United States Patent [19]
Grimm et al.

[11] Patent Number: 5,837,542
[45] Date of Patent: Nov. 17, 1998

[54] INTERCELLULAR ADHESION MOLECULE-1 (ICAM-1) RIBOZYMES

[75] Inventors: Susan Grimm; Dan T. Stinchcomb; James McSwiggen; Sean Sullivan; Kenneth G. Draper, all of Boulder, Colo.

[73] Assignee: Ribozyme Pharmaceuticals, Inc., Boulder, Colo.

[21] Appl. No.: 292,620

[22] Filed: Aug. 17, 1994

Related U.S. Application Data

[63] Continuation-in-part of Ser. No. 8,895, Jan. 19, 1993, abandoned, which is a continuation-in-part of Ser. No. 989,849, Dec. 7, 1992, abandoned.

[51] Int. Cl.[6] .............................. C12Q 1/68; C12N 15/85; A61K 48/00

[52] U.S. Cl. ........................... 435/366; 435/6; 435/91.31; 435/172.3; 435/320.1; 435/325; 536/23.1; 536/23.2; 536/24.5

[58] Field of Search ........................ 435/6, 91.31, 172.1, 435/172.3, 320.1, 325, 366; 536/23.1, 23.2, 24.5; 514/44

[56] References Cited

PUBLICATIONS

Stuel et al. Phesm Res.12:465–483 (1995).

*Primary Examiner*—John L. LeGuyader
*Attorney, Agent, or Firm*—Lyon & Lyon LLP

[57] ABSTRACT

Enzymatic RNA molecules which cleave ICAM-1 mRNA.

13 Claims, 6 Drawing Sheets

HAMMERHEAD RIBOZYME SUBSTRATE MOTIFS

HEPATITIS DELTA VIRUS RIBOZYME

RNase H Assay

- Body-labeled transcript (not purified)
- DNA oligo (10 nM, 100 nM and 1000 nM)
- RNAse H (0.08 - 1.0 u/µl)
- 37°C, 10 min

INTERCELLULAR ADHESION MOLECULE-1 (ICAM-1) RIBOZYMES

RELATED APPLICATIONS

This application is a continuation-in-part of Sullivan et al., "Method and Reagent for Treatment of inflammatory Disease" filed Jan. 19, 1993, U.S. Ser. No. 08/008,895, now abandoned, which is a continuation-in-part of Sullivan et al., having the same title filed Dec. 7, 1992, U.S. Ser. No. 07/989,849, now abandoned, both applications are hereby incorporated by reference herein.

FIELD OF THE INVENTION

The present invention relates to therapeutic compositions and methods for the treatment or diagnosis of diseases or conditions related to ICAM-1 levels, such as transplant rejection, cancer, rheumatoid arthritis, asthma, reperfusion injury, and inflammatory or autoimmune disorders. For example, such treatments will be useful for transplant rejection, myocardial ischemia, stroke, psoriasis, and Kawasaki disease.

BACKGROUND OF THE INVENTION

The following is a brief description of the physiological role of ICAM-1. The discussion is not meant to be complete and is provided only for understanding of the invention that follows. This summary is not an admission that any of the work described below is prior art to the claimed invention.

Intercellular adhesion molecule-1 (ICAM-1) is a cell surface protein whose expression is induced by inflammatory mediators. ICAM-1 is required for adhesion of leukocytes to endothelial cells and for several immunological functions including antigen presentation, immunoglobulin production and cytotoxic cell activity. Blocking ICAM-1 function prevents immune cell recognition and activity during transplant rejection and in animal models of rheumatoid arthritis, asthma and reperfusion injury.

Cell-cell adhesion plays a pivotal role in inflammatory and immune responses (Springer et al., 1987 *Ann. Rev. Immunol.* 5, 223–252). Cell adhesion is required for leukocytes to bind to and migrate through vascular endothelial cells. In addition, cell—cell adhesion is required for antigen presentation to T cells, for B cell induction by T cells, as well as for the cytotoxicity activity of T cells, NK cells, monocytes or granulocytes. Intercellular adhesion molecule-1 (ICAM-1) is a 110 kilodalton member of the immunoglobulin superfamily that is involved in all of these cell—cell interactions (Simmons et al., 1988 *Nature* (London) 331, 624–627).

ICAM-1 is expressed on only a limited number of cells and at low levels in the absence of stimulation (Dustin et al., 1986 *J. Immunol.* 137, 245–254). Upon treatment with a number of inflammatory mediators (lipopolysaccharide, 65-interferon, tumor necrosis factor-60, or interleukin-1), a variety of cell types (endothelial, epithelial, fibroblastic and hematopoietic cells) in a variety of tissues express high levels of ICAM-1 on their surface (Sringer et. al. supra; Dustin et al., supra; and Rothlein et al., 1988 *J. Immunol.* 141, 1665–1669). Induction occurs via increased transcription of ICAM-1 mRNA (Simmons et al., supra). Elevated expression is detectable after 4 hours and peaks after 16–24 hours of induction.

ICAM-1 induction is critical for a number of inflammatory and immune responses. In vitro, antibodies to ICAM-1 block adhesion of leukocytes to cytokine-activated endothelial cells (Boyd, 1988 *Proc. Natl. Acad. Sci. USA* 85, 3095–3099; Dustin and Springer, 1988 *J. Cell Biol.* 107, 321–331). Thus, ICAM-1 expression may be required for the extravasation of immune cells to sites of inflammation. Antibodies to ICAM-1 also block T cell killing, mixed lymphocyte reactions, and T cell-mediated B cell differentiation, suggesting that ICAM-1 is required for these cognate cell interactions (Boyd et al., supra). The importance of ICAM-1 in antigen presentation is underscored by the inability of ICAM-1 defective murine B cell mutants to stimulate antigen-dependent T cell proliferation (Dang et al., 1990 *J. Immuno.* 144, 4082–4091). Conversely, murine L cells require transfection with human ICAM-1 in addition to HLA-DR in order to present antigen to human T cells (Altmann et al., 1989 *Nature* (London) 338, 512–514). In summary, evidence in vitro indicates that ICAM-1 is required for cell—cell interactions critical to inflammatory responses, cellular immune responses, and humoral antibody responses.

SUMMARY OF THE INVENTION

This invention relates to ribozymes, or enzymatic RNA molecules, directed to cleave mRNA species encoding ICAM-1. In particular, applicant describes the selection and function of ribozymes capable of cleaving this RNA and their use to reduce levels of ICAM-1 in various tissues to treat the diseases discussed herein. Such ribozymes are also useful for diagnostic uses.

Ribozymes that cleave ICAM-1 mRNA represent a novel therapeutic approach to inflammatory or autoimmune disorders. ICAM-1 function can be blocked therapeutically using monoclonal antibodies. Ribozymes have the advantage of being generally immunologically inert, whereas significant neutralizing anti-IgG responses can be observed with some monoclonal antibody treatments. Antisense DNA molecules have been described that block ICAM-1 expression (Chiang et al., 1991 *J. Biol. Chem.* 266, 18162–18171). However, ribozymes may show greater perdurance or lower effective doses than antisense molecules due to their catalytic properties and their inherent secondary and tertiary structures. Such ribozymes, with their catalytic activity and increased site specificity (as described below), represent more potent and safe therapeutic molecules than antisense oligonucleotides.

Applicant indicates that these ribozymes are able to inhibit expression of ICAM-1 and that the catalytic activity of the ribozymes is required for their inhibitory effect. Those of ordinary skill in the art, will find that it is clear from the examples described that other ribozymes that cleave target ICAM-1 encoding mRNAs may be readily designed and are within the invention.

Six basic varieties of naturaliy-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992 *Proc. Natl. Acad. Sci. USA*, 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence). Examples of such hammerhead motifs are described by Rossi et al., 1992 *Aids Research and Human Retroviruses*, 8, 183, of hairpin motifs by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, 1989 *Biochemistry*, 28, 4929 and Hampel et al., 1990 *Nucleic Acids Res.earch* 18, 299, and an example of the hepatitis delta virus motif is described by Perrotta and Been, 1992, *Biochemistry* 31, 16, of the RNaseP motif by Guerrier-Takada et al., 1983 *Cell* 35, 849, of the *Neurospora* VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target ICAM-1 encoding mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs, (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991 *Proc. Natl. Acad. Sci. USA*, 88, 10591–5; Kashani-Sabet et al., 1992 *Antisense Res. Dev.* 2, 3–15; Dropulic et al., 1992 *J Virol.* 66, 1432–41; Weerasinghe et al., 1991 *J Virol.* 65, 5531–5534; Ojwang et al., 1992 *Proc. Natl. Acad. Sci. USA*, 89, 10802–10806; Chen et al., 1992 *Nucleic Acids Res.*, 20, 4581–1589; Sarver et al., 1990 *Science*, 247, 1222–1225). Those skilled in the art realize that any ribozyme can be expressed in eukaryotic cells from the appropriate DNA vector. The activity of such ribozymes can be augmented by their release from the primary transcript by a second ribozyme (Draper et al., PCT WO93/23569, and Sullivan et al., PCT WO94/02595, both 35 hereby incorporated in their totality by reference herein; Ohkawa et al., 1992, *Nucleic Acids Symp. Ser.*, 27, 15–6; Taira et al., 1991 *Nucleic Acids Res.*, 19, 5125–5130; Ventura et al., 1993 *Nucleic Acids Res.*, 21, 3249–55).

Thus, in a first aspect, the invention features ribozymes that inhibit ICAM-1 production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target ICAM-1 encoding mRNAs, preventing translation and protein accumulation. In the absence of the expression of the target gene, a therapeutic effect may be observed.

By "inhibit" is meant that the activity or level of ICAM-1 encoding mRNA is reduced below that observed in the absense of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of ICAM-1 activity in a cell or tissue. By "related" is meant that the inhibition of ICAM-1 mRNA and thus reduction in the level of ICAM-1 will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues or cells ex vivo or in vivo by injection or through the use of a catheter, infusion pump or stent, with or without their incorporation in biopolymers. In preferred embodiments, the ribozymes have binding arms which are complementary to the sequences in Tables II, III, VI–IX. Examples of such ribozymes are shown in Tables IV–VIII and X. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit ICAM-1 activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.

Drawings:

FIG. 1 is a diagrammatic representation of the hammerhead ribozyme domain known in the art.

FIG. 2a is a diagrammatic representation of the hammerhead ribozyme domain known in the art; FIG. 2b is a diagrammatic representation of the hammerhead ribozyme as divided by Uhlenbeck (1987, *Nature* 327, 596–600) into a substrate and enzyme portion; FIG. 2c is a similar diagram showing the hammerhead divided by Haseloff and Gerlach (1988, *Nature* 334, 585–591) into two portions; and FIG. 2d is a similar diagram showing the hammerhead divided by Jeffries and Symons (1989, *Nucl. Acids. Res.* 17, 1371–1371) into two portions.

Figure 6A:
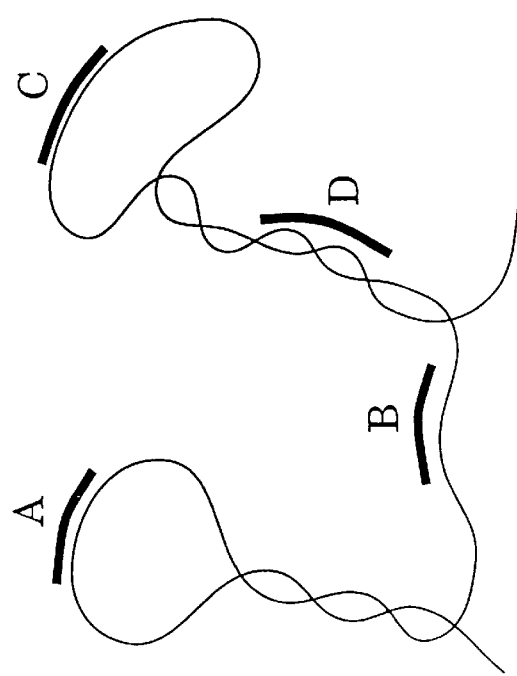
Figure 6B:
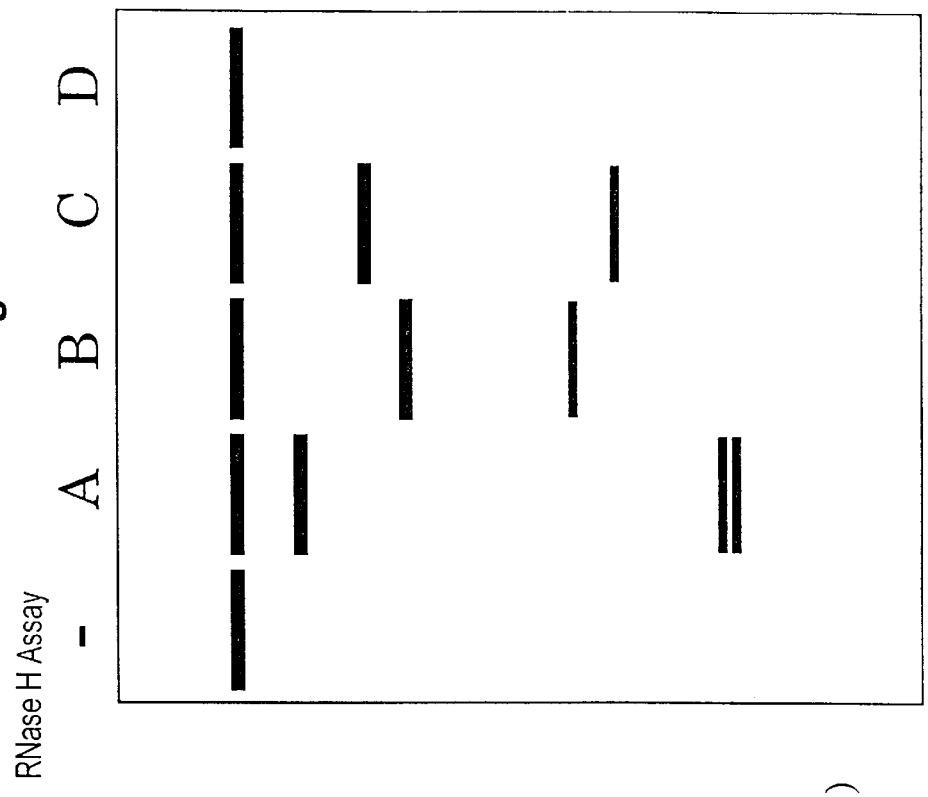

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Ribozymes

Ribozymes of this invention block to some extent ICAM-1 expression and can be used to treat disease or diagnose such disease. Ribozymes will be delivered to cells in culture and to tissues in animal models of transplant rejection and rheumatoid arthritis. Ribozyme cleavage of ICAM-1 mRNA in these systems may prevent inflammatory cell function and alleviate disease symptoms.

Target Sites

Targets for useful ribozymes can be determined as disclosed in Draper et al supra. Sullivan et al., supra, as well as by Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to rat, mouse and human RNA are provided, those in the art will recognize that the equivalent human RNA targets described can be used as described below. Thus, the same target may be used, but binding arms suitable for targetting human RNA sequences are present in the ribozyme. Such targets may also be selected as described below.

The sequence of human, rat and mouse ICAM-1 mRNA can be screened for accessible sites using a computer folding algorithm. Regions of the mRNA that did not form secondary folding structures and that contain potential hammerhead or hairpin ribozyme cleavage sites can be identified. These sites are shown in Tables II, III, and VI–IX. (All sequences are 5' to 3' in the tables.) While rat, mouse and human sequences can be screened and ribozymes thereafter designed, the human targetted sequences are of most utility. However, as discussed in Stinchcomb et al. "Method and Composition for Treatment of Restenosis and Cancer Using Ribozymes," U.S. Ser. No. 08/245,466, filed May 18, 1994, and hereby incorporated by reference herein, rat and mouse targetted ribozmes are useful to test efficacy of action of the ribozyme prior to testing in humans. The nucleotide base position is noted in the Tables as that site to be cleaved by the designated type of ribozyme. (In Table III, lower case letters indicate positions that are not conserved between the Human and the Mouse ICAM sequences.)

To test whether the sites predicted by the computer-based RNA folding algorithm correspond to accessible sites in the target mRNA, hammerhead sites are selected for analysis. Hammerhead ribozymes are designed that could bind and are individually analyzed by computer folding (Jaeger et al., 1989, *Proc. Nati. Acad. Sci. USA*, 86, 7706–7710) to assess whether the ribozyme sequences fold into the appropriate secondary structure. Those ribozymes with unfavorable intramolecular interactions between the binding arms and the catalytic core are eliminated from consideration. Varying binding arms lengths can be chosen to optimize activity. Generally, at least 5 bases on each arm are able to bind to, or otherwise interact with, the target RNA.

Referring to FIG. 6, mRNA is screened for accessible cleavage sites by the method described generally in Draper et al., WO/US93/04020 and McSwiggen, U.S. patent application Ser. No. 07/883,849 filed May 1, 1992, entitled "Assay for ribozyme target site," both hereby incorporated by reference herein. Briefly, DNA oligonucleotides representing potential hammerhead ribozyme cleavage sites are synthesized. A polymerase chain reaction is used to generate a substrate for T7 RNA polymerase transcription from human or murine ICAM-1 cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a phosphor imaging system. From these data, hammerhead ribozyme sites are chosen as the most accessible.

Ribozymes of the hammerhead motif are designed to anneal to various sites in the mRNA message. The binding arms are complementary to the target site sequences described above. The ribozymes were chemically synthesized. The method of synthesis used follows the procedure for normal RNA synthesis as described in Usman et al., 1987 *J. Am. Chem. Soc.*, 109, 7845–7854 and in Scaringe et al., 1990 *Nucleic Acids Res.*, 18, 5433–5441, and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from (Hertel et al., 1992 *Nucleic Acids Res.*, 20, 3252). Hairpin ribozymes are synthesized in two parts and annealed to reconstruct the active ribozyme (Chowrira and Burke, 1992 *Nucleic Acids Res.*, 20, 2835–2840). All ribozymes are modified to enhance stability by modification of five ribonucleotides at both the 5' and 3' ends with 2'-O-methyl groups. Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736) the totality of which is hereby incorporated herein by reference) and were resuspended in water.

The sequences of the chemically synthesized ribozymes useful in this study are shown in Tables IV–VIII and X. Those in the art will recognize that these sequences are representative only of many more such sequences where the enzymatic portion of the ribozyme (all but the binding arms) is altered to affect activity and may be formed of ribonucleotides or other nucleotides or non-nucleotides. Such ribozymes are equivalent to the ribozymes described specifically in the Tables.

Optimizing Ribozyme Activity

Figure 2A:
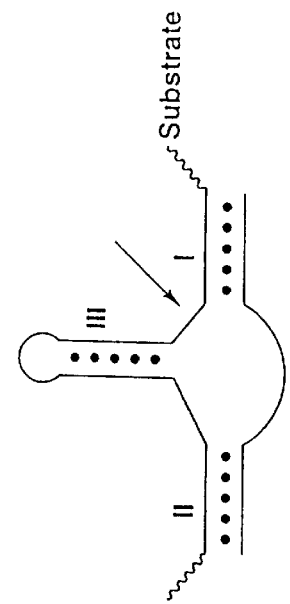
Figure 2B:
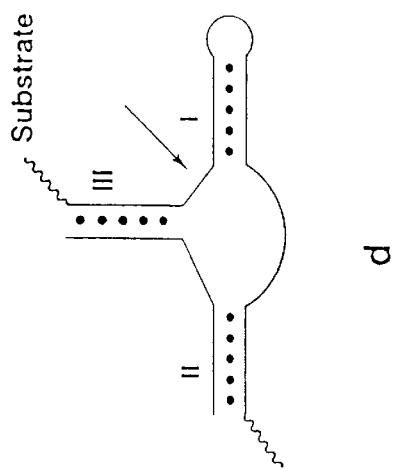
Figure 2C:
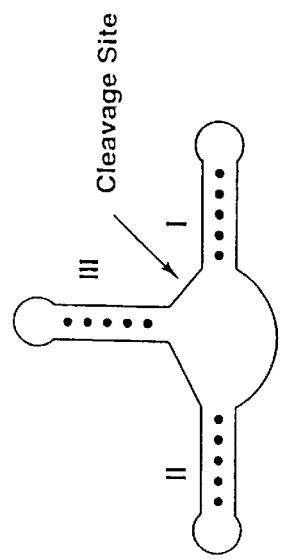
Figure 2D:
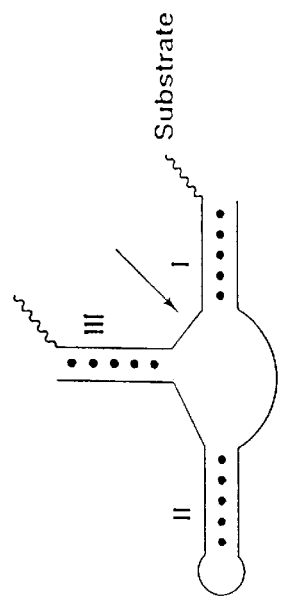

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., Nature 1990, 344:565; Pieken et al., Science 1991, 253:314; Usman and Cedergren, *Trends in Biochem. Sci.* 1992, 17:334; Usman et al., International Publication No. WO 93/15187; and Rossi et al., International Publication No. WO 91/03162, as well as Usman,N. et al. U.S. patent application Ser. No. 07/829,729, and Sproat,B. European Patent Application 92110298.4 which describe various chemical modifications that can be made to the sugar moieties of enzymatic RNA molecules. All these publications are hereby incorporated by reference herein.), modifications which enhance their efficacy in cells, and removal of stem II bases to shorten RNA synthesis times and reduce chemical requirements.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. The RNA/vehicle combination is locally delivered by direct injection or by use of a catheter, infusion pump or stent. Alternative routes of delivery include, but are not limited to, intramuscular injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol I or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. U S A*, 87, 6743–7; Gao, and Huang, 1993 *Nucleic Acids Res.*, 21, 2867–72; Lieber et al., 1993 *Methods Enzymol.*, 217, 47–66; Zhou et al., 1990 *Mol. Cell. Biol.*, 4529–37). Several investigators have demonstrated that ribozymes expressed from such promoters can function in mammalian cells (e.g. Kashani-Sabet, et al., 1992 *Antisense Res. Dev.* 2, 3–15; Ojwang et al., 1992 *Proc. Natl. Acad. Sci. U S A* 89, 10802–6; Chen et al., 1992 *Nucleic Acids Res.*, 20, 4581–9; Yu et al., 1993 *Proc. Natl. Acad. Sci. U S A* 90, 6340–4; L'Huillier, et al., 1992 *EMBO J.* 11, 4411–8; Lisziewicz et al., 1993 *Proc. Natl. Acad. Sci. U. S. A.* 90, 8000–4). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral vectors).

In a preferred embodiment of the invention, a transcription unit expressing a ribozyme that cleaves ICAM-1 RNA is inserted into a plasmid DNA vector or an adenovirus DNA viral vector. Both vectors have been used to transfer genes to the intact vasculature of live animals (Willard et al., 1992 *Circulation*, 86, I-473.; Nabel et al., 1990 *Science* 249, 1285–1288) and both vectors lead to transient gene expression. The adenovirus vector is delivered as recombinant adenoviral particles. DNA may be delivered alone or complexed with vehicles (as described for RNA above). The DNA, DNA/vehicle complexes, or the recombinant adenovirus particles are locally administered to the site of treatment, e.g., through the use of a catheter, stent or infusion pump.

EXAMPLE 1

ICAM-1 Hammerhead Ribozymes

By engineering ribozyme motifs we have designed several ribozymes directed against ICAM-1 mRNA sequences. These have been synthesized with modifications that improve their nuclease resistance. These ribozymes cleave ICAM-1 target sequences in vitro.

The ribozymes will be tested for function in vivo by exogenous delivery to human umbilical vein endothelial cells (HUVEC). Ribozymes will be delivered by incorporation into liposomes, by complexing with cationic lipids, by microinjection, or by expression from DNA vectors. Cytokine-induced ICAM-1 expression will be monitored by ELISA, by indirect immunofluoresence, and/or by FACS analysis. ICAM-1 mRNA levels will be assessed by Northern, by RNAse protection, by primer extension or by quantitative RT-PCR analysis. Ribozymes that block the induction of ICAM-1 protein and mRNA by more than 90% will be identified.

RNA ribozymes and/or genes encoding them will be locally delivered to transplant tissue ex vivo in animal models. Expression of the ribozyme will be monitored by its ability to block ex vivo induction of ICAM-1 mRNA and protein. The effect of the anti-ICAM-1 ribozymes on graft rejection will then be assessed. Similarly, ribozymes will be introduced into joints of mice with collagen-induced arthritis or rabbits with Streptococcal cell wall-induced arthritis. Liposome delivery, cationic lipid delivery, or adeno-associated virus vector delivery can be used. One dose (or a few infrequent doses) of a stable anti-ICAM-1 ribozyme or a gene construct that constitutively expresses the ribozyme may abrogate inflammatory and immune responses in these diseases.

Uses

ICAM-1 plays a central role in immune cell recognition and function. Ribozyme inhibition of ICAM-1 expression can reduce transplant rejection and alleviate symptoms in patients with rheumatoid arthritis, asthma or other acute and chronic inflammatory disorders. We have engineered several ribozymes that cleave ICAM-1 mRNA. Ribozymes that efficiently inhibit ICAM-1 expression in cells can be readily found and their activity measured with regard to their ability to block transplant rejection and arthritis symptoms in animal models. These anti-ICAM-1 ribozymes represent a novel therapeutic for the treatment of immunological or inflammatory disorders.

The therapeutic utility of reduction of activity of ICAM-1 function is evident in the following disease targets. The noted references indicate the role of ICAM-1 and the therapeutic potential of ribozymes described herein. Thus, these targets can be therapeutically treated with agents that reduce ICAM-1 expression or function. These diseases and the studies that support a critical role for ICAM-1 in their pathology are listed below. This list is not meant to be complete and those in the art will recognize further conditions and diseases that can be effectively treated using ribozymes of the present invention.

Transplant rejection

ICAM-1 is expressed on venules and capillaries of human cardiac biopsies with histological evidence of graft rejection (Briscoe et al., 1991 *Transplantation* 51, 537–539).

Antibody to ICAM-1 blocks renal (Cosimi et al., 1990 *J. Immunol.* 144, 4604–4612) and cardiac (Flavin et al., 1991 *Transplant. Proc.* 23, 533–534) graft rejection in primates.

A Phase I clinical trial of a monoclonal anti-ICAM-1 antibody showed significant reduction in rejection and a significant increase in graft function in human kidney transplant patients (Haug, et al., 1993 *Transplantation* 55, 766–72).

Rheumatoid arthritis

ICAM-1 overexpression is seen on synovial fibroblasts, endothelial cells, macrophages, and some lymphocytes (Chin et al., 1990 *Arthritis Rheum* 33, 1776–86; Koch et al., 1991 *Lab Invest* 64, 313–20).

Soluble ICAM-1 levels correlate with disease severity (Mason et al., 1993 *Arthritis Rheum* 36, 519–27).

Anti-ICAM antibody inhibits collagen-induced arthritis in mice (Kakimoto et al., 1992 *Cell Immunol* 142, 326–37).

Anti-ICAM antibody inhibits adjuvant-induced arthritis in rats (Iigo et al., 1991 *J Immunol* 147, 4167–71).

Myocardial ischemia, stroke, and reperfusion injury

Anti-ICAM-1 antibody blocks adherence of neutrophils to anoxic endothelial cells (Yoshida et al., 1992 *Am J Physiol* 262, H1891–8).

Anti-ICAM-1 antibody reduces neurological damage in a rabbit model of cerebral stroke (Bowes et al., 1993 *Exp Neurol* 119, 215–9).

Anti-ICAM-1 antibody protects against reperfusion injury in a cat model of myocardial ischemia (Ma et al., 1992 *Circulation* 86, 937–46).

Asthma

Antibody to ICAM-1 partially blocks eosinophil adhesion to endothelial cells and is overexpressed on inflamed airway endothelium and epithelium in vivo (Wegner et al., 1990 *Science* 247, 456–9).

In a primate model of asthma, anti-ICAM-1 antibody blocks airway eosinophilia (Wegner et al., supra) and prevents the resurgence of airway inflammation and hyper-responsiveness after dexamethosone treatment (Gundel et al., 1992 *Clin Exp Allergy* 22, 569–75).

Psoriasis

Surface ICAM-1 and a clipped, soluble version of ICAM-1 is expressed in psoriatic lesions and expression correlates with inflammation (Kellner et al., 1991 *Br J Dermatol* 125, 211–6; Griffiths 1989 *J Am Acad Dermatol* 20, 617–29; Schopf et al., 1993 *Br J Dermatol* 128, 34–7).

Anti-ICAM antibody blocks keratinocyte antigen presentation to T cells (Nickoloff et al., 1993 *J Immunol* 150, 2148–59).

Kawasaki disease

Surface ICAM-1 expression correlates with the disease and is reduced by effective immunoglobulin treatment (Leung, et al., 1989 *Lancet* 2, 1298–302).

Soluble ICAM levels are elevated in Kawasaki disease patients; particularly high levels are observed in patients with coronary artery lesions (Furukawa et al., 1992 *Arthritis Rheum* 35, 672–7; Tsuji, 1992 *Arerugi* 41, 1507–14).

Circulating LFA-1$^+$ T cells are depleted (presumably due to ICAM-1 mediated extravasation) in Kawasaki disease patients (Furukawa et al., 1993 *Scand J Immunol* 37, 377–80).

Diagnostic Uses

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an ICAM-1 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., ICAM-1) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena* thermophila rRNA, fungal mitochondria, chloroplasts, phage T4, blue-green algae, and others.

RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

TABLE I-continued

Characteristics of Ribozymes

Hammerhead Ribozyme

Figure 1:
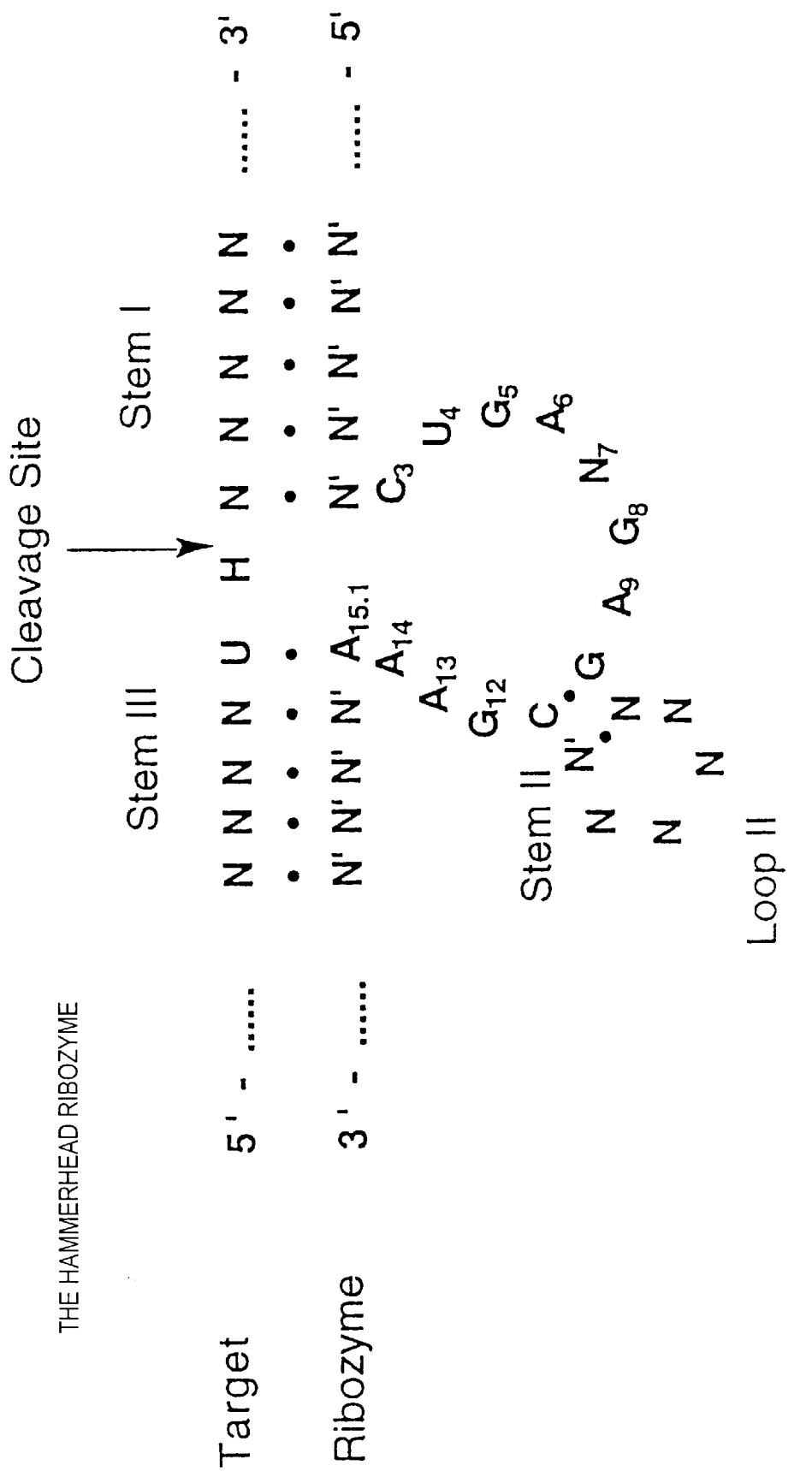

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIGS. 1 and 2 show examples of various manifestations as used in the art).

Hairpin Ribozyme

Figure 3:
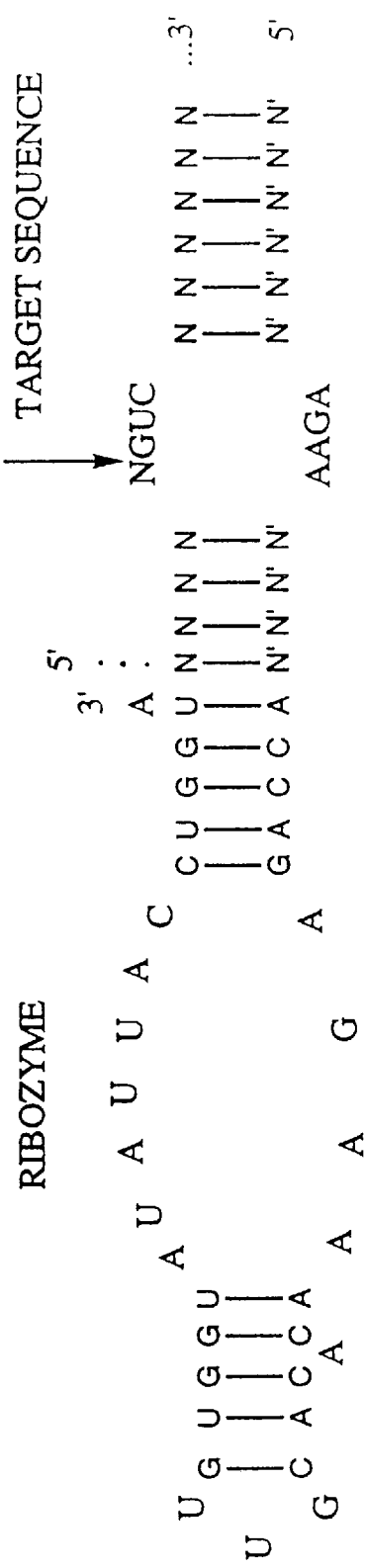
FIG. 3 is a representation of the general structure of the hairpin ribozyme domain known in the art.

Size: ~50 nucleotides.
Requires the target sequence GUC immediately 3' of the cleavage site.
Binds 4–6 nucleotides at 5' site of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Figure 4:
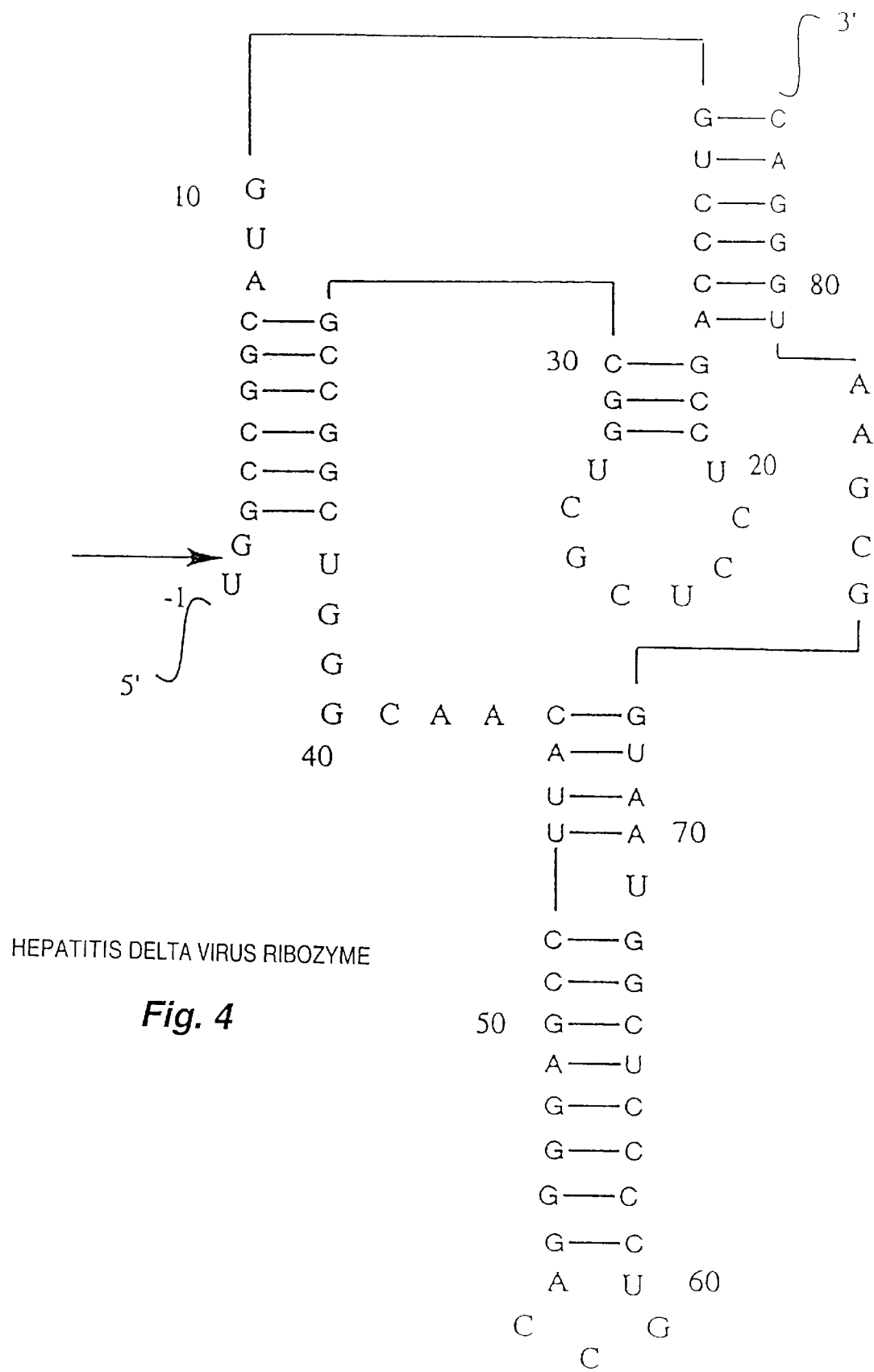
FIG. 4 is a representation of the general structure of the hepatitis delta virus ribozyme domain known in the art.

Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Neurospora VS RNA Ribozyme

Figure 5:
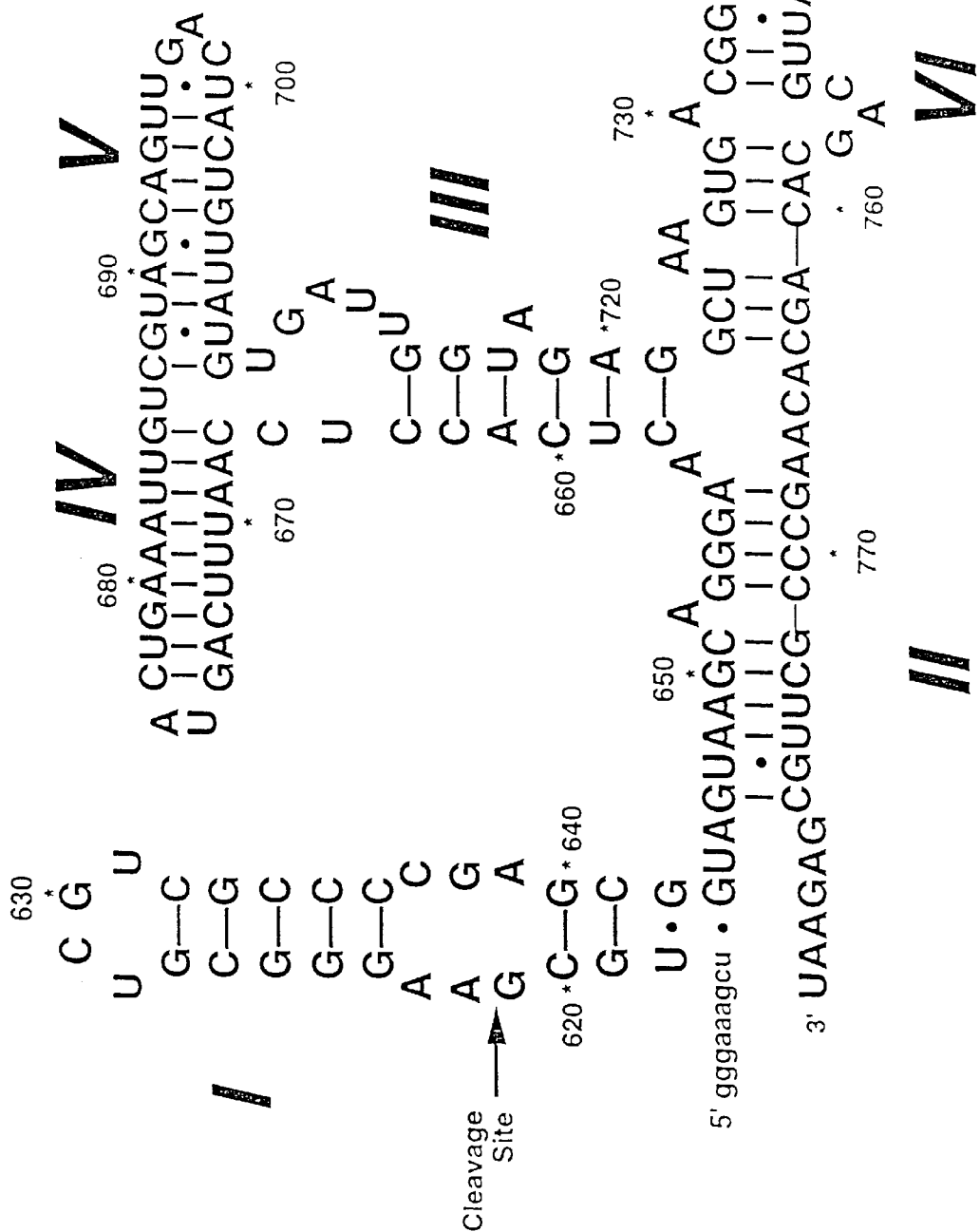
FIG. 5 is a representation of the general structure of the VS RNA ribozyme domain known in the art.

Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Human ICAM HH Target sequence

| nt. Position | Target Sequences | Seq. ID No. | nt. Position | Target Sequences | Seq. ID No. |
|---|---|---|---|---|---|
| 11 | CCCCAGU C GACGCUG | 7 | 386 | ACCGUGU A CUGGACU | 47 |
| 23 | CUGAGCU C CUCUGCU | 8 | 394 | CUGGACU C CAGAACG | 48 |
| 26 | AGCUCCU C UGCUACU | 9 | 420 | CACCCCU C CCCUCUU | 49 |
| 31 | CUCUGCU A CUCAGAG | 10 | 425 | CUCCCCU C UUGGCAG | 50 |
| 34 | UGCUACU C AGAGUUG | 11 | 427 | CCCCUCU U GGCAGCC | 51 |
| 40 | UCAGAGU U GCAACCU | 12 | 450 | AGAACCU U ACCCUAC | 52 |
| 48 | GCAACCU C AGCCUCG | 13 | 451 | GAACCUU A CCCUACG | 53 |
| 54 | UCAGCCU C GCUAUGG | 14 | 456 | UUACCCU A CGCUGCC | 54 |
| 58 | CCUCGCU A UGGCUCC | 15 | 495 | CCAACCU C ACCGUGG | 55 |
| 64 | UAUGGCU C CCAGCAG | 16 | 510 | UGCUGCU C CGUGGGG | 56 |
| 96 | CCGCACU C CUGGUCC | 17 | 564 | CUGAGGU C ACGACCA | 57 |
| 102 | UCCUGGU C CUGCUCG | 18 | 592 | GAGAGAU C ACCAUGG | 58 |
| 108 | UCCGCU C GGGGCUC | 19 | 607 | AGCCAAU U UCUCGUG | 59 |
| 115 | CGGGGCU C UGUUCCC | 20 | 608 | GCCAAUU U CUCGUGC | 60 |
| 119 | GCUCUGU U CCCAGGA | 21 | 609 | CCAAUUU C UCGUGCC | 61 |
| 120 | CUCUGUU C CCAGGAC | 22 | 611 | AAUUUCU C GUGCCGC | 62 |
| 146 | CAGACAU C UGUGUCC | 23 | 656 | GAGCUGU U UGAGAAC | 63 |
| 152 | UCUGUGU C CCCCUCA | 24 | 657 | AGCUGUU U GAGAACA | 64 |
| 158 | UCCCCCU C AAAAGUC | 25 | 668 | AACACCU C GGCCCCC | 65 |
| 165 | CAAAAGU C AUCCUGC | 26 | 677 | GCCCCCU A CCAGCUC | 66 |
| 168 | AAGUCAU C CUGCCCC | 27 | 684 | ACCAGCU C CAGACCU | 67 |
| 185 | GGAGGCU C CGUGCUG | 28 | 692 | CAGACCU U UGUCCUG | 68 |
| 209 | AGCACCU C CUGUGAC | 29 | 693 | AGACCUU U GUCCUGC | 69 |
| 227 | CCCAAGU U GUUGGGC | 30 | 696 | CCUUUGU C CUGCCAG | 70 |
| 230 | AAGUUGU U GGGCAUA | 31 | 709 | AGCGACU C CCCCACA | 71 |

TABLE II-continued

Human ICAM HH Target sequence

| nt. Position | Target Sequences | Seq. ID No. | nt. Position | Target Sequences | Seq. ID No. |
|---|---|---|---|---|---|
| 237 | UGGGCAU A GAGACCC | 32 | 720 | CACAACU U GUCAGCC | 72 |
| 248 | ACCCCGU U GCCUAAA | 33 | 723 | AACUUGU C AGCCCCC | 73 |
| 253 | GUUGCCU A AAAAGGA | 34 | 735 | CCCGGGU C CUAGAGG | 74 |
| 263 | AAGGAGU U GCUCCUG | 35 | 738 | GGGUCCU A GAGGUGG | 75 |
| 267 | AGUUGCU C CUGCCUG | 36 | 765 | CCGUGGU C UGUUCCC | 76 |
| 293 | AAGGUGU A UGAACUG | 37 | 769 | GGUCUGU U CCCUGGA | 77 |
| 319 | AGAAGAU A GCCAACC | 38 | 770 | GUCUGUU C CCUGGAC | 78 |
| 335 | AUGCUAU A UUCAAAC | 39 | 785 | GGGCUGU U CCCAGUC | 79 |
| 337 | GUGCUAU U CAAACUG | 40 | 786 | GGCUGUU C CCAGUCU | 80 |
| 338 | UGCUAUU C AAACUGC | 41 | 792 | UCCCAGU C UCGGAGG | 81 |
| 359 | GGGCAGU C AACAGCU | 42 | 794 | CCAGUCU C GGAGGCC | 82 |
| 367 | AACAGCU A AAACCUU | 43 | 807 | CCCAGGU C CACCUGG | 83 |
| 374 | AAAACCU U CCUCACC | 44 | 833 | CAGAGGU U GAACCCC | 84 |
| 375 | AAACCUU C CUCACCG | 45 | 846 | CCACAGU C ACCUAUG | 85 |
| 378 | CCUUCCU C ACCGUGU | 46 | 851 | GUCACCU A UGGCAAC | 86 |
| 863 | AACGACU C CUUCUCG | 87 | 1408 | UCGAGAU C UUGAGGG | 136 |
| 866 | GACUCCU U CUCGGCC | 88 | 1410 | GAGAUCU U GAGGGCA | 137 |
| 867 | ACUCCUU C UCGGCCA | 89 | 1421 | GGCACCU A CCUCUGU | 138 |
| 869 | UCCUUCU C GGCCAAG | 90 | 1425 | CCUACCU C UGUCGGG | 139 |
| 881 | AAGGCCU C AGUCAGU | 91 | 1429 | CCUCUGU C GGGCCAG | 140 |
| 885 | CCUCAGU C AGUGUGA | 92 | 1444 | GAGCACU C AAGGGGA | 141 |
| 933 | GUGCAGU A AUACUGG | 93 | 1455 | GGGAGGU C ACCCGCG | 142 |
| 936 | CAGUAAU A CUGGGGA | 94 | 1482 | AUGUGCU C UCCCCCC | 143 |
| 978 | UGACCAU C UACAGCU | 95 | 1484 | GUGCUCU C CCCCCGG | 144 |
| 980 | ACCAUCU A CAGCUUU | 96 | 1493 | CCCCGGU A UGAGAUU | 145 |
| 986 | UACAGCU U UCCGGCG | 97 | 1500 | AUGAGAU U GUCAUCA | 146 |
| 987 | ACAGCUU U CCGGCGC | 98 | 1503 | AGAUUGU C AUCAUCA | 147 |
| 988 | CAGCUUU C CGGCGCC | 99 | 1506 | UUGUCAU C AUCACUG | 148 |
| 1005 | ACGUGAU U CUGACGA | 100 | 1509 | UCAUCAU C ACUGUGG | 149 |
| 1006 | CGUGAUU C UGACGAA | 101 | 1518 | CUGUGGU A GCAGCCG | 150 |
| 1023 | CAGAGGU C UCAGAAG | 102 | 1530 | CCGCAGU C AUAAUGG | 151 |
| 1025 | GAGGUCU C AGAAGGG | 103 | 1533 | CAGUCAU A AUGGGCA | 152 |
| 1066 | CCACCCU A GAGCCAA | 104 | 1551 | CAGGCCU C AGCACGU | 153 |
| 1092 | AUGGGGU U CCAGCCC | 105 | 1559 | AGCACGU A CCUCUAU | 154 |
| 1093 | UGGGGUU C CAGCCCA | 106 | 1563 | CGUACCU C UAUAACC | 155 |
| 1125 | CCCAGCU C CUGCUGA | 107 | 1565 | UACCUCU A UAACCGC | 156 |
| 1163 | CGCAGCU U CUCCUGC | 108 | 1567 | CCUCUAU A ACCGCCA | 157 |
| 1164 | GCAGCUU C UCCUGCU | 109 | 1584 | GGAAGAU C AAGAAAU | 158 |
| 1166 | AGCUUCU C CUGCUCU | 110 | 1592 | AAGAAAU A CAGACUA | 159 |
| 1172 | UCCUGCU U UGCAACC | 111 | 1599 | ACAGACU A CAACAGG | 160 |
| 1200 | GCCAGCU U AUACACA | 112 | 1651 | CACGCCU C CCUGAAC | 161 |
| 1201 | CCAGCUU A UACACAA | 113 | 1661 | UGAACCU A UCCCGGG | 162 |
| 1203 | AGCUUAU A CACAAGA | 114 | 1663 | AACCUAU C CCGGGAC | 163 |
| 1227 | GGGAGCU U CGUGUCC | 115 | 1678 | AGGGCCU C UUCCUCG | 164 |
| 1228 | GGAGCUU C GUGUCCU | 116 | 1680 | GGCUCUU C CUCGGCC | 165 |
| 1233 | UUCGUGU C CUGUAUG | 117 | 1681 | GCCUCUU C CUCGGCC | 166 |
| 1238 | GUCCUGU A UGGCCCC | 118 | 1684 | UCUUCCU C GGCCUUC | 167 |
| 1264 | GAGGGAU U GUCCGGG | 119 | 1690 | UCGGCCU U CCCAUAU | 168 |
| 1267 | GGAUUGU C CGGGAAA | 120 | 1691 | CGGCCUU C CCAUAUU | 169 |
| 1294 | AGAAAAU U CCCAGCA | 121 | 1696 | UUCCCAU A UUGGUGG | 170 |
| 1295 | GAAAAUU C CCAGCAG | 122 | 1698 | CCCAUAU U GGUGGCA | 171 |
| 1306 | GCAGACU C CAAUGUG | 123 | 1737 | AAGACAU A UGCCAUG | 172 |
| 1321 | CCAGGCU U GGGGGAA | 124 | 1750 | UGCAGCU A CACCUAC | 173 |
| 1334 | AACCCAU U GCCCGAG | 125 | 1756 | UACACCU A CCGGCCC | 174 |
| 1344 | CCGAGCU C AAGUGUC | 126 | 1787 | AGGGCAU U GUCCUCA | 175 |
| 1351 | CAAGUGU C UAAAGGA | 127 | 1790 | GCAUUGU C CUCAGUC | 176 |
| 1353 | AGUGUCU A AAGGAUG | 128 | 1793 | UUGUCCU C AGUCAGA | 177 |
| 1366 | UGGCACU U UCCCACU | 129 | 1797 | CCUCAGU C AGAUACA | 178 |
| 1367 | GGCACUU U CCCACUG | 130 | 1802 | GUCAGAU A CAACAGC | 179 |
| 1368 | GCACUUU C CCACUGC | 131 | 1812 | ACAGCAU U UGGGGCC | 180 |
| 1380 | UGCCCAU C GGGGAAU | 132 | 1813 | CAGCAUU U GGGGCCA | 181 |
| 1388 | GGGGAAU C AGUGACU | 133 | 1825 | CCAUGGU A CCUGCAC | 182 |
| 1398 | UGACUGU C ACUCGAG | 134 | 1837 | CACACCU A AAACACU | 183 |
| 1402 | UGUCACU C GAGAUCU | 135 | 1845 | AAACACU A GGCCACG | 184 |
| 1856 | CACGCAU C UGAUCUG | 185 | 2189 | UAUUUAU U GAGUGUC | 234 |
| 1861 | AUCUGAU C UGUAGUC | 186 | 2196 | UGAGUGU C UUUUAUG | 235 |
| 1865 | GAUCUGU A GUCACAU | 187 | 2198 | AGUGUCU U UUAUGUA | 236 |
| 1868 | CUGUAGU C ACAUGAC | 188 | 2199 | GUGUCUU U UAUGUAG | 237 |
| 1877 | CAUGACU A AGCCAAG | 189 | 2200 | UGUCUUU U AUGUAGG | 238 |
| 1901 | CAAGACU C AAGACAU | 190 | 2201 | GUCUUUU A UGUAGGC | 239 |
| 1912 | ACAUGAU U GAUGGAU | 191 | 2205 | UUUAUGU A GGCUAAA | 240 |
| 1922 | UGGAUGU U AAAGUCU | 192 | 2210 | GUAGGCU A AAUGAAC | 241 |
| 1923 | GGAUGUU A AAGUCUA | 193 | 2220 | UGAACAU A GGUCUCU | 242 |
| 1928 | UUAAAGU C UAGCCUG | 194 | 2224 | CAUAGGU C UCUGGCC | 243 |

TABLE II-continued

Human ICAM HH Target sequence

| nt. Position | Target Sequences | Seq. ID No. | nt. Position | Target Sequences | Seq. ID No. |
|---|---|---|---|---|---|
| 1930 | AAAGUCU A GCCUGAU | 195 | 2226 | UAGGUCU C UGGCCUC | 244 |
| 1964 | GAGACAU A GCCCCAC | 196 | 2233 | CUGGCCU C ACGGAGC | 245 |
| 1983 | AGGACAU A CAACUGG | 197 | 2242 | CGGAGCU C CCAGUCC | 246 |
| 1996 | GGGAAAU A CUGAAAC | 198 | 2248 | UCCCAGU C CAUGUCA | 247 |
| 2005 | UGAAACU U GCUGCCU | 199 | 2254 | UCCAUGU C ACAUUCA | 248 |
| 2013 | GCUGCCU A UUGGGUA | 200 | 2259 | GUCACAU U CAAGGUC | 249 |
| 2015 | UGCCUAU U GGGUAUG | 201 | 2260 | UCACAUU C AAGGUCA | 250 |
| 2020 | AUUGGGU A UGCUGAG | 202 | 2266 | UCAAGGU C ACCAGGU | 251 |
| 2039 | ACAGACU U ACAGAAG | 203 | 2274 | ACCAGGU A CAGUUGU | 252 |
| 2040 | CAGACUU A CAGAAGA | 204 | 2279 | GUACAGU U GUACAGG | 253 |
| 2057 | UGGCCCU C CAUAGAC | 205 | 2282 | CAGUUGU A CAGGUUG | 254 |
| 2061 | CCUCCAU A GACAUGU | 206 | 2288 | UACAGGU U GUACACU | 255 |
| 2071 | CAUGUGU A GCAUCAA | 207 | 2291 | AGGUUGU A CACUGCA | 256 |
| 2076 | GUAGCAU C AAAACAC | 208 | 2321 | AAAAGAU C AAAUGGG | 257 |
| 2097 | CCACACU U CCUGACG | 209 | 2338 | UGGGACU U CUCAUUG | 258 |
| 2098 | CACACUU C CUGACGG | 210 | 2339 | GGGACUU C UCAUUGG | 259 |
| 2115 | GCCAGCU U GGGCACU | 211 | 2341 | GACUUCU C AUUGGCC | 260 |
| 2128 | CUGCUGU C UACUGAC | 212 | 2344 | UUCUCAU U GGCCAAC | 261 |
| 2130 | GCUGUCU A CUGACCC | 213 | 2358 | CCUGCCU U UCCCCAG | 262 |
| 2145 | CAACCCU U GAUGAUA | 214 | 2359 | CUGCCUU U CCCCAGA | 263 |
| 2152 | UGAUGAU A UGUAUUU | 215 | 2360 | UGCCUUU C CCCAGAA | 264 |
| 2156 | GAUAUGU A UUUAUUC | 216 | 2376 | GAGUGAU U UUUCUAU | 265 |
| 2158 | UAUGUAU U UAUUCAU | 217 | 2377 | AGUGAUU U UUCUAUC | 266 |
| 2159 | AUGUAUU U AUUCAUU | 218 | 2378 | GUGAUUU U UCUAUCG | 267 |
| 2160 | UGUAUUU A UUCAUUU | 219 | 2379 | UGAUUUU U CUAUCGG | 268 |
| 2162 | UAUUUAU U CAUUUGU | 220 | 2380 | GAUUUUU C UAUCGGC | 269 |
| 2163 | AUUUAUU C AUUUGUU | 221 | 2382 | UUUUUCU A UCGGCAC | 270 |
| 2166 | UAUUCAU U UGUUAUU | 222 | 2384 | UUUCUAU C GGCACAA | 271 |
| 2167 | AUUCAUU U GUUAUUU | 223 | 2399 | AAGCACU A UAUGGAC | 272 |
| 2170 | CAUUUGU U AUUUUAC | 224 | 2401 | GCACUAU A UGGACUG | 273 |
| 2171 | AUUUGUU A UUUUACC | 225 | 2411 | GACUGGU A AUGGUUC | 274 |
| 2173 | UUGUUAU U UUACCAG | 226 | 2417 | UAAUGGU U CACAGGU | 275 |
| 2174 | UGUUAUU U UACCAGC | 227 | 2418 | AAUGGUU C ACAGGUU | 276 |
| 2175 | GUUAUUU U ACCAGCU | 228 | 2425 | CACAGGU U CAGAGAU | 277 |
| 2176 | UUAUUUU A CCAGCUA | 229 | 2426 | ACAGGUU C AGAGAUU | 278 |
| 2183 | ACCAGCU A UUUAUUG | 230 | 2433 | CAGAGAU U ACCCAGU | 279 |
| 2185 | CAGCUAU U UAUUGAG | 231 | 2434 | AGAGAUU A CCCAGUG | 280 |
| 2186 | AGCUAUU U AUUGAGU | 232 | 2448 | GAGGCCU U AUUCCUC | 281 |
| 2187 | GCUAUUU A UUGAGUG | 233 | 2449 | AGGCCUU A UUCCUCC | 282 |
| 2451 | GCCUUAU U CCUCCCU | 283 | 2750 | UAUGUGU A GACAAGC | 332 |
| 2452 | CCUUAUU C CUCCCUU | 284 | 2759 | ACAAGCU C UCGCUCU | 333 |
| 2455 | UAUUCCU C CCUUCCC | 285 | 2761 | AAGCUCU C GCUCUGU | 334 |
| 2459 | CCUCCCU U CCCCCCA | 286 | 2765 | UCUCGCU C UGUCACC | 335 |
| 2460 | CUCCCUU C CCCCCAA | 287 | 2769 | GCUCUGU C ACCCAGG | 336 |
| 2479 | GACACCU U UGUUAGC | 288 | 2797 | GUGCAAU C AUGGUUC | 337 |
| 2480 | ACACCUU U GUUAGCC | 289 | 2803 | UCAUGGU U CACUGCA | 338 |
| 2483 | CCUUUGU U AGCCACC | 290 | 2804 | CAUGGUU C ACUGCAG | 339 |
| 2484 | CUUUGUU A GCCACCU | 291 | 2813 | CUGCAGU C UUGACCU | 340 |
| 2492 | GCCACCU C CCCACCC | 292 | 2815 | GCAGUCU U GACCUUU | 341 |
| 2504 | CCCACAU A CAUUUCU | 293 | 2821 | UUGACCU U UGGGCU | 342 |
| 2508 | CAUACAU U UCUGCCA | 294 | 2822 | UGACCUU U GGGCUC | 343 |
| 2509 | AUACAUU U CUGCCAG | 295 | 2823 | GACCUUU U GGGCUCA | 344 |
| 2510 | UACAUUU C UGCCAGU | 296 | 2829 | UUGGGCU C AAGUGAU | 345 |
| 2520 | CCAGUGU U CACAAUG | 297 | 2837 | AAGUGAU C CUCCCAC | 346 |
| 2521 | CAGUGUU C ACAAUGA | 298 | 2840 | UGAUCCU C CCACCUC | 347 |
| 2533 | UGACACU C AGCGGUC | 299 | 2847 | CCCACCU C AGCCUCC | 348 |
| 2540 | CAGCGGU C AUGUCUG | 300 | 2853 | UCAGCCU C CUGAGUA | 349 |
| 2545 | GUCAUGU C UGGACAU | 301 | 2860 | CCUGAGU A GCUGGGA | 350 |
| 2568 | AGGGAAU A UGCCCAA | 302 | 2872 | GGACCAU A GGCUCAC | 351 |
| 2579 | CCAAGCU A UGCCUUG | 303 | 2877 | AUAGGCU C ACAACAC | 352 |
| 2585 | UAUGCCU U GUCCUCU | 304 | 2899 | GGCAAAU U UGAUUUU | 353 |
| 2588 | GCCUUGU C CUCUUGU | 305 | 2900 | GCAAAUU U GAUUUUU | 354 |
| 2591 | UUGUCCU C UUGUCCU | 306 | 2904 | AUUUGAU U UUUUUUU | 355 |
| 2593 | GUCCUCU U GUCCUGU | 307 | 2905 | UUUGAUU U UUUUUUU | 356 |
| 2596 | CUCUUGU C CUGUUUG | 308 | 2906 | UUGAUUU U UUUUUUU | 357 |
| 2601 | GUCCUGU U UGCAUUU | 309 | 2907 | UGAUUUU U UUUUUUU | 358 |
| 2602 | UCCUGUU U GCAUUUC | 310 | 2908 | GAUUUUU U UUUUUUU | 359 |
| 2607 | UUUGCAU U UCACUGG | 311 | 2909 | AUUUUUU U UUUUUUU | 360 |
| 2608 | UUGCAUU U CACUGGG | 312 | 2910 | UUUUUUU U UUUUUUU | 361 |
| 2609 | UGCAUUU C ACUGGGA | 313 | 2911 | UUUUUUU U UUUUUUU | 362 |
| 2620 | GGGAGCU U GCACUAU | 314 | 2912 | UUUUUUU U UUUUUUC | 363 |
| 2626 | UUGCACU A UUGCAGC | 315 | 2913 | UUUUUUU U UUUUUCA | 364 |
| 2628 | GCACUAU U GCAGCUC | 316 | 2914 | UUUUUUU U UUUUCAG | 365 |
| 2635 | UGCAGCU C CAGUUUC | 317 | 2915 | UUUUUUU U UUUCAGA | 366 |

TABLE II-continued

Human ICAM HH Target sequence

| nt. Position | Target Sequences | Seq. ID No. | nt. Position | Target Sequences | Seq. ID No. |
|---|---|---|---|---|---|
| 2640 | CUCCAGU U UCCUGCA | 318 | 2916 | UUUUUUU U UUCAGAG | 367 |
| 2641 | UCCAGUU U CCUGCAG | 319 | 2917 | UUUUUUU U UCAGAGA | 368 |
| 2642 | CCAGUUU C CUGCAGU | 320 | 2918 | UUUUUUU U CAGAGAC | 369 |
| 2653 | CAGUGAU C AGGGUCC | 321 | 2919 | UUUUUUU C AGAGACG | 370 |
| 2659 | UCAGGGU C CUGCAAG | 322 | 2931 | ACGGGGU C UCGCAAC | 371 |
| 2689 | CCAAGGU A UUGGAGG | 323 | 2933 | GGGGUCU C GCAACAU | 372 |
| 2691 | AAGGUAU U GGAGGAC | 324 | 2941 | GCAACAU U GCCCAGA | 373 |
| 2700 | GAGGACU C CCUCCCA | 325 | 2951 | CCAGACU U CCUUUGU | 374 |
| 2704 | ACUCCCU C CCAGCUU | 326 | 2952 | CAGACUU C CUUUGUG | 375 |
| 2711 | CCCAGCU U UGGAAGG | 327 | 2955 | ACUUCCU U UGUGUUA | 378 |
| 2712 | CCAGCUU U GGAAGGG | 328 | 2956 | CUUCCUU U GUGUUAG | 377 |
| 2721 | GAAGGGU C AUCCGCG | 329 | 2961 | UUUGUGU U AGUUAAU | 378 |
| 2724 | GGGUCAU C CGCGUGU | 330 | 2962 | UUGUGUU A GUUAAUA | 379 |
| 2744 | UGUGUGU A UGUGUAG | 331 | 2965 | UGUUAGU U AAUAAAG | 380 |
| 2966 | GUUAGUU A AUAAAGC | 381 | | | |
| 2969 | AGUUAAU A AAGCUUU | 382 | | | |
| 2975 | UAAAGCU U UCUCAAC | 383 | | | |
| 2976 | AAAGCUU U CUCAACU | 384 | | | |
| 2977 | AAGCUUU C UCAACUG | 385 | | | |
| 2979 | GCUUUCU C AACUGCC | 386 | | | |

TABLE III

Mouse ICAM HH Target Sequence

| nt. Position | Target Sequence | Seq. ID No. | nt. Position | Target Sequence | Seq. ID No. |
|---|---|---|---|---|---|
| 11 | CCCugGU C acCGuUG | 387 | 367 | AAugGCU u cAACCcg | 584 |
| 23 | CaGuGgU u CUCUGCU | 388 | 374 | gAAgCCU U CCUgcCC | 585 |
| 26 | uGgUuCU C UGCUcCU | 389 | 375 | AAgCCUU C CUgcCCc | 586 |
| 31 | CUCUGCU c CUCcaca | 390 | 378 | CuacCaU C ACCGUGU | 587 |
| 34 | UuCUcaU a AGgGUcG | 391 | 386 | ACCGUGU A uUcGuuU | 588 |
| 40 | gCAcAcU U GuAgCCU | 392 | 394 | CcGGACU u ucGAuCu | 589 |
| 48 | aggACCU C AGCCUgG | 393 | 420 | CACaCuU C CCCcCcg | 590 |
| 54 | UggGCCU C GugAUGG | 394 | 425 | CaCCCCU C ccaGCAG | 591 |
| 58 | CaUgcCU u UaGCUCC | 395 | 427 | CagCUCU c aGCAGug | 592 |
| 64 | cAcccCU C CCAGCAG | 396 | 450 | AGgACCU c ACCCUgC | 593 |
| 96 | CucugCU C CUGGcCC | 397 | 451 | GAAaCcU u uCCUuuG | 594 |
| 102 | UgCcaGU a CUGCUgG | 398 | 456 | UUACCCU c aGCcaCu | 595 |
| 108 | cuCUGCU C cuGGCcC | 399 | 495 | CuAcCaU C ACCGUGu | 596 |
| 115 | uGGuuCU C UGcUCCu | 400 | 510 | UGCUGCU C CGUGGGG | 597 |
| 119 | GgaaUGU c aCCAGGA | 401 | 564 | CUcAGGU a uCcAuCc | 598 |
| 120 | CUCUGcU C CugGccC | 402 | 592 | GAaAGAU C ACaugGG | 599 |
| 146 | CAGuCgU C cGcuUcc | 403 | 607 | AGCCAAU U UCUCaUG | 600 |
| 152 | UCUGUGU C agCCaCu | 404 | 608 | GCCAAUU U CUCaUGC | 601 |
| 158 | UCCuguU u AAAAacC | 405 | 609 | CCAAUUU C UCaUGCC | 602 |
| 165 | CAgAAGU u gUuuUGC | 406 | 611 | AAUUUCU c aUGCCGC | 603 |
| 168 | AAGcCuU C CUGCCCC | 407 | 656 | aAGCUGU U UGAGcug | 604 |
| 185 | GGuGGgU C CGUGCaG | 408 | 657 | AGCUGUU U GAGcugA | 605 |
| 209 | gcCACuU C CUcUGgC | 409 | 668 | cgagCCU a GGCCaCC | 606 |
| 227 | CagAAGU U GUUuuGC | 410 | 677 | GaCCuCU A CCAGCcu | 607 |
| 230 | AAGUUGU U uuGCucc | 411 | 684 | uuCAGCU C CgGuCCU | 608 |
| 237 | UGuGCuU u GAGAaCu | 412 | 692 | CgGACuU U cGauCUu | 609 |
| 248 | AaCCCaU c uCCUAAA | 413 | 693 | AGgaCcU c acCCUGC | 610 |
| 253 | ccUGCCU A AggAaGA | 414 | 696 | CCUgUuU C UGCCCuc | 611 |
| 263 | AgGGuuU c uCUaCUG | 415 | 709 | gGCGgCU C CaCCuCA | 612 |
| 267 | AGggGCU C CUGCCUa | 416 | 720 | uACAACU U uUCAGCu | 613 |
| 293 | AAGcUGU u UGAgCUG | 417 | 723 | AACUUuU C AGCuCCg | 614 |
| 319 | AGgAGAU A cugAgCC | 418 | 735 | aCCaGaU C CUgGAGa | 615 |
| 335 | cUGUGCU u UgagAAC | 419 | 738 | uGGgCCU c GuGaUGG | 616 |
| 337 | GUcCAaU U CAcACUG | 420 | 765 | CaGUcGU C cGcUuCC | 617 |
| 338 | aGCUgUU u gAgCUGa | 421 | 769 | GGcCUGU U uCCUGcc | 618 |
| 359 | GuGCAGU C guCcGCU | 422 | 770 | uUuUGcU C CCUGGAa | 619 |
| 785 | GGcCUGU U uCCuGcC | 423 | 1353 | AGUGggU c gAaGgUG | 620 |
| 786 | GcCUGUU u CCuGcCU | 424 | 1366 | UaaCAgU c UaCaACU | 621 |
| 792 | UggagGU C UCGGAaG | 425 | 1367 | aGCACcU c CCCACcu | 622 |
| 794 | CugGgCU u GGAGaCu | 426 | 1368 | GuACUgU a CCACUcu | 623 |
| 807 | CuCgGaU a uACCUGG | 427 | 1380 | UGCCCAU C GGGGugg | 624 |
| 833 | GAaAGcU c GAcaCCC | 428 | 1388 | GGaGacU C AGUGgCU | 625 |
| 846 | CCcugGU C ACCguUG | 429 | 1398 | UGgCUGU C ACagaAc | 626 |

TABLE III-continued

Mouse ICAM HH Target Sequence

| nt. Position | Target Sequence | Seq. ID No. | nt. Position | Target Sequence | Seq. ID No. |
|---|---|---|---|---|---|
| 851 | GagACCU c UacCAgC | 430 | 1402 | UGUgcuU u GAGAaCU | 627 |
| 863 | AgCcACU u CcUCUgG | 431 | 1408 | gCGAGAU C ggGgaGG | 628 |
| 866 | GAagCCU U CcuGcCC | 432 | 1410 | GAggUCU c GgaaGgg | 629 |
| 867 | AuUCgUU u cCGGagA | 433 | 1421 | ccCACCU A CuUuUGU | 630 |
| 869 | UCuUcCU C augCAAG | 434 | 1425 | aCUgCCU u gGUaGaG | 631 |
| 881 | AuGGCuU C AacCcGU | 435 | 1429 | uCUCUaU u GccCCuG | 632 |
| 885 | CCUugGU a gagGUGA | 436 | 1444 | GAaggCU C AgGaGGA | 633 |
| 993 | cUauAaU c AUuCUGG | 437 | 1455 | GGaAuGU C ACCaGga | 634 |
| 936 | uAaUcAU u CUGGuGc | 438 | 1482 | AguUGuU u UgCuCCC | 635 |
| 978 | UaACagU C UACAaCU | 439 | 1484 | cUGuUCU u CCuCauG | 636 |
| 980 | ACagUCU A CAaCUUU | 440 | 1493 | CuguGcU u UGAGAac | 637 |
| 986 | UACAaCU U UuCaGCu | 441 | 1500 | AUGAaAU c aUggUCc | 638 |
| 987 | ACAaCUU U uCaGCuC | 442 | 1503 | gGAcUaU a AUCAUuc | 639 |
| 988 | CAaCUUU u CaGCuCC | 443 | 1506 | UUaUguU u AUaACcG | 640 |
| 1005 | ACcaGAU c CUGgaGA | 444 | 1509 | cuAcCAU C ACcGUGu | 641 |
| 1006 | uGaGAgU C UGggGAA | 445 | 1518 | ucaUGGU c cCAGgCG | 642 |
| 1023 | ugGAGGU C UCgGAAG | 446 | 1530 | CuauAaU C AUucUGG | 643 |
| 1025 | GAGGUCU C gGAAGGG | 447 | 1533 | ugGUCAU u gUGGGCc | 644 |
| 1066 | CCACuCU c aAaauAA | 448 | 1551 | CAuGCCU u AGCAgcU | 645 |
| 1092 | AcuGGaU c uCAGgCC | 449 | 1559 | AGCACcU c CCcaccU | 646 |
| 1093 | UGGaccU u CAGCCaA | 450 | 1563 | CuUAugU u UAUAACC | 647 |
| 1125 | CCCAaCU C uUcuUGA | 451 | 1565 | UAugUuU A UAACCGC | 648 |
| 1163 | CGaACCU U CUuuUGC | 452 | 1567 | ugUuUAU A ACCGCCA | 649 |
| 1164 | GaAGCUU C UuuUGCU | 453 | 1584 | GaAAGAU C AgGAuAU | 650 |
| 1166 | AGCUUCU u uUGCUCU | 454 | 1592 | AgGAuAU A CAaguUA | 651 |
| 1172 | UCCUGuU u aaaAACC | 455 | 1599 | ACAaguU A CAgaAGG | 652 |
| 1200 | cuCuGCU c cUcCAVA | 456 | 1651 | CcCaCCU C CCUGAgC | 653 |
| 1201 | gCuGCUU u UgaACAg | 457 | 1661 | gaAACCU u UCCuuuG | 654 |
| 1203 | AcuUUuU u CACcAGu | 458 | 1663 | AACCUuU C CuuuGAa | 655 |
| 1227 | GGuAcaU a CGUGUgC | 459 | 1678 | AGGaCCU C agCCUgG | 656 |
| 1228 | GaAGCUU C uUuUgCU | 460 | 1680 | aGCCaCU U CCUCuGg | 657 |
| 1233 | UUCGUuU C CgGagaG | 461 | 1681 | GCCaCUU C CUCuGgC | 658 |
| 1238 | GUgCUGU A UGGuCCu | 462 | 1684 | aCUUCUU c uGgCUgu | 659 |
| 1264 | GAaGGgU c GUgCaaG | 463 | 1690 | cCGGaCU U uCgAUcU | 660 |
| 1267 | uGAgaGU C uGGGgAA | 464 | 1691 | CGGaCUU u CgAUcUU | 661 |
| 1294 | AGgAgAU a CugAGCc | 465 | 1696 | UgCCCAU c ggGGUGG | 662 |
| 1295 | GAggggU C uCAGCAG | 466 | 1698 | CggAUAU a ccUGGag | 663 |
| 1306 | GCAGACU C ugAaaUG | 467 | 1737 | gAGACcU c UaCCAgc | 664 |
| 1321 | gaAGGCU c aGGaGgA | 468 | 1750 | gCgGCU c CACCUca | 665 |
| 1334 | AACCCAU c uCCuaAa | 469 | 1756 | gAagCCU u CCuGCCC | 666 |
| 1344 | auGAGCU c gAGaGUg | 470 | 1787 | gaGaCAU U GUCCcCA | 667 |
| 1351 | ugAaUGU a UAAguuA | 471 | 1790 | GCAUUGU u CUCuaau | 668 |
| 1793 | UgGUCCU C gGcugGA | 472 | 2173 | UUagagU U UUACCAG | 669 |
| 1797 | CacCAGU C AcAUAaA | 473 | 2174 | UagagUU U UACCAGC | 670 |
| 1802 | acCAGAU c CuggAGa | 474 | 2175 | agagUUU U ACCAGCU | 671 |
| 1812 | ACuGgAU c UcaGGCC | 475 | 2176 | gagUUUU A CCAGCUA | 672 |
| 1813 | CAGCAUU U acccuCA | 476 | 2183 | ACCAGCU A UUUAUUG | 673 |
| 1825 | CCAcGcU A CCUcugC | 477 | 2185 | CAGCUAU U UAUUGAG | 674 |
| 1837 | CAugCCU u uAgCuCc | 478 | 2186 | AGCUAUU U AUUGAGU | 675 |
| 1845 | cgAgcCU A GGCCACc | 479 | 2187 | GCUAUUU A UUGAGUa | 676 |
| 1856 | CggaCuU u cGAUCUu | 480 | 2189 | UAUUUAU U GAGUacC | 677 |
| 1861 | AcaUGAU a UccAGUa | 481 | 2196 | caAcUcU u cUUgAUG | 678 |
| 1865 | cAcuUGU A GcCuCAg | 482 | 2198 | gcaGcCU c UUUAUGUu | 679 |
| 1868 | CaccAGU C ACAUaAa | 483 | 2199 | GccUCUU a UgUuUAu | 680 |
| 1877 | CAUGcCU u AGCagcu | 484 | 2200 | UcUuccU c AUGcAaG | 681 |
| 1901 | uAAaACU C AAGggAc | 484 | 2201 | aagUUUU A UGUcGGC | 682 |
| 1912 | AuAUagU a gAUcagU | 486 | 2205 | UUUAUGU c GGCcugA | 683 |
| 1922 | UGaAUGU a uAAGUua | 487 | 2210 | GgAGaCU c AgUGgcu | 684 |
| 1923 | uGAUGcU c AgGUaUc | 488 | 2220 | cuggCAU u GuUCUCU | 685 |
| 1928 | UUAgAGU u UuaCCaG | 489 | 2224 | CucAGGU a UCcauCC | 686 |
| 1930 | AgAGUuU u aCCaGcU | 490 | 2226 | UgGaUCU C aGGCCgC | 687 |
| 1964 | GAGACAU u GuCCCca | 491 | 2233 | CUGaCCU C cuGGAGg | 688 |
| 1983 | AGGAuAU A CAAgUua | 492 | 2242 | uGGAGCU a gCgGaCC | 689 |
| 1996 | aGGAgAU A CUGAgcC | 493 | 2248 | UauCcaU C CAUccCA | 690 |
| 2005 | UGgAgCU a GCgGaCc | 494 | 2254 | UCCAauU C ACAcUgA | 691 |
| 2013 | GCUauuU A UUGaGUA | 495 | 2259 | aUCACAU U CAcGGUg | 692 |
| 2015 | UGCCcAU c GGGgugG | 496 | 2260 | UCACAUU C AcGGUgc | 693 |
| 2020 | ggUGGuU c UuCUGAG | 497 | 2266 | ggAAuGU C ACCAGGa | 694 |
| 2039 | gCuGgCU a gCAGAgG | 498 | 2274 | ACCAGaU c CuGgaGa | 695 |
| 2040 | CuGACcU c CuGgAGg | 499 | 2279 | GaAggGU c GUgCAaG | 696 |
| 2057 | UGcuCCU C CAcAucC | 500 | 2282 | aAGcUGU u ugaGcUG | 697 |
| 2061 | CuaCCAU c acCgUGU | 501 | 2299 | UAuAaGU U aUggcCU | 698 |
| 2071 | CAcuUGU A GCcUCAg | 502 | 2291 | caGUgCU u CuCUGCu | 699 |
| 2076 | GUAGCcU C AgAgCua | 503 | 2321 | gAAAGAU C AcAUGGG | 700 |

TABLE III-continued

Mouse ICAM HH Target Sequence

| nt. Position | Target Sequence | Seq. ID No. | nt. Position | Target Sequence | Seq. ID No. |
|---|---|---|---|---|---|
| 2097 | CaACuCU U CuUGAuG | 504 | 2338 | UGaGACU c CUgccUG | 701 |
| 2098 | CACACUU C CccCcG | 505 | 2339 | GaaACcU u UCcUUuG | 702 |
| 2115 | GCCAGCU c GGaggaU | 506 | 2341 | GACcUCU a ccaGcCu | 703 |
| 2128 | CaGCUaU u UAuUGAg | 507 | 2344 | UUucgAU c uuCCAgC | 704 |
| 2130 | cCUGUuU c CUGcCuC | 508 | 2358 | CCcagCU c UCagCAG | 705 |
| 2145 | CAACuCU U cuUGAUg | 509 | 2359 | CUGCuUU U gasCAGA | 706 |
| 2152 | UauUaAU u UagAgUU | 510 | 2360 | aaCCUUU C CuuuGAA | 707 |
| 2156 | uugAUGU A UUUAUUa | 511 | 2376 | agGUGgU U cUUCUga | 708 |
| 2158 | gAUGUAU U UAUUaAU | 512 | 2377 | gGUGgUU c UUCUgag | 709 |
| 2159 | AUGUAUU U AUUaAUU | 513 | 2378 | agGgUUU c UCUAcuG | 710 |
| 2160 | UGUAUUU A UUaAUUU | 514 | 2379 | UGcUUUU c ucAUaaG | 711 |
| 2162 | UAUUUAU U aAUUUag | 515 | 2380 | aAgUUUU a UgUCGGC | 712 |
| 2163 | AUgUAUU u AUUaaUU | 516 | 2383 | aUUcUCU A UuGcCcC | 713 |
| 2166 | acUUCAU U cucUAUU | 517 | 2384 | aUcCagU a GaCACAA | 714 |
| 2167 | AUguAUU U aUUAaUU | 518 | 2399 | AAaCACU A UgUGGAC | 715 |
| 2170 | uAUUUaU U AaUUUAg | 519 | 2401 | aagCUgU u UGagCUG | 716 |
| 2171 | AgUUGUU u UgcUcCC | 520 | 2411 | uACUGGU c AgGaUgC | 717 |
| 2417 | gAAUGGU a CAuAcGU | 521 | 2691 | AAuGUcU c cGAGGcC | 718 |
| 2418 | AcUGGaU C uCAGGcc | 522 | 2700 | GAaGcCU u CCUgCCc | 719 |
| 2425 | CAugGGU c gAGgGuU | 523 | 2704 | gacCuCU a CCAGCcU | 720 |
| 2426 | AuuaaUU u AGAGuUU | 524 | 2711 | CCCAGCU c UcagcaG | 721 |
| 2433 | uAGAGuU U uaCCAGc | 525 | 2712 | gagGucU c GGAAGGG | 722 |
| 2434 | AGAGuUU u aCCAGcu | 526 | 2721 | GAAGGGU C gUgCaaG | 723 |
| 2448 | GAaGCCU U ccUgCcC | 527 | 2724 | GGuaCAU a CGuGUGc | 724 |
| 2449 | AaGCCUU c cUgCcCC | 528 | 2744 | gGUGgGU c cGUGcAG | 725 |
| 2451 | GCCUguU U CCUgCCU | 529 | 2750 | UAUuUaU u GAguAcC | 726 |
| 2452 | CCUguUU C CUgCCUc | 530 | 2759 | cCggaCU u UCGaUCU | 727 |
| 2455 | gAagCCU u CCUgCCC | 531 | 2761 | AgGacCU C aCcCUGc | 728 |
| 2459 | CCaCaCU U CCCCCCc | 532 | 2765 | UuUuGCU C UGcCgCu | 729 |
| 2460 | CaCaCUU C CCCCCcg | 533 | 2769 | agUCUGU C AaaCAGG | 730 |
| 2479 | GAgACCU c UaccAGC | 534 | 2797 | aUGaAAU A AUGGUcC | 731 |
| 2480 | uCACCgU U GUgAuCC | 535 | 2803 | UCAUGGU c CcagGCg | 732 |
| 2483 | CCaaUGU c AGCCACC | 536 | 2804 | ggUGGgU C cgUGCAG | 733 |
| 2484 | CUUUuUU c aCCAguc | 537 | 2813 | CUcCgGU C cUGACCc | 734 |
| 2492 | agCACCU C CCCACCu | 538 | 2815 | aCAGUCU a cAaCUUU | 735 |
| 2504 | CCCACcU A CuUUUgU | 539 | 2821 | cUGACCU c cUGGagg | 736 |
| 2508 | uAUcCAU c caUcCCA | 540 | 2822 | gGAgCcU c cGGaCUu | 737 |
| 2509 | uUAgAgU U uUaCCAG | 541 | 2823 | ugCCUUU a GcuCcCA | 738 |
| 2510 | UAgAgUU U UaCCAGc | 542 | 2829 | cUGGaCU a uAaUcAU | 739 |
| 2520 | CuuuUGU U CcCAAUG | 543 | 2837 | AgGUGgU u CUuCuga | 740 |
| 2521 | CAGcaUU u ACccUcA | 544 | 2840 | UGAgaCU C CugCCUg | 741 |
| 2533 | UGAugCU C AGguaUC | 545 | 2847 | CCaAugU C AGCCaCC | 742 |
| 2540 | CAGCaGU C cgcUgUG | 546 | 2853 | gCAGCCU C uUauGUu | 743 |
| 2545 | GUgcUGU a UGGuCcU | 547 | 2860 | gCcaAGU A aCUGuGA | 744 |
| 2568 | guGaAgU c UGuCaAA | 548 | 2872 | GGACCuU c aGCcaAg | 745 |
| 2579 | auAAGuU A UGgCcUG | 549 | 2877 | uUccGCU a cCAuCAC | 746 |
| 2585 | cugGCaU U GUuCUCU | 550 | 2899 | cGgAcuU U cGAUcUU | 747 |
| 2588 | GCaUUGU u UCUaaU | 551 | 2900 | uuAAuUU a GAgUUUU | 748 |
| 2591 | UgGUuCU C UgcUCCU | 552 | 2904 | AcUUcAU U cUcUaUU | 749 |
| 2593 | cUuCUuU U GcuCUGc | 553 | 2905 | cUUcAUU c UcUaUUg | 750 |
| 2596 | CUuUUGU u CccaaUG | 554 | 2906 | UUGAUgU a UUUaUUa | 751 |
| 2601 | acCgUGU a UuCgUUU | 555 | 2907 | UGuaUUU a UUaaUUU | 752 |
| 2602 | UCCaGcU a cCAUccC | 556 | 2908 | GAagcUU c UUUUgcU | 753 |
| 2607 | cUcGgAU a UacCUGG | 557 | 2909 | AgcUUcU U UUgcUcU | 754 |
| 2608 | caGCAgU c CgCUGuG | 558 | 2910 | UgUaUUU a UUaaUUU | 755 |
| 2609 | gGaAUgU C ACcaGGA | 559 | 2911 | UgUaUUU a UUaaUUU | 756 |
| 2620 | aGGAcCU c aCcCUgc | 560 | 2912 | UUgUUcU C UaaUgUC | 757 |
| 2626 | UUuCgaU c UUcCAGC | 561 | 2913 | UUUcUcU a cUggUCA | 758 |
| 2628 | GCACacU U GuAGCcu | 562 | 2914 | UgcUUUU c UcaUaAG | 759 |
| 2635 | UuCAGCU C CgGUccu | 563 | 2915 | aUUUaUU a aUUuAGA | 760 |
| 2640 | ggCCUGU U UCCUGCc | 564 | 2916 | UaUUcgU U UcCgGAG | 761 |
| 2641 | cCCAGcU c uCaGCAG | 565 | 2917 | aUUcgUU U cCgGAGA | 762 |
| 2642 | CCuGUUU C CUGCcuc | 566 | 2918 | UUcgUUU c CgGAGAg | 763 |
| 2653 | uAcUGgU C AGGaUgC | 567 | 2919 | UUcUcaU a AggGuCG | 764 |
| 2659 | gaAGGGU C gUGCAAG | 568 | 2931 | ugGaGGU C UCGgAAg | 765 |
| 2689 | CuAAuGU c UccGAGG | 569 | 2933 | GaGGUCU C GgAAggg | 766 |
| 2941 | GagACAU U GuCCcca | 570 | | | |
| 2951 | CCAcgCU a CCUcUGc | 571 | | | |
| 2952 | CAGcagU C CgcUGUG | 572 | | | |
| 2955 | AgUgaCU c UGUGUcA | 573 | | | |
| 2956 | uUUCCUU U GaaUcAa | 574 | | | |
| 2961 | UcUGUGU c AGccAcU | 575 | | | |
| 2962 | aUGUaUU u aUUAAUu | 576 | | | |
| 2965 | UuUgAaU c AAUAAAG | 577 | | | |

TABLE III-continued

Mouse ICAM HH Target Sequence

| nt. Position | Target Sequence | Seq. ID No. | nt. Position | Target Sequence | Seq. ID No. |
|---|---|---|---|---|---|
| 2966 | GcUgGcU A gcAgAGg | 578 | | | |
| 2969 | AaUcAAU A AAGuUUU | 579 | | | |
| 2975 | UAgAGuU U UacCAgC | 580 | | | |
| 2976 | gAgGgUU U CUCuACU | 581 | | | |
| 2977 | AAGCUgU u UgAgCUG | 582 | | | |
| 2979 | uCaUUCU C uAuUGCC | 583 | | | |

TABLE IV

Human ICAM HH Ribozyme Sequences

| nt. Position | Ribozyme Sequence | Seq. ID No. |
|---|---|---|
| 11 | CAGCGUC CUGAUGAGGCCGAAAGGCCGAA ACUGGGG | 767 |
| 23 | AGCAGAG CUGAUGAGGCCGAAAGGCCGAA AGCUCAG | 768 |
| 26 | AGUAGCA CUGAUGAGGCCGAAAGGCCGAA AGGAGCU | 769 |
| 31 | CUCUGAG CUGAUGAGGCCGAAAGGCCGAA AGCAGAG | 770 |
| 34 | CAACUCU CUGAUGAGGCCGAAAGGCCGAA AGUAGCA | 771 |
| 40 | AGGUUGC CUGAUGAGGCCGAAAGGCCGAA ACUCUGA | 772 |
| 48 | CGAGGCU CUGAUGAGGCCGAAAGGCCGAA AGGUUGC | 773 |
| 54 | CCAUAGC CUGAUGAGGCCGAAAGGCCGAA AGGCUGA | 774 |
| 58 | GGAGCCA CUGAUGAGGCCGAAAGGCCGAA AGCGAGG | 775 |
| 64 | CUGCUGG CUGAUGAGGCCGAAAGGCCGAA AGCCAUA | 776 |
| 96 | GGACCAG CUGAUGAGGCCGAAAGGCCGAA AGUGCAG | 777 |
| 102 | CGAGCAG CUGAUGAGGCCGAAAGGCCGAA ACCAGGA | 778 |
| 108 | GAGCCCC CUGAUGAGGCCGAAAGGCCGAA AGCAGGA | 779 |
| 115 | GGGAACA CUGAUGAGGCCGAAAGGCCGAA AGCCCCG | 780 |
| 119 | UCCUGGG CUGAUGAGGCCGAAAGGCCGAA ACAGAGC | 781 |
| 120 | GUCCUGG CUGAUGAGGCCGAAAGGCCGAA AACAGAG | 782 |
| 146 | GGACACA CUGAUGAGGCCGAAAGGCCGAA AUGUCUG | 783 |
| 152 | UGAGGGG CUGAUGAGGCCGAAAGGCCGAA ACACAGA | 784 |
| 158 | GACUUUU CUGAUGAGGCCGAAAGGCCGAA AGGGGGA | 785 |
| 165 | GCAGGAU CUGAUGAGGCCGAAAGGCCGAA ACUUUUG | 786 |
| 168 | GGGGCAG CUGAUGAGGCCGAAAGGCCGAA AUGACUU | 787 |
| 185 | CAGCACG CUGAUGAGGCCGAAAGGCCGAA AGCCUCC | 788 |
| 209 | GUCACAG CUGAUGAGGCCGAAAGGCCGAA AGGUGCU | 789 |
| 227 | GCCCAAC CUGAUGAGGCCGAAAGGCCGAA ACUUGGG | 790 |
| 230 | UAUGCCC CUGAUGAGGCCGAAAGGCCGAA ACAACUU | 791 |
| 237 | GGGUCUC CUGAUGAGGCCGAAAGGCCGAA AUGCCCA | 792 |
| 248 | UUUAGGC CUGAUGAGGCCGAAAGGCCGAA ACGGGGU | 793 |
| 253 | UCCUUUU CUGAUGAGGCCGAAAGGCCGAA AGGCAAC | 794 |
| 263 | CAGGAGC CUGAUGAGGCCGAAAGGCCGAA ACUCCUU | 795 |
| 267 | CAGGCAG CUGAUGAGGCCGAAAGGCCGAA AGCAACU | 796 |
| 293 | CAGUUCA CUGAUGAGGCCGAAAGGCCGAA ACACCUU | 797 |
| 319 | GGUUGGC CUGAUGAGGCCGAAAGGCCGAA AUCUUCU | 798 |
| 335 | GUUUGAA CUGAUGAGGCCGAAAGGCCGAA AGCACAU | 799 |
| 337 | CAGUUUG CUGAUGAGGCCGAAAGGCCGAA AUAGCAC | 800 |
| 338 | GCAGUUU CUGAUGAGGCCGAAAGGCCGAA AAUAGCA | 801 |
| 359 | AGCUGUU CUGAUGAGGCCGAAAGGCCGAA ACUGCCC | 802 |
| 367 | AAGGUUU CUGAUGAGGCCGAAAGGCCGAA AGCUGUU | 803 |
| 374 | GGUGAGG CUGAUGAGGCCGAAAGGCCGAA AGGUUUU | 804 |
| 375 | CGGUGAG CUGAUGAGGCCGAAAGGCCGAA AAGGUUU | 805 |
| 378 | ACACGGU CUGAUGAGGCCGAAAGGCCGAA AGGAAGG | 806 |
| 386 | AGUCCAG CUGAUGAGGCCGAAAGGCCGAA ACACGGU | 807 |
| 394 | CGUUCUG CUGAUGAGGCCGAAAGGCCGAA AGUCCAG | 808 |
| 420 | AAGAGGG CUGAUGAGGCCGAAAGGCCGAA AGGGGUG | 809 |
| 425 | CUGCCAA CUGAUGAGGCCGAAAGGCCGAA AGGGGAG | 810 |
| 427 | GGCUGCC CUGAUGAGGCCGAAAGGCCGAA AGAGGGG | 811 |
| 450 | GUAGGGU CUGAUGAGGCCGAAAGGCCGAA AGGUUCU | 812 |
| 451 | CGUAGGG CUGAUGAGGCCGAAAGGCCGAA AAGGUUC | 813 |
| 456 | GGCAGCG CUGAUGAGGCCGAAAGGCCGAA AGGGUAA | 814 |
| 495 | CCACGGU CUGAUGAGGCCGAAAGGCCGAA AGGUUGG | 815 |
| 510 | CCCCACG CUGAUGAGGCCGAAAGGCCGAA AGCAGCA | 816 |
| 564 | UGGUCGU CUGAUGAGGCCGAAAGGCCGAA ACCUCAG | 817 |
| 592 | CCAUGGU CUGAUGAGGCCGAAAGGCCGAA AUCUCUC | 818 |
| 607 | CACGAGA CUGAUGAGGCCGAAAGGCCGAA AUUGGCU | 819 |
| 608 | GCACGAG CUGAUGAGGCCGAAAGGCCGAA AAUUGGC | 820 |
| 609 | GGCACGA CUGAUGAGGCCGAAAGGCCGAA AAAUUGG | 821 |
| 611 | GCGGCAC CUGAUGAGGCCGAAAGGCCGAA AGAAAUU | 822 |
| 656 | GUUCUCA CUGAUGAGGCCGAAAGGCCGAA ACAGCUC | 823 |
| 657 | UGUUCUC CUGAUGAGGCCGAAAGGCCGAA AACAGCU | 824 |

TABLE IV-continued

Human ICAM HH Ribozyme Sequences

| nt. Position | Ribozyme Sequence | | | Seq. ID No. |
|---|---|---|---|---|
| 668 | GGGGGCC | CUGAUGAGGCCGAAAGGCCGAA | AGGUGUU | 825 |
| 677 | GAGCUGG | CUGAUGAGGCCGAAAGGCCGAA | AGGGGGC | 826 |
| 684 | AGGUCUG | CUGAUGAGGCCGAAAGGCCGAA | AGCUGGU | 827 |
| 692 | CAGGACA | CUGAUGAGGCCGAAAGGCCGAA | AGGUCUG | 828 |
| 693 | GCAGGAC | CUGAUGAGGCCGAAAGGCCGAA | AAGGUCU | 829 |
| 696 | CUGGCAG | CUGAUGAGGCCGAAAGGCCGAA | ACAAAGG | 830 |
| 709 | UGUGGGG | CUGAUGAGGCCGAAAGGCCGAA | AGUCGCU | 831 |
| 720 | GGCUGAC | CUGAUGAGGCCGAAAGGCCGAA | AGUUGUG | 832 |
| 723 | GGGGGCU | CUGAUGAGGCCGAAAGGCCGAA | ACAAGUU | 833 |
| 735 | CCUCUAG | CUGAUGAGGCCGAAAGGCCGAA | ACCCGGG | 834 |
| 738 | CCACCUC | CUGAUGAGGCCGAAAGGCCGAA | AGGACCC | 835 |
| 765 | GGGAACA | CUGAUGAGGCCGAAAGGCCGAA | ACCACGG | 836 |
| 769 | UCCAGGG | CUGAUGAGGCCGAAAGGCCGAA | ACAGACC | 837 |
| 770 | GUCCAGG | CUGAUGAGGCCGAAAGGCCGAA | AACAGAC | 838 |
| 785 | GACUGGG | CUGAUGAGGCCGAAAGGCCGAA | ACAGCCC | 839 |
| 786 | AGACUGG | CUGAUGAGGCCGAAAGGCCGAA | AACAGCC | 840 |
| 792 | CCUCCGA | CUGAUGAGGCCGAAAGGCCGAA | ACUGGGA | 841 |
| 794 | GGCCUCC | CUGAUGAGGCCGAAAGGCCGAA | AGACUGG | 842 |
| 807 | CCAGGUG | CUGAUGAGGCCGAAAGGCCGAA | ACCUGGG | 843 |
| 833 | GGGGUUC | CUGAUGAGGCCGAAAGGCCGAA | ACCUCUG | 844 |
| 846 | CAUAGGU | CUGAUGAGGCCGAAAGGCCGAA | ACUGUGG | 845 |
| 851 | GUUGCCA | CUGAUGAGGCCGAAAGGCCGAA | AGGUGAC | 846 |
| 863 | CGAGAAG | CUGAUGAGGCCGAAAGGCCGAA | AGUCGUU | 847 |
| 866 | GGCCGAG | CUGAUGAGGCCGAAAGGCCGAA | AGGAGUC | 848 |
| 867 | UGGCCGA | CUGAUGAGGCCGAAAGGCCGAA | AAGGAGU | 849 |
| 869 | CUUGGCC | CUGAUGAGGCCGAAAGGCCGAA | AGAAGGA | 850 |
| 881 | ACUGACU | CUGAUGAGGCCGAAAGGCCGAA | AGGCCUU | 851 |
| 885 | UCACACU | CUGAUGAGGCCGAAAGGCCGAA | ACUGAGG | 852 |
| 933 | CCAGUAU | CUGAUGAGGCCGAAAGGCCGAA | ACUGCAC | 853 |
| 936 | UCCCCAG | CUGAUGAGGCCGAAAGGCCGAA | AUUACUG | 854 |
| 978 | AGCUGUA | CUGAUGAGGCCGAAAGGCCGAA | AUGGUCA | 855 |
| 980 | AAAGCUG | CUGAUGAGGCCGAAAGGCCGAA | AGAUGGU | 856 |
| 986 | CGCCGGA | CUGAUGAGGCCGAAAGGCCGAA | AGCUGUA | 857 |
| 987 | GCGCCGG | CUGAUGAGGCCGAAAGGCCGAA | AAGCUGU | 858 |
| 988 | GGCGCCG | CUGAUGAGGCCGAAAGGCCGAA | AAAGCUG | 859 |
| 1005 | UCGUCAG | CUGAUGAGGCCGAAAGGCCGAA | AUCACGU | 860 |
| 1006 | UUCGUCA | CUGAUGAGGCCGAAAGGCCGAA | AAUCACG | 861 |
| 1023 | CUUCUGA | CUGAUGAGGCCGAAAGGCCGAA | ACCUCUG | 862 |
| 1025 | CCCUUCU | CUGAUGAGGCCGAAAGGCCGAA | AGACCUC | 863 |
| 1066 | UUGGCUC | CUGAUGAGGCCGAAAGGCCGAA | AGGGUGG | 864 |
| 1092 | GGGCUGG | CUGAUGAGGCCGAAAGGCCGAA | ACCCCAU | 865 |
| 1093 | UGGGCUG | CUGAUGAGGCCGAAAGGCCGAA | AACCCCA | 866 |
| 1125 | UCAGCAG | CUGAUGAGGCCGAAAGGCCGAA | AGCUGGG | 867 |
| 1163 | GCAGGAG | CUGAUGAGGCCGAAAGGCCGAA | AGCUGCG | 868 |
| 1164 | AGCAGGA | CUGAUGAGGCCGAAAGGCCGAA | AAGCUGC | 869 |
| 1166 | AGAGCAG | CUGAUGAGGCCGAAAGGCCGAA | AGAAGCU | 870 |
| 1172 | GGUUGCA | CUGAUGAGGCCGAAAGGCCGAA | AGCAGGA | 871 |
| 1200 | UGUGUAU | CUGAUGAGGCCGAAAGGCCGAA | AGCUGGC | 872 |
| 1201 | UUGUGUA | CUGAUGAGGCCGAAAGGCCGAA | AAGCUGG | 873 |
| 1203 | UCUUGUG | CUGAUGAGGCCGAAAGGCCGAA | AUAAGCU | 874 |
| 1227 | GGACACG | CUGAUGAGGCCGAAAGGCCGAA | AGCUCCC | 875 |
| 1228 | AGGACAC | CUGAUGAGGCCGAAAGGCCGAA | AAGCUCC | 876 |
| 1233 | CAUACAG | CUGAUGAGGCCGAAAGGCCGAA | ACACGAA | 877 |
| 1238 | GGGGCCA | CUGAUGAGGCCGAAAGGCCGAA | ACAGGAC | 878 |
| 1264 | CCCGGAC | CUGAUGAGGCCGAAAGGCCGAA | AUCCCUC | 879 |
| 1267 | UUUCCCG | CUGAUGAGGCCGAAAGGCCGAA | ACAAUCC | 880 |
| 1294 | UGCUGGG | CUGAUGAGGCCGAAAGGCCGAA | AUUUUCU | 881 |
| 1295 | CUGCUGG | CUGAUGAGGCCGAAAGGCCGAA | AAUUUUC | 882 |
| 1306 | CACAUUG | CUGAUGAGGCCGAAAGGCCGAA | AGUCUGC | 883 |
| 1321 | UUCCCCC | CUGAUGAGGCCGAAAGGCCGAA | AGCCUGG | 884 |
| 1334 | CUCGGGC | CUGAUGAGGCCGAAAGGCCGAA | AUGGGUU | 885 |
| 1344 | GACACUU | CUGAUGAGGCCGAAAGGCCGAA | AGCUCGG | 886 |
| 1351 | UCCUUUA | CUGAUGAGGCCGAAAGGCCGAA | ACACUUG | 887 |
| 1353 | CAUCCUU | CUGAUGAGGCCGAAAGGCCGAA | AGACACU | 888 |
| 1366 | AGUGGGA | CUGAUGAGGCCGAAAGGCCGAA | AGUGCCA | 889 |
| 1367 | CAGUGGG | CUGAUGAGGCCGAAAGGCCGAA | AAGUGCC | 890 |
| 1368 | GCAGUGG | CUGAUGAGGCCGAAAGGCCGAA | AAAGUGC | 891 |
| 1380 | AUUCCCC | CUGAUGAGGCCGAAAGGCCGAA | AUGGGCA | 892 |
| 1388 | AGUCACU | CUGAUGAGGCCGAAAGGCCGAA | AUUCCCC | 893 |
| 1398 | CUCGAGU | CUGAUGAGGCCGAAAGGCCGAA | ACAGUCA | 894 |
| 1402 | AGAUCUC | CUGAUGAGGCCGAAAGGCCGAA | AGUGACA | 895 |
| 1408 | CCCUCAA | CUGAUGAGGCCGAAAGGCCGAA | AUCUCGA | 896 |
| 1410 | UGCCCUC | CUGAUGAGGCCGAAAGGCCGAA | AGAUCUC | 897 |
| 1421 | ACAGAGG | CUGAUGAGGCCGAAAGGCCGAA | AGGUGCC | 898 |
| 1425 | CCCGACA | CUGAUGAGGCCGAAAGGCCGAA | AGGUAGG | 899 |

TABLE IV-continued

Human ICAM HH Ribozyme Sequences

| nt. Position | Ribozyme Sequence | | | Seq. ID No. |
|---|---|---|---|---|
| 1429 | CUGGCCC | CUGAUGAGGCCGAAAGGCCGAA | ACAGAGG | 900 |
| 1444 | UCCCCUU | CUGAUGAGGCCGAAAGGCCGAA | AGUGCUC | 901 |
| 1455 | CGCGGGU | CUGAUGAGGCCGAAAGGCCGAA | ACCUCCC | 902 |
| 1482 | GGGGGGA | CUGAUGAGGCCGAAAGGCCGAA | AGCACAU | 903 |
| 1484 | CCGGGGG | CUGAUGAGGCCGAAAGGCCGAA | AGAGCAC | 904 |
| 1493 | AAUCUCA | CUGAUGAGGCCGAAAGGCCGAA | ACCGGGG | 905 |
| 1500 | UGAUGAC | CUGAUGAGGCCGAAAGGCCGAA | AUCUCAU | 906 |
| 1503 | UGAUGAU | CUGAUGAGGCCGAAAGGCCGAA | ACAAUCU | 907 |
| 1506 | CAGUGAU | CUGAUGAGGCCGAAAGGCCGAA | AUGACAA | 908 |
| 1509 | CCACAGU | CUGAUGAGGCCGAAAGGCCGAA | AUGAUGA | 909 |
| 1518 | CGGCUGC | CUGAUGAGGCCGAAAGGCCGAA | ACCACAG | 910 |
| 1530 | CCAUUAU | CUGAUGAGGCCGAAAGGCCGAA | ACUGCGG | 911 |
| 1533 | UGCCCAU | CUGAUGAGGCCGAAAGGCCGAA | AUGACUG | 912 |
| 1551 | ACGUGCU | CUGAUGAGGCCGAAAGGCCGAA | AGGCCUG | 913 |
| 1559 | AUAGAGG | CUGAUGAGGCCGAAAGGCCGAA | ACGUGCU | 914 |
| 1563 | GGUUAUA | CUGAUGAGGCCGAAAGGCCGAA | AGGUACG | 915 |
| 1565 | GCGGUUA | CUGAUGAGGCCGAAAGGCCGAA | AGAGGUA | 916 |
| 1567 | UGGCGGU | CUGAUGAGGCCGAAAGGCCGAA | AUAGAGG | 917 |
| 1584 | AUUUCUU | CUGAUGAGGCCGAAAGGCCGAA | ACUUCC | 918 |
| 1592 | UAGUCUG | CUGAUGAGGCCGAAAGGCCGAA | AUUUCUU | 919 |
| 1599 | CCUGUUG | CUGAUGAGGCCGAAAGGCCGAA | AGUCUGU | 920 |
| 1651 | GUUCAGG | CUGAUGAGGCCGAAAGGCCGAA | AGGCGUG | 921 |
| 1661 | CCCGGGA | CUGAUGAGGCCGAAAGGCCGAA | AGGUUCA | 922 |
| 1663 | GUCCCGG | CUGAUGAGGCCGAAAGGCCGAA | AUAGGUU | 923 |
| 1678 | CGAGGAA | CUGAUGAGGCCGAAAGGCCGAA | AGGCCCU | 924 |
| 1680 | GCCGAGG | CUGAUGAGGCCGAAAGGCCGAA | AGAGGCC | 925 |
| 1681 | GGCCGAG | CUGAUGAGGCCGAAAGGCCGAA | AAGAGGC | 926 |
| 1684 | GAAGGCC | CUGAUGAGGCCGAAAGGCCGAA | AGGAAGA | 927 |
| 1690 | AUAUGGG | CUGAUGAGGCCGAAAGGCCGAA | AGGCCGA | 928 |
| 1691 | AAUAUGG | CUGAUGAGGCCGAAAGGCCGAA | AAGGCCG | 929 |
| 1696 | CCACCAA | CUGAUGAGGCCGAAAGGCCGAA | AUGGGAA | 930 |
| 1698 | UGCCACC | CUGAUGAGGCCGAAAGGCCGAA | AUAUGGG | 931 |
| 1737 | CAUGGCA | CUGAUGAGGCCGAAAGGCCGAA | AUGUCUU | 932 |
| 1750 | GUAGGUG | CUGAUGAGGCCGAAAGGCCGAA | AGCUGCA | 933 |
| 1756 | GGGCCGG | CUGAUGAGGCCGAAAGGCCGAA | AGGUGUA | 934 |
| 1787 | UGAGGAC | CUGAUGAGGCCGAAAGGCCGAA | AUGCCCU | 935 |
| 1790 | GACUGAG | CUGAUGAGGCCGAAAGGCCGAA | ACAAUGC | 936 |
| 1793 | UCUGACU | CUGAUGAGGCCGAAAGGCCGAA | AGGACAA | 937 |
| 1797 | UGUAUCU | CUGAUGAGGCCGAAAGGCCGAA | ACUGAGG | 938 |
| 1802 | GCUGUUG | CUGAUGAGGCCGAAAGGCCGAA | AUCUGAC | 939 |
| 1812 | GGCCCCA | CUGAUGAGGCCGAAAGGCCGAA | AUGCUGU | 940 |
| 1813 | UGGCCCC | CUGAUGAGGCCGAAAGGCCGAA | AAUGCUG | 941 |
| 1825 | GUGCAGG | CUGAUGAGGCCGAAAGGCCGAA | ACCAUGG | 942 |
| 1837 | AGUGUUU | CUGAUGAGGCCGAAAGGCCGAA | AGGUGUU | 943 |
| 1845 | CGUGGCC | CUGAUGAGGCCGAAAGGCCGAA | AGUGUUU | 944 |
| 1856 | CAGAUCA | CUGAUGAGGCCGAAAGGCCGAA | AUGCGUG | 945 |
| 1861 | GACUACA | CUGAUGAGGCCGAAAGGCCGAA | AUCAGAU | 946 |
| 1865 | AUGUGAC | CUGAUGAGGCCGAAAGGCCGAA | ACAGAUC | 947 |
| 1868 | GUCAUGU | CUGAUGAGGCCGAAAGGCCGAA | ACUACAG | 948 |
| 1877 | CUUGGCU | CUGAUGAGGCCGAAAGGCCGAA | AGUCAUG | 949 |
| 1901 | AUGUCUU | CUGAUGAGGCCGAAAGGCCGAA | AGUCUUG | 950 |
| 1912 | AUCCAUC | CUGAUGAGGCCGAAAGGCCGAA | AUCAUGU | 951 |
| 1922 | AGACUUU | CUGAUGAGGCCGAAAGGCCGAA | ACAUCCA | 952 |
| 1923 | UAGACUU | CUGAUGAGGCCGAAAGGCCGAA | AACAUCC | 953 |
| 1928 | CAGGCUA | CUGAUGAGGCCGAAAGGCCGAA | ACUUUAA | 954 |
| 1930 | AUCAGGC | CUGAUGAGGCCGAAAGGCCGAA | AGACUUU | 955 |
| 1964 | GUGGGGC | CUGAUGAGGCCGAAAGGCCGAA | AUGUCUC | 956 |
| 1983 | CCAGUUG | CUGAUGAGGCCGAAAGGCCGAA | AUGUCCU | 957 |
| 1996 | GUUUCAG | CUGAUGAGGCCGAAAGGCCGAA | AUUUCCC | 958 |
| 2005 | AGGCAGC | CUGAUGAGGCCGAAAGGCCGAA | AGUUUCA | 959 |
| 2013 | UACCCAA | CUGAUGAGGCCGAAAGGCCGAA | AGGCAGC | 960 |
| 2015 | CAUACCC | CUGAUGAGGCCGAAAGGCCGAA | AUAGGCA | 961 |
| 2020 | CUCAGCA | CUGAUGAGGCCGAAAGGCCGAA | ACCCAAU | 962 |
| 2039 | CUUCUGU | CUGAUGAGGCCGAAAGGCCGAA | AGUCUGU | 963 |
| 2040 | UCUUCUG | CUGAUGAGGCCGAAAGGCCGAA | AAGUCUG | 964 |
| 2057 | GUCUAUG | CUGAUGAGGCCGAAAGGCCGAA | AGGGCCA | 965 |
| 2061 | ACAUGUC | CUGAUGAGGCCGAAAGGCCGAA | AUGGAGG | 966 |
| 2071 | UUGAUGC | CUGAUGAGGCCGAAAGGCCGAA | ACACAUG | 967 |
| 2076 | GUGUUUU | CUGAUGAGGCCGAAAGGCCGAA | AUGCUAC | 968 |
| 2097 | CGUCAGG | CUGAUGAGGCCGAAAGGCCGAA | AGUGUCG | 969 |
| 2098 | CCGUCAG | CUGAUGAGGCCGAAAGGCCGAA | AAGUGUG | 970 |
| 2115 | AGUGCCC | CUGAUGAGGCCGAAAGGCCGAA | AGCUGGC | 971 |
| 2128 | GUCAGUA | CUGAUGAGGCCGAAAGGCCGAA | ACAGCAG | 972 |
| 2130 | GGGUCAG | CUGAUGAGGCCGAAAGGCCGAA | AGACAGC | 973 |
| 2145 | UAUCAUC | CUGAUGAGGCCGAAAGGCCGAA | AGGGUUG | 974 |

TABLE IV-continued

Human ICAM HH Ribozyme Sequences

| nt. Position | Ribozyme Sequence | | | Seq. ID No. |
|---|---|---|---|---|
| 2152 | AAAUACA | CUGAUGAGGCCGAAAGGCCGAA | AUCAUCA | 975 |
| 2156 | GAAUAAA | CUGAUGAGGCCGAAAGGCCGAA | ACAUAUC | 976 |
| 2158 | AUGAAUA | CUGAUGAGGCCGAAAGGCCGAA | AUACAUA | 977 |
| 2159 | AAUGAAU | CUGAUGAGGCCGAAAGGCCGAA | AAUACAU | 978 |
| 2160 | AAAUGAA | CUGAUGAGGCCGAAAGGCCGAA | AAAUACA | 979 |
| 2162 | ACAAAUG | CUGAUGAGGCCGAAAGGCCGAA | AUAAAUA | 980 |
| 2163 | AACAAAU | CUGAUGAGGCCGAAAGGCCGAA | AAUAAAU | 981 |
| 2166 | AAUAACA | CUGAUGAGGCCGAAAGGCCGAA | AUGAAUA | 982 |
| 2167 | AAAUAAC | CUGAUGAGGCCGAAAGGCCGAA | AAUGAAU | 983 |
| 2170 | GUAAAUU | CUGAUGAGGCCGAAAGGCCGAA | ACAAAUG | 984 |
| 2171 | GGUAAAA | CUGAUGAGGCCGAAAGGCCGAA | AACAAAU | 985 |
| 2173 | CUGGUAA | CUGAUGAGGCCGAAAGGCCGAA | AUAACAA | 986 |
| 2174 | GCUGGUA | CUGAUGAGGCCGAAAGGCCGAA | AAUAACA | 987 |
| 2175 | AGCUGGU | CUGAUGAGGCCGAAAGGCCGAA | AAAUAAC | 988 |
| 2176 | UAGCUGG | CUGAUGAGGCCGAAAGGCCGAA | AAAAUAA | 989 |
| 2183 | CAAUAAA | CUGAUGAGGCCGAAAGGCCGAA | AGCUGGU | 990 |
| 2185 | CUCAAUA | CUGAUGAGGCCGAAAGGCCGAA | AUAGCUG | 991 |
| 2186 | ACUCAAU | CUGAUGAGGCCGAAAGGCCGAA | AAUAGCU | 992 |
| 2187 | CACUCAA | CUGAUGAGGCCGAAAGGCCGAA | AAAUAGC | 993 |
| 2189 | GACACUC | CUGAUGAGGCCGAAAGGCCGAA | AUAAAUA | 994 |
| 2196 | CAUAAAA | CUGAUGAGGCCGAAAGGCCGAA | ACACUCA | 995 |
| 2198 | UACAUAA | CUGAUGAGGCCGAAAGGCCGAA | AGACACU | 996 |
| 2199 | CUACAUA | CUGAUGAGGCCGAAAGGCCGAA | AAGACAC | 997 |
| 2200 | CCUACAU | CUGAUGAGGCCGAAAGGCCGAA | AAAGACA | 998 |
| 2201 | GCCUACA | CUGAUGAGGCCGAAAGGCCGAA | AAAAGAC | 999 |
| 2205 | UUUAGCC | CUGAUGAGGCCGAAAGGCCGAA | ACAUAAA | 1000 |
| 2210 | GUUCAUU | CUGAUGAGGCCGAAAGGCCGAA | AGCCUAC | 1001 |
| 2220 | AGAGACC | CUGAUGAGGCCGAAAGGCCGAA | AUGUUCA | 1002 |
| 2224 | GGCCAGA | CUGAUGAGGCCGAAAGGCCGAA | ACCUAUG | 1003 |
| 2226 | GAGGCCA | CUGAUGAGGCCGAAAGGCCGAA | AGACCUA | 1004 |
| 2233 | GCUCCGU | CUGAUGAGGCCGAAAGGCCGAA | AGGCCAG | 1005 |
| 2242 | GGACUGG | CUGAUGAGGCCGAAAGGCCGAA | AGCUCCG | 1006 |
| 2248 | UGACAUG | CUGAUGAGGCCGAAAGGCCGAA | ACUGGGA | 1007 |
| 2254 | UGAAUGU | CUGAUGAGGCCGAAAGGCCGAA | ACAUGGA | 1008 |
| 2259 | GACCUUG | CUGAUGAGGCCGAAAGGCCGAA | AUGUGAC | 1009 |
| 2260 | UGACCUU | CUGAUGAGGCCGAAAGGCCGAA | AAUGUGA | 1010 |
| 2266 | ACCUGGU | CUGAUGAGGCCGAAAGGCCGAA | ACCUUGA | 1011 |
| 2274 | ACAACUG | CUGAUGAGGCCGAAAGGCCGAA | ACCUGGU | 1012 |
| 2279 | CCUGUAC | CUGAUGAGGCCGAAAGGCCGAA | ACUGUAC | 1013 |
| 2282 | CAACCUG | CUGAUGAGGCCGAAAGGCCGAA | ACAACUG | 1014 |
| 2288 | AGUGUAC | CUGAUGAGGCCGAAAGGCCGAA | ACCUGUA | 1015 |
| 2291 | UGCAGUG | CUGAUGAGGCCGAAAGGCCGAA | ACAACCU | 1016 |
| 2321 | CCCAUUU | CUGAUGAGGCCGAAAGGCCGAA | AUCUUUU | 1017 |
| 2338 | CAAUGAG | CUGAUGAGGCCGAAAGGCCGAA | AGUCCCA | 1018 |
| 2339 | CCAAUGA | CUGAUGAGGCCGAAAGGCCGAA | AAGUCCC | 1019 |
| 2341 | GGCCAAU | CUGAUGAGGCCGAAAGGCCGAA | AGAAGUC | 1020 |
| 2344 | GUUGGCC | CUGAUGAGGCCGAAAGGCCGAA | AUGAGAA | 1021 |
| 2358 | CUGGGGA | CUGAUGAGGCCGAAAGGCCGAA | AGGCAGG | 1022 |
| 2359 | UCUGGGG | CUGAUGAGGCCGAAAGGCCGAA | AAGGCAG | 1023 |
| 2360 | UUCUGGG | CUGAUGAGGCCGAAAGGCCGAA | AAAGGCA | 1024 |
| 2376 | AUAGAAA | CUGAUGAGGCCGAAAGGCCGAA | AUCACUC | 1025 |
| 2377 | GAUAGAA | CUGAUGAGGCCGAAAGGCCGAA | AAUCACU | 1026 |
| 2378 | CGAUAGA | CUGAUGAGGCCGAAAGGCCGAA | AAAUCAC | 1027 |
| 2379 | CCGAUAG | CUGAUGAGGCCGAAAGGCCGAA | AAAAUCA | 1028 |
| 2380 | GCCGAUA | CUGAUGAGGCCGAAAGGCCGAA | AAAAAUC | 1029 |
| 2382 | GUGCCGA | CUGAUGAGGCCGAAAGGCCGAA | AGAAAAA | 1030 |
| 2384 | UUGUGCC | CUGAUGAGGCCGAAAGGCCGAA | AUAGAAA | 1031 |
| 2399 | GUCCAUA | CUGAUGAGGCCGAAAGGCCGAA | AGUGCUU | 1032 |
| 2401 | CAGUCCA | CUGAUGAGGCCGAAAGGCCGAA | AUAGUGC | 1033 |
| 2411 | GAACCAU | CUGAUGAGGCCGAAAGGCCGAA | ACCAGUC | 1034 |
| 2417 | ACCUGUG | CUGAUGAGGCCGAAAGGCCGAA | ACCAUUA | 1035 |
| 2418 | AACCUGU | CUGAUGAGGCCGAAAGGCCGAA | AACCAUU | 1036 |
| 2425 | AUCUCUG | CUGAUGAGGCCGAAAGGCCGAA | ACCUGUG | 1037 |
| 2426 | AAUCUCU | CUGAUGAGGCCGAAAGGCCGAA | AACCUGU | 1038 |
| 2433 | ACUGGGU | CUGAUGAGGCCGAAAGGCCGAA | AUCUCUG | 1039 |
| 2434 | CACUGGG | CUGAUGAGGCCGAAAGGCCGAA | AAUCUCU | 1040 |
| 2448 | GAGGAAU | CUGAUGAGGCCGAAAGGCCGAA | AGGCCUC | 1041 |
| 2449 | GGAGGAA | CUGAUGAGGCCGAAAGGCCGAA | AAGGCCU | 1042 |
| 2451 | AGGGAGG | CUGAUGAGGCCGAAAGGCCGAA | AUAAGGC | 1043 |
| 2452 | AAGGGAG | CUGAUGAGGCCGAAAGGCCGAA | AAUAAGG | 1044 |
| 2455 | GGGAAGG | CUGAUGAGGCCGAAAGGCCGAA | AGGAAUA | 1045 |
| 2459 | UGGGGGG | CUGAUGAGGCCGAAAGGCCGAA | AGGGAGG | 1046 |
| 2460 | UUGGGGG | CUGAUGAGGCCGAAAGGCCGAA | AAGGGAG | 1047 |
| 2479 | GCUAACA | CUGAUGAGGCCGAAAGGCCGAA | AGGUGUC | 1048 |
| 2480 | GGCUAAC | CUGAUGAGGCCGAAAGGCCGAA | AAGGUGU | 1049 |

TABLE IV-continued

Human ICAM HH Ribozyme Sequences

| nt. Position | Ribozyme Sequence | | | Seq. ID No. |
|---|---|---|---|---|
| 2483 | GGUGGCU | CUGAUGAGGCCGAAAGGCCGAA | ACAAAGG | 1050 |
| 2484 | AGGUGGC | CUGAUGAGGCCGAAAGGCCGAA | AACAAAG | 1051 |
| 2492 | GGGUGGG | CUGAUGAGGCCGAAAGGCCGAA | AGGUGGC | 1052 |
| 2504 | AGAAAUG | CUGAUGAGGCCGAAAGGCCGAA | AUGUGGG | 1053 |
| 2508 | UGGCAGA | CUGAUGAGGCCGAAAGGCCGAA | AUGUAUG | 1054 |
| 2509 | CUGGCAG | CUGAUGAGGCCGAAAGGCCGAA | AAUGUAU | 1055 |
| 2510 | ACUGGCA | CUGAUGAGGCCGAAAGGCCGAA | AAAUGUA | 1056 |
| 2520 | CAUUGUG | CUGAUGAGGCCGAAAGGCCGAA | ACACUGG | 1057 |
| 2521 | UCAUUGU | CUGAUGAGGCCGAAAGGCCGAA | AACACUG | 1058 |
| 2533 | GACCGCU | CUGAUGAGGCCGAAAGGCCGAA | AGUGUCA | 1059 |
| 2540 | CAGACAU | CUGAUGAGGCCGAAAGGCCGAA | ACCGCUG | 1060 |
| 2545 | AUGUCCA | CUGAUGAGGCCGAAAGGCCGAA | ACAUGAC | 1061 |
| 2568 | UUGGGCA | CUGAUGAGGCCGAAAGGCCGAA | AUUCCCU | 1062 |
| 2579 | CAAGGCA | CUGAUGAGGCCGAAAGGCCGAA | AGCUUGG | 1063 |
| 2585 | AGAGGAC | CUGAUGAGGCCGAAAGGCCGAA | AGGCAUA | 1064 |
| 2588 | ACAAGAG | CUGAUGAGGCCGAAAGGCCGAA | ACAAGGC | 1065 |
| 2591 | AGGACAA | CUGAUGAGGCCGAAAGGCCGAA | AGGACAA | 1066 |
| 2593 | ACAGGAC | CUGAUGAGGCCGAAAGGCCGAA | AGAGGAC | 1067 |
| 2596 | CAAACAG | CUGAUGAGGCCGAAAGGCCGAA | ACAAGAG | 1068 |
| 2601 | AAAUGCA | CUGAUGAGGCCGAAAGGCCGAA | ACAGGAC | 1069 |
| 2602 | GAAAUGC | CUGAUGAGGCCGAAAGGCCGAA | AACAGGA | 1070 |
| 2607 | CCAGUGA | CUGAUGAGGCCGAAAGGCCGAA | AUGCAAA | 1071 |
| 2608 | CCCAGUG | CUGAUGAGGCCGAAAGGCCGAA | AAUGCAA | 1072 |
| 2609 | UCCCAGU | CUGAUGAGGCCGAAAGGCCGAA | AAAUGCA | 1073 |
| 2620 | AUAGUGC | CUGAUGAGGCCGAAAGGCCGAA | AGCUCCC | 1074 |
| 2626 | GCUGCAA | CUGAUGAGGCCGAAAGGCCGAA | AGUGCAA | 1075 |
| 2628 | GAGCUGC | CUGAUGAGGCCGAAAGGCCGAA | AUAGUGC | 1076 |
| 2635 | GAAACUG | CUGAUGAGGCCGAAAGGCCGAA | AGCUGCA | 1077 |
| 2640 | UGCAGGA | CUGAUGAGGCCGAAAGGCCGAA | ACUGGAG | 1078 |
| 2641 | CUGCAGG | CUGAUGAGGCCGAAAGGCCGAA | AACUGGA | 1079 |
| 2642 | ACUGCAG | CUGAUGAGGCCGAAAGGCCGAA | AAACUGG | 1080 |
| 2653 | GGACCCU | CUGAUGAGGCCGAAAGGCCGAA | AUCACUG | 1081 |
| 2659 | CUUGCAG | CUGAUGAGGCCGAAAGGCCGAA | ACCCUGA | 1082 |
| 2689 | CCUCCAA | CUGAUGAGGCCGAAAGGCCGAA | ACCUUGG | 1083 |
| 2691 | GUCCUCC | CUGAUGAGGCCGAAAGGCCGAA | AUACCUU | 1084 |
| 2700 | UGGGAGG | CUGAUGAGGCCGAAAGGCCGAA | AGUCCUC | 1085 |
| 2704 | AAGCUGG | CUGAUGAGGCCGAAAGGCCGAA | AGGGAGU | 1086 |
| 2711 | CCUUCCA | CUGAUGAGGCCGAAAGGCCGAA | AGCUGGG | 1087 |
| 2712 | CCCUUCC | CUGAUGAGGCCGAAAGGCCGAA | AAGCUGG | 1088 |
| 2721 | CGCGGAU | CUGAUGAGGCCGAAAGGCCGAA | ACCCUUC | 1089 |
| 2724 | ACACGCG | CUGAUGAGGCCGAAAGGCCGAA | AUGACCC | 1090 |
| 2744 | CUACACA | CUGAUGAGGCCGAAAGGCCGAA | ACACACA | 1091 |
| 2750 | GCUUGUC | CUGAUGAGGCCGAAAGGCCGAA | ACACAUA | 1092 |
| 2759 | AGAGCGA | CUGAUGAGGCCGAAAGGCCGAA | AGCUUGU | 1093 |
| 2761 | ACAGAGC | CUGAUGAGGCCGAAAGGCCGAA | AGAGCUU | 1094 |
| 2765 | GGUGACA | CUGAUGAGGCCGAAAGGCCGAA | AGCGAGA | 1095 |
| 2769 | CCUGGGU | CUGAUGAGGCCGAAAGGCCGAA | ACAGAGC | 1096 |
| 2797 | GAACCAU | CUGAUGAGGCCGAAAGGCCGAA | AUUGCAC | 1097 |
| 2803 | UGCAGUG | CUGAUGAGGCCGAAAGGCCGAA | ACCAUGA | 1098 |
| 2804 | CUGCAGU | CUGAUGAGGCCGAAAGGCCGAA | AACCAUG | 1099 |
| 2813 | AGGUCAA | CUGAUGAGGCCGAAAGGCCGAA | ACUGCAG | 1100 |
| 2315 | AAAGGUC | CUGAUGAGGCCGAAAGGCCGAA | AGACUGC | 1101 |
| 2821 | AGCCCAA | CUGAUGAGGCCGAAAGGCCGAA | AGGUCAA | 1102 |
| 2822 | GAGCCCA | CUGAUGAGGCCGAAAGGCCGAA | AAGGUCA | 1103 |
| 2823 | UGAGCCC | CUGAUGAGGCCGAAAGGCCGAA | AAAGGUC | 1104 |
| 2829 | AUCACUU | CUGAUGAGGCCGAAAGGCCGAA | AGCCCAA | 1105 |
| 2837 | GUGGGAG | CUGAUGAGGCCGAAAGGCCGAA | AUCACUU | 1106 |
| 2840 | GAGGUGG | CUGAUGAGGCCGAAAGGCCGAA | AGGAUCA | 1107 |
| 2847 | GGAGGCU | CUGAUGAGGCCGAAAGGCCGAA | AGGUGGG | 1108 |
| 2853 | UACUCAG | CUGAUGAGGCCGAAAGGCCGAA | AGGCUGA | 1109 |
| 2860 | UCCCAGC | CUGAUGAGGCCGAAAGGCCGAA | ACUCAGG | 1110 |
| 2872 | GUGAGCC | CUGAUGAGGCCGAAAGGCCGAA | AUGGUCC | 1111 |
| 2877 | GUGUUGU | CUGAUGAGGCCGAAAGGCCGAA | AGCCUAU | 1112 |
| 2899 | AAAAUCA | CUGAUGAGGCCGAAAGGCCGAA | AUUUGCC | 1113 |
| 2900 | AAAAAUC | CUGAUGAGGCCGAAAGGCCGAA | AAUUUGC | 1114 |
| 2904 | AAAAAAA | CUGAUGAGGCCGAAAGGCCGAA | AUCAAAU | 1115 |
| 2905 | AAAAAAA | CUGAUGAGGCCGAAAGGCCGAA | AAUCAAA | 1116 |
| 2906 | AAAAAAA | CUGAUGAGGCCGAAAGGCCGAA | AAAUCAA | 1117 |
| 2907 | AAAAAAA | CUGAUGAGGCCGAAAGGCCGAA | AAAAUCA | 1118 |
| 2908 | AAAAAAA | CUGAUGAGGCCGAAAGGCCGAA | AAAAAUC | 1119 |
| 2909 | AAAAAAA | CUGAUGAGGCCGAAAGGCCGAA | AAAAAAU | 1120 |
| 2910 | AAAAAAA | CUGAUGAGGCCGAAAGGCCGAA | AAAAAAA | 1121 |
| 2911 | AAAAAAA | CUGAUGAGGCCGAAAGGCCGAA | AAAAAAA | 1122 |
| 2912 | GAAAAAA | CUGAUGAGGCCGAAAGGCCGAA | AAAAAAA | 1123 |
| 2913 | UGAAAAA | CUGAUGAGGCCGAAAGGCCGAA | AAAAAAA | 1124 |

TABLE IV-continued

Human ICAM HH Ribozyme Sequences

| nt. Position | Ribozyme Sequence | | | Seq. ID No. |
|---|---|---|---|---|
| 2914 | CUGAAAA | CUGAUGAGGCCGAAAGGCCGAA | AAAAAAA | 1125 |
| 2915 | UCUGAAA | CUGAUGAGGCCGAAAGGCCGAA | AAAAAAA | 1126 |
| 2916 | CUCUGAA | CUGAUGAGGCCGAAAGGCCGAA | AAAAAAA | 1127 |
| 2917 | UCUCUGA | CUGAUGAGGCCGAAAGGCCGAA | AAAAAAA | 1128 |
| 2918 | GUCUCUG | CUGAUGAGGCCGAAAGGCCGAA | AAAAAAA | 1129 |
| 2919 | CGUCUCU | CUGAUGAGGCCGAAAGGCCGAA | AAAAAAA | 1130 |
| 2931 | GUUGCGA | CUGAUGAGGCCGAAAGGCCGAA | ACCCCGU | 1131 |
| 2933 | AUGUUGC | CUGAUGAGGCCGAAAGGCCGAA | AGACCCC | 1132 |
| 2941 | UCUGGGC | CUGAUGAGGCCGAAAGGCCGAA | AUGUUGC | 1133 |
| 2951 | ACAAAGG | CUGAUGAGGCCGAAAGGCCGAA | AGUCUGG | 1134 |
| 2952 | CACAAAG | CUGAUGAGGCCGAAAGGCCGAA | AAGUCUG | 1135 |
| 2955 | UAACACA | CUGAUGAGGCCGAAAGGCCGAA | AGGAAGU | 1136 |
| 2956 | CUAACAC | CUGAUGAGGCCGAAAGGCCGAA | AAGGAAG | 1137 |
| 2961 | AUUAACU | CUGAUGAGGCCGAAAGGCCGAA | ACACAAA | 1138 |
| 2962 | UAUUAAC | CUGAUGAGGCCGAAAGGCCGAA | AACACAA | 1139 |
| 2965 | CUUUAUU | CUGAUGAGGCCGAAAGGCCGAA | ACUAACA | 1140 |
| 2966 | GCUUUAU | CUGAUGAGGCCGAAAGGCCGAA | AACUAAC | 1141 |
| 2969 | AAAGCUU | CUGAUGAGGCCGAAAGGCCGAA | AUUAACU | 1142 |
| 2975 | GUUGAGA | CUGAUGAGGCCGAAAGGCCGAA | AGCUUUA | 1143 |
| 2976 | AGUUGAG | CUGAUGAGGCCGAAAGGCCGAA | AAGCUUU | 1144 |
| 2977 | CAGUUGA | CUGAUGAGGCCGAAAGGCCGAA | AAAGCUU | 1145 |
| 2979 | GGCAGUU | CUGAUGAGGCCGAAAGGCCGAA | AGAAAGC | 1146 |

TABLE V

Mouse ICAM HH Ribozyme Sequence

| nt. Position | Ribozyme Sequence | | | Seq. ID No. |
|---|---|---|---|---|
| 11 | CAACGGU | CUGAUGAGGCCGAAAGGCCGAA | ACCAGGG | 1147 |
| 23 | AGCAGAG | CUGAUGAGGCCGAAAGGCCGAA | ACCACUG | 1148 |
| 26 | AGGAGCA | CUGAUGAGGCCGAAAGGCCGAA | AGAACCA | 1149 |
| 31 | UGUGGAG | CUGAUGAGGCCGAAAGGCCGAA | AGCAGAG | 1150 |
| 34 | CGACCCU | CUGAUGAGGCCGAAAGGCCGAA | AUGAGAA | 1151 |
| 40 | AGGCUAC | CUGAUGAGGCCGAAAGGCCGAA | AGUGUGC | 1152 |
| 48 | CCAGGCU | CUGAUGAGGCCGAAAGGCCGAA | AGGUCCU | 1153 |
| 54 | CCAUCAC | CUGAUGAGGCCGAAAGGCCGAA | AGGCCCA | 1154 |
| 58 | GGAGCUA | CUGAUGAGGCCGAAAGGCCGAA | AGGCAUG | 1155 |
| 64 | CUGCUGG | CUGAUGAGGCCGAAAGGCCGAA | AGGGGUG | 1156 |
| 96 | GGGCCAG | CUGAUGAGGCCGAAAGGCCGAA | AGCAGAG | 1157 |
| 102 | CCAGCAG | CUGAUGAGGCCGAAAGGCCGAA | ACUGGCA | 1158 |
| 108 | GGGCCAG | CUGAUGAGGCCGAAAGGCCGAA | AGCAGAG | 1159 |
| 115 | AGGAGCA | CUGAUGAGGCCGAAAGGCCGAA | AGAACCA | 1160 |
| 119 | UCCUGGU | CUGAUGAGGCCGAAAGGCCGAA | ACAUUCC | 1161 |
| 120 | GGGCCAG | CUGAUGAGGCCGAAAGGCCGAA | AGCAGAG | 1162 |
| 146 | GGAAGCG | CUGAUGAGGCCGAAAGGCCGAA | ACGACUG | 1163 |
| 152 | AGUGGCU | CUGAUGAGGCCGAAAGGCCGAA | ACACAGA | 1164 |
| 158 | GGUUUUU | CUGAUGAGGCCGAAAGGCCGAA | AACAGGA | 1165 |
| 165 | GCAAAAC | CUGAUGAGGCCGAAAGGCCGAA | ACUUCUG | 1166 |
| 168 | GGGGCAG | CUGAUGAGGCCGAAAGGCCGAA | AAGGCUU | 1167 |
| 185 | CUGCACG | CUGAUGAGGCCGAAAGGCCGAA | ACCCACC | 1168 |
| 209 | GCCAGAG | CUGAUGAGGCCGAAAGGCCGAA | AAGUGGC | 1169 |
| 227 | GCAAAAC | CUGAUGAGGCCGAAAGGCCGAA | ACUUCUG | 1170 |
| 230 | GGAGCAA | CUGAUGAGGCCGAAAGGCCGAA | ACAACUU | 1171 |
| 237 | AGUUCUC | CUGAUGAGGCCGAAAGGCCGAA | AAGCACA | 1172 |
| 248 | UUUAGGA | CUGAUGAGGCCGAAAGGCCGAA | AUGGGUU | 1173 |
| 253 | UCUUCCU | CUGAUGAGGCCGAAAGGCCGAA | AGGCAGG | 1174 |
| 263 | CAGUAGA | CUGAUGAGGCCGAAAGGCCGAA | AAACCCU | 1175 |
| 267 | UAGGCAG | CUGAUGAGGCCGAAAGGCCGAA | AGCCCCU | 1176 |
| 293 | CAGCUCA | CUGAUGAGGCCGAAAGGCCGAA | ACAGCUU | 1177 |
| 319 | GGCUCAG | CUGAUGAGGCCGAAAGGCCGAA | AUCUCCU | 1178 |
| 335 | GUUCUCA | CUGAUGAGGCCGAAAGGCCGAA | AGCACAG | 1179 |
| 337 | CAGUGUG | CUGAUGAGGCCGAAAGGCCGAA | AUUGGAC | 1180 |
| 338 | UCAGCUC | CUGAUGAGGCCGAAAGGCCGAA | AACAGCU | 1181 |
| 359 | AGCGGAC | CUGAUGAGGCCGAAAGGCCGAA | ACUGCAC | 1182 |
| 367 | CGGGUUG | CUGAUGAGGCCGAAAGGCCGAA | AGCCAUU | 1183 |
| 374 | GGGCAGG | CUGAUGAGGCCGAAAGGCCGAA | AGGCUUC | 1184 |
| 375 | GGGGCAG | CUGAUGAGGCCGAAAGGCCGAA | AAGGCUU | 1185 |
| 378 | ACACGGU | CUGAUGAGGCCGAAAGGCCGAA | AUGGUAG | 1186 |
| 386 | AAACGAA | CUGAUGAGGCCGAAAGGCCGAA | ACACGGU | 1187 |
| 394 | AGAUCGA | CUGAUGAGGCCGAAAGGCCGAA | AGUCCGG | 1188 |
| 420 | CGGGGGG | CUGAUGAGGCCGAAAGGCCGAA | AAGUGUG | 1189 |

TABLE V-continued

Mouse ICAM HH Ribozyme Sequence

| nt. Position | Ribozyme Sequence | | | Seq. ID No. |
|---|---|---|---|---|
| 425 | CUGCUGG | CUGAUGAGGCCGAAAGGCCGAA | AGGGGUG | 1190 |
| 427 | CACUGCU | CUGAUGAGGCCGAAAGGCCGAA | AGAGCUG | 1191 |
| 450 | GCAGGGU | CUGAUGAGGCCGAAAGGCCGAA | AGGUCCU | 1192 |
| 451 | CAAAGGA | CUGAUGAGGCCGAAAGGCCGAA | AGGUUUC | 1193 |
| 456 | AGUGGCU | CUGAUGAGGCCGAAAGGCCGAA | AGGGUAA | 1194 |
| 495 | ACACGGU | CUGAUGAGGCCGAAAGGCCGAA | AUGGUAG | 1195 |
| 510 | CCCCACG | CUGAUGAGGCCGAAAGGCCGAA | AGCAGCA | 1196 |
| 564 | GGAUGGA | CUGAUGAGGCCGAAAGGCCGAA | ACCUGAG | 1197 |
| 592 | CCCAUGU | CUGAUGAGGCCGAAAGGCCGAA | AUCUUUC | 1198 |
| 607 | CAUGAGA | CUGAUGAGGCCGAAAGGCCGAA | AUUGGCU | 1199 |
| 608 | GCAUGAG | CUGAUGAGGCCGAAAGGCCGAA | AAUUGGC | 1200 |
| 609 | GGCAUGA | CUGAUGAGGCCGAAAGGCCGAA | AAAUUGG | 1201 |
| 611 | GCGGCAU | CUGAUGAGGCCGAAAGGCCGAA | AGAAAUU | 1202 |
| 656 | CAGCUCA | CUGAUGAGGCCGAAAGGCCGAA | ACAGCUU | 1203 |
| 657 | UCAGCUC | CUGAUGAGGCCGAAAGGCCGAA | AACAGCU | 1204 |
| 668 | GGUGGCC | CUGAUGAGGCCGAAAGGCCGAA | AGGCUCG | 1205 |
| 677 | AGGCUGG | CUGAUGAGGCCGAAAGGCCGAA | AGAGGUC | 1206 |
| 684 | AGGACCG | CUGAUGAGGCCGAAAGGCCGAA | AGCUGAA | 1207 |
| 692 | AAGAUCG | CUGAUGAGGCCGAAAGGCCGAA | AAGUCCG | 1208 |
| 693 | GCAGGGU | CUGAUGAGGCCGAAAGGCCGAA | AGGUCCU | 1209 |
| 696 | GAGGCAG | CUGAUGAGGCCGAAAGGCCGAA | AAACAGG | 1210 |
| 709 | UGAGGUG | CUGAUGAGGCCGAAAGGCCGAA | AGCCGCC | 1211 |
| 720 | AGCUGAA | CUGAUGAGGCCGAAAGGCCGAA | AGUUGUA | 1212 |
| 723 | CGGAGCU | CUGAUGAGGCCGAAAGGCCGAA | AAAAGUU | 1213 |
| 735 | UCUCCAG | CUGAUGAGGCCGAAAGGCCGAA | AUCUGGU | 1214 |
| 738 | CCAUCAC | CUGAUGAGGCCGAAAGGCCGAA | AGGCCCA | 1215 |
| 765 | GGAAGCG | CUGAUGAGGCCGAAAGGCCGAA | ACGACUG | 1216 |
| 769 | GGCAGGA | CUGAUGAGGCCGAAAGGCCGAA | ACAGGCC | 1217 |
| 770 | UUCCAGG | CUGAUGAGGCCGAAAGGCCGAA | AGCAAAA | 1218 |
| 785 | GGCAGGA | CUGAUGAGGCCGAAAGGCCGAA | ACAGGCC | 1219 |
| 786 | AGGCAGG | CUGAUGAGGCCGAAAGGCCGAA | AACAGGC | 1220 |
| 792 | CUUCCGA | CUGAUGAGGCCGAAAGGCCGAA | ACCUCCA | 1221 |
| 794 | AGUCUCC | CUGAUGAGGCCGAAAGGCCGAA | AGCCCAG | 1222 |
| 807 | CCAGGUA | CUGAUGAGGCCGAAAGGCCGAA | AUCCGAG | 1223 |
| 833 | GGGUGUC | CUGAUGAGGCCGAAAGGCCGAA | AGCUUUG | 1224 |
| 846 | CAACGGU | CUGAUGAGGCCGAAAGGCCGAA | ACCAGGG | 1225 |
| 851 | GCUGGUA | CUGAUGAGGCCGAAAGGCCGAA | AGGUCUC | 1226 |
| 863 | CCAGAGG | CUGAUGAGGCCGAAAGGCCGAA | AGUGGCU | 1227 |
| 866 | GGGCAGG | CUGAUGAGGCCGAAAGGCCGAA | AGGCUUC | 1228 |
| 867 | UCUCCGG | CUGAUGAGGCCGAAAGGCCGAA | AACGAAU | 1229 |
| 869 | CUUGCAU | CUGAUGAGGCCGAAAGGCCGAA | AGGAAGA | 1230 |
| 881 | ACGGGUU | CUGAUGAGGCCGAAAGGCCGAA | AAGCCAU | 1231 |
| 885 | UCACCUC | CUGAUGAGGCCGAAAGGCCGAA | ACCAAGG | 1232 |
| 933 | CCAGAAU | CUGAUGAGGCCGAAAGGCCGAA | AUUAUAG | 1233 |
| 936 | GCACCAG | CUGAUGAGGCCGAAAGGCCGAA | AUGAUUA | 1234 |
| 978 | AGUUGUA | CUGAUGAGGCCGAAAGGCCGAA | ACUGUUA | 1235 |
| 980 | AAAGUUG | CUGAUGAGGCCGAAAGGCCGAA | AGACUGU | 1236 |
| 986 | AGCUGAA | CUGAUGAGGCCGAAAGGCCGAA | AGUUGUA | 1237 |
| 987 | GAGCUGA | CUGAUGAGGCCGAAAGGCCGAA | AAGUUGU | 1238 |
| 988 | GGAGCUG | CUGAUGAGGCCGAAAGGCCGAA | AAAGUUG | 1239 |
| 1005 | UCUCCAG | CUGAUGAGGCCGAAAGGCCGAA | AUCUGGU | 1240 |
| 1006 | UUCCCCA | CUGAUGAGGCCGAAAGGCCGAA | ACUCUCA | 1241 |
| 1023 | CUUCCGA | CUGAUGAGGCCGAAAGGCCGAA | ACCUCCA | 1242 |
| 1025 | CCCUUCC | CUGAUGAGGCCGAAAGGCCGAA | AGACCUC | 1243 |
| 1066 | UUAUUUU | CUGAUGAGGCCGAAAGGCCGAA | AGAGUGG | 1244 |
| 1092 | GGCCUGA | CUGAUGAGGCCGAAAGGCCGAA | AUCCAGU | 1245 |
| 1093 | UUGGCUG | CUGAUGAGGCCGAAAGGCCGAA | AGGUCCA | 1246 |
| 1125 | UCAAGAA | CUGAUGAGGCCGAAAGGCCGAA | AGUUGGG | 1247 |
| 1163 | GCAAAAG | CUGAUGAGGCCGAAAGGCCGAA | AGCUUCG | 1248 |
| 1164 | AGCAAAA | CUGAUGAGGCCGAAAGGCCGAA | AAGCUUC | 1249 |
| 1166 | AGAGCAA | CUGAUGAGGCCGAAAGGCCGAA | AGAAGCU | 1250 |
| 1172 | GGUUUUU | CUGAUGAGGCCGAAAGGCCGAA | AACAGGA | 1251 |
| 1200 | UGUGGAG | CUGAUGAGGCCGAAAGGCCGAA | AGCAGAG | 1252 |
| 1201 | CUGUUCA | CUGAUGAGGCCGAAAGGCCGAA | AAGCAGC | 1253 |
| 1203 | ACUGGUG | CUGAUGAGGCCGAAAGGCCGAA | AAAAAGU | 1254 |
| 1227 | GCACACG | CUGAUGAGGCCGAAAGGCCGAA | AUGUACC | 1255 |
| 1228 | AGCAAAA | CUGAUGAGGCCGAAAGGCCGAA | AAGCUUC | 1256 |
| 1233 | CUCUCCG | CUGAUGAGGCCGAAAGGCCGAA | AAACGAA | 1257 |
| 1238 | AGGACCA | CUGAUGAGGCCGAAAGGCCGAA | ACAGCAC | 1258 |
| 1264 | CUUGCAC | CUGAUGAGGCCGAAAGGCCGAA | ACCCUUC | 1259 |
| 1267 | UUCCCCA | CUGAUGAGGCCGAAAGGCCGAA | ACUCUCA | 1260 |
| 1294 | GGCUCAG | CUGAUGAGGCCGAAAGGCCGAA | AUCUCCU | 1261 |
| 1295 | CUGCUGA | CUGAUGAGGCCGAAAGGCCGAA | ACCCCUC | 1262 |
| 1306 | CAUUUCA | CUGAUGAGGCCGAAAGGCCGAA | AGCUGC | 1263 |
| 1321 | UCCUCCU | CUGAUGAGGCCGAAAGGCCGAA | AGCCUUC | 1264 |

TABLE V-continued

Mouse ICAM HH Ribozyme Sequence

| nt. Position | Ribozyme Sequence | | | Seq. ID No. |
|---|---|---|---|---|
| 1334 | UUUAGGA | CUGAUGAGGCCGAAAGGCCGAA | AUGGGUU | 1265 |
| 1344 | CACUCUC | CUGAUGAGGCCGAAAGGCCGAA | AGCUCAU | 1266 |
| 1351 | UAACUUA | CUGAUGAGGCCGAAAGGCCGAA | ACAUUCA | 1267 |
| 1353 | CACCUUC | CUGAUGAGGCCGAAAGGCCGAA | ACCCACU | 1268 |
| 1366 | AGUUGUA | CUGAUGAGGCCGAAAGGCCGAA | ACUGUUA | 1269 |
| 1367 | AGGUGGG | CUGAUGAGGCCGAAAGGCCGAA | AGGUGCU | 1270 |
| 1368 | AGAGUGG | CUGAUGAGGCCGAAAGGCCGAA | ACAGUAC | 1271 |
| 1380 | CCACCCC | CUGAUGAGGCCGAAAGGCCGAA | AUGGGCA | 1272 |
| 1388 | AGCCACU | CUGAUGAGGCCGAAAGGCCGAA | AGUCUCC | 1273 |
| 1398 | GUUCUGU | CUGAUGAGGCCGAAAGGCCGAA | ACAGCCA | 1274 |
| 1402 | AGUUCUC | CUGAUGAGGCCGAAAGGCCGAA | AAGCACA | 1275 |
| 1408 | CCUCCCC | CUGAUGAGGCCGAAAGGCCGAA | AUCUCGC | 1276 |
| 1410 | CCCUUCC | CUGAUGAGGCCGAAAGGCCGAA | AGACCUC | 1277 |
| 1421 | ACAAAAG | CUGAUGAGGCCGAAAGGCCGAA | AGGUGGG | 1278 |
| 1425 | CUCUACC | CUGAUGAGGCCGAAAGGCCGAA | AGGCAGU | 1279 |
| 1429 | CAGGGGC | CUGAUGAGGCCGAAAGGCCGAA | AUAGAGA | 1280 |
| 1444 | UCCUCCU | CUGAUGAGGCCGAAAGGCCGAA | AGCCUUC | 1281 |
| 1455 | UCCUGGU | CUGAUGAGGCCGAAAGGCCGAA | ACAUUCC | 1282 |
| 1482 | GGGAGCA | CUGAUGAGGCCGAAAGGCCGAA | AACAACU | 1283 |
| 1484 | CAUGAGG | CUGAUGAGGCCGAAAGGCCGAA | AGAACAG | 1284 |
| 1493 | GUUCUCA | CUGAUGAGGCCGAAAGGCCGAA | AGCACAG | 1285 |
| 1500 | GGACCAU | CUGAUGAGGCCGAAAGGCCGAA | AUUUCAU | 1286 |
| 1503 | GAAUGAU | CUGAUGAGGCCGAAAGGCCGAA | AUAGUCC | 1287 |
| 1506 | CGGUUAU | CUGAUGAGGCCGAAAGGCCGAA | AACAUAA | 1288 |
| 1509 | ACACGGU | CUGAUGAGGCCGAAAGGCCGAA | AUGGUAG | 1289 |
| 1518 | CGCCUGG | CUGAUGAGGCCGAAAGGCCGAA | ACCAUGA | 1290 |
| 1530 | CCAGAAU | CUGAUGAGGCCGAAAGGCCGAA | AUUAUAG | 1291 |
| 1533 | GGCCCAC | CUGAUGAGGCCGAAAGGCCGAA | AUGACCA | 1292 |
| 1551 | AGCUGCU | CUGAUGAGGCCGAAAGGCCGAA | AGGCAUG | 1293 |
| 1559 | AGGUGGG | CUGAUGAGGCCGAAAGGCCGAA | AGGUGCU | 1294 |
| 1563 | GGUUAUA | CUGAUGAGGCCGAAAGGCCGAA | ACAUAAG | 1295 |
| 1565 | GCGGUUA | CUGAUGAGGCCGAAAGGCCGAA | AAACAUA | 1296 |
| 1567 | UGGCGGU | CUGAUGAGGCCGAAAGGCCGAA | AUAAACA | 1297 |
| 1584 | AUAUCCU | CUGAUGAGGCCGAAAGGCCGAA | AUCUUUC | 1298 |
| 1592 | UAACUUG | CUGAUGAGGCCGAAAGGCCGAA | AUAUCCU | 1299 |
| 1599 | CCUUCUG | CUGAUGAGGCCGAAAGGCCGAA | AACUUGU | 1300 |
| 1651 | GCUCAGG | CUGAUGAGGCCGAAAGGCCGAA | AGGUGGG | 1301 |
| 1661 | CAAAGGA | CUGAUGAGGCCGAAAGGCCGAA | AGGUUUC | 1302 |
| 1663 | UUCAAAG | CUGAUGAGGCCGAAAGGCCGAA | AAAGGUU | 1303 |
| 1678 | CCAGGCU | CUGAUGAGGCCGAAAGGCCGAA | AGGUCCU | 1304 |
| 1680 | CCAGAGG | CUGAUGAGGCCGAAAGGCCGAA | AGUGGCU | 1305 |
| 1681 | GCCAGAG | CUGAUGAGGCCGAAAGGCCGAA | AAGUGGC | 1306 |
| 1684 | ACAGCCA | CUGAUGAGGCCGAAAGGCCGAA | AGGAAGU | 1307 |
| 1690 | AGAUCGA | CUGAUGAGGCCGAAAGGCCGAA | AGUCCGG | 1308 |
| 1691 | AAGAUCG | CUGAUGAGGCCGAAAGGCCGAA | AAGUCCG | 1309 |
| 1696 | CCACCCC | CUGAUGAGGCCGAAAGGCCGAA | AUGGGCA | 1310 |
| 1698 | CUCCAGG | CUGAUGAGGCCGAAAGGCCGAA | AUAUCCG | 1311 |
| 1737 | GCUGGUA | CUGAUGAGGCCGAAAGGCCGAA | AGGUCUC | 1312 |
| 1750 | UGAGGUG | CUGAUGAGGCCGAAAGGCCGAA | AGCCGCC | 1313 |
| 1756 | GGGCAGG | CUGAUGAGGCCGAAAGGCCGAA | AGGCUUC | 1314 |
| 1787 | UGGGGAC | CUGAUGAGGCCGAAAGGCCGAA | AUGUCUC | 1315 |
| 1790 | AUUAGAG | CUGAUGAGGCCGAAAGGCCGAA | ACAAUGC | 1316 |
| 1793 | UCCAGCC | CUGAUGAGGCCGAAAGGCCGAA | AGGACCA | 1317 |
| 1797 | UUUAUGU | CUGAUGAGGCCGAAAGGCCGAA | ACUGGUG | 1318 |
| 1802 | UCUCCAG | CUGAUGAGGCCGAAAGGCCGAA | AUCUGGU | 1319 |
| 1812 | GGCCUGA | CUGAUGAGGCCGAAAGGCCGAA | AUCCAGU | 1320 |
| 1813 | UGAGGGU | CUGAUGAGGCCGAAAGGCCGAA | AAUGCUG | 1321 |
| 1825 | GCAGAGG | CUGAUGAGGCCGAAAGGCCGAA | AGCGUGG | 1322 |
| 1837 | GGAGCUA | CUGAUGAGGCCGAAAGGCCGAA | AGGCAUG | 1323 |
| 1845 | GGUGGCC | CUGAUGAGGCCGAAAGGCCGAA | AGGCUCG | 1324 |
| 1856 | AAGAUCG | CUGAUGAGGCCGAAAGGCCGAA | AAGUCCG | 1325 |
| 1861 | UACUGGA | CUGAUGAGGCCGAAAGGCCGAA | AUCAUGU | 1326 |
| 1865 | CUGAGGC | CUGAUGAGGCCGAAAGGCCGAA | ACAAGUG | 1327 |
| 1868 | UUUAUGU | CUGAUGAGGCCGAAAGGCCGAA | ACUGGUG | 1328 |
| 1877 | AGCUGCU | CUGAUGAGGCCGAAAGGCCGAA | AGGCAUG | 1329 |
| 1901 | GUCCCUU | CUGAUGAGGCCGAAAGGCCGAA | AGUUUUA | 1330 |
| 1912 | ACUGAUC | CUGAUGAGGCCGAAAGGCCGAA | ACUAUAU | 1331 |
| 1922 | UAACUUA | CUGAUGAGGCCGAAAGGCCGAA | ACAUUCA | 1332 |
| 1923 | GAUACCU | CUGAUGAGGCCGAAAGGCCGAA | AGCAUCA | 1333 |
| 1928 | CUGGUAA | CUGAUGAGGCCGAAAGGCCGAA | ACUCUAA | 1334 |
| 1930 | AGCUGGU | CUGAUGAGGCCGAAAGGCCGAA | AAACUCU | 1335 |
| 1964 | UGGGGAC | CUGAUGAGGCCGAAAGGCCGAA | AUGUCUC | 1336 |
| 1983 | UAACUUG | CUGAUGAGGCCGAAAGGCCGAA | AUAUCCU | 1337 |
| 1996 | GGCUCAG | CUGAUGAGGCCGAAAGGCCGAA | AUCUCCU | 1338 |
| 2005 | GGUCCGC | CUGAUGAGGCCGAAAGGCCGAA | AGCUCCA | 1339 |

TABLE V-continued

Mouse ICAM HH Ribozyme Sequence

| nt. Position | Ribozyme Sequence | | | Seq. ID No. |
|---|---|---|---|---|
| 2013 | UACUCAA | CUGAUGAGGCCGAAAGGCCGAA | AAAUAGC | 1340 |
| 2015 | CCACCCC | CUGAUGAGGCCGAAAGGCCGAA | AUGGGCA | 1341 |
| 2020 | CUCAGAA | CUGAUGAGGCCGAAAGGCCGAA | AACCACC | 1342 |
| 2039 | CCUCUGC | CUGAUGAGGCCGAAAGGCCGAA | AGCCAGC | 1343 |
| 2040 | CCUCCAG | CUGAUGAGGCCGAAAGGCCGAA | AGGUCAG | 1344 |
| 2057 | GGAUGUG | CUGAUGAGGCCGAAAGGCCGAA | AGGAGCA | 1345 |
| 2061 | ACACGGU | CUGAUGAGGCCGAAAGGCCGAA | AUGGUAG | 1346 |
| 2071 | CUGAGGC | CUGAUGAGGCCGAAAGGCCGAA | ACAAGUG | 1347 |
| 2076 | UAGCUCU | CUGAUGAGGCCGAAAGGCCGAA | AGGCUAC | 1348 |
| 2097 | CAUCAAG | CUGAUGAGGCCGAAAGGCCGAA | AGAGUUG | 1349 |
| 2098 | CGGGGGG | CUGAUGAGGCCGAAAGGCCGAA | AAGUGUG | 1350 |
| 2115 | AUCCUCC | CUGAUGAGGCCGAAAGGCCGAA | AGCUGGC | 1351 |
| 2128 | CUCAAUA | CUGAUGAGGCCGAAAGGCCGAA | AUAGCUG | 1352 |
| 2130 | GAGGCAG | CUGAUGAGGCCGAAAGGCCGAA | AAACAGG | 1353 |
| 2145 | CAUCAAG | CUGAUGAGGCCGAAAGGCCGAA | AGAGUUG | 1354 |
| 2152 | AACUCUA | CUGAUGAGGCCGAAAGGCCGAA | AUUAAUA | 1355 |
| 2156 | UAAUAAA | CUGAUGAGGCCGAAAGGCCGAA | ACAUCAA | 1356 |
| 2158 | AUUAAUA | CUGAUGAGGCCGAAAGGCCGAA | AUACAUC | 1357 |
| 2159 | AAUUAAU | CUGAUGAGGCCGAAAGGCCGAA | AAUACAU | 1358 |
| 2160 | AAAUUAA | CUGAUGAGGCCGAAAGGCCGAA | AAAUACA | 1359 |
| 2162 | CUAAAUU | CUGAUGAGGCCGAAAGGCCGAA | AUAAAUA | 1360 |
| 2163 | AAUUAAU | CUGAUGAGGCCGAAAGGCCGAA | AAUACAU | 1361 |
| 2166 | AAUAGAG | CUGAUGAGGCCGAAAGGCCGAA | AUGAAGU | 1362 |
| 2167 | AAUUAAU | CUGAUGAGGCCGAAAGGCCGAA | AAUACAU | 1363 |
| 2170 | CUAAAUU | CUGAUGAGGCCGAAAGGCCGAA | AUAAAUA | 1364 |
| 2171 | GGGAGCA | CUGAUGAGGCCGAAAGGCCGAA | AACAACU | 1365 |
| 2173 | CUGGUAA | CUGAUGAGGCCGAAAGGCCGAA | ACUCUAA | 1366 |
| 2174 | GCUGGUA | CUGAUGAGGCCGAAAGGCCGAA | AACUCUA | 1367 |
| 2175 | AGCUGGU | CUGAUGAGGCCGAAAGGCCGAA | AAACUCU | 1368 |
| 2176 | UAGCUGG | CUGAUGAGGCCGAAAGGCCGAA | AAAACUC | 1369 |
| 2183 | CAAUAAA | CUGAUGAGGCCGAAAGGCCGAA | AGCUGGU | 1370 |
| 2185 | CUCAAUA | CUGAUGAGGCCGAAAGGCCGAA | AUAGCUG | 1371 |
| 2186 | ACUCAAU | CUGAUGAGGCCGAAAGGCCGAA | AAUAGCU | 1372 |
| 2187 | UACUCAA | CUGAUGAGGCCGAAAGGCCGAA | AAAUAGC | 1373 |
| 2189 | GGUACUC | CUGAUGAGGCCGAAAGGCCGAA | AUAAAUA | 1374 |
| 2196 | CAUCAAG | CUGAUGAGGCCGAAAGGCCGAA | AGAGUUG | 1375 |
| 2198 | AACAUAA | CUGAUGAGGCCGAAAGGCCGAA | AGGCUGC | 1376 |
| 2199 | AUAAACA | CUGAUGAGGCCGAAAGGCCGAA | AAGAGGC | 1377 |
| 2200 | CUUGCAU | CUGAUGAGGCCGAAAGGCCGAA | AGGAAGA | 1378 |
| 2201 | GCCGACA | CUGAUGAGGCCGAAAGGCCGAA | AAAACUU | 1379 |
| 2205 | UCAGGCC | CUGAUGAGGCCGAAAGGCCGAA | ACAUAAA | 1380 |
| 2210 | AGCCACU | CUGAUGAGGCCGAAAGGCCGAA | AGUCUCC | 1381 |
| 2220 | AGAGAAC | CUGAUGAGGCCGAAAGGCCGAA | AUGCCAG | 1382 |
| 2224 | GGAUGGA | CUGAUGAGGCCGAAAGGCCGAA | ACCUGAG | 1383 |
| 2226 | GCGGCCU | CUGAUGAGGCCGAAAGGCCGAA | AGAUCCA | 1384 |
| 2233 | CCUCCAG | CUGAUGAGGCCGAAAGGCCGAA | AGGUCAG | 1385 |
| 2242 | GGUCCGC | CUGAUGAGGCCGAAAGGCCGAA | AGCUCCA | 1386 |
| 2248 | UGGGAUG | CUGAUGAGGCCGAAAGGCCGAA | AUGGAUA | 1387 |
| 2254 | UCAGUGU | CUGAUGAGGCCGAAAGGCCGAA | AAUUGGA | 1388 |
| 2259 | CACCGUG | CUGAUGAGGCCGAAAGGCCGAA | AUGUGAU | 1389 |
| 2260 | GCACCGU | CUGAUGAGGCCGAAAGGCCGAA | AAUGUGA | 1390 |
| 2266 | UCCUGGU | CUGAUGAGGCCGAAAGGCCGAA | ACAUUCC | 1391 |
| 2274 | UCUCCAG | CUGAUGAGGCCGAAAGGCCGAA | AUCUGGU | 1392 |
| 2279 | CUUGCAC | CUGAUGAGGCCGAAAGGCCGAA | ACCCUUC | 1393 |
| 2282 | CAGCUCA | CUGAUGAGGCCGAAAGGCCGAA | ACAGCUU | 1394 |
| 2288 | AGGCCAU | CUGAUGAGGCCGAAAGGCCGAA | ACUUAUA | 1395 |
| 2291 | AGCAGAG | CUGAUGAGGCCGAAAGGCCGAA | ACCACUG | 1396 |
| 2321 | CCCAUGU | CUGAUGAGGCCGAAAGGCCGAA | AUCUUUC | 1397 |
| 2338 | CAGGCAG | CUGAUGAGGCCGAAAGGCCGAA | AGUCUCA | 1398 |
| 2339 | CAAAGGA | CUGAUGAGGCCGAAAGGCCGAA | AGGUUUC | 1399 |
| 2341 | AGGCUGG | CUGAUGAGGCCGAAAGGCCGAA | AGAGGUC | 1400 |
| 2344 | GCUGGAA | CUGAUGAGGCCGAAAGGCCGAA | AUCGAAA | 1401 |
| 2358 | CUGCUGA | CUGAUGAGGCCGAAAGGCCGAA | AGCUGGG | 1402 |
| 2359 | UCUGUUC | CUGAUGAGGCCGAAAGGCCGAA | AAAGCAG | 1403 |
| 2360 | UUCAAAG | CUGAUGAGGCCGAAAGGCCGAA | AAAGGUU | 1404 |
| 2376 | UCAGAAG | CUGAUGAGGCCGAAAGGCCGAA | ACCACCU | 1405 |
| 2377 | CUCAGAA | CUGAUGAGGCCGAAAGGCCGAA | AACCACC | 1406 |
| 2378 | CAGUAGA | CUGAUGAGGCCGAAAGGCCGAA | AAACCCU | 1407 |
| 2379 | CUUAUGA | CUGAUGAGGCCGAAAGGCCGAA | AAAAGCA | 1408 |
| 2380 | GCCGACA | CUGAUGAGGCCGAAAGGCCGAA | AAAACUU | 1409 |
| 2382 | GGGGCAA | CUGAUGAGGCCGAAAGGCCGAA | AGAGAAU | 1410 |
| 2384 | UUGUGUC | CUGAUGAGGCCGAAAGGCCGAA | ACUGGAU | 1411 |
| 2399 | GUCCACA | CUGAUGAGGCCGAAAGGCCGAA | AGUGUUU | 1412 |
| 2401 | CAGCUCA | CUGAUGAGGCCGAAAGGCCGAA | ACAGCUU | 1413 |
| 2411 | GCAUCCU | CUGAUGAGGCCGAAAGGCCGAA | ACCAGUA | 1414 |

TABLE V-continued

Mouse ICAM HH Ribozyme Sequence

| nt. Position | Ribozyme Sequence | | | Seq. ID No. |
|---|---|---|---|---|
| 2417 | ACGUAUG | CUGAUGAGGCCGAAAGGCCGAA | ACCAUUC | 1415 |
| 2418 | GGCCUGA | CUGAUGAGGCCGAAAGGCCGAA | AUCCAGU | 1416 |
| 2425 | AACCCUC | CUGAUGAGGCCGAAAGGCCGAA | ACCCAUG | 1417 |
| 2426 | AAACUCU | CUGAUGAGGCCGAAAGGCCGAA | AAUUAAU | 1418 |
| 2433 | GCUGGUA | CUGAUGAGGCCGAAAGGCCGAA | AACUCUA | 1419 |
| 2434 | AGCUGGU | CUGAUGAGGCCGAAAGGCCGAA | AAACUCU | 1420 |
| 2448 | GGGCAGG | CUGAUGAGGCCGAAAGGCCGAA | AGGCUUC | 1421 |
| 2449 | GGGGCAG | CUGAUGAGGCCGAAAGGCCGAA | AAGGCUU | 1422 |
| 2451 | AGGCAGG | CUGAUGAGGCCGAAAGGCCGAA | AACAGGC | 1423 |
| 2452 | GAGGCAG | CUGAUGAGGCCGAAAGGCCGAA | AAACAGG | 1424 |
| 2455 | GGGCAGG | CUGAUGAGGCCGAAAGGCCGAA | AGGCUUC | 1425 |
| 2459 | GGGGGGG | CUGAUGAGGCCGAAAGGCCGAA | AGUGUGG | 1426 |
| 2460 | CGGGGGG | CUGAUGAGGCCGAAAGGCCGAA | AAGUGUG | 1427 |
| 2479 | GCUGGUA | CUGAUGAGGCCGAAAGGCCGAA | AGGUCUC | 1428 |
| 2480 | GGAUCAC | CUGAUGAGGCCGAAAGGCCGAA | ACGGUGA | 1429 |
| 2483 | GGUGGCU | CUGAUGAGGCCGAAAGGCCGAA | ACAUUGG | 1430 |
| 2484 | GACUGGU | CUGAUGAGGCCGAAAGGCCGAA | AAAAAAG | 1431 |
| 2492 | AGGUGGG | CUGAUGAGGCCGAAAGGCCGAA | AGGUGCU | 1432 |
| 2504 | ACAAAAG | CUGAUGAGGCCGAAAGGCCGAA | AGGUGGG | 1433 |
| 2508 | UGGGAUG | CUGAUGAGGCCGAAAGGCCGAA | AUGGAUA | 1434 |
| 2509 | CUGGUAA | CUGAUGAGGCCGAAAGGCCGAA | ACUCUAA | 1435 |
| 2510 | GCUGGUA | CUGAUGAGGCCGAAAGGCCGAA | AACUCUA | 1436 |
| 2520 | CAUUGGG | CUGAUGAGGCCGAAAGGCCGAA | ACAAAAG | 1437 |
| 2521 | UGAGGGU | CUGAUGAGGCCGAAAGGCCGAA | AAUGCUG | 1438 |
| 2533 | GAUACCU | CUGAUGAGGCCGAAAGGCCGAA | AGCAUCA | 1439 |
| 2540 | CACAGCG | CUGAUGAGGCCGAAAGGCCGAA | ACUGCUG | 1440 |
| 2545 | AGGACCA | CUGAUGAGGCCGAAAGGCCGAA | ACAGCAC | 1441 |
| 2568 | UUUGACA | CUGAUGAGGCCGAAAGGCCGAA | ACUUCAC | 1442 |
| 2579 | CAGGCCA | CUGAUGAGGCCGAAAGGCCGAA | AACUUAU | 1443 |
| 2585 | AGAGAAC | CUGAUGAGGCCGAAAGGCCGAA | AUGCCAG | 1444 |
| 2588 | AUUAGAG | CUGAUGAGGCCGAAAGGCCGAA | ACAAUGC | 1445 |
| 2591 | AGGAGCA | CUGAUGAGGCCGAAAGGCCGAA | AGAACCA | 1446 |
| 2593 | GCAGAGC | CUGAUGAGGCCGAAAGGCCGAA | AAAGAAG | 1447 |
| 2596 | CAUUGGG | CUGAUGAGGCCGAAAGGCCGAA | ACAAAAG | 1448 |
| 2601 | AAACGAA | CUGAUGAGGCCGAAAGGCCGAA | ACACGGU | 1449 |
| 2602 | GGGAUGG | CUGAUGAGGCCGAAAGGCCGAA | AGCUGGA | 1450 |
| 2607 | CCAGGUA | CUGAUGAGGCCGAAAGGCCGAA | AUCCGAG | 1451 |
| 2608 | CACAGCG | CUGAUGAGGCCGAAAGGCCGAA | ACUGCUG | 1452 |
| 2609 | UCCUGGU | CUGAUGAGGCCGAAAGGCCGAA | ACAUUCC | 1453 |
| 2620 | GCAGGGU | CUGAUGAGGCCGAAAGGCCGAA | AGGUCCU | 1454 |
| 2626 | GCUGGAA | CUGAUGAGGCCGAAAGGCCGAA | AUCGAAA | 1455 |
| 2628 | AGGCUAC | CUGAUGAGGCCGAAAGGCCGAA | AGUGUGC | 1456 |
| 2635 | AGGACCG | CUGAUGAGGCCGAAAGGCCGAA | AGCUGAA | 1457 |
| 2640 | GGCAGGA | CUGAUGAGGCCGAAAGGCCGAA | ACAGGCC | 1458 |
| 2641 | CUGCUGA | CUGAUGAGGCCGAAAGGCCGAA | AGCUGGG | 1459 |
| 2642 | GAGGCAG | CUGAUGAGGCCGAAAGGCCGAA | AAACAGG | 1460 |
| 2653 | GCAUCCU | CUGAUGAGGCCGAAAGGCCGAA | ACCAGUA | 1461 |
| 2659 | CUUGCAC | CUGAUGAGGCCGAAAGGCCGAA | ACCCUUC | 1462 |
| 2689 | CCUCGGA | CUGAUGAGGCCGAAAGGCCGAA | ACAUUAG | 1463 |
| 2691 | GGCCUCG | CUGAUGAGGCCGAAAGGCCGAA | AGACAUU | 1464 |
| 2700 | GGGCAGG | CUGAUGAGGCCGAAAGGCCGAA | AGGCUUC | 1465 |
| 2704 | AGGCUGG | CUGAUGAGGCCGAAAGGCCGAA | AGAGGUC | 1466 |
| 2711 | CUGCUGA | CUGAUGAGGCCGAAAGGCCGAA | AGCUGGG | 1467 |
| 2712 | CCCUUCC | CUGAUGAGGCCGAAAGGCCGAA | AGACCUC | 1468 |
| 2721 | CUUGCAC | CUGAUGAGGCCGAAAGGCCGAA | ACCCUUC | 1469 |
| 2724 | GCACACG | CUGAUGAGGCCGAAAGGCCGAA | AUGUACC | 1470 |
| 2744 | CUGCACG | CUGAUGAGGCCGAAAGGCCGAA | ACCCACC | 1471 |
| 2750 | GGUACUC | CUGAUGAGGCCGAAAGGCCGAA | AUAAAUA | 1472 |
| 2759 | AGAUCGA | CUGAUGAGGCCGAAAGGCCGAA | AGUCCGG | 1473 |
| 2761 | GCAGGGU | CUGAUGAGGCCGAAAGGCCGAA | AGGUCCU | 1474 |
| 2765 | AGCGGCA | CUGAUGAGGCCGAAAGGCCGAA | AGCAAAA | 1475 |
| 2769 | CCUGUUU | CUGAUGAGGCCGAAAGGCCGAA | ACAGACU | 1476 |
| 2797 | GGACCAU | CUGAUGAGGCCGAAAGGCCGAA | AUUUCAU | 1477 |
| 2803 | CGCCUGG | CUGAUGAGGCCGAAAGGCCGAA | ACCAUGA | 1478 |
| 2804 | CUGCACG | CUGAUGAGGCCGAAAGGCCGAA | ACCCACC | 1479 |
| 2813 | GGGUCAG | CUGAUGAGGCCGAAAGGCCGAA | ACCGGAG | 1480 |
| 2815 | AAAGUUG | CUGAUGAGGCCGAAAGGCCGAA | AGACUGU | 1481 |
| 2821 | CCUCCAG | CUGAUGAGGCCGAAAGGCCGAA | AGGUCAG | 1482 |
| 2822 | AAGUCCG | CUGAUGAGGCCGAAAGGCCGAA | AGGCUCC | 1483 |
| 2823 | UGGGAGC | CUGAUGAGGCCGAAAGGCCGAA | AAAGGCA | 1484 |
| 2829 | AUGAUUA | CUGAUGAGGCCGAAAGGCCGAA | AGUCCAG | 1485 |
| 2837 | UCAGAAG | CUGAUGAGGCCGAAAGGCCGAA | ACCACCU | 1486 |
| 2840 | CAGGCAG | CUGAUGAGGCCGAAAGGCCGAA | AGUCUCA | 1487 |
| 2847 | GGUGGCU | CUGAUGAGGCCGAAAGGCCGAA | ACAUUGG | 1488 |
| 2853 | AACAUAA | CUGAUGAGGCCGAAAGGCCGAA | AGGCUGC | 1489 |

TABLE V-continued

Mouse ICAM HH Ribozyme Sequence

| nt. Position | Ribozyme Sequence | | | Seq. ID No. |
|---|---|---|---|---|
| 2860 | UCACAGU | CUGAUGAGGCCGAAAGGCCGAA | ACUUGGC | 1490 |
| 2872 | CUUGGCU | CUGAUGAGGCCGAAAGGCCGAA | AAGGUCC | 1491 |
| 2877 | GUGAUGG | CUGAUGAGGCCGAAAGGCCGAA | AGCGGAA | 1492 |
| 2899 | AAGAUCG | CUGAUGAGGCCGAAAGGCCGAA | AAGUCCG | 1493 |
| 2900 | AAAACUC | CUGAUGAGGCCGAAAGGCCGAA | AAAUUAA | 1494 |
| 2904 | AAUAGAG | CUGAUGAGGCCGAAAGGCCGAA | AUGAAGU | 1495 |
| 2905 | CAAUAGA | CUGAUGAGGCCGAAAGGCCGAA | AAUGAAG | 1496 |
| 2906 | UAAUAAA | CUGAUGAGGCCGAAAGGCCGAA | ACAUCAA | 1497 |
| 2907 | AAAUUAA | CUGAUGAGGCCGAAAGGCCGAA | AAAUACA | 1498 |
| 2908 | AGCAAAA | CUGAUGAGGCCGAAAGGCCGAA | AAGCUUC | 1499 |
| 2909 | AGAGCAA | CUGAUGAGGCCGAAAGGCCGAA | AGAAGCU | 1500 |
| 2910 | AAAUUAA | CUGAUGAGGCCGAAAGGCCGAA | AAAUACA | 1501 |
| 2911 | AAAUUAA | CUGAUGAGGCCGAAAGGCCGAA | AAAUACA | 1502 |
| 2912 | GACAUUA | CUGAUGAGGCCGAAAGGCCGAA | AGAACAA | 1503 |
| 2913 | UGACCAG | CUGAUGAGGCCGAAAGGCCGAA | AGAGAAA | 1504 |
| 2914 | CUUAUGA | CUGAUGAGGCCGAAAGGCCGAA | AAAAGCA | 1505 |
| 2915 | UCUAAAU | CUGAUGAGGCCGAAAGGCCGAA | AAUAAAU | 1506 |
| 2916 | CUCCGGA | CUGAUGAGGCCGAAAGGCCGAA | ACGAAUA | 1507 |
| 2917 | UCUCCGG | CUGAUGAGGCCGAAAGGCCGAA | AACGAAU | 1508 |
| 2918 | CUCUCCG | CUGAUGAGGCCGAAAGGCCGAA | AAACGAA | 1509 |
| 2919 | CGACCCU | CUGAUGAGGCCGAAAGGCCGAA | AUGAGAA | 1510 |
| 2931 | CUUCCGA | CUGAUGAGGCCGAAAGGCCGAA | ACCUCCA | 1511 |
| 2933 | CCCUUCC | CUGAUGAGGCCGAAAGGCCGAA | AGACCUC | 1512 |
| 2941 | UGGGGAC | CUGAUGAGGCCGAAAGGCCGAA | AUGUCUC | 1513 |
| 2951 | GCAGAGG | CUGAUGAGGCCGAAAGGCCGAA | AGCGUGG | 1514 |
| 2952 | CACAGCG | CUGAUGAGGCCGAAAGGCCGAA | ACUGCUG | 1515 |
| 2955 | UGACACA | CUGAUGAGGCCGAAAGGCCGAA | AGUCACU | 1516 |
| 2956 | UUGAUUC | CUGAUGAGGCCGAAAGGCCGAA | AAGGAAA | 1517 |
| 2961 | AGUGGCU | CUGAUGAGGCCGAAAGGCCGAA | ACACAGA | 1518 |
| 2962 | AAUUAAU | CUGAUGAGGCCGAAAGGCCGAA | AAAUACAU | 1519 |
| 2965 | CUUUAUU | CUGAUGAGGCCGAAAGGCCGAA | AUUCAAA | 1520 |
| 2966 | CCUCUGC | CUGAUGAGGCCGAAAGGCCGAA | AGCCAGC | 1521 |
| 2969 | AAAACUU | CUGAUGAGGCCGAAAGGCCGAA | AUUGAUU | 1522 |
| 2975 | GCUGGUA | CUGAUGAGGCCGAAAGGCCGAA | AACUCUA | 1523 |
| 2976 | AGUAGAG | CUGAUGAGGCCGAAAGGCCGAA | AACCCUC | 1524 |
| 2977 | CAGCUCA | CUGAUGAGGCCGAAAGGCCGAA | ACAGCUU | 1525 |
| 2979 | GGCAAUA | CUGAUGAGGCCGAAAGGCCGAA | AGAAUGA | 1526 |

TABLE VI

Human ICAM Hairpin Ribozyme/Substrate Sequences

| nt. Position | Hairpin Ribozyme Sequence | Seq. ID No. | Substrate | Seq. ID No. |
|---|---|---|---|---|
| 70 | GGGCCGGG AGAA GCUG ACCAGAGAAACACACGUUGUGGUACAUUACCUGGUA | 1527 | CAGCA GCC CCCGGCCC | 1544 |
| 86 | GGAGUGCG AGAA GCGC ACCAGAGAAACACACGUUGUGGUACAUUACCUGGUA | 1528 | GCGCU GCC CGCACUCC | 1545 |
| 343 | CCCAUCAG AGAA GUUU ACCAGAGAAACACACGUUGUGGUACAUUACCUGGUA | 1529 | AAACU GCC CUGAUGGG | 1546 |
| 635 | GCCCUUGG AGAA GCAG ACCAGAGAAACACACGUUGUGGUACAUUACCUGGUA | 1530 | CUGCG GCC CCAAGGGC | 1547 |
| 653 | UGUUCUCA AGAA GCUC ACCAGAGAAACACACGUUGUGGUACAUUACCUGGUA | 1531 | GAGCU GUU UGAGAACA | 1548 |
| 782 | AGACUGGG AGAA GCCC ACCAGAGAAACACACGUUGUGGUACAUUACCUGGUA | 1532 | GGGCU GUU CCCAGUCU | 1549 |
| 920 | CUGCACAC AGAA GCCG ACCAGAGAAACACACGUUGUGGUACAUUACCUGGUA | 1533 | CGGCU GAC GUGUGCAG | 1550 |
| 1301 | ACAUUGGA AGAA GCUG ACCAGAGAAACACACGUUGUGGUACAUUACCUGGUA | 1534 | CAGCA GAC UCCAAUGU | 1551 |
| 1373 | CCCCGAUG AGAA GUGG ACCAGAGAAACACACGUUGUGGUACAUUACCUGGUA | 1535 | CCACU GCC CAUCGGGG | 1552 |
| 1521 | AUGACUGC AGAA GCUA ACCAGAGAAACACACGUUGUGGUACAUUACCUGGUA | 1536 | UAGCA GCC GCAGUCAU | 1553 |
| 1594 | CUGUUGUA AGAA GUAU ACCAGAGAAACACACGUUGUGGUACAUUACCUGGUA | 1537 | AUACA GAC UACAACAG | 1554 |
| 2008 | ACCCAAUA AGAA GCAA ACCAGAGAAACACACGUUGUGGUACAUUACCUGGUA | 1538 | UUGCU GCC UAUUGGGU | 1555 |
| 2034 | UUCUGUAA AGAA GUGG ACCAGAGAAACACACGUUGUGGUACAUUACCUGGUA | 1539 | CCACA GAC UUACAGAA | 1556 |
| 2125 | GGUCAGUA AGAA GCAC ACCAGAGAAACACACGUUGUGGUACAUUACCUGGUA | 1540 | CUGCU GUC UACUGACC | 1557 |
| 2132 | GGGUUGGG AGAA GUAG ACCAGAGAAACACACGUUGUGGUACAUUACCUGGUA | 1541 | CUACU GAC CCCAACCC | 1558 |
| 2276 | ACCUGUAC AGAA GUAC ACCAGAGAAACACACGUUGUGGUACAUUACCUGGUA | 1542 | GUACA GUU GUACAGGU | 1559 |
| 2810 | AAGGUCAA AGAA GCAG ACCAGAGAAACACACGUUGUGGUACAUUACCUGGUA | 1543 | CUGCA GUC UUGACCUU | 1560 |

TABLE VII

Mouse ICAM Hairpin Ribozyme/Substrate Sequences

| nt. Position | Hairpin Ribozyme Sequence | Seq. ID No. | Substrate | Seq. ID No. |
|---|---|---|---|---|
| 76 | GGGAUCAC AGAA GUGA ACCAGAGAAACACACGUUGUGGUACAUUACCUGGUA | 1561 | UCACC GUU GUGAUCCC | 1578 |
| 164 | UGAGGAAG AGAA GUUC ACCAGAGAAACACACGUUGUGGUACAUUACCUGGUA | 1562 | GAACU GUU CUUCCUCA | 1579 |
| 252 | UCAGCUCA AGAA GCUU ACCAGAGAAACACACGUUGUGGUACAUUACCUGGUA | 1563 | AAGCU GUU UGAGCUGA | 1580 |
| 284 | GCACAGCG AGAA GCUG ACCAGAGAAACACACGUUGUGGUACAUUACCUGGUA | 1564 | CAGCA GUC CGCUGUGC | 1581 |
| 318 | AAGCGGAC AGAA GCAC ACCAGAGAAACACACGUUGUGGUACAUUACCUGGUA | 1565 | GUGCA GUC GUCCGCUU | 1582 |
| 447 | AGAGCUGG AGAA GCGG ACCAGAGAAACACACGUUGUGGUACAUUACCUGGUA | 1566 | CCGCG GAC CCAGCUCU | 1583 |
| 804 | UCUCCUGG AGAA GCAU ACCAGAGAAACACACGUUGUGGUACAUUACCUGGUA | 1567 | AUGCC GAC CCAGGAGA | 1584 |
| 847 | UCUACCAA AGAA GUGG ACCAGAGAAACACACGUUGUGGUACAUUACCUGGUA | 1568 | CCACU GCC UUGGUAGA | 1585 |
| 913 | AGGAUCUG AGAA GCUA ACCAGAGAAACACACGUUGUGGUACAUUACCUGGUA | 1569 | UAGCG GAC CAGAUCCU | 1586 |
| 946 | AAGUUGUA AGAA GUUA ACCAGAGAAACACACGUUGUGGUACAUUACCUGGUA | 1570 | UAACA GUC UACAACUU | 1587 |
| 1234 | CCCAAGCA AGAA GUCU ACCAGAGAAACACACGUUGUGGUACAUUACCUGGUA | 1571 | AGACG GAC UGCUUGGG | 1588 |
| 1275 | AUUUCAGA AGAA GCUG ACCAGAGAAACACACGUUGUGGUACAUUACCUGGUA | 1572 | CAGCA GAC UCUGAAAU | 1589 |
| 1325 | UGCCUUCC AGAA GCAG ACCAGAGAAACACACGUUGUGGUACAUUACCUGGUA | 1573 | CUGCA GAC GGAAGGCA | 1590 |
| 1350 | CCCCGAUG AGAA GCAG ACCAGAGAAACACACGUUGUGGUACAUUACCUGGUA | 1574 | CUGCU GCC CAUCGGGG | 1591 |
| 1534 | ACAUAAGA AGAA GCCA ACCAGAGAAACACACGUUGUGGUACAUUACCUGGUA | 1575 | UGGCA GCC UCUUAUGU | 1592 |
| 1851 | GUCCACCG AGAA GUAG ACCAGAGAAACACACGUUGUGGUACAUUACCUGGUA | 1576 | CUACA GCC CGGUGGAC | 1593 |
| 1880 | AGAAUGAA AGAA GCGU ACCAGAGAAACACACGUUGUGGUACAUUACCUGGUA | 1577 | ACGCU GAC UUCAUUCU | 1594 |

TABLE VIII

Mouse ICAM Hairpin Ribozyme/Substrate Sequences

| nt. Position | Hairpin Ribozyme Sequence | Seq. ID No. | Substrate | Seq. ID No. |
|---|---|---|---|---|
| 5 | AAAGUGCA AGAA GCAG ACCAGAGAAACACACGUUGUGGUACAUUACCUGGUA | 1595 | CUGCU GCC UGCACUUU | 1614 |
| 59 | GGAGCAGA AGAA GCAU ACCAGAGAAACACACGUUGUGGUACAUUACCUGGUA | 1596 | AUGCU GCC UCUGCUCC | 1615 |
| 84 | GGGAUCAC AGAA GCGA ACCAGAGAAACACACGUUGUGGUACAUUACCUGGUA | 1597 | UCGCC GUU GUGAUCCC | 1616 |
| 295 | GCACAGUG AGAA GCUG ACCAGAGAAACACACGUUGUGGUACAUUACCUGGUA | 1598 | CAGCA GAC CACUGUGC | 1617 |
| 329 | AAGCCGAG AGAA GCGU ACCAGAGAAACACACGUUGUGGUACAUUACCUGGUA | 1599 | ACGCA GUC CUCGGCUU | 1618 |
| 433 | UUCCACCA AGAA GCGC ACCAGAGAAACACACGUUGUGGUACAUUACCUGGUA | 1600 | GCGCU GCC UGGUGGAA | 1619 |
| 626 | CAUUCUUG AGAA GUGA ACCAGAGAAACACACGUUGUGGUACAUUACCUGGUA | 1601 | UCACU GUU CAAGAAUG | 1620 |
| 806 | UCUCCAGG AGAA GCAU ACCAGAGAAACACACGUUGUGGUACAUUACCUGGUA | 1602 | AUGCU GAC CUGGAGA | 1621 |
| 849 | UCCACUGA AGAA GUGG ACCAGAGAAACACACGUUGUGGUACAUUACCUGGUA | 1603 | CCACU GCC UCAGUGGA | 1622 |
| 915 | AGGGUCUG AGAA GCCA ACCAGAGAAACACACGUUGUGGUACAUUACCUGGUA | 1604 | UGGCG GAC CAGACCCU | 1623 |
| 1182 | ACCUCCAA AGAA GCAG ACCAGAGAAACACACGUUGUGGUACAUUACCUGGUA | 1605 | CUGCG GCC UUGGAGGU | 1624 |
| 1307 | AUGUAAGA AGAA GCUG ACCAGAGAAACACACGUUGUGGUACAUUACCUGGUA | 1606 | CAGCA GAC UCUUACAU | 1625 |
| 1357 | UGCUUUCC AGAA GCAG ACCAGAGAAACACACGUUGUGGUACAUUACCUGGUA | 1607 | CUGCA GCC GGAAAGCA | 1626 |
| 1382 | UCCCGAUA AGAA GCGG ACCAGAGAAACACACGUUGUGGUACAUUACCUGGUA | 1608 | CCGCU GCC UAUCGGGA | 1627 |
| 1858 | GCCCACCA AGAA GUAG ACCAGAGAAACACACGUUGUGGUACAUUACCUGGUA | 1609 | CUACA GCC UGGUGGGC | 1628 |
| 1887 | AGAAGGAA AGAA GCCU ACCAGAGAAACACACGUUGUGGUACAUUACCUGGUA | 1610 | AGGCU GAC UUCCUUCU | 1629 |
| 2012 | GAGUUGGG AGAA GUGU ACCAGAGAAACACACGUUGUGGUACAUUACCUGGUA | 1611 | ACACU GUC CCCAACUC | 1630 |
| 2303 | AGACUCCA AGAA GUGG ACCAGAGAAACACACGUUGUGGUACAUUACCUGGUA | 1612 | CCACA GCC UGGAGUCU | 1631 |
| 2539 | CCUCCCAC AGAA GCUU ACCAGAGAAACACACGUUGUGGUACAUUACCUGGUA | 1613 | AAGCU GUU GUGGGAGG | 1632 |

TABLE IX

Rat ICAM HH Ribozyme Target Sequence

| nt. Position | HH Target sequence | | | Seq. ID No. |
|---|---|---|---|---|
| 11 | GAUCCAAU | U | CACACUGA | 1633 |
| 23 | GCUGACUU | C | CUUCUCUA | 1634 |
| 26 | GAACUGCU | C | UUCCUCUU | 1635 |
| 31 | CCUCUGCU | C | CUGGUCCU | 1636 |
| 34 | CUGAAGCU | C | AGAUAUAC | 1637 |
| 40 | CUCAAGGU | A | CAAGCCCC | 1638 |
| 48 | GAGAACCU | C | GGCCUGGG | 1639 |
| 54 | CCCCGCCU | C | CCUGAGCC | 1640 |
| 58 | CCGUGCCU | U | UAGCUCCC | 1641 |
| 64 | CAAUGGCU | U | CAACCCGU | 1642 |
| 96 | CCUCUGCU | C | CUGGUCCU | 1643 |
| 102 | CUCCUGGU | C | CUGGUCGC | 1644 |
| 108 | GGACUGCU | U | GGGGAACU | 1645 |
| 115 | UCCUACCU | U | UGUUCCCA | 1646 |
| 119 | GACACUGU | C | CCCAACUC | 1647 |
| 120 | GUUGUGAU | C | CCCGGGCC | 1648 |
| 146 | CCAGACCU | U | GGAACUCC | 1649 |
| 152 | ACCCGGCU | C | CACCUCAA | 1650 |
| 158 | AUUUCUUU | C | ACGAGUCA | 1651 |
| 165 | UGAACAGU | A | CUUCCCCC | 1652 |
| 168 | GAAGCCUU | C | UGCCUCG | 1653 |
| 185 | GGGUGGAU | C | CGUGCAGG | 1654 |

TABLE IX-continued

Rat ICAM HH Ribozyme Target Sequence

| nt. Position | HH Target sequence | | | Seq. ID No. |
|---|---|---|---|---|
| 209 | CAGCCCCU | A | AUCUGACC | 1655 |
| 227 | GACCAAGU | A | ACUGUGAA | 1656 |
| 230 | CAAGCUGU | U | GUGGGAGG | 1657 |
| 237 | CUGAAGCU | C | GACACCCC | 1658 |
| 248 | GGCCCCCU | A | CCUUAGGA | 1659 |
| 253 | CACUGCCJ | C | AGUGGAGG | 1660 |
| 263 | GAGCCAAU | U | UCUCAUGC | 1661 |
| 267 | GAAGCCUU | C | CUGCCUCG | 1662 |
| 293 | GAAGCUCU | U | CAAGCUGA | 1663 |
| 319 | CGGAGGAU | C | ACAAACGA | 1664 |
| 335 | ACUGUGCU | U | UGAGAACU | 1665 |
| 337 | UGUGCUAU | A | UGGUCCUC | 1666 |
| 338 | AAGCUCUU | C | AAGCUGAG | 1667 |
| 359 | CACGCAGU | C | CUCGGCUU | 1668 |
| 367 | CAAUGGCU | U | CAACCCGU | 1669 |
| 374 | UUACCCCU | C | ACCCACCU | 1670 |
| 375 | AGAAGCCU | U | CCUGCCUC | 1671 |
| 378 | ACCCACCU | C | ACAGGGUA | 1672 |
| 386 | CGCUGUGU | U | UUGGAGCU | 1673 |
| 394 | GUGGUGCU | U | CUGAACAG | 1674 |
| 420 | GCACCCCU | C | CCAGCGCA | 1675 |
| 425 | CCUCGGCU | U | CUGCCACC | 1676 |
| 427 | UCCCUGUU | U | AAAAACCA | 1677 |
| 450 | AAGAACCU | C | AUCCUGCG | 1678 |
| 451 | GGGUACUU | C | CCCCAGGC | 1679 |
| 456 | CUCGGCUU | C | UGCCACCA | 1680 |
| 495 | GCCACCAU | C | ACUGUGUA | 1681 |
| 510 | GUGCUGCU | C | CGUGGGAA | 1682 |
| 564 | GAAAAUGU | U | CCAACCAC | 1683 |
| 592 | GGGAGUAU | C | ACCAGGGA | 1684 |
| 607 | GAGCCAAU | U | UCUCAUGC | 1685 |
| 608 | AGCCAAUU | U | CUCAUGCU | 1686 |
| 609 | GCCAAUUU | C | UCAUGCUU | 1687 |
| 611 | CAAUUUCU | C | AUGCUUCA | 1688 |
| 656 | GUCACUGU | U | CAAGAAUG | 1689 |
| 657 | UCACUGUU | C | AAGAAUGU | 1690 |
| 668 | GAACUGCU | C | UUCCUCUU | 1691 |
| 677 | GCACCCCU | C | CCAGCGCA | 1692 |
| 684 | AGGCAGCU | C | CGGACUUU | 1693 |
| 692 | CCAGACCU | U | GGAACUCC | 1694 |
| 693 | CGGACUUU | C | GAUCUUCC | 1695 |
| 696 | GCCUGUUU | C | CUGCCUCU | 1696 |
| 709 | CAGCAUUU | A | CCCCUCAC | 1697 |
| 720 | CUACAACU | U | UUCAGCUC | 1698 |
| 723 | CAACUUUU | C | AGCUCCCA | 1699 |
| 735 | CUCCUGGU | C | CUGGUCGC | 1700 |
| 738 | UCCUGCCU | C | GGGGUGGA | 1701 |
| 765 | ACUGUGCU | U | UGAGAACU | 1702 |
| 769 | UCUUGUGU | U | CCCUGGAA | 1703 |
| 770 | CUUGUGUU | C | CCUGGAAG | 1704 |
| 785 | AGGCCUGU | U | UCCUGCCU | 1705 |
| 786 | GGCCUGUU | U | CCUGCCUC | 1706 |
| 792 | CUCCUGGU | C | CUGGUCGC | 1707 |
| 794 | UCCUGCCU | C | UGAAGCUC | 1708 |
| 807 | GCUCAGAU | A | UACCUGGA | 1709 |
| 833 | CCUGGGGU | U | GGAGACUA | 1710 |
| 846 | CUGACAGU | U | AUUUAUUG | 1711 |
| 851 | GCUCACCU | U | UAGCAGCU | 1712 |
| 863 | CAAUGGCU | U | CAACCCGU | 1713 |
| 866 | CCAUGCUU | C | CUCUGACA | 1714 |
| 867 | GACCACCU | C | CCCACCUA | 1715 |
| 869 | CUCUUCCU | C | UUGCGAAG | 1716 |
| 881 | AAUGGCUU | C | AACCGUG | 1717 |
| 885 | GACCAAGU | A | ACUGUGAA | 1718 |
| 933 | UGUGUAUU | C | GUUCCCAG | 1719 |
| 936 | GCAGAGAU | U | UUGUGUCA | 1720 |
| 978 | UUGAGAAU | C | UACAACUU | 1721 |
| 980 | GAGAAUCU | A | CAACUUUU | 1722 |
| 986 | CUACAACU | U | UUCAGCUC | 1723 |
| 987 | UACAACUU | U | UCAGCUCC | 1724 |
| 988 | ACAACUUU | U | CAGCUCCC | 1725 |
| 1005 | UUCGUGAU | C | GUGGCGUC | 1726 |
| 1006 | GUGGGAGU | A | UCACCAGG | 1727 |
| 1023 | CCGGAGGU | C | UCAGAAGG | 1728 |
| 1025 | GGAGGUCU | C | AGAAGGGG | 1729 |
| 1066 | CCUACCUU | U | GUUCCCAA | 1730 |
| 1092 | AGAGGGGU | C | UCAGCAGA | 1731 |
| 1093 | AGGGGAAU | C | CAGCCCCU | 1732 |
| 1125 | CCCCAACU | C | UUGUUGAU | 1733 |
| 1163 | ACGACGCU | U | CUUUUGCU | 1734 |
| 1164 | CGACGCUU | C | UUUUGCUC | 1735 |
| 1166 | ACGCUUCU | U | UUGCUCUG | 1736 |
| 1172 | CUUUUGCU | C | UGCGGCCU | 1737 |
| 1200 | AUCCAAUU | C | ACACUGAA | 1738 |
| 1201 | UUGGGCUU | C | UCCACAGG | 1739 |
| 1203 | GGGCUUCU | C | CACAGGUC | 1740 |
| 1227 | UUGGAACU | C | CAUGUGCU | 1741 |
| 1228 | GCGGGCUU | C | GUGAUCGU | 1742 |
| 1233 | CUCCUGGU | C | CUGGUCGC | 1743 |
| 1238 | UGUGCUAU | A | UGGUCCUC | 1744 |
| 1264 | GGAAAGAU | C | AUACGGGU | 1745 |
| 1267 | GUCACUGU | U | CAAGAAUG | 1746 |
| 1294 | CAGAGAUU | U | UGUGUCAG | 1747 |
| 1295 | AGAGGGGU | C | UCAGCAGA | 1748 |
| 1306 | AGCAGACU | C | UUACAUGC | 1749 |
| 1321 | AACAGAGU | C | UGGGGAAA | 1750 |
| 1334 | GUAUUCGU | U | CCCAGAGC | 1751 |
| 1344 | UCGGUGCU | C | AGGUAUCC | 1752 |
| 1351 | UCAGGCCU | A | AGAGGACU | 1753 |
| 1353 | UAGCAGCU | C | AACAAUGG | 1754 |
| 1366 | AGGGUACU | U | CCCCAGGC | 1755 |
| 1367 | GGGUACUU | C | CCCCAGGC | 1756 |
| 1368 | GAUGGUGU | C | CCGCUGCC | 1757 |
| 1380 | CUGCCUAU | C | GGGAUGGU | 1758 |
| 1388 | UGGAGACU | A | ACUGGAUG | 1759 |
| 1398 | CUGGCUGU | C | ACAGGACA | 1760 |
| 1402 | CUGUGCUU | U | GAGAACUG | 1761 |
| 1408 | UUCGUGAU | C | GUGGCGUC | 1762 |
| 1410 | CGAACUAU | C | GAGUGGAC | 1763 |
| 1421 | GGGUACUU | C | CCCCAGGC | 1764 |
| 1425 | ACCCACCU | C | CUCUGGCU | 1765 |
| 1429 | AUACUUGU | A | GCCUCAGG | 1766 |
| 1444 | AGAAGCCU | C | AGGAGGAG | 1767 |
| 1455 | GGGAGUAU | C | ACCAGGGA | 1768 |
| 1482 | AGGGUACU | U | CCCCAGG | 1769 |
| 1484 | ACUGCUCU | U | CCUCUUGC | 1770 |
| 1493 | CCUGGGGU | U | GGAGACUA | 1771 |
| 1500 | CGUGAAAU | U | AUGGUCAA | 1772 |
| 1503 | GAAAAUGU | U | CCAACCAC | 1773 |
| 1506 | UGGGUCAU | A | AUUGUUGG | 1774 |
| 1509 | GCCACCAU | C | ACUGUGUA | 1775 |
| 1518 | GUCCUGGU | C | GCCGUUGU | 1776 |
| 1530 | ACCUGGGU | C | AUAAUUGU | 1777 |
| 1533 | CUGAUCAU | U | GCGGGCUU | 1778 |
| 1551 | GUGGCCCU | C | UGCUCGUA | 1779 |
| 1559 | UGGGAAGU | C | CCUGUUUA | 1780 |
| 1563 | UCCUACCU | U | UGUUCCCA | 1781 |
| 1565 | UUACACCU | A | UUACCGCC | 1782 |
| 1567 | ACACCUAU | U | ACCGCCAG | 1783 |
| 1584 | AGGAAGAU | C | AGGAUAUA | 1784 |
| 1592 | CAGGAUAU | A | CAAGUUAC | 1785 |
| 1599 | UACAAGUU | A | CAGAAGGC | 1786 |
| 1651 | CCCCGCCU | C | CCUGAGCC | 1787 |
| 1661 | CUGCACUU | U | GCCCUGGU | 1788 |
| 1663 | GAACAGAU | C | AAUGGACA | 1789 |
| 1678 | GAGAACCU | C | GGCCUGGG | 1790 |
| 1680 | GGGCUUCU | C | CACAGGUC | 1791 |
| 1681 | GGCCUGUU | U | CCUGCCUC | 1792 |
| 1684 | CUGCUCGU | A | GACCUCUC | 1793 |
| 1690 | CCCCACCU | A | CAUACAUU | 1794 |
| 1691 | CCGGACUU | U | CGAUCUUC | 1795 |
| 1696 | CUCCUGGU | C | CUGGUCGC | 1796 |
| 1698 | UCAGAUAU | A | CCUGGAGA | 1797 |
| 1737 | GAUCACAU | U | CACGGUGC | 1798 |
| 1750 | GUCCAUUU | A | CACCUAUU | 1799 |
| 1756 | CCUCUGCU | C | CUGGUCCU | 1800 |
| 1787 | GAGAACCU | C | GGCCUGGG | 1801 |
| 1790 | GACACUGU | C | CCCAACUC | 1802 |

TABLE IX-continued

Rat ICAM HH Ribozyme Target Sequence

| nt. Position | HH Target sequence | | | Seq. ID No. |
|---|---|---|---|---|
| 1793 | AUGGUCCU | C | ACCUGGAC | 1803 |
| 1797 | UCCCUGUU | U | AAAAACCA | 1804 |
| 1802 | GCUCAGAU | A | UACCUGGA | 1805 |
| 1812 | AACAGAGU | C | UGGGGAAA | 1806 |
| 1813 | GCGGGCUU | C | GUGAUCGU | 1807 |
| 1825 | GCCACCAU | C | ACUGUGUA | 1808 |
| 1837 | ACCCACCU | C | ACAGGGUA | 1809 |
| 1845 | AGAGGACU | C | GGAGGGGC | 1810 |
| 1856 | CCCCUAAU | C | UGACCUGC | 1811 |
| 1861 | CAUGUGCU | A | UAUGGUCC | 1812 |
| 1865 | UAUCCGGU | A | GACACAAG | 1813 |
| 1868 | UCACGAGU | C | AUAUAAAU | 1814 |
| 1877 | ACAGUACU | U | CCCCCAGG | 1815 |
| 1901 | CUAAAACU | C | AAGGUACA | 1816 |
| 1912 | GAACAGAU | C | AAUGGACA | 1817 |
| 1922 | AUGUAAGU | U | AUUGCCUA | 1818 |
| 1923 | UGGACGCU | C | ACCUUUAG | 1819 |
| 1928 | GCUCAGAU | A | UACCUGGA | 1820 |
| 1930 | UGGAGACU | A | ACUGGAUG | 1821 |
| 1964 | AGAGAUUU | U | GUGUCAGC | 1822 |
| 1983 | GAGAACCU | C | GGCCUGGG | 1823 |
| 1996 | UGGAAGCU | C | UUCAAGCU | 1824 |
| 2005 | AUGUAAGU | U | AUUGCCUA | 1825 |
| 2013 | CGCUGCCU | A | UCGGGAUG | 1826 |
| 2015 | CUGCCUAU | C | GGGAUGGU | 1827 |
| 2020 | UAUUGAGU | A | CCCUGUAC | 1828 |
| 2039 | CGGAGGAU | C | ACAAACGA | 1829 |
| 2040 | CCUGACCU | C | CUGGAGGU | 1830 |
| 2057 | CUGGUCCU | C | CAAUGGCU | 1831 |
| 2061 | GCGUCCAU | U | UACACCUA | 1832 |
| 2071 | AUACUUGU | A | GCCUCAGG | 1833 |
| 2076 | UGUAGCCU | C | AGGCCUAA | 1834 |
| 2097 | CCAACUCU | U | GUUGAUGU | 1835 |
| 2098 | CCUGACCU | C | CUGGAGGU | 1836 |
| 2115 | UUCCGACU | A | GGGUCCUG | 1837 |
| 2128 | AGUGCUGU | A | CCAUGAUC | 1838 |
| 2130 | GCCUGUUU | C | CUGCCUCU | 1839 |
| 2145 | CCAACUCU | U | GUUGAUGU | 1840 |
| 2152 | UUGAGAAU | C | UACAACUU | 1841 |
| 2156 | UGACAGUU | A | UUUAUUGA | 1842 |
| 2158 | UGAUGUAU | U | UAUUAAUU | 1843 |
| 2159 | GAUGUAUU | U | AUUAAUUC | 1844 |
| 2160 | AUGUAUUU | A | UUAAUUCA | 1845 |
| 2162 | ACAUUCCU | A | CCUUUGUU | 1846 |
| 2163 | UAUUUAUU | A | AUUCAGAG | 1847 |
| 2166 | UGAUGUAU | U | UAUUAAUU | 1848 |
| 2167 | GAUGUAUU | U | AUUAAUUC | 1849 |
| 2170 | GUAUUUAU | U | AAUUCAGA | 1850 |
| 2171 | CAGUUAUU | U | AUUGAGUA | 1851 |
| 2173 | UGUGCUAU | A | UGGUCCUC | 1852 |
| 2174 | UCUCUAUU | A | CCCCUGCU | 1853 |
| 2175 | AUUUCUUU | C | ACGAGUCA | 1854 |
| 2176 | GAAAAUGU | U | CCAACCAC | 1855 |
| 2183 | UGACAGUU | A | UUUAUUGA | 1856 |
| 2185 | ACAGUUAU | U | UAUUGAGU | 1857 |
| 2186 | CAGUUAUU | U | AUUGAGUA | 1858 |
| 2187 | AGUUAUUU | A | UUGAGUAC | 1859 |
| 2189 | UUAUUUAU | U | GAGUACCC | 1860 |
| 2196 | CUGACAGU | U | AUUUAUUG | 1861 |
| 2198 | GAAUGUCU | C | CGAGGUCA | 1862 |
| 2199 | AGACUCUU | A | CAUGCCAG | 1863 |
| 2200 | GGGUACUU | C | CCCCAGGC | 1864 |
| 2201 | GGGCUUCU | C | CACAGGUC | 1865 |
| 2205 | UUUUGUGU | C | AGCCACUG | 1866 |
| 2210 | UGGAGACU | A | ACUGGAUG | 1867 |
| 2220 | GAGAACCU | C | GGCCUGGG | 1868 |
| 2224 | ACAUACAU | U | CCUACCUU | 1869 |
| 2226 | CUGGACCU | C | AGGCCACA | 1870 |
| 2233 | UCAUGCUU | C | ACAGAACU | 1871 |
| 2242 | ACACAGCU | U | UCAGUAGU | 1872 |
| 2248 | CUCCUGGU | C | CUGGUCGC | 1873 |
| 2254 | AUCCAAUU | C | ACACUGAA | 1874 |
| 2259 | GAUCACAU | U | CACGGUGC | 1875 |
| 2260 | AUCACAUU | C | ACGGUGCU | 1876 |
| 2266 | AUCAGGAU | A | UACAAGUU | 1877 |
| 2274 | GAGCAGGU | U | AACAUGUA | 1878 |
| 2279 | GGAAAGAU | C | AUACGGGU | 1879 |
| 2282 | ACAGUUAU | U | UAUUGAGU | 1880 |
| 2288 | GCCCUGGU | C | CUCCAAUG | 1881 |
| 2291 | CAGGAUAU | A | CAAGUUAC | 1882 |
| 2321 | GGAAAGAU | C | AUACGGGU | 1883 |
| 2338 | UUGGGCUU | C | UCCACAGG | 1884 |
| 2339 | GGGUACUU | C | CCCCAGGC | 1885 |
| 2341 | GGGCCUGU | C | GGUGCUCA | 1886 |
| 2344 | CUGCUCGU | A | GACCUCUC | 1887 |
| 2358 | CCCUGCCU | C | CUCCCACA | 1888 |
| 2359 | CCAUCCAU | C | CCACAGAA | 1889 |
| 2360 | CUUGCUGU | C | CCUGGAAG | 1890 |
| 2376 | GAACUGCU | C | UUCCUCUU | 1891 |
| 2377 | GACUUCCU | U | CUCUAUUA | 1892 |
| 2378 | GCUGAUUU | C | UUUCACGA | 1893 |
| 2379 | CUGCUCUU | C | CUCUUGCG | 1894 |
| 2380 | UGAUUUCU | U | UCACGAGU | 1895 |
| 2382 | AUUUCUUU | C | ACGAGUCA | 1896 |
| 2384 | UAUCCGGU | A | GACACAAG | 1897 |
| 2399 | UAAAUACU | A | UGUGGACG | 1898 |
| 2401 | UGUGCUAU | A | UGGUCCUC | 1899 |
| 2411 | CAAUUUCU | C | AUGCUUCA | 1900 |
| 2417 | AUCAGGAU | A | UACAAGUU | 1901 |
| 2418 | UCAUGCUU | C | ACAGAACU | 1902 |
| 2425 | UUAAUAAU | U | CAGAGUUC | 1903 |
| 2426 | CCUGGGGU | U | GGAGACUA | 1904 |
| 2433 | UCAGAGUU | C | UGACAGUU | 1905 |
| 2434 | CGGAGGAU | C | ACAAACGA | 1906 |
| 2448 | UGAACAGU | A | CUUCCCCC | 1907 |
| 2449 | GAAGCCUU | C | CUGCCUGG | 1908 |
| 2451 | GGCCUGUU | U | CCUGCCUC | 1909 |
| 2452 | GCCUGUUU | C | CUGCCUCU | 1910 |
| 2455 | ACAUUCCU | A | CCUUUGUU | 1911 |
| 2459 | CCCUGCCU | C | CUCCCACA | 1912 |
| 2460 | CCUACCUU | U | GUUCCAA | 1913 |
| 2479 | UUACACCU | A | UUACCGCC | 1914 |
| 2480 | GUCGCCAU | U | GUGAUCCC | 1915 |
| 2483 | ACCUUUGU | U | CCCAAUGU | 1916 |
| 2484 | CCUUUGUU | C | CCAAUGUC | 1917 |
| 2492 | GACCACCU | C | CCCACCUA | 1918 |
| 2504 | ACCUACAU | A | CAUUCCUA | 1919 |
| 2508 | ACAUACAU | U | CCUACCUU | 1920 |
| 2509 | CAUACAUU | C | CUACCUUU | 1921 |
| 2510 | GUCCAUUU | A | CACCUAUU | 1922 |
| 2520 | ACCUUUGU | U | CCCAAUGU | 1923 |
| 2521 | CCUUUGUU | C | CCAAUGUC | 1924 |
| 2533 | ACAGCAUU | U | ACCCCUCA | 1925 |
| 2540 | UCGGUGCU | C | AGGUAUCC | 1926 |
| 2545 | AGGCAGCU | C | CGGACUUU | 1927 |
| 2568 | CAGAGAUU | U | UGUGUCAG | 1928 |
| 2579 | CCUGCACU | U | UGCCCUGG | 1929 |
| 2585 | CUGCUCGU | A | GACCUCUC | 1930 |
| 2588 | UGCCUCCU | C | CCACAGCC | 1931 |
| 2591 | CUCUUCCU | C | UUGCGAAG | 1932 |
| 2593 | UCUCUAUU | A | CCCCUGCU | 1933 |
| 2596 | CUCCUGGU | C | CUGGUCGC | 1934 |
| 2601 | UGUGCUAU | A | UGGUCCUC | 1935 |
| 2602 | GUCCUGGU | C | GCCGUUGU | 1936 |
| 2607 | GUGGGAGU | A | UCACCAGG | 1937 |
| 2608 | CUUUAGCU | C | CCGUGGGA | 1938 |
| 2609 | UGGAGACU | A | ACUGGAUG | 1939 |
| 2620 | UCAGAGUU | C | UGACAGUU | 1940 |
| 2626 | CUCUCAGU | A | GUGCUGCU | 1941 |
| 2628 | UACAACUU | U | UCAGCUCC | 1942 |
| 2635 | UCACAGAU | C | CAAUUCAC | 1943 |
| 2640 | GCUCAGGU | A | UCCAUCCA | 1944 |
| 2641 | CCCCACCU | A | CAUACAUU | 1945 |
| 2642 | GCCUGUUU | C | CUGCCUCU | 1946 |
| 2653 | CCACAGGU | C | AGGGUGCU | 1947 |
| 2659 | AGAAGGGU | C | CUGCAAGC | 1948 |
| 2689 | ACUAGGGU | C | CUGAAGCU | 1949 |
| 2691 | UCAGGCCU | A | AGAGGACU | 1950 |

TABLE IX-continued

Rat ICAM HH Ribozyme Target Sequence

| nt. Position | HH Target sequence | | | Seq. ID No. |
|---|---|---|---|---|
| 2700 | AGGGUACU | U | CCCCCAGG | 1951 |
| 2704 | GACCACCU | C | CCCACCUA | 1952 |
| 2711 | CCCUACCU | U | AGGAAGGU | 1953 |
| 2712 | CCUACCUU | A | GGAAGGUG | 1954 |
| 2721 | GGAAAGAU | C | AUACGGGU | 1955 |
| 2724 | AAGAUCAU | A | CGGGUUUG | 1956 |
| 2744 | GGGUGGAU | C | CGUGCAGG | 1957 |
| 2750 | GUCCCUGU | U | UAAAAACC | 1958 |
| 2759 | GACGAACU | A | UCGAGUGG | 1959 |
| 2761 | CGGACUUU | C | GAUCUUCC | 1960 |
| 2765 | CUUUUGCU | C | UGCGGCCU | 1961 |
| 2769 | UUCUCUAU | U | ACCCCUGC | 1962 |
| 2797 | CGUGAAAU | U | AUGGUCAA | 1963 |
| 2803 | CUCAUGCU | U | CACAGAAC | 1964 |
| 2804 | UCAUGCUU | C | ACAGAACU | 1965 |
| 2813 | GCUCCCAU | C | CUGACCCU | 1966 |
| 2815 | CGGACUUU | C | GAUCUUCC | 1967 |
| 2821 | CCUGACCU | C | CUGGAGGU | 1968 |
| 2822 | UACAACUU | U | UCAGCUCC | 1969 |
| 2823 | CAACUUUU | C | AGCUCCCA | 1970 |
| 2829 | UCGGUGCU | C | AGGUAUCC | 1971 |
| 2837 | CACAGGGU | A | CUUCCCCC | 1972 |
| 2840 | GCACCCCU | C | CCAGCGCA | 1973 |
| 2847 | UUACCCCU | C | ACCCACCU | 1974 |
| 2853 | UUCGAUCU | U | CCGACUAG | 1975 |
| 2860 | UCUUGUGU | U | CCCUGGAA | 1976 |
| 2872 | GGGCCUGU | C | GGUGCUCA | 1977 |
| 2877 | UGGAGUCU | C | CCAGCACC | 1978 |
| 2899 | AGGCAGCU | C | CGGACUUU | 1979 |
| 2900 | GGCUGACU | U | CCUUCUCU | 1980 |
| 2904 | GAACUGCU | C | UUCCUCUU | 1981 |
| 2905 | GGCUGACU | U | CCUUCUCU | 1982 |
| 2906 | GUUGAUGU | A | UUUAUUAA | 1983 |
| 2907 | CUGCUCUU | C | CUCUUGCG | 1984 |
| 2908 | UGAUGUAU | U | UAUUAAUU | 1985 |
| 2909 | GAACUGCU | C | UUCCUCUU | 1986 |
| 2910 | ACUUCCUU | C | UCUAUUAC | 1987 |
| 2911 | UUCCUUCU | C | UAUUACCC | 1988 |
| 2912 | AUGUAUUU | A | UUAAUUCA | 1989 |
| 2913 | UGUGUAUU | C | GUUCCCAG | 1990 |
| 2914 | GUAUUUAU | U | AAUUCAGA | 1991 |
| 2915 | UAUUUAUU | A | AUUCAGAG | 1992 |
| 2916 | CUCUUCCU | C | UUGCGAAG | 1993 |
| 2917 | CUUCCUCU | U | GCGAAGAC | 1994 |
| 2918 | AUUUCUUU | C | ACGAGUCA | 1995 |
| 2919 | UUUUGUGU | C | AGCCACUG | 1996 |
| 2931 | GAUGGUGU | C | CCGCUGCC | 1997 |
| 2933 | UGGAGUCU | C | CCAGCACC | 1998 |
| 2941 | CAGUACUU | C | CCCCAGGC | 1999 |
| 2951 | ACCAUGCU | U | CCUCUGAC | 2000 |
| 2952 | CCGGACUU | U | CGAUCUUC | 2001 |
| 2955 | UGCUUCCU | C | UGACAUGG | 2002 |
| 2956 | CUUUCCUU | U | GAAUCAAU | 2003 |
| 2961 | UUUUGUGU | C | AGCCACUG | 2004 |
| 2962 | UGUGUAUU | C | GUUCCCAG | 2005 |
| 2965 | CUUUGAAU | C | AAUAAAGU | 2006 |
| 2966 | UGGAAGCU | C | UUCAAGCU | 2007 |
| 2969 | GAAUCAAU | A | AAGUUUUA | 2008 |
| 2975 | UGGAAGCU | C | UUCAAGCU | 2009 |
| 2976 | UAUAUGGU | C | CUCACCUG | 2010 |
| 2977 | GAAGCUCU | U | CAAGCUGA | 2011 |

TABLE X

Rat ICAM HH Ribozyme Sequences

| nt. Position | Rat HH Ribozyme Sequence | | | Seq. ID No. |
|---|---|---|---|---|
| 11 | UCAGUGUG | CUGAUGAGGCCGAAAGGCCGAA | AUUGGAUC | 2012 |
| 23 | UAGAGAAG | CUGAUGAGGCCGAAAGGCCGAA | AAGUCAGC | 2013 |
| 26 | AAGAGGAA | CUGAUGAGGCCGAAAGGCCGAA | AGCAGUUC | 2014 |
| 31 | AGGACCAG | CUGAUGAGGCCGAAAGGCCGAA | AGCAGAGG | 2015 |
| 34 | GUAUAUCU | CUGAUGAGGCCGAAAGGCCGAA | AGCUUCAG | 2016 |
| 40 | GGGCUUG | CUGAUGAGGCCGAAAGGCCGAA | ACCUUGAG | 2017 |
| 48 | CCCAGGCC | CUGAUGAGGCCGAAAGGCCGAA | AGGUUCUC | 2018 |
| 54 | GGCUCAGG | CUGAUGAGGCCGAAAGGCCGAA | AGGCGGGG | 2019 |
| 58 | GGGAGCUA | CUGAUGAGGCCGAAAGGCCGAA | AGGCACGG | 2020 |
| 64 | ACGGGUUG | CUGAUGAGGCCGAAAGGCCGAA | AGCCAUUG | 2021 |
| 96 | AGGACCAG | CUGAUGAGGCCGAAAGGCCGAA | AGCAGAGG | 2022 |
| 102 | GCGACCAG | CUGAUGAGGCCGAAAGGCCGAA | ACCAGGAG | 2023 |
| 108 | AGUUCCCC | CUGAUGAGGCCGAAAGGCCGAA | AGCAGUCC | 2024 |
| 115 | UGGGAACA | CUGAUGAGGCCGAAAGGCCGAA | AGGUAGGA | 2025 |
| 119 | GAGUUGGG | CUGAUGAGGCCGAAAGGCCGAA | ACAGUGUC | 2026 |
| 120 | GGCCCGGG | CUGAUGAGGCCGAAAGGCCGAA | AUCACAAC | 2027 |
| 146 | GGAGUUCC | CUGAUGAGGCCGAAAGGCCGAA | AGGUCUGG | 2028 |
| 152 | UUGAGGUG | CUGAUGAGGCCGAAAGGCCGAA | AGCCGGGU | 2029 |
| 158 | UGACUCGU | CUGAUGAGGCCGAAAGGCCGAA | AAAGAAAU | 2030 |
| 165 | GGGGGAAG | CUGAUGAGGCCGAAAGGCCGAA | ACUGUUCA | 2031 |
| 168 | CGAGGCAG | CUGAUGAGGCCGAAAGGCCGAA | AAGGCUUC | 2032 |
| 185 | CCUGCACG | CUGAUGAGGCCGAAAGGCCGAA | AUCCACCC | 2033 |
| 209 | GGUCAGAU | CUGAUGAGGCCGAAAGGCCGAA | AGGGGCUG | 2034 |
| 227 | UUCACAGU | CUGAUGAGGCCGAAAGGCCGAA | ACUGGUC | 2035 |
| 230 | CCUCCCAC | CUGAUGAGGCCGAAAGGCCGAA | ACAGCUUG | 2036 |
| 237 | GGGUGUC | CUGAUGAGGCCGAAAGGCCGAA | AGCUUCAG | 2037 |
| 248 | UCCUAAGG | CUGAUGAGGCCGAAAGGCCGAA | AGGGGGCC | 2038 |

TABLE X-continued

Rat ICAM HH Ribozyme Sequences

| nt. Position | Rat HH Ribozyme Sequence | | | Seq. ID No. |
|---|---|---|---|---|
| 253 | CCUCCACU | CUGAUGAGGCCGAAAGGCCGAA | AGGCAGUG | 2039 |
| 263 | GCAUGAGA | CUGAUGAGGCCGAAAGGCCGAA | AUUGGCUC | 2040 |
| 267 | CGAGGCAG | CUGAUGAGGCCGAAAGGCCGAA | AAGGCUUC | 2041 |
| 293 | UCAGCUUG | CUGAUGAGGCCGAAAGGCCGAA | AGAGCUUC | 2042 |
| 319 | UCGUUUGU | CUGAUGAGGCCGAAAGGCCGAA | AUCCUCCG | 2043 |
| 335 | AGUUCUCA | CUGAUGAGGCCGAAAGGCCGAA | AGCACAGU | 2044 |
| 337 | GAGGACCA | CUGAUGAGGCCGAAAGGCCGAA | AUAGCACA | 2045 |
| 338 | CUCAGCUU | CUGAUGAGGCCGAAAGGCCGAA | AAGAGCUU | 2046 |
| 359 | AAGCCGAG | CUGAUGAGGCCGAAAGGCCGAA | ACUGCGUG | 2047 |
| 367 | ACGGGUUG | CUGAUGAGGCCGAAAGGCCGAA | AGCCAUUG | 2048 |
| 374 | AGGUGGGU | CUGAUGAGGCCGAAAGGCCGAA | AGGGGUAA | 2049 |
| 375 | GAGGCAGG | CUGAUGAGGCCGAAAGGCCGAA | AGGCUUCU | 2050 |
| 378 | UACCCUGU | CUGAUGAGGCCGAAAGGCCGAA | AGGUGGGU | 2051 |
| 386 | AGCUCCAA | CUGAUGAGGCCGAAAGGCCGAA | ACACAGCG | 2052 |
| 394 | CUGUUCAG | CUGAUGAGGCCGAAAGGCCGAA | AGCACCAC | 2053 |
| 420 | UGCGCUGG | CUGAUGAGGCCGAAAGGCCGAA | AGGGGUGC | 2054 |
| 425 | GGUGGCAG | CUGAUGAGGCCGAAAGGCCGAA | AGCCGAGG | 2055 |
| 427 | UGGUUUUU | CUGAUGAGGCCGAAAGGCCGAA | AACAGGGA | 2056 |
| 450 | CGCAGGAU | CUGAUGAGGCCGAAAGGCCGAA | AGGUUCUU | 2057 |
| 451 | GCCUGGGG | CUGAUGAGGCCGAAAGGCCGAA | AAGUACCC | 2058 |
| 456 | UGGUGGCA | CUGAUGAGGCCGAAAGGCCGAA | AAGCCGAG | 2059 |
| 495 | UACACAGU | CUGAUGAGGCCGAAAGGCCGAA | AUGGUGGC | 2060 |
| 510 | UUCCCACG | CUGAUGAGGCCGAAAGGCCGAA | AGCAGCAC | 2061 |
| 564 | GUGGUUGG | CUGAUGAGGCCGAAAGGCCGAA | ACAUUUUC | 2062 |
| 592 | UCCCUGGU | CUGAUGAGGCCGAAAGGCCGAA | AUACUCCC | 2063 |
| 607 | GCAUGAGA | CUGAUGAGGCCGAAAGGCCGAA | AUUGGCUU | 2064 |
| 608 | AGCAUGAG | CUGAUGAGGCCGAAAGGCCGAA | AAUUGGCU | 2065 |
| 609 | AAGCAUGA | CUGAUGAGGCCGAAAGGCCGAA | AAAUUGGC | 2066 |
| 611 | UGAAGCAU | CUGAUGAGGCCGAAAGGCCGAA | AGAAAUUG | 2067 |
| 656 | CAUUCUUG | CUGAUGAGGCCGAAAGGCCGAA | ACAGUGAC | 2068 |
| 657 | ACAUUCUU | CUGAUGAGGCCGAAAGGCCGAA | AACAGUGA | 2069 |
| 668 | AAGAGGAA | CUGAUGAGGCCGAAAGGCCGAA | AGCAGUUC | 2070 |
| 677 | UGCGCUGG | CUGAUGAGGCCGAAAGGCCGAA | AGGGGUGC | 2071 |
| 684 | AAAGUCCG | CUGAUGAGGCCGAAAGGCCGAA | AGCUGCCU | 2072 |
| 692 | GGAGUUCC | CUGAUGAGGCCGAAAGGCCGAA | AGGUCUGG | 2073 |
| 693 | CGAAGAUC | CUGAUGAGGCCGAAAGGCCGAA | AAAGUCCG | 2074 |
| 696 | AGAGGCAG | CUGAUGAGGCCGAAAGGCCGAA | AAACAGGC | 2075 |
| 709 | GUGAGGGG | CUGAUGAGGCCGAAAGGCCGAA | AAAUGCUG | 2076 |
| 720 | GAGCUGAA | CUGAUGAGGCCGAAAGGCCGAA | AGUUGUAG | 2077 |
| 723 | UGGGAGCU | CUGAUGAGGCCGAAAGGCCGAA | AAAAGUUG | 2078 |
| 735 | GCGACCAG | CUGAUGAGGCCGAAAGGCCGAA | ACCAGGAG | 2079 |
| 738 | UCCACCCC | CUGAUGAGGCCGAAAGGCCGAA | AGGCAGGA | 2080 |
| 765 | AGUUCUCA | CUGAUGAGGCCGAAAGGCCGAA | AGCACAGU | 2081 |
| 769 | UUCCAGGG | CUGAUGAGGCCGAAAGGCCGAA | ACACAAGA | 2082 |
| 770 | CUUCCAGG | CUGAUGAGGCCGAAAGGCCGAA | AACACAAG | 2083 |
| 785 | AGGCAGGA | CUGAUGAGGCCGAAAGGCCGAA | ACAGGCCU | 2084 |
| 786 | GAGGCAGG | CUGAUGAGGCCGAAAGGCCGAA | AACAGGCC | 2085 |
| 792 | GCGACCAG | CUGAUGAGGCCGAAAGGCCGAA | ACCAGGAG | 2086 |
| 794 | GAGCUUCA | CUGAUGAGGCCGAAAGGCCGAA | AGGCAGGA | 2087 |
| 807 | UCCAGGUA | CUGAUGAGGCCGAAAGGCCGAA | AUCUGAGC | 2088 |
| 833 | UAGUCUCC | CUGAUGAGGCCGAAAGGCCGAA | ACCCCAGG | 2089 |
| 846 | CAAUAAAU | CUGAUGAGGCCGAAAGGCCGAA | ACUGUCAG | 2090 |
| 851 | AGCUGCUA | CUGAUGAGGCCGAAAGGCCGAA | AGGUGAGC | 2091 |
| 863 | ACGGGUUG | CUGAUGAGGCCGAAAGGCCGAA | AGCCAUUG | 2092 |
| 866 | UGUCAGAG | CUGAUGAGGCCGAAAGGCCGAA | AAGCAUGG | 2093 |
| 867 | UAGGUGGG | CUGAUGAGGCCGAAAGGCCGAA | AGGUGGUC | 2094 |
| 869 | CUUCGCAA | CUGAUGAGGCCGAAAGGCCGAA | AGGAAGAG | 2095 |
| 881 | CACGGGUU | CUGAUGAGGCCGAAAGGCCGAA | AAGCCAUU | 2096 |
| 885 | UUCACAGU | CUGAUGAGGCCGAAAGGCCGAA | ACUUGGUC | 2097 |
| 933 | CUGGGAAC | CUGAUGAGGCCGAAAGGCCGAA | AAUACACA | 2098 |
| 936 | UGACACAA | CUGAUGAGGCCGAAAGGCCGAA | AUCUCUGC | 2099 |
| 978 | AAGUUGUA | CUGAUGAGGCCGAAAGGCCGAA | AUUCUCAA | 2100 |
| 980 | AAAAGUUG | CUGAUGAGGCCGAAAGGCCGAA | AGAUUCUC | 2101 |
| 986 | GAGCUGAA | CUGAUGAGGCCGAAAGGCCGAA | AGUUGUAG | 2102 |
| 987 | GGAGCUGA | CUGAUGAGGCCGAAAGGCCGAA | AAGUUGUA | 2103 |
| 988 | GGGAGCUG | CUGAUGAGGCCGAAAGGCCGAA | AAAGUUGU | 2104 |
| 1005 | GACGCCAC | CUGAUGAGGCCGAAAGGCCGAA | AUCACGAA | 2105 |
| 1006 | CCUGGUGA | CUGAUGAGGCCGAAAGGCCGAA | ACUCCCAC | 2106 |
| 1023 | CCUUCUGA | CUGAUGAGGCCGAAAGGCCGAA | ACCUCCGG | 2107 |
| 1025 | CCCCUUCU | CUGAUGAGGCCGAAAGGCCGAA | AGACCUCC | 2108 |
| 1066 | UUGGGAAC | CUGAUGAGGCCGAAAGGCCGAA | AAGGUAGG | 2109 |
| 1092 | UCUGCUGA | CUGAUGAGGCCGAAAGGCCGAA | ACCCCUCU | 2110 |
| 1093 | AGGGGCUG | CUGAUGAGGCCGAAAGGCCGAA | AUUCCCCU | 2111 |
| 1125 | AUCAACAA | CUGAUGAGGCCGAAAGGCCGAA | AGUUGGGG | 2112 |
| 1163 | AGCAAAAG | CUGAUGAGGCCGAAAGGCCGAA | AGCGUCGU | 2113 |

TABLE X-continued

Rat ICAM HH Ribozyme Sequences

| nt. Position | Rat HH Ribozyme Sequence | | | Seq. ID No. |
|---|---|---|---|---|
| 1164 | GAGCAAAA | CUGAUGAGGCCGAAAGGCCGAA | AAGCGUCG | 2114 |
| 1166 | CAGAGCAA | CUGAUGAGGCCGAAAGGCCGAA | AGAAGCGU | 2115 |
| 1172 | AGGCCGCA | CUGAUGAGGCCGAAAGGCCGAA | AGCAAAAG | 2116 |
| 1200 | UUCAGUGU | CUGAUGAGGCCGAAAGGCCGAA | AAUUGGAU | 2117 |
| 1201 | CCUGUGGA | CUGAUGAGGCCGAAAGGCCGAA | AAGCCCAA | 2118 |
| 1203 | GACCUGUG | CUGAUGAGGCCGAAAGGCCGAA | AGAAGCCC | 2119 |
| 1227 | AGCACAUG | CUGAUGAGGCCGAAAGGCCGAA | AGUUCCAA | 2120 |
| 1228 | ACGAUCAC | CUGAUGAGGCCGAAAGGCCGAA | AAGCCCGC | 2121 |
| 1233 | GCGACCAG | CUGAUGAGGCCGAAAGGCCGAA | ACCAGGAG | 2122 |
| 1238 | GAGGACCA | CUGAUGAGGCCGAAAGGCCGAA | AUAGCACA | 2123 |
| 1264 | ACCCGUAU | CUGAUGAGGCCGAAAGGCCGAA | AUCUUUCC | 2124 |
| 1267 | CAUUCUUG | CUGAUGAGGCCGAAAGGCCGAA | ACAGUGAC | 2125 |
| 1294 | CUGACACA | CUGAUGAGGCCGAAAGGCCGAA | AAUCUCUG | 2126 |
| 1295 | UCUGCUGA | CUGAUGAGGCCGAAAGGCCGAA | ACCCCUCU | 2127 |
| 1306 | GCAUGUAA | CUGAUGAGGCCGAAAGGCCGAA | AGUCUGCU | 2128 |
| 1321 | UUUCCCCA | CUGAUGAGGCCGAAAGGCCGAA | ACUCUGUU | 3129 |
| 1334 | GCUCUGGG | CUGAUGAGGCCGAAAGGCCGAA | ACGAAUAC | 2130 |
| 1344 | GGAUACCU | CUGAUGAGGCCGAAAGGCCGAA | AGCACCGA | 2131 |
| 1351 | AGUCCUCU | CUGAUGAGGCCGAAAGGCCGAA | AGGCCUGA | 2132 |
| 1353 | CCAUUGUU | CUGAUGAGGCCGAAAGGCCGAA | AGCUGCUA | 2133 |
| 1366 | CCUGGGGG | CUGAUGAGGCCGAAAGGCCGAA | AGUACCCU | 2134 |
| 1367 | GCCUGGGG | CUGAUGAGGCCGAAAGGCCGAA | AAGUACCC | 2135 |
| 1368 | GGCAGCGG | CUGAUGAGGCCGAAAGGCCGAA | ACACCAUC | 2136 |
| 1380 | ACCAUCCC | CUGAUGAGGCCGAAAGGCCGAA | AUAGGCAG | 2137 |
| 1388 | CAUCCAGU | CUGAUGAGGCCGAAAGGCCGAA | AGUCUCCA | 2138 |
| 1398 | UGUCCUGU | CUGAUGAGGCCGAAAGGCCGAA | ACAGCCAG | 2139 |
| 1402 | CAGUUCUC | CUGAUGAGGCCGAAAGGCCGAA | AAGCACAG | 2140 |
| 1408 | GACGCCAC | CUGAUGAGGCCGAAAGGCCGAA | AUCACGAA | 2141 |
| 1410 | GUCCACUC | CUGAUGAGGCCGAAAGGCCGAA | AUAGUUCG | 2142 |
| 1421 | GCCUGGGG | CUGAUGAGGCCGAAAGGCCGAA | AAGUACCC | 2143 |
| 1425 | AGCCAGAG | CUGAUGAGGCCGAAAGGCCGAA | AGGUGGGU | 2144 |
| 1429 | CCUGAGGC | CUGAUGAGGCCGAAAGGCCGAA | ACAAGUAU | 2145 |
| 1444 | CUCCUCCU | CUGAUGAGGCCGAAAGGCCGAA | AGCCUUCU | 2146 |
| 1455 | UCCCUGGU | CUGAUGAGGCCGAAAGGCCGAA | AUACUCCC | 2147 |
| 1482 | CCUGGGGG | CUGAUGAGGCCGAAAGGCCGAA | AGUACCCU | 2148 |
| 1484 | GCAAGAGG | CUGAUGAGGCCGAAAGGCCGAA | AGAGCAGU | 2149 |
| 1493 | UAGUCUCC | CUGAUGAGGCCGAAAGGCCGAA | ACCCCAGG | 2150 |
| 1500 | UUGACCAU | CUGAUGAGGCCGAAAGGCCGAA | AUUUCACG | 2151 |
| 1503 | GUGGUUGG | CUGAUGAGGCCGAAAGGCCGAA | ACAUUUUC | 2152 |
| 1506 | CCAACAAU | CUGAUGAGGCCGAAAGGCCGAA | AUGACCCA | 2153 |
| 1509 | UACACAGU | CUGAUGAGGCCGAAAGGCCGAA | AUGGUGGC | 2154 |
| 1518 | ACAACGGC | CUGAUGAGGCCGAAAGGCCGAA | ACCAGGAC | 2155 |
| 1530 | ACAAUUAU | CUGAUGAGGCCGAAAGGCCGAA | ACCCAGGU | 2156 |
| 1533 | AAGCCCGC | CUGAUGAGGCCGAAAGGCCGAA | AUGAUCAG | 2157 |
| 1551 | UACGAGCA | CUGAUGAGGCCGAAAGGCCGAA | AGGGCCAC | 2158 |
| 1559 | UAAACAGG | CUGAUGAGGCCGAAAGGCCGAA | ACUUCCCA | 2159 |
| 1563 | UGGGAACA | CUGAUGAGGCCGAAAGGCCGAA | AGGUAGGA | 2160 |
| 1565 | GGCGGUAA | CUGAUGAGGCCGAAAGGCCGAA | AGGUGUAA | 2161 |
| 1567 | CUGGCGGU | CUGAUGAGGCCGAAAGGCCGAA | AUAGGUGU | 2162 |
| 1584 | UAUAUCCU | CUGAUGAGGCCGAAAGGCCGAA | AUCUUCCU | 2163 |
| 1592 | GUAACUUG | CUGAUGAGGCCGAAAGGCCGAA | AUAUCCUG | 2164 |
| 1599 | GCCUUCUG | CUGAUGAGGCCGAAAGGCCGAA | AACUUGUA | 2165 |
| 1651 | GGCUCAGG | CUGAUGAGGCCGAAAGGCCGAA | AGGCGGGG | 2166 |
| 1661 | ACCAGGGC | CUGAUGAGGCCGAAAGGCCGAA | AAGUGCAG | 2167 |
| 1663 | UGUCCAUU | CUGAUGAGGCCGAAAGGCCGAA | AUCUGUUC | 2168 |
| 1678 | CCCAGGCC | CUGAUGAGGCCGAAAGGCCGAA | AGGUUCUC | 2169 |
| 1680 | GACCUGUG | CUGAUGAGGCCGAAAGGCCGAA | AGAAGCCC | 2170 |
| 1681 | GAGGCAGG | CUGAUGAGGCCGAAAGGCCGAA | AACAGGCC | 2171 |
| 1684 | GAGAGGUC | CUGAUGAGGCCGAAAGGCCGAA | ACGAGCAG | 2172 |
| 1690 | AAUGUAUG | CUGAUGAGGCCGAAAGGCCGAA | AGGUGGGG | 2173 |
| 1691 | GAAGAUCG | CUGAUGAGGCCGAAAGGCCGAA | AAGUCCGG | 2174 |
| 1696 | GCGACCAG | CUGAUGAGGCCGAAAGGCCGAA | ACCAGGAG | 2175 |
| 1698 | UCUCCAGG | CUGAUGAGGCCGAAAGGCCGAA | AUAUCUGA | 2176 |
| 1737 | GCACCGUG | CUGAUGAGGCCGAAAGGCCGAA | AUGUGAUC | 2177 |
| 1750 | AAUAGGUG | CUGAUGAGGCCGAAAGGCCGAA | AAAUGGAC | 2178 |
| 1756 | AGGACCAG | CUGAUGAGGCCGAAAGGCCGAA | AGCAGAGG | 2179 |
| 1787 | CCCAGGCC | CUGAUGAGGCCGAAAGGCCGAA | AGGUUCUC | 2180 |
| 1790 | GAGUUGGG | CUGAUGAGGCCGAAAGGCCGAA | ACAGUGUC | 2181 |
| 1793 | GUCCAGGU | CUGAUGAGGCCGAAAGGCCGAA | AGGACCAU | 2182 |
| 1797 | UGGUUUUU | CUGAUGAGGCCGAAAGGCCGAA | AACAGGGA | 2183 |
| 1802 | UCCAGGUA | CUGAUGAGGCCGAAAGGCCGAA | AUCUGAGC | 2184 |
| 1812 | UUUCCCCA | CUGAUGAGGCCGAAAGGCCGAA | ACUCUGUU | 2185 |
| 1825 | UACACAGU | CUGAUGAGGCCGAAAGGCCGAA | AUGGUGGC | 2187 |
| 1837 | UACCCUGU | CUGAUGAGGCCGAAAGGCCGAA | AGGUGGGU | 2188 |
| 1845 | GCCCCUCC | CUGAUGAGGCCGAAAGGCCGAA | AGUCCUCU | 2189 |

TABLE X-continued

Rat ICAM HH Ribozyme Sequences

| nt. Position | Rat HH Ribozyme Sequence | | | Seq. ID No. |
|---|---|---|---|---|
| 1856 | GCAGGUCA | CUGAUGAGGCCGAAAGGCCGAA | AUUAGGGG | 2190 |
| 1861 | GGACCAUA | CUGAUGAGGCCGAAAGGCCGAA | AGCACAUG | 2191 |
| 1865 | CUUGUGUC | CUGAUGAGGCCGAAAGGCCGAA | ACCGGAUA | 2192 |
| 1868 | AUUUAUAU | CUGAUGAGGCCGAAAGGCCGAA | ACUCGUGA | 2193 |
| 1877 | CCUGGGGG | CUGAUGAGGCCGAAAGGCCGAA | AGUACUGU | 2194 |
| 1901 | UGUACCUU | CUGAUGAGGCCGAAAGGCCGAA | AGUUUUAG | 2195 |
| 1912 | UGUCCAUU | CUGAUGAGGCCGAAAGGCCGAA | AUCUGUUC | 2196 |
| 1922 | UAGGCAAU | CUGAUGAGGCCGAAAGGCCGAA | ACUUACAU | 2197 |
| 1923 | CUAAAGGU | CUGAUGAGGCCGAAAGGCCGAA | AGCGUCCA | 2198 |
| 1928 | UCCAGGUA | CUGAUGAGGCCGAAAGGCCGAA | AUCUGAGC | 2199 |
| 1930 | CAUCCAGU | CUGAUGAGGCCGAAAGGCCGAA | AGUCUCCA | 2200 |
| 1964 | GCUGACAC | CUGAUGAGGCCGAAAGGCCGAA | AAAUCUCU | 2201 |
| 1983 | CCCAGGCC | CUGAUGAGGCCGAAAGGCCGAA | AGGUUCUC | 2202 |
| 1996 | AGCUUGAA | CUGAUGAGGCCGAAAGGCCGAA | AGCUUCCA | 2203 |
| 2005 | UAGGCAAU | CUGAUGAGGCCGAAAGGCCGAA | ACUUACAU | 2204 |
| 2013 | CAUCCCGA | CUGAUGAGGCCGAAAGGCCGAA | AGGCAGCG | 2205 |
| 2015 | ACCAUCCC | CUGAUGAGGCCGAAAGGCCGAA | AUAGGCAG | 2206 |
| 2020 | GUACAGGG | CUGAUGAGGCCGAAAGGCCGAA | ACUCAAUA | 2207 |
| 2039 | UCGUUUGU | CUGAUGAGGCCGAAAGGCCGAA | AUCCUCCG | 2208 |
| 2040 | ACCUCCAG | CUGAUGAGGCCGAAAGGCCGAA | AGGUCAGG | 2209 |
| 2057 | AGCCAUUG | CUGAUGAGGCCGAAAGGCCGAA | AGGACCAG | 2210 |
| 2061 | UAGGUGUA | CUGAUGAGGCCGAAAGGCCGAA | AUGGACGC | 2211 |
| 2071 | CCUGAGGC | CUGAUGAGGCCGAAAGGCCGAA | ACAAGUAU | 2212 |
| 2076 | UUAGGCCU | CUGAUGAGGCCGAAAGGCCGAA | AGGCUACA | 2213 |
| 2097 | ACAUCAAC | CUGAUGAGGCCGAAAGGCCGAA | AGAGUUGG | 2214 |
| 2098 | ACCUCCAG | CUGAUGAGGCCGAAAGGCCGAA | AGGUCAGG | 2215 |
| 2115 | CAGGACCC | CUGAUGAGGCCGAAAGGCCGAA | AGUCGGAA | 2216 |
| 2128 | GAUCAUGG | CUGAUGAGGCCGAAAGGCCGAA | ACAGCACU | 2217 |
| 2130 | AGAGGCAG | CUGAUGAGGCCGAAAGGCCGAA | AAACAGGC | 2218 |
| 2145 | ACAUCAAC | CUGAUGAGGCCGAAAGGCCGAA | AGAGUUGG | 2219 |
| 2152 | AAGUUGUA | CUGAUGAGGCCGAAAGGCCGAA | AUUCUCAA | 2220 |
| 2156 | UCAAUAAA | CUGAUGAGGCCGAAAGGCCGAA | AACUGUCA | 2221 |
| 2158 | AAUUAAUA | CUGAUGAGGCCGAAAGGCCGAA | AUACAUCA | 2222 |
| 2159 | GAAUUAAU | CUGAUGAGGCCGAAAGGCCGAA | AAUACAUC | 2223 |
| 2160 | UGAAUUAA | CUGAUGAGGCCGAAAGGCCGAA | AAAUACAU | 2224 |
| 2162 | AACAAAGG | CUGAUGAGGCCGAAAGGCCGAA | AGGAAUGU | 2225 |
| 2163 | CUCUGAAU | CUGAUGAGGCCGAAAGGCCGAA | AAUAAAUA | 2226 |
| 2166 | AAUUAAUA | CUGAUGAGGCCGAAAGGCCGAA | AUACAUCA | 2227 |
| 2167 | GAAUUAAU | CUGAUGAGGCCGAAAGGCCGAA | AAUACAUC | 2228 |
| 2170 | UCUGAAUU | CUGAUGAGGCCGAAAGGCCGAA | AUAAAUAC | 2229 |
| 2171 | UACUCAAU | CUGAUGAGGCCGAAAGGCCGAA | AAUAACUG | 2230 |
| 2173 | GAGGACCA | CUGAUGAGGCCGAAAGGCCGAA | AUAGCACA | 2231 |
| 2174 | AGCAGGGG | CUGAUGAGGCCGAAAGGCCGAA | AAUAGAGA | 2232 |
| 2175 | UGACUCGU | CUGAUGAGGCCGAAAGGCCGAA | AAAGAAAU | 2233 |
| 2176 | GUGGUUGG | CUGAUGAGGCCGAAAGGCCGAA | ACAUUUUC | 2234 |
| 2183 | UCAAUAAA | CUGAUGAGGCCGAAAGGCCGAA | AACUGUCA | 2235 |
| 2185 | ACUCAAUA | CUGAUGAGGCCGAAAGGCCGAA | AUAACUGU | 2236 |
| 2186 | UACUCAAU | CUGAUGAGGCCGAAAGGCCGAA | AAUAACUG | 2237 |
| 2187 | GUACUCAA | CUGAUGAGGCCGAAAGGCCGAA | AAAUAACU | 2238 |
| 2189 | GGGUACUC | CUGAUGAGGCCGAAAGGCCGAA | AUAAAUAA | 2239 |
| 2196 | CAAUAAAU | CUGAUGAGGCCGAAAGGCCGAA | ACUGUCAG | 2240 |
| 2198 | UGACCUCG | CUGAUGAGGCCGAAAGGCCGAA | AGACAUUC | 2241 |
| 2199 | CUGGCAUG | CUGAUGAGGCCGAAAGGCCGAA | AAGAGUCU | 2242 |
| 2200 | GCCUGGGG | CUGAUGAGGCCGAAAGGCCGAA | AAGUACCC | 2243 |
| 2201 | GACCUGUG | CUGAUGAGGCCGAAAGGCCGAA | AGAAGCCC | 2244 |
| 2205 | CAGUGGCU | CUGAUGAGGCCGAAAGGCCGAA | ACACAAAA | 2245 |
| 2210 | CAUCCAGU | CUGAUGAGGCCGAAAGGCCGAA | AGUCUCCA | 2246 |
| 2220 | CCCAGGCC | CUGAUGAGGCCGAAAGGCCGAA | AGGUUCUC | 2247 |
| 2224 | AAGGUAGG | CUGAUGAGGCCGAAAGGCCGAA | AUGUAUGU | 2248 |
| 2226 | UGUGGCCU | CUGAUGAGGCCGAAAGGCCGAA | AGGUCCAG | 2249 |
| 2233 | AGUUCUGU | CUGAUGAGGCCGAAAGGCCGAA | AAGCAUGA | 2250 |
| 2242 | ACUACUGA | CUGAUGAGGCCGAAAGGCCGAA | AGCUGUGU | 2251 |
| 2248 | GCGACCAG | CUGAUGAGGCCGAAAGGCCGAA | ACCAGGAG | 2252 |
| 2254 | UUCAGUGU | CUGAUGAGGCCGAAAGGCCGAA | AAUUGGAU | 2253 |
| 2259 | GCACCGUG | CUGAUGAGGCCGAAAGGCCGAA | AUGUGAUC | 2254 |
| 2260 | AGCACCGU | CUGAUGAGGCCGAAAGGCCGAA | AAUGUGAU | 2255 |
| 2266 | AACUUGUA | CUGAUGAGGCCGAAAGGCCGAA | AUCCUGAU | 2256 |
| 2274 | UACAUGUU | CUGAUGAGGCCGAAAGGCCGAA | ACCUGCUC | 2257 |
| 2279 | ACCCGUAU | CUGAUGAGGCCGAAAGGCCGAA | AUCUUUCC | 2258 |
| 2282 | ACUCAAUA | CUGAUGAGGCCGAAAGGCCGAA | AUAACUGU | 2259 |
| 2288 | CAUUGGAG | CUGAUGAGGCCGAAAGGCCGAA | ACCAGGGC | 2260 |
| 2291 | GUAACUUG | CUGAUGAGGCCGAAAGGCCGAA | AUAUCCUG | 2261 |
| 2321 | ACCCGUAU | CUGAUGAGGCCGAAAGGCCGAA | AUCUUUCC | 2262 |
| 2338 | CCUGUGGA | CUGAUGAGGCCGAAAGGCCGAA | AAGCCCAA | 2263 |
| 2339 | GCCUGGGG | CUGAUGAGGCCGAAAGGCCGAA | AAGUACCC | 2264 |

TABLE X-continued

Rat ICAM HH Ribozyme Sequences

| nt. Position | | Rat HH Ribozyme Sequence | | Seq. ID No. |
|---|---|---|---|---|
| 2341 | UGAGCACC | CUGAUGAGGCCGAAAGGCCGAA | ACAGGCCC | 2265 |
| 2344 | GAGAGGUC | CUGAUGAGGCCGAAAGGCCGAA | ACGAGCAG | 2266 |
| 2358 | UGUGGGAG | CUGAUGAGGCCGAAAGGCCGAA | AGGCAGGG | 2267 |
| 2359 | UUCUGUGG | CUGAUGAGGCCGAAAGGCCGAA | AUGGAUGG | 2268 |
| 2360 | CUUCCAGG | CUGAUGAGGCCGAAAGGCCGAA | AACACAAG | 2269 |
| 2376 | AAGAGGAA | CUGAUGAGGCCGAAAGGCCGAA | AGCAGUUC | 2270 |
| 2377 | UAAUAGAG | CUGAUGAGGCCGAAAGGCCGAA | AGGAAGUC | 2271 |
| 2378 | UCGUGAAA | CUGAUGAGGCCGAAAGGCCGAA | AAAUCAGC | 2272 |
| 2379 | CGCAAGAG | CUGAUGAGGCCGAAAGGCCGAA | AAGAGCAG | 2273 |
| 2380 | ACUCGUGA | CUGAUGAGGCCGAAAGGCCGAA | AGAAAUCA | 2274 |
| 2382 | UGACUCGU | CUGAUGAGGCCGAAAGGCCGAA | AAAGAAAU | 2275 |
| 2384 | CUUGUGUC | CUGAUGAGGCCGAAAGGCCGAA | ACCGGAUA | 2276 |
| 2399 | CGUCCACA | CUGAUGAGGCCGAAAGGCCGAA | AGUAUUUA | 2277 |
| 2401 | GAGGACCA | CUGAUGAGGCCGAAAGGCCGAA | AUAGCACA | 2278 |
| 2411 | UGAAGCAU | CUGAUGAGGCCGAAAGGCCGAA | AGAAAUUG | 2279 |
| 2417 | AACUUGUA | CUGAUGAGGCCGAAAGGCCGAA | AUCCUGAU | 2280 |
| 2418 | AGUUCUGU | CUGAUGAGGCCGAAAGGCCGAA | AAGCAUGA | 2281 |
| 2425 | GAACUCUG | CUGAUGAGGCCGAAAGGCCGAA | AUUAAUAA | 2282 |
| 2426 | UAGUCUCC | CUGAUGAGGCCGAAAGGCCGAA | ACCCCAGG | 2283 |
| 2433 | AACUGUCA | CUGAUGAGGCCGAAAGGCCGAA | AACUCUGA | 2284 |
| 2434 | UCGUUUGU | CUGAUGAGGCCGAAAGGCCGAA | AUCCUCCG | 2285 |
| 2448 | GGGGGAAG | CUGAUGAGGCCGAAAGGCCGAA | ACUGUUCA | 2286 |
| 2449 | CGAGGCAG | CUGAUGAGGCCGAAAGGCCGAA | AAGGCUUC | 2287 |
| 2451 | GAGGCAGG | CUGAUGAGGCCGAAAGGCCGAA | AACAGGCC | 2288 |
| 2452 | AGAGGCAG | CUGAUGAGGCCGAAAGGCCGAA | AAACAGGC | 2289 |
| 2455 | AACAAAGG | CUGAUGAGGCCGAAAGGCCGAA | AGGAAUGU | 2290 |
| 2459 | UGUGGGAG | CUGAUGAGGCCGAAAGGCCGAA | AGGCAGGG | 2291 |
| 2460 | UUGGGAAC | CUGAUGAGGCCGAAAGGCCGAA | AAGGUAGG | 2292 |
| 2479 | GGCGGUAA | CUGAUGAGGCCGAAAGGCCGAA | AGGUGUAA | 2293 |
| 2480 | GGGAUCAC | CUGAUGAGGCCGAAAGGCCGAA | ACGGCGAC | 2294 |
| 2483 | ACAUUGGG | CUGAUGAGGCCGAAAGGCCGAA | ACAAAGGU | 2295 |
| 2484 | GACAUUGG | CUGAUGAGGCCGAAAGGCCGAA | AACAAAGG | 2296 |
| 2492 | UAGGUGGG | CUGAUGAGGCCGAAAGGCCGAA | AGGUGGUC | 2297 |
| 2504 | UAGGAAUG | CUGAUGAGGCCGAAAGGCCGAA | AUGUAGGU | 2298 |
| 2508 | AAGGUAGG | CUGAUGAGGCCGAAAGGCCGAA | AUGUAUGU | 2299 |
| 2509 | AAAGGUAG | CUGAUGAGGCCGAAAGGCCGAA | AAUGUAUG | 2300 |
| 2510 | AAUAGGUG | CUGAUGAGGCCGAAAGGCCGAA | AAAUGGAC | 2301 |
| 2520 | ACAUUGGG | CUGAUGAGGCCGAAAGGCCGAA | ACAAAGGU | 2302 |
| 2521 | GACAUUGG | CUGAUGAGGCCGAAAGGCCGAA | AACAAAGG | 2303 |
| 2533 | UGAGGGGU | CUGAUGAGGCCGAAAGGCCGAA | AAUGCUGU | 2304 |
| 2540 | GGAUACCU | CUGAUGAGGCCGAAAGGCCGAA | AGCACCGA | 2305 |
| 2545 | AAAGUCCG | CUGAUGAGGCCGAAAGGCCGAA | AGCUGCCU | 2306 |
| 2568 | CUGACACA | CUGAUGAGGCCGAAAGGCCGAA | AAUCUCUG | 2307 |
| 2579 | CCAGGGCA | CUGAUGAGGCCGAAAGGCCGAA | AGUGCAGG | 2308 |
| 2585 | GAGAGGUC | CUGAUGAGGCCGAAAGGCCGAA | ACGAGCAG | 2309 |
| 2588 | GGCUGUGG | CUGAUGAGGCCGAAAGGCCGAA | AGGAGGCA | 2310 |
| 2591 | CUUCGCAA | CUGAUGAGGCCGAAAGGCCGAA | AGGAAGAG | 2311 |
| 2593 | AGCAGGGG | CUGAUGAGGCCGAAAGGCCGAA | AAUAGAGA | 2312 |
| 2596 | GCGACCAG | CUGAUGAGGCCGAAAGGCCGAA | ACCAGGAG | 2313 |
| 2601 | GAGGACCA | CUGAUGAGGCCGAAAGGCCGAA | AUAGCACA | 2314 |
| 2602 | ACAACGGC | CUGAUGAGGCCGAAAGGCCGAA | ACCAGGAC | 2315 |
| 2607 | CCUGGUGA | CUGAUGAGGCCGAAAGGCCGAA | ACUCCCAC | 2316 |
| 2608 | UCCCACGG | CUGAUGAGGCCGAAAGGCCGAA | AGCUAAAG | 2317 |
| 2609 | CAUCCAGU | CUGAUGAGGCCGAAAGGCCGAA | AGUCUCCA | 2318 |
| 2620 | AACUGUCA | CUGAUGAGGCCGAAAGGCCGAA | AACUCUGA | 2319 |
| 2626 | AGCAGCAC | CUGAUGAGGCCGAAAGGCCGAA | ACUGAGAG | 2320 |
| 2628 | GGAGCUGA | CUGAUGAGGCCGAAAGGCCGAA | AAGUUGUA | 2321 |
| 2635 | GUGAAUUG | CUGAUGAGGCCGAAAGGCCGAA | AUCUGUGA | 2322 |
| 2640 | UGGAUGGA | CUGAUGAGGCCGAAAGGCCGAA | ACCUGAGC | 2323 |
| 2641 | AAUGUAUG | CUGAUGAGGCCGAAAGGCCGAA | AGGUGGGG | 2324 |
| 2642 | AGAGGCAG | CUGAUGAGGCCGAAAGGCCGAA | AAACAGGC | 2325 |
| 2653 | AGCACCCU | CUGAUGAGGCCGAAAGGCCGAA | ACCUGUGG | 2326 |
| 2659 | GCUUGCAG | CUGAUGAGGCCGAAAGGCCGAA | ACCCUUCU | 2327 |
| 2689 | AGCUUCAG | CUGAUGAGGCCGAAAGGCCGAA | ACCCUAGU | 2328 |
| 2691 | AGUCCUCU | CUGAUGAGGCCGAAAGGCCGAA | AGGCCUGA | 2329 |
| 2700 | CCUGGGGG | CUGAUGAGGCCGAAAGGCCGAA | AGUACCCU | 2330 |
| 2704 | UAGGUGGG | CUGAUGAGGCCGAAAGGCCGAA | AGGUGGUC | 2331 |
| 2711 | ACCUUCCU | CUGAUGAGGCCGAAAGGCCGAA | AGGUAGGG | 2332 |
| 2712 | CACCUUCC | CUGAUGAGGCCGAAAGGCCGAA | AAGGUAGG | 2333 |
| 2721 | ACCCGUAU | CUGAUGAGGCCGAAAGGCCGAA | AUCUUUCC | 2334 |
| 2724 | CAAACCCG | CUGAUGAGGCCGAAAGGCCGAA | AUGAUCUU | 2335 |
| 2744 | CCUGCACG | CUGAUGAGGCCGAAAGGCCGAA | AUCCACCC | 2336 |
| 2750 | GGUUUUUA | CUGAUGAGGCCGAAAGGCCGAA | ACAGGGAC | 2337 |
| 2759 | CCACUCGA | CUGAUGAGGCCGAAAGGCCGAA | AGUUCGUC | 2338 |
| 2761 | GGAAGAUC | CUGAUGAGGCCGAAAGGCCGAA | AAAGUCCG | 2339 |

TABLE X-continued

Rat ICAM HH Ribozyme Sequences

| nt. Position | Rat HH Ribozyme Sequence | | | Seq. ID No. |
|---|---|---|---|---|
| 2765 | AGGCCGCA | CUGAUGAGGCCGAAAGGCCGAA | AGCAAAAG | 2340 |
| 2769 | GCAGGGGU | CUGAUGAGGCCGAAAGGCCGAA | AUAGAGAA | 2341 |
| 2797 | UUGACCAU | CUGAUGAGGCCGAAAGGCCGAA | AUUUCACG | 2342 |
| 2803 | GUUCUGUG | CUGAUGAGGCCGAAAGGCCGAA | AGCAUGAG | 2343 |
| 2804 | AGUUCUGU | CUGAUGAGGCCGAAAGGCCGAA | AAGCAUGA | 2344 |
| 2813 | AGGGUCAG | CUGAUGAGGCCGAAAGGCCGAA | AUGGGAGC | 2345 |
| 2815 | GGAAGAUC | CUGAUGAGGCCGAAAGGCCGAA | AAAGUCCG | 2346 |
| 2821 | ACCUCCAG | CUGAUGAGGCCGAAAGGCCGAA | AGGUCAGG | 2347 |
| 2822 | GGAGCUGA | CUGAUGAGGCCGAAAGGCCGAA | AAGUUGUA | 2348 |
| 2823 | UGGGAGCU | CUGAUGAGGCCGAAAGGCCGAA | AAAAGUUG | 2349 |
| 2829 | GGAUACCU | CUGAUGAGGCCGAAAGGCCGAA | AGCACCGA | 2350 |
| 2837 | GGGGGAAG | CUGAUGAGGCCGAAAGGCCGAA | ACCCUGUG | 2351 |
| 2840 | UGCGCUGG | CUGAUGAGGCCGAAAGGCCGAA | AGGGGUGC | 2352 |
| 2847 | AGGUGGGU | CUGAUGAGGCCGAAAGGCCGAA | AGGGGUAA | 2353 |
| 2853 | CUAGUCGG | CUGAUGAGGCCGAAAGGCCGAA | AGAUCGAA | 2354 |
| 2860 | UUCCAGGG | CUGAUGAGGCCGAAAGGCCGAA | ACACAAGA | 2355 |
| 2872 | UGAGCACC | CUGAUGAGGCCGAAAGGCCGAA | ACAGGCCC | 2356 |
| 2877 | GGUGCUGG | CUGAUGAGGCCGAAAGGCCGAA | AGACUCCA | 2357 |
| 2899 | AAAGUCCG | CUGAUGAGGCCGAAAGGCCGAA | AGCUGCCU | 2358 |
| 2900 | AGAGAAGG | CUGAUGAGGCCGAAAGGCCGAA | AGUCAGCC | 2359 |
| 2904 | AAGAGGAA | CUGAUGAGGCCGAAAGGCCGAA | AGCAGUUC | 2360 |
| 2905 | AGAGAAGG | CUGAUGAGGCCGAAAGGCCGAA | AGUCAGCC | 2361 |
| 2906 | UUAAUAAA | CUGAUGAGGCCGAAAGGCCGAA | ACAUCAAC | 2362 |
| 2907 | CGCAAGAG | CUGAUGAGGCCGAAAGGCCGAA | AAGAGCAG | 2363 |
| 2908 | AAUUAAUA | CUGAUGAGGCCGAAAGGCCGAA | AUACAUCA | 2364 |
| 2909 | AAGAGGAA | CUGAUGAGGCCGAAAGGCCGAA | AGCAGUUC | 2365 |
| 2910 | GUAAUAGA | CUGAUGAGGCCGAAAGGCCGAA | AAGGAAGU | 2366 |
| 2911 | GGGUAAUA | CUGAUGAGGCCGAAAGGCCGAA | AGAAGGAA | 2367 |
| 2912 | UGAAUUAA | CUGAUGAGGCCGAAAGGCCGAA | AAAUACAU | 2368 |
| 2913 | CUGGGAAC | CUGAUGAGGCCGAAAGGCCGAA | AAUACACA | 2369 |
| 2914 | UCUGAAUU | CUGAUGAGGCCGAAAGGCCGAA | AUAAAUAC | 2370 |
| 2915 | CUCUGAAU | CUGAUGAGGCCGAAAGGCCGAA | AAUAAAUA | 2371 |
| 2916 | CUUCGCAA | CUGAUGAGGCCGAAAGGCCGAA | AGGAAGAG | 2372 |
| 2917 | GUCUUCGC | CUGAUGAGGCCGAAAGGCCGAA | AGAGGAAG | 2373 |
| 2918 | UGACUCGU | CUGAUGAGGCCGAAAGGCCGAA | AAAGAAAU | 2374 |
| 2919 | CAGUGGCU | CUGAUGAGGCCGAAAGGCCGAA | ACACAAAA | 2375 |
| 2931 | GGCAGCGG | CUGAUGAGGCCGAAAGGCCGAA | ACACCAUC | 2376 |
| 2933 | GGUGCUGG | CUGAUGAGGCCGAAAGGCCGAA | AGACUCCA | 2377 |
| 2941 | GCCUGGGG | CUGAUGAGGCCGAAAGGCCGAA | AAGUACUG | 2378 |
| 2951 | GUCAGAGG | CUGAUGAGGCCGAAAGGCCGAA | AGCAUGGU | 2379 |
| 2952 | GAAGAUCG | CUGAUGAGGCCGAAAGGCCGAA | AAGUCCGG | 2380 |
| 2955 | CCAUGUCA | CUGAUGAGGCCGAAAGGCCGAA | AGGAAGCA | 2381 |
| 2956 | AUUGAUUC | CUGAUGAGGCCGAAAGGCCGAA | AAGGAAAG | 2382 |
| 2961 | CAGUGGCU | CUGAUGAGGCCGAAAGGCCGAA | ACACAAAA | 2383 |
| 2962 | CUGGGAAC | CUGAUGAGGCCGAAAGGCCGAA | AAUACACA | 2384 |
| 2965 | ACUUUAUU | CUGAUGAGGCCGAAAGGCCGAA | AUUCAAAG | 2385 |
| 2966 | AGCUUGAA | CUGAUGAGGCCGAAAGGCCGAA | AGCUUCCA | 2386 |
| 2969 | UAAAACUU | CUGAUGAGGCCGAAAGGCCGAA | AUUGAUUC | 2387 |
| 2975 | AGCUUGAA | CUGAUGAGGCCGAAAGGCCGAA | AGCUUCCA | 2388 |
| 2976 | CAGGUGAG | CUGAUGAGGCCGAAAGGCCGAA | ACCAUAUA | 2389 |
| 2977 | UCAGCUUG | CUGAUGAGGCCGAAAGGCCGAA | AGAGCUUC | 2390 |

We claim:

1. An enzymatic RNA molecule which specifically cleaves intercellular adhesion molecule-1(ICAM-1) mRNA.

2. The enzymatic RNA molecule of claim 1, wherein said enzymatic RNA molecule is in a hammerhead motif.

3. The enzymatic RNA molecule of claim 1, wherein said enzymatic RNA molecule is in a hairpin, hepatitis delta virus, group 1 intron, or RNAseP RNA motif.

4. The enzymatic RNA molecule of any claims 1, 2 or 3, wherein said enzymatic RNA molecule comprises between 12 and 100 bases complementary to said mRNA.

5. The enzymatic RNA molecule of claim 4, wherein said enzymatic RNA molecule comprises between 14 and 24 bases complementary to said mRNA.

6. The enzymatic RNA molecule of claim 2 consisting essentially of any sequence defined as Seq. ID. Nos. 767–1526 and 2012–2390.

7. A mammalian cell including an enzymatic RNA molecule of any of claims 1, 2 or 3.

8. The mammalian cell of claim 7, wherein said mammalian cell is a human cell.

9. An expression vector including nucleic acid sequence encoding at least one enzymatic RNA molecule of any of claims 1, 2 or 3, in a manner which allows expression of that enzymatic RNA molecule.

10. A mammalian cell including the expression vector of claim 9.

11. The mammalian cell of claim 10, wherein said mammalian cell is a human cell.

12. The enzymatic RNA molecule of claim 2, wherein the binding arms of said enzymatic RNA molecule comprise sequences complementary to any of the sequences defined as Seq. ID. Nos. 7–776 and 1633–2011.

13. The enzymatic RNA molecule of claim 3, wherein the binding arms of said hairpin enzymatic RNA molecule comprise sequences complementary to any of the sequences defined as Seq. ID. Nos. 1544–1560, 1578–1594 and 1614–1632.

* * * * *

SEQUENCE LISTING ( 1 ) GENERAL INFORMATION:

( i i i ) NUMBER OF SEQUENCES: 2390

( 2 ) INFORMATION FOR SEQ ID NO: 1:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
        any base. "H"represents nucleotide C, A, or U.

(xi) SEQUENCE DESCRIPTION: SEQ ID NO: 1:

NNNNUHNNNN N                                                                                          11

(2) INFORMATION FOR SEQ ID NO: 2:

(i) SEQUENCE CHARACTERISTICS:
        (A) LENGTH: 32
        (B) TYPE: nucleic acid
        (C) STRANDEDNESS: single
        (D) TOPOLOGY: linear (ix) FEATURE:
        (D) OTHER INFORMATION: The letter "N" stands for
            any base.

(xi) SEQUENCE DESCRIPTION: SEQ ID NO: 2:

NNNNCUGAN GAGNNNNNNN NNNCGAAANN NN                                                                    32

(2) INFORMATION FOR SEQ ID NO: 3:

(i) SEQUENCE CHARACTERISTICS:
        (A) LENGTH: 14
        (B) TYPE: nucleic acid
        (C) STRANDEDNESS: single
        (D) TOPOLOGY: linear (ix) FEATURE:
        (D) OTHER INFORMATION: The letter "N" stands for
            any base.

(xi) SEQUENCE DESCRIPTION: SEQ ID NO: 3:

NNNNGUCNN NNNN                                                                                        14

(2) INFORMATION FOR SEQ ID NO: 4:

(i) SEQUENCE CHARACTERISTICS:
        (A) LENGTH: 50
        (B) TYPE: nucleic acid
        (C) STRANDEDNESS: single
        (D) TOPOLOGY: linear (ix) FEATURE:
        (D) OTHER INFORMATION: The letter "N" stands for
            any base.

(xi) SEQUENCE DESCRIPTION: SEQ ID NO: 4:

NNNNNNAGAA NNNNACCAGA GAAACACACG UUGUGGUAUA UUACCUGGUA                                                 50

(2) INFORMATION FOR SEQ ID NO: 5:

(i) SEQUENCE CHARACTERISTICS:
        (A) LENGTH: 85
        (B) TYPE: nucleic acid
        (C) STRANDEDNESS: single
        (D) TOPOLOGY: linear (xi) SEQUENCE DESCRIPTION: SEQ ID NO: 5:

UGGCCGGCAU GGUCCAGCC UCCUCGCUGG CGCCGGCUGG GCAACAUUCC GAGGGGACCG                                       60

UCCCCUCGGU AAUGGCGAAU GGGAC                                                                           85

(2) INFORMATION FOR SEQ ID NO: 6:

(i) SEQUENCE CHARACTERISTICS:
        (A) LENGTH: 176
        (B) TYPE: nucleic acid
        (C) STRANDEDNESS: single
        (D) TOPOLOGY: linear (x i) SEQUENCE DESCRIPTION: SEQ ID NO: 6:

| | | | | | | |
|---|---|---|---|---|---|---|
| GGGAAAGCUU | GCGAAGGGCG | UCGUCGCCCC | GAGCGGUAGU | AAGCAGGGAA | CUCACCUCCA | 60 |
| AUUUCAGUAC | UGAAAUUGUC | GUAGCAGUUG | ACUACUGUUA | UGUGAUGGU | AGAGGCUAAG | 120 |
| UGACGGUAUU | GGCGUAAGUC | AGUAUUGCAG | CACAGCACAA | GCCCGCUUGC | GAGAAU | 176 |

(2) INFORMATION FOR SEQ ID NO: 7:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (x i) SEQUENCE DESCRIPTION: SEQ ID NO: 7:

CCCCAGUCGA CGCUG                      15

(2) INFORMATION FOR SEQ ID NO: 8:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (x i) SEQUENCE DESCRIPTION: SEQ ID NO: 8:

CUGAGCUCCU CUGCU                      15

(2) INFORMATION FOR SEQ ID NO: 9:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (x i) SEQUENCE DESCRIPTION: SEQ ID NO: 9:

AGCUCCUCUG CUACU                      15

(2) INFORMATION FOR SEQ ID NO: 10:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (x i) SEQUENCE DESCRIPTION: SEQ ID NO: 10:

CUCUGCUACU CAGAG                      15

(2) INFORMATION FOR SEQ ID NO: 11:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (x i) SEQUENCE DESCRIPTION: SEQ ID NO: 11:

UGCUACUCAG AGUUG                      15

(2) INFORMATION FOR SEQ ID NO: 12:

(i) SEQUENCE CHARACTERISTICS:
    (A) LENGTH: 15 base pairs
    (B) TYPE: nucleic acid ( C ) STRANDEDNESS: single
( D ) TOPOLOGY: linear ( x i ) SEQUENCE DESCRIPTION: SEQ ID NO: 12:

UCAGAGUUGC AACCU 15

( 2 ) INFORMATION FOR SEQ ID NO: 13:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 13:

GCAACCUCAG CCUCG 15

( 2 ) INFORMATION FOR SEQ ID NO: 14:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 14:

UCAGCCUCGC UAUGG 15

( 2 ) INFORMATION FOR SEQ ID NO: 15:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 15:

CCUCGCUAUG GCUCC 15

( 2 ) INFORMATION FOR SEQ ID NO: 16:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 16:

UAUGGCUCCC AGCAG 15

( 2 ) INFORMATION FOR SEQ ID NO: 17:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 17:

CCGCACUCCU GGUCC 15

( 2 ) INFORMATION FOR SEQ ID NO: 18:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 18:

UCCUGGUCCU GCUCG 15

( 2 ) INFORMATION FOR SEQ ID NO: 19:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 19:

UCCUGCUCGG GGCUC 15

( 2 ) INFORMATION FOR SEQ ID NO: 20:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

CGGGGCUCUG UUCCC 15

( 2 ) INFORMATION FOR SEQ ID NO: 21:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 21:

GCUCUGUUCC CAGGA 15

( 2 ) INFORMATION FOR SEQ ID NO: 22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 22:

CUCUGUUCCC AGGAC 15

( 2 ) INFORMATION FOR SEQ ID NO: 23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 23:

CAGACAUCUG UGUCC 15

( 2 ) INFORMATION FOR SEQ ID NO: 24:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 24:

```
UCUGUGUCCC CCUCA                                                            15
```

( 2 ) INFORMATION FOR SEQ ID NO: 25:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 25:

```
UCCCCCUCAA AAGUC                                                            15
```

( 2 ) INFORMATION FOR SEQ ID NO: 26:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 26:

```
CAAAAGUCAU CCUGC                                                            15
```

( 2 ) INFORMATION FOR SEQ ID NO: 27:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

```
AAGUCAUCCU GCCCC                                                            15
```

( 2 ) INFORMATION FOR SEQ ID NO: 28:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:

```
GGAGGCUCCG UGCUG                                                            15
```

( 2 ) INFORMATION FOR SEQ ID NO: 29:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 29:

```
AGCACCUCCU GUGAC                                                            15
```

( 2 ) INFORMATION FOR SEQ ID NO: 30:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 30:

```
CCCAAGUUGU UGGGC                                                            15
```

( 2 ) INFORMATION FOR SEQ ID NO: 31:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 31:

AAGUUGUUGG GCAUA 15

( 2 ) INFORMATION FOR SEQ ID NO: 32:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 32:

UGGGCAUAGA GACCC 15

( 2 ) INFORMATION FOR SEQ ID NO: 33:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 33:

ACCCCGUUGC CUAAA 15

( 2 ) INFORMATION FOR SEQ ID NO: 34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 34:

GUUGCCUAAA AAGGA 15

( 2 ) INFORMATION FOR SEQ ID NO: 35:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 35:

AAGGAGUUGC UCCUG 15

( 2 ) INFORMATION FOR SEQ ID NO: 36:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 36:

AGUUGCUCCU GCCUG 15

( 2 ) INFORMATION FOR SEQ ID NO: 37:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 37:

AAGGUGUAUG AACUG    15

( 2 ) INFORMATION FOR SEQ ID NO: 38:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 38:

AGAAGAUAGC CAACC    15

( 2 ) INFORMATION FOR SEQ ID NO: 39:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 39:

AUGUGCUAUU CAAAC    15

( 2 ) INFORMATION FOR SEQ ID NO: 40:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 40:

GUGCUAUUCA AACUG    15

( 2 ) INFORMATION FOR SEQ ID NO: 41:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 41:

UGCUAUUCAA ACUGC    15

( 2 ) INFORMATION FOR SEQ ID NO: 42:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 42:

GGGCAGUCAA CAGCU    15

( 2 ) INFORMATION FOR SEQ ID NO: 43:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 43:

AACAGCUAAA ACCUU                    15

( 2 ) INFORMATION FOR SEQ ID NO: 44:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 44:

AAAACCUUCC UCACC                    15

( 2 ) INFORMATION FOR SEQ ID NO: 45:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 45:

AAACCUUCCU CACCG                    15

( 2 ) INFORMATION FOR SEQ ID NO: 46:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 46:

CCUUCCUCAC CGUGU                    15

( 2 ) INFORMATION FOR SEQ ID NO: 47:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 47:

ACCGUGUACU GGACU                    15

( 2 ) INFORMATION FOR SEQ ID NO: 48:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 48:

CUGGACUCCA GAACG                    15

( 2 ) INFORMATION FOR SEQ ID NO: 49:

( i ) SEQUENCE CHARACTERISTICS:
        ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 49:

CACCCCUCCC CUCUU 15

(2) INFORMATION FOR SEQ ID NO: 50:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 50:

CUCCCCUCUU GGCAG 15

(2) INFORMATION FOR SEQ ID NO: 51:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 51:

CCCCUCUUGG CAGCC 15

(2) INFORMATION FOR SEQ ID NO: 52:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 52:

AGAACCUUAC CCUAC 15

(2) INFORMATION FOR SEQ ID NO: 53:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 53:

GAACCUUACC CUACG 15

(2) INFORMATION FOR SEQ ID NO: 54:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 54:

UUACCCUACG CUGCC 15

(2) INFORMATION FOR SEQ ID NO: 55:

(i) SEQUENCE CHARACTERISTICS:
(A) LENGTH: 15 base pairs
(B) TYPE: nucleic acid
(C) STRANDEDNESS: single (D) TOPOLOGY: linear (xi) SEQUENCE DESCRIPTION: SEQ ID NO: 55:

CCAACCUCAC CGUGG                                                                                   15

(2) INFORMATION FOR SEQ ID NO: 56:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 56:

UGCUGCUCCG UGGGG                                                                                   15

(2) INFORMATION FOR SEQ ID NO: 57:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 57:

CUGAGGUCAC GACCA                                                                                   15

(2) INFORMATION FOR SEQ ID NO: 58:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 58:

GAGAGAUCAC CAUGG                                                                                   15

(2) INFORMATION FOR SEQ ID NO: 59:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 59:

AGCCAAUUUC UCGUG                                                                                   15

(2) INFORMATION FOR SEQ ID NO: 60:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 60:

GCCAAUUUCU CGUGC                                                                                   15

(2) INFORMATION FOR SEQ ID NO: 61:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (x i) SEQUENCE DESCRIPTION: SEQ ID NO: 61:

CCAAUUUCUC GUGCC    15

(2) INFORMATION FOR SEQ ID NO: 62:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 62:

AAUUUCUCGU GCCGC    15

(2) INFORMATION FOR SEQ ID NO: 63:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 63:

GAGCUGUUUG AGAAC    15

(2) INFORMATION FOR SEQ ID NO: 64:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 64:

AGCUGUUUGA GAACA    15

(2) INFORMATION FOR SEQ ID NO: 65:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 65:

AACACCUCGG CCCCC    15

(2) INFORMATION FOR SEQ ID NO: 66:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 66:

GCCCCCUACC AGCUC    15

(2) INFORMATION FOR SEQ ID NO: 67:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 67:

ACCAGCUCCA GACCU 15

( 2 ) INFORMATION FOR SEQ ID NO: 68:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 68:

CAGACCUUUG UCCUG 15

( 2 ) INFORMATION FOR SEQ ID NO: 69:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 69:

AGACCUUUGU CCUGC 15

( 2 ) INFORMATION FOR SEQ ID NO: 70:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 70:

CCUUUGUCCU GCCAG 15

( 2 ) INFORMATION FOR SEQ ID NO: 71:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 71:

AGCGACUCCC CCACA 15

( 2 ) INFORMATION FOR SEQ ID NO: 72:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 72:

CACAACUUGU CAGCC 15

( 2 ) INFORMATION FOR SEQ ID NO: 73:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 73:

AACUUGUCAG CCCCC 15

( 2 ) INFORMATION FOR SEQ ID NO: 74:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 74:

CCCGGGUCCU AGAGG                15

( 2 ) INFORMATION FOR SEQ ID NO: 75:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 75:

GGGUCCUAGA GGUGG                15

( 2 ) INFORMATION FOR SEQ ID NO: 76:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 76:

CCGUGGUCUG UUCCC                15

( 2 ) INFORMATION FOR SEQ ID NO: 77:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 77:

GGUCUGUUCC CUGGA                15

( 2 ) INFORMATION FOR SEQ ID NO: 78:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 78:

GUCUGUUCCC UGGAC                15

( 2 ) INFORMATION FOR SEQ ID NO: 79:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 79:

GGGCUGUUCC CAGUC                15

( 2 ) INFORMATION FOR SEQ ID NO: 80:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 80:

GGCUGUUCCC AGUCU                                                              15

( 2 ) INFORMATION FOR SEQ ID NO: 81:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 81:

UCCCAGUCUC GGAGG                                                              15

( 2 ) INFORMATION FOR SEQ ID NO: 82:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 82:

CCAGUCUCGG AGGCC                                                              15

( 2 ) INFORMATION FOR SEQ ID NO: 83:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 83:

CCCAGGUCCA CCUGG                                                              15

( 2 ) INFORMATION FOR SEQ ID NO: 84:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 84:

CAGAGGUUGA ACCCC                                                              15

( 2 ) INFORMATION FOR SEQ ID NO: 85:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 85:

CCACAGUCAC CUAUG                                                              15

( 2 ) INFORMATION FOR SEQ ID NO: 86:

( i ) SEQUENCE CHARACTERISTICS:

(A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 86:

GUCACCUAUG GCAAC 15

(2) INFORMATION FOR SEQ ID NO: 87:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 87:

AACGACUCCU UCUCG 15

(2) INFORMATION FOR SEQ ID NO: 88:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 88:

GACUCCUUCU CGGCC 15

(2) INFORMATION FOR SEQ ID NO: 89:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 89:

ACUCCUUCUC GGCCA 15

(2) INFORMATION FOR SEQ ID NO: 90:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 90:

UCCUUCUCGG CCAAG 15

(2) INFORMATION FOR SEQ ID NO: 91:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 91:

AAGGCCUCAG UCAGU 15

(2) INFORMATION FOR SEQ ID NO: 92:

(i) SEQUENCE CHARACTERISTICS:
            (A) LENGTH: 15 base pairs
            (B) TYPE: nucleic acid (C) STRANDEDNESS: single
(D) TOPOLOGY: linear (x i) SEQUENCE DESCRIPTION: SEQ ID NO: 92:

CCUCAGUCAG UGUGA 15

(2) INFORMATION FOR SEQ ID NO: 93:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 93:

GUGCAGUAAU ACUGG 15

(2) INFORMATION FOR SEQ ID NO: 94:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 94:

CAGUAAUACU GGGGA 15

(2) INFORMATION FOR SEQ ID NO: 95:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 95:

UGACCAUCUA CAGCU 15

(2) INFORMATION FOR SEQ ID NO: 96:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 96:

ACCAUCUACA GCUUU 15

(2) INFORMATION FOR SEQ ID NO: 97:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 97:

UACAGCUUUC CGGCG 15

(2) INFORMATION FOR SEQ ID NO: 98:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO: 98:

ACAGCUUUCC GGCGC 15

( 2 ) INFORMATION FOR SEQ ID NO: 99:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 99:

CAGCUUUCCG GCGCC 15

( 2 ) INFORMATION FOR SEQ ID NO: 100:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 100:

ACGUGAUUCU GACGA 15

( 2 ) INFORMATION FOR SEQ ID NO: 101:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 101:

CGUGAUUCUG ACGAA 15

( 2 ) INFORMATION FOR SEQ ID NO: 102:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 102:

CAGAGGUCUC AGAAG 15

( 2 ) INFORMATION FOR SEQ ID NO: 103:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 103:

GAGGUCUCAG AAGGG 15

( 2 ) INFORMATION FOR SEQ ID NO: 104:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 104:

CCACCCUAGA GCCAA 15

(2) INFORMATION FOR SEQ ID NO: 105:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 105:

AUGGGGUUCC AGCCC 15

(2) INFORMATION FOR SEQ ID NO: 106:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 106:

UGGGGUUCCA GCCCA 15

(2) INFORMATION FOR SEQ ID NO: 107:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 107:

CCCAGCUCCU GCUGA 15

(2) INFORMATION FOR SEQ ID NO: 108:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 108:

CGCAGCUUCU CCUGC 15

(2) INFORMATION FOR SEQ ID NO: 109:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 109:

GCAGCUUCUC CUGCU 15

(2) INFORMATION FOR SEQ ID NO: 110:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 110:

AGCUUCUCCU GCUCU 15

( 2 ) INFORMATION FOR SEQ ID NO: 111:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 111:

UCCUGCUCUG CAACC 15

( 2 ) INFORMATION FOR SEQ ID NO: 112:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 112:

GCCAGCUUAU ACACA 15

( 2 ) INFORMATION FOR SEQ ID NO: 113:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 113:

CCAGCUUAUA CACAA 15

( 2 ) INFORMATION FOR SEQ ID NO: 114:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 114:

AGCUUAUACA CAAGA 15

( 2 ) INFORMATION FOR SEQ ID NO: 115:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 115:

GGGAGCUUCG UGUCC 15

( 2 ) INFORMATION FOR SEQ ID NO: 116:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 116:

GGAGCUUCGU GUCCU 15

( 2 ) INFORMATION FOR SEQ ID NO: 117:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 117:

UUCGUGUCCU GUAUG       15

( 2 ) INFORMATION FOR SEQ ID NO: 118:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 118:

GUCCUGUAUG GCCCC       15

( 2 ) INFORMATION FOR SEQ ID NO: 119:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 119:

GAGGGAUUGU CCGGG       15

( 2 ) INFORMATION FOR SEQ ID NO: 120:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 120:

GGAUUGUCCG GGAAA       15

( 2 ) INFORMATION FOR SEQ ID NO: 121:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 121:

AGAAAAUUCC CAGCA       15

( 2 ) INFORMATION FOR SEQ ID NO: 122:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 122:

GAAAAUUCCC AGCAG       15

( 2 ) INFORMATION FOR SEQ ID NO: 123:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 123:

GCAGACUCCA AUGUG                15

( 2 ) INFORMATION FOR SEQ ID NO: 124:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 124:

CCAGGCUUGG GGGAA                15

( 2 ) INFORMATION FOR SEQ ID NO: 125:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 125:

AACCCAUUGC CCGAG                15

( 2 ) INFORMATION FOR SEQ ID NO: 126:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 126:

CCGAGCUCAA GUGUC                15

( 2 ) INFORMATION FOR SEQ ID NO: 127:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 127:

CAAGUGUCUA AAGGA                15

( 2 ) INFORMATION FOR SEQ ID NO: 128:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 128:

AGUGUCUAAA GGAUG                15

( 2 ) INFORMATION FOR SEQ ID NO: 129:

( i ) SEQUENCE CHARACTERISTICS:
        ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 129:

UGGCACUUUC CCACU 15

(2) INFORMATION FOR SEQ ID NO: 130:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 130:

GGCACUUUCC CACUG 15

(2) INFORMATION FOR SEQ ID NO: 131:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 131:

GCACUUUCCC ACUGC 15

(2) INFORMATION FOR SEQ ID NO: 132:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 132:

UGCCCAUCGG GGAAU 15

(2) INFORMATION FOR SEQ ID NO: 133:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 133:

GGGGAAUCAG UGACU 15

(2) INFORMATION FOR SEQ ID NO: 134:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 134:

UGACUGUCAC UCGAG 15

(2) INFORMATION FOR SEQ ID NO: 135:

(i) SEQUENCE CHARACTERISTICS:
(A) LENGTH: 15 base pairs
(B) TYPE: nucleic acid
(C) STRANDEDNESS: single ( D ) TOPOLOGY: linear ( x i ) SEQUENCE DESCRIPTION: SEQ ID NO: 135:

UGUCACUCGA GAUCU    15

( 2 ) INFORMATION FOR SEQ ID NO: 136:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 136:

UCGAGAUCUU GAGGG    15

( 2 ) INFORMATION FOR SEQ ID NO: 137:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 137:

GAGAUCUUGA GGGCA    15

( 2 ) INFORMATION FOR SEQ ID NO: 138:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 138:

GGCACCUACC UCUGU    15

( 2 ) INFORMATION FOR SEQ ID NO: 139:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 139:

CCUACCUCUG UCGGG    15

( 2 ) INFORMATION FOR SEQ ID NO: 140:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 140:

CCUCUGUCGG GCCAG    15

( 2 ) INFORMATION FOR SEQ ID NO: 141:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 141:

GAGCACUCAA GGGGA 15

( 2 ) INFORMATION FOR SEQ ID NO: 142:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 142:

GGGAGGUCAC CCGCG 15

( 2 ) INFORMATION FOR SEQ ID NO: 143:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 143:

AUGUGCUCUC CCCCC 15

( 2 ) INFORMATION FOR SEQ ID NO: 144:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 144:

GUGCUCUCCC CCCGG 15

( 2 ) INFORMATION FOR SEQ ID NO: 145:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 145:

CCCCGGUAUG AGAUU 15

( 2 ) INFORMATION FOR SEQ ID NO: 146:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 146:

AUGAGAUUGU CAUCA 15

( 2 ) INFORMATION FOR SEQ ID NO: 147:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 147:

AGAUUGUCAU CAUCA 15

(2) INFORMATION FOR SEQ ID NO: 148:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 148:

UUGUCAUCAU CACUG 15

(2) INFORMATION FOR SEQ ID NO: 149:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 149:

UCAUCAUCAC UGUGG 15

(2) INFORMATION FOR SEQ ID NO: 150:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 150:

CUGUGGUAGC AGCCG 15

(2) INFORMATION FOR SEQ ID NO: 151:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 151:

CCGCAGUCAU AAUGG 15

(2) INFORMATION FOR SEQ ID NO: 152:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 152:

CAGUCAUAAU GGGCA 15

(2) INFORMATION FOR SEQ ID NO: 153:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 153:

CAGGCCUCAG CACGU 15

(2) INFORMATION FOR SEQ ID NO: 154:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 154:

AGCACGUACC UCUAU 15

(2) INFORMATION FOR SEQ ID NO: 155:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 155:

CGUACCUCUA UAACC 15

(2) INFORMATION FOR SEQ ID NO: 156:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 156:

UACCUCUAUA ACCGC 15

(2) INFORMATION FOR SEQ ID NO: 157:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 157:

CCUCUAUAAC CGCCA 15

(2) INFORMATION FOR SEQ ID NO: 158:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 158:

GGAAGAUCAA GAAAU 15

(2) INFORMATION FOR SEQ ID NO: 159:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 159:

AAGAAAUACA GACUA 15

(2) INFORMATION FOR SEQ ID NO: 160:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 160:

ACAGACUACA ACAGG 15

(2) INFORMATION FOR SEQ ID NO: 161:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 161:

CACGCCUCCC UGAAC 15

(2) INFORMATION FOR SEQ ID NO: 162:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 162:

UGAACCUAUC CCGGG 15

(2) INFORMATION FOR SEQ ID NO: 163:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 163:

AACCUAUCCC GGGAC 15

(2) INFORMATION FOR SEQ ID NO: 164:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 164:

AGGGCCUCUU CCUCG 15

(2) INFORMATION FOR SEQ ID NO: 165:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 165:

GGCCUCUUCC UCGGC 15

(2) INFORMATION FOR SEQ ID NO: 166:

(i) SEQUENCE CHARACTERISTICS:

(A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 166:

GCCUCUUCCU CGGCC                                                                        15

(2) INFORMATION FOR SEQ ID NO: 167:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 167:

UCUUCCUCGG CCUUC                                                                        15

(2) INFORMATION FOR SEQ ID NO: 168:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 168:

UCGGCCUUCC CAUAU                                                                        15

(2) INFORMATION FOR SEQ ID NO: 169:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 169:

CGGCCUUCCC AUAUU                                                                        15

(2) INFORMATION FOR SEQ ID NO: 170:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 170:

UUCCCAUAUU GGUGG                                                                        15

(2) INFORMATION FOR SEQ ID NO: 171:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 171:

CCCAUAUUGG UGGCA                                                                        15

(2) INFORMATION FOR SEQ ID NO: 172:

(i) SEQUENCE CHARACTERISTICS:
                (A) LENGTH: 15 base pairs
                (B) TYPE: nucleic acid ( C ) STRANDEDNESS: single
( D ) TOPOLOGY: linear ( x i ) SEQUENCE DESCRIPTION: SEQ ID NO: 172:

AAGACAUAUG CCAUG 15

( 2 ) INFORMATION FOR SEQ ID NO: 173:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 173:

UGCAGCUACA CCUAC 15

( 2 ) INFORMATION FOR SEQ ID NO: 174:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 174:

UACACCUACC GGCCC 15

( 2 ) INFORMATION FOR SEQ ID NO: 175:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 175:

AGGGCAUUGU CCUCA 15

( 2 ) INFORMATION FOR SEQ ID NO: 176:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 176:

GCAUUGUCCU CAGUC 15

( 2 ) INFORMATION FOR SEQ ID NO: 177:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 177:

UUGUCCUCAG UCAGA 15

( 2 ) INFORMATION FOR SEQ ID NO: 178:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 178:

CCUCAGUCAG AUACA 15

( 2 ) INFORMATION FOR SEQ ID NO: 179:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 179:

GUCAGAUACA ACAGC 15

( 2 ) INFORMATION FOR SEQ ID NO: 180:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 180:

ACAGCAUUUG GGGCC 15

( 2 ) INFORMATION FOR SEQ ID NO: 181:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 181:

CAGCAUUUGG GGCCA 15

( 2 ) INFORMATION FOR SEQ ID NO: 182:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 182:

CCAUGGUACC UGCAC 15

( 2 ) INFORMATION FOR SEQ ID NO: 183:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 183:

CACACCUAAA ACACU 15

( 2 ) INFORMATION FOR SEQ ID NO: 184:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 184:

AAACACUAGG CCACG  15

(2) INFORMATION FOR SEQ ID NO: 185:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 185:

CACGCAUCUG AUCUG  15

(2) INFORMATION FOR SEQ ID NO: 186:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 186:

AUCUGAUCUG UAGUC  15

(2) INFORMATION FOR SEQ ID NO: 187:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 187:

GAUCUGUAGU CACAU  15

(2) INFORMATION FOR SEQ ID NO: 188:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 188:

CUGUAGUCAC AUGAC  15

(2) INFORMATION FOR SEQ ID NO: 189:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 189:

CAUGACUAAG CCAAG  15

(2) INFORMATION FOR SEQ ID NO: 190:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 190:

CAAGACUCAA GACAU  15

( 2 ) INFORMATION FOR SEQ ID NO: 191:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 191:

ACAUGAUUGA UGGAU     15

( 2 ) INFORMATION FOR SEQ ID NO: 192:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 192:

UGGAUGUUAA AGUCU     15

( 2 ) INFORMATION FOR SEQ ID NO: 193:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 193:

GGAUGUUAAA GUCUA     15

( 2 ) INFORMATION FOR SEQ ID NO: 194:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 194:

UUAAAGUCUA GCCUG     15

( 2 ) INFORMATION FOR SEQ ID NO: 195:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 195:

AAAGUCUAGC CUGAU     15

( 2 ) INFORMATION FOR SEQ ID NO: 196:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 196:

GAGACAUAGC CCCAC     15

( 2 ) INFORMATION FOR SEQ ID NO: 197:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 197:

AGGACAUACA ACUGG 15

( 2 ) INFORMATION FOR SEQ ID NO: 198:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 198:

GGGAAAUACU GAAAC 15

( 2 ) INFORMATION FOR SEQ ID NO: 199:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 199:

UGAAACUUGC UGCCU 15

( 2 ) INFORMATION FOR SEQ ID NO: 200:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 200:

GCUGCCUAUU GGGUA 15

( 2 ) INFORMATION FOR SEQ ID NO: 201:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 201:

UGCCUAUUGG GUAUG 15

( 2 ) INFORMATION FOR SEQ ID NO: 202:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 202:

AUUGGGUAUG CUGAG 15

( 2 ) INFORMATION FOR SEQ ID NO: 203:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 203:

ACAGACUUAC AGAAG 15

( 2 ) INFORMATION FOR SEQ ID NO: 204:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 204:

CAGACUUACA GAAGA 15

( 2 ) INFORMATION FOR SEQ ID NO: 205:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 205:

UGGCCCUCCA UAGAC 15

( 2 ) INFORMATION FOR SEQ ID NO: 206:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 206:

CCUCCAUAGA CAUGU 15

( 2 ) INFORMATION FOR SEQ ID NO: 207:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 207:

CAUGUGUAGC AUCAA 15

( 2 ) INFORMATION FOR SEQ ID NO: 208:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 208:

GUAGCAUCAA AACAC 15

( 2 ) INFORMATION FOR SEQ ID NO: 209:

( i ) SEQUENCE CHARACTERISTICS:
        ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 209:

CCACACUUCC UGACG 15

(2) INFORMATION FOR SEQ ID NO: 210:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 210:

CACACUUCCU GACGG 15

(2) INFORMATION FOR SEQ ID NO: 211:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 211:

GCCAGCUUGG GCACU 15

(2) INFORMATION FOR SEQ ID NO: 212:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 212:

CUGCUGUCUA CUGAC 15

(2) INFORMATION FOR SEQ ID NO: 213:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 213:

GCUGUCUACU GACCC 15

(2) INFORMATION FOR SEQ ID NO: 214:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 214:

CAACCCUUGA UGAUA 15

(2) INFORMATION FOR SEQ ID NO: 215:

(i) SEQUENCE CHARACTERISTICS:
(A) LENGTH: 15 base pairs
(B) TYPE: nucleic acid
(C) STRANDEDNESS: single ( D ) TOPOLOGY: linear ( x i ) SEQUENCE DESCRIPTION: SEQ ID NO: 215:

UGAUGAUAUG UAUUU 15

( 2 ) INFORMATION FOR SEQ ID NO: 216:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 216:

GAUAUGUAUU UAUUC 15

( 2 ) INFORMATION FOR SEQ ID NO: 217:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 217:

UAUGUAUUUA UUCAU 15

( 2 ) INFORMATION FOR SEQ ID NO: 218:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 218:

AUGUAUUUAU UCAUU 15

( 2 ) INFORMATION FOR SEQ ID NO: 219:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 219:

UGUAUUUAUU CAUUU 15

( 2 ) INFORMATION FOR SEQ ID NO: 220:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 220:

UAUUUAUUCA UUUGU 15

( 2 ) INFORMATION FOR SEQ ID NO: 221:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (x i) SEQUENCE DESCRIPTION: SEQ ID NO: 221:

AUUUAUUCAU UUGUU                                                                                     15

(2) INFORMATION FOR SEQ ID NO: 222:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 222:

UAUUCAUUUG UUAUU                                                                                     15

(2) INFORMATION FOR SEQ ID NO: 223:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 223:

AUUCAUUUGU UAUUU                                                                                     15

(2) INFORMATION FOR SEQ ID NO: 224:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 224:

CAUUUGUUAU UUUAC                                                                                     15

(2) INFORMATION FOR SEQ ID NO: 225:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 225:

AUUUGUUAUU UUACC                                                                                     15

(2) INFORMATION FOR SEQ ID NO: 226:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 226:

UUGUUAUUUU ACCAG                                                                                     15

(2) INFORMATION FOR SEQ ID NO: 227:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO: 227:

UGUUAUUUUA CCAGC 15

(2) INFORMATION FOR SEQ ID NO: 228:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 228:

GUUAUUUUAC CAGCU 15

(2) INFORMATION FOR SEQ ID NO: 229:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 229:

UUAUUUUACC AGCUA 15

(2) INFORMATION FOR SEQ ID NO: 230:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 230:

ACCAGCUAUU UAUUG 15

(2) INFORMATION FOR SEQ ID NO: 231:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 231:

CAGCUAUUUA UUGAG 15

(2) INFORMATION FOR SEQ ID NO: 232:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 232:

AGCUAUUUAU UGAGU 15

(2) INFORMATION FOR SEQ ID NO: 233:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 233:

GCUAUUUAUU GAGUG 15

( 2 ) INFORMATION FOR SEQ ID NO: 234:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 234:

UAUUUAUUGA GUGUC        15

( 2 ) INFORMATION FOR SEQ ID NO: 235:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 235:

UGAGUGUCUU UUAUG        15

( 2 ) INFORMATION FOR SEQ ID NO: 236:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 236:

AGUGUCUUUU AUGUA        15

( 2 ) INFORMATION FOR SEQ ID NO: 237:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 237:

GUGUCUUUUA UGUAG        15

( 2 ) INFORMATION FOR SEQ ID NO: 238:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 238:

UGUCUUUUAU GUAGG        15

( 2 ) INFORMATION FOR SEQ ID NO: 239:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 239:

GUCUUUUAUG UAGGC        15

( 2 ) INFORMATION FOR SEQ ID NO: 240:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 240:

UUUAUGUAGG CUAAA           15

( 2 ) INFORMATION FOR SEQ ID NO: 241:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 241:

GUAGGCUAAA UGAAC           15

( 2 ) INFORMATION FOR SEQ ID NO: 242:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 242:

UGAACAUAGG UCUCU           15

( 2 ) INFORMATION FOR SEQ ID NO: 243:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 243:

CAUAGGUCUC UGGCC           15

( 2 ) INFORMATION FOR SEQ ID NO: 244:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 244:

UAGGUCUCUG GCCUC           15

( 2 ) INFORMATION FOR SEQ ID NO: 245:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 245:

CUGGCCUCAC GGAGC           15

( 2 ) INFORMATION FOR SEQ ID NO: 246:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 246:

CGGAGCUCCC AGUCC  15

(2) INFORMATION FOR SEQ ID NO: 247:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 247:

UCCCAGUCCA UGUCA  15

(2) INFORMATION FOR SEQ ID NO: 248:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 248:

UCCAUGUCAC AUUCA  15

(2) INFORMATION FOR SEQ ID NO: 249:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 249:

GUCACAUUCA AGGUC  15

(2) INFORMATION FOR SEQ ID NO: 250:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 250:

UCACAUUCAA GGUCA  15

(2) INFORMATION FOR SEQ ID NO: 251:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 251:

UCAAGGUCAC CAGGU  15

(2) INFORMATION FOR SEQ ID NO: 252:

(i) SEQUENCE CHARACTERISTICS:
(A) LENGTH: 15 base pairs
(B) TYPE: nucleic acid ( C ) STRANDEDNESS: single
( D ) TOPOLOGY: linear ( x i ) SEQUENCE DESCRIPTION: SEQ ID NO: 252:

ACCAGGUACA GUUGU                                                                                            15

( 2 ) INFORMATION FOR SEQ ID NO: 253:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 253:

GUACAGUUGU ACAGG                                                                                            15

( 2 ) INFORMATION FOR SEQ ID NO: 254:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 254:

CAGUUGUACA GGUUG                                                                                            15

( 2 ) INFORMATION FOR SEQ ID NO: 255:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 255:

UACAGGUUGU ACACU                                                                                            15

( 2 ) INFORMATION FOR SEQ ID NO: 256:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 256:

AGGUUGUACA CUGCA                                                                                            15

( 2 ) INFORMATION FOR SEQ ID NO: 257:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 257:

AAAAGAUCAA AUGGG                                                                                            15

( 2 ) INFORMATION FOR SEQ ID NO: 258:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 258:

UGGGACUUCU CAUUG 15

( 2 ) INFORMATION FOR SEQ ID NO: 259:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 259:

GGGACUUCUC AUUGG 15

( 2 ) INFORMATION FOR SEQ ID NO: 260:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 260:

GACUUCUCAU UGGCC 15

( 2 ) INFORMATION FOR SEQ ID NO: 261:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 261:

UUCUCAUUGG CCAAC 15

( 2 ) INFORMATION FOR SEQ ID NO: 262:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 262:

CCUGCCUUUC CCCAG 15

( 2 ) INFORMATION FOR SEQ ID NO: 263:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 263:

CUGCCUUUCC CCAGA 15

( 2 ) INFORMATION FOR SEQ ID NO: 264:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 264:

UGCCUUUCCC CAGAA 15

( 2 ) INFORMATION FOR SEQ ID NO: 265:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 265:

GAGUGAUUUU UCUAU 15

( 2 ) INFORMATION FOR SEQ ID NO: 266:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 266:

AGUGAUUUUU CUAUC 15

( 2 ) INFORMATION FOR SEQ ID NO: 267:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 267:

GUGAUUUUUC UAUCG 15

( 2 ) INFORMATION FOR SEQ ID NO: 268:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 268:

UGAUUUUUCU AUCGG 15

( 2 ) INFORMATION FOR SEQ ID NO: 269:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 269:

GAUUUUUCUA UCGGC 15

( 2 ) INFORMATION FOR SEQ ID NO: 270:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 270:

UUUUUCUAUC GGCAC 15

( 2 ) INFORMATION FOR SEQ ID NO: 271:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 271:

UUUCUAUCGG CACAA 15

( 2 ) INFORMATION FOR SEQ ID NO: 272:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 272:

AAGCACUAUA UGGAC 15

( 2 ) INFORMATION FOR SEQ ID NO: 273:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 273:

GCACUAUAUG GACUG 15

( 2 ) INFORMATION FOR SEQ ID NO: 274:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 274:

GACUGGUAAU GGUUC 15

( 2 ) INFORMATION FOR SEQ ID NO: 275:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 275:

UAAUGGUUCA CAGGU 15

( 2 ) INFORMATION FOR SEQ ID NO: 276:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 276:

AAUGGUUCAC AGGUU 15

( 2 ) INFORMATION FOR SEQ ID NO: 277:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 277:

CACAGGUUCA GAGAU 15

( 2 ) INFORMATION FOR SEQ ID NO: 278:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 278:

ACAGGUUCAG AGAUU 15

( 2 ) INFORMATION FOR SEQ ID NO: 279:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 279:

CAGAGAUUAC CCAGU 15

( 2 ) INFORMATION FOR SEQ ID NO: 280:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 280:

AGAGAUUACC CAGUG 15

( 2 ) INFORMATION FOR SEQ ID NO: 281:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 281:

GAGGCCUUAU UCCUC 15

( 2 ) INFORMATION FOR SEQ ID NO: 282:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 282:

AGGCCUUAUU CCUCC 15

( 2 ) INFORMATION FOR SEQ ID NO: 283:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 283:

GCCUUAUUCC UCCCU 15

( 2 ) INFORMATION FOR SEQ ID NO: 284:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 284:

CCUUAUUCCU CCCUU 15

( 2 ) INFORMATION FOR SEQ ID NO: 285:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 285:

UAUUCCUCCC UUCCC 15

( 2 ) INFORMATION FOR SEQ ID NO: 286:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 286:

CCUCCCUUCC CCCCA 15

( 2 ) INFORMATION FOR SEQ ID NO: 287:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 287:

CUCCCUUCCC CCCAA 15

( 2 ) INFORMATION FOR SEQ ID NO: 288:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 288:

GACACCUUUG UUAGC 15

( 2 ) INFORMATION FOR SEQ ID NO: 289:

( i ) SEQUENCE CHARACTERISTICS:
      ( A ) LENGTH: 15 base pairs (B) TYPE: nucleic acid
        (C) STRANDEDNESS: single
        (D) TOPOLOGY: linear (xi) SEQUENCE DESCRIPTION: SEQ ID NO: 289:

ACACCUUUGU UAGCC 15

(2) INFORMATION FOR SEQ ID NO: 290:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 290:

CCUUUGUUAG CCACC 15

(2) INFORMATION FOR SEQ ID NO: 291:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 291:

CUUUGUUAGC CACCU 15

(2) INFORMATION FOR SEQ ID NO: 292:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 292:

GCCACCUCCC CACCC 15

(2) INFORMATION FOR SEQ ID NO: 293:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 293:

CCCACAUACA UUUCU 15

(2) INFORMATION FOR SEQ ID NO: 294:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 294:

CAUACAUUUC UGCCA 15

(2) INFORMATION FOR SEQ ID NO: 295:

(i) SEQUENCE CHARACTERISTICS:
        (A) LENGTH: 15 base pairs
        (B) TYPE: nucleic acid
        (C) STRANDEDNESS: single ( D ) TOPOLOGY: linear ( x i ) SEQUENCE DESCRIPTION: SEQ ID NO: 295:

AUACAUUUCU GCCAG 15

( 2 ) INFORMATION FOR SEQ ID NO: 296:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 296:

UACAUUUCUG CCAGU 15

( 2 ) INFORMATION FOR SEQ ID NO: 297:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 297:

CCAGUGUUCA CAAUG 15

( 2 ) INFORMATION FOR SEQ ID NO: 298:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 298:

CAGUGUUCAC AAUGA 15

( 2 ) INFORMATION FOR SEQ ID NO: 299:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 299:

UGACACUCAG CGGUC 15

( 2 ) INFORMATION FOR SEQ ID NO: 300:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 300:

CAGCGGUCAU GUCUG 15

( 2 ) INFORMATION FOR SEQ ID NO: 301:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 301:

GUCAUGUCUG GACAU 15

( 2 ) INFORMATION FOR SEQ ID NO: 302:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 302:

AGGGAAUAUG CCCAA 15

( 2 ) INFORMATION FOR SEQ ID NO: 303:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 303:

CCAAGCUAUG CCUUG 15

( 2 ) INFORMATION FOR SEQ ID NO: 304:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 304:

UAUGCCUUGU CCUCU 15

( 2 ) INFORMATION FOR SEQ ID NO: 305:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 305:

GCCUUGUCCU CUUGU 15

( 2 ) INFORMATION FOR SEQ ID NO: 306:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 306:

UUGUCCUCUU GUCCU 15

( 2 ) INFORMATION FOR SEQ ID NO: 307:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 307:

GUCCUCUUGU CCUGU 15

( 2 ) INFORMATION FOR SEQ ID NO: 308:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 308:

CUCUUGUCCU GUUUG 15

( 2 ) INFORMATION FOR SEQ ID NO: 309:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 309:

GUCCUGUUUG CAUUU 15

( 2 ) INFORMATION FOR SEQ ID NO: 310:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 310:

UCCUGUUUGC AUUUC 15

( 2 ) INFORMATION FOR SEQ ID NO: 311:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 311:

UUUGCAUUUC ACUGG 15

( 2 ) INFORMATION FOR SEQ ID NO: 312:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 312:

UUGCAUUUCA CUGGG 15

( 2 ) INFORMATION FOR SEQ ID NO: 313:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 313:

UGCAUUUCAC UGGGA 15

( 2 ) INFORMATION FOR SEQ ID NO: 314:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 314:

GGGAGCUUGC ACUAU 15

( 2 ) INFORMATION FOR SEQ ID NO: 315:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 315:

UUGCACUAUU GCAGC 15

( 2 ) INFORMATION FOR SEQ ID NO: 316:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 316:

GCACUAUUGC AGCUC 15

( 2 ) INFORMATION FOR SEQ ID NO: 317:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 317:

UGCAGCUCCA GUUUC 15

( 2 ) INFORMATION FOR SEQ ID NO: 318:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 318:

CUCCAGUUUC CUGCA 15

( 2 ) INFORMATION FOR SEQ ID NO: 319:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 319:

UCCAGUUUCC UGCAG 15

( 2 ) INFORMATION FOR SEQ ID NO: 320:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 320:

CCAGUUUCCU GCAGU     15

( 2 ) INFORMATION FOR SEQ ID NO: 321:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 321:

CAGUGAUCAG GGUCC     15

( 2 ) INFORMATION FOR SEQ ID NO: 322:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 322:

UCAGGGUCCU GCAAG     15

( 2 ) INFORMATION FOR SEQ ID NO: 323:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 323:

CCAAGGUAUU GGAGG     15

( 2 ) INFORMATION FOR SEQ ID NO: 324:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 324:

AAGGUAUUGG AGGAC     15

( 2 ) INFORMATION FOR SEQ ID NO: 325:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 325:

GAGGACUCCC UCCCA     15

( 2 ) INFORMATION FOR SEQ ID NO: 326:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 326:

ACUCCCUCCC AGCUU 15

(2) INFORMATION FOR SEQ ID NO: 327:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 327:

CCCAGCUUUG GAAGG 15

(2) INFORMATION FOR SEQ ID NO: 328:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 328:

CCAGCUUUGG AAGGG 15

(2) INFORMATION FOR SEQ ID NO: 329:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 329:

GAAGGGUCAU CCGCG 15

(2) INFORMATION FOR SEQ ID NO: 330:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 330:

GGGUCAUCCG CGUGU 15

(2) INFORMATION FOR SEQ ID NO: 331:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 331:

UGUGUGUAUG UGUAG 15

(2) INFORMATION FOR SEQ ID NO: 332:

(i) SEQUENCE CHARACTERISTICS:
(A) LENGTH: 15 base pairs
(B) TYPE: nucleic acid (C) STRANDEDNESS: single
(D) TOPOLOGY: linear (xi) SEQUENCE DESCRIPTION: SEQ ID NO: 332:

UAUGUGUAGA CAAGC 15

(2) INFORMATION FOR SEQ ID NO: 333:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 333:

ACAAGCUCUC GCUCU 15

(2) INFORMATION FOR SEQ ID NO: 334:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 334:

AAGCUCUCGC UCUGU 15

(2) INFORMATION FOR SEQ ID NO: 335:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 335:

UCUCGCUCUG UCACC 15

(2) INFORMATION FOR SEQ ID NO: 336:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 336:

GCUCUGUCAC CCAGG 15

(2) INFORMATION FOR SEQ ID NO: 337:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 337:

GUGCAAUCAU GGUUC 15

(2) INFORMATION FOR SEQ ID NO: 338:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO: 338:

UCAUGGUUCA CUGCA 15

( 2 ) INFORMATION FOR SEQ ID NO: 339:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 339:

CAUGGUUCAC UGCAG 15

( 2 ) INFORMATION FOR SEQ ID NO: 340:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 340:

CUGCAGUCUU GACCU 15

( 2 ) INFORMATION FOR SEQ ID NO: 341:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 341:

GCAGUCUUGA CCUUU 15

( 2 ) INFORMATION FOR SEQ ID NO: 342:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 342:

UUGACCUUUU GGGCU 15

( 2 ) INFORMATION FOR SEQ ID NO: 343:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 343:

UGACCUUUUG GGCUC 15

( 2 ) INFORMATION FOR SEQ ID NO: 344:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 344:

```
GACCUUUUGG GCUCA                                                                                    15
```

( 2 ) INFORMATION FOR SEQ ID NO: 345:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 345:

```
UUGGGCUCAA GUGAU                                                                                    15
```

( 2 ) INFORMATION FOR SEQ ID NO: 346:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 346:

```
AAGUGAUCCU CCCAC                                                                                    15
```

( 2 ) INFORMATION FOR SEQ ID NO: 347:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 347:

```
UGAUCCUCCC ACCUC                                                                                    15
```

( 2 ) INFORMATION FOR SEQ ID NO: 348:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 348:

```
CCCACCUCAG CCUCC                                                                                    15
```

( 2 ) INFORMATION FOR SEQ ID NO: 349:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 349:

```
UCAGCCUCCU GAGUA                                                                                    15
```

( 2 ) INFORMATION FOR SEQ ID NO: 350:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 350:

```
CCUGAGUAGC UGGGA                                                                                    15
```

( 2 ) INFORMATION FOR SEQ ID NO: 351:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 351:

GGACCAUAGG CUCAC     15

( 2 ) INFORMATION FOR SEQ ID NO: 352:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 352:

AUAGGCUCAC AACAC     15

( 2 ) INFORMATION FOR SEQ ID NO: 353:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 353:

GGCAAAUUUG AUUUU     15

( 2 ) INFORMATION FOR SEQ ID NO: 354:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 354:

GCAAAUUUGA UUUUU     15

( 2 ) INFORMATION FOR SEQ ID NO: 355:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 355:

AUUUGAUUUU UUUUU     15

( 2 ) INFORMATION FOR SEQ ID NO: 356:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 356:

UUUGAUUUUU UUUUU     15

( 2 ) INFORMATION FOR SEQ ID NO: 357:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 357:

UUGAUUUUUU UUUUU 15

( 2 ) INFORMATION FOR SEQ ID NO: 358:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 358:

UGAUUUUUUU UUUUU 15

( 2 ) INFORMATION FOR SEQ ID NO: 359:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 359:

GAUUUUUUUU UUUUU 15

( 2 ) INFORMATION FOR SEQ ID NO: 360:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 360:

AUUUUUUUUU UUUUU 15

( 2 ) INFORMATION FOR SEQ ID NO: 361:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 361:

UUUUUUUUUU UUUUU 15

( 2 ) INFORMATION FOR SEQ ID NO: 362:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 362:

UUUUUUUUUU UUUUU 15

( 2 ) INFORMATION FOR SEQ ID NO: 363:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 363:

UUUUUUUUUU UUUUC 15

( 2 ) INFORMATION FOR SEQ ID NO: 364:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 364:

UUUUUUUUUU UUUCA 15

( 2 ) INFORMATION FOR SEQ ID NO: 365:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 365:

UUUUUUUUUU UUCAG 15

( 2 ) INFORMATION FOR SEQ ID NO: 366:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 366:

UUUUUUUUUU UCAGA 15

( 2 ) INFORMATION FOR SEQ ID NO: 367:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 367:

UUUUUUUUUU CAGAG 15

( 2 ) INFORMATION FOR SEQ ID NO: 368:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 368:

UUUUUUUUUC AGAGA 15

( 2 ) INFORMATION FOR SEQ ID NO: 369:

( i ) SEQUENCE CHARACTERISTICS:
    ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 369:

UUUUUUUUCA GAGAC 15

(2) INFORMATION FOR SEQ ID NO: 370:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 370:

UUUUUUUCAG AGACG 15

(2) INFORMATION FOR SEQ ID NO: 371:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 371:

ACGGGGUCUC GCAAC 15

(2) INFORMATION FOR SEQ ID NO: 372:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 372:

GGGGUCUCGC AACAU 15

(2) INFORMATION FOR SEQ ID NO: 373:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 373:

GCAACAUUGC CCAGA 15

(2) INFORMATION FOR SEQ ID NO: 374:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 374:

CCAGACUUCC UUUGU 15

(2) INFORMATION FOR SEQ ID NO: 375:

(i) SEQUENCE CHARACTERISTICS:
(A) LENGTH: 15 base pairs
(B) TYPE: nucleic acid
(C) STRANDEDNESS: single ( D ) TOPOLOGY: linear ( x i ) SEQUENCE DESCRIPTION: SEQ ID NO: 375:

CAGACUUCCU UUGUG 15

( 2 ) INFORMATION FOR SEQ ID NO: 376:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 376:

ACUUCCUUUG UGUUA 15

( 2 ) INFORMATION FOR SEQ ID NO: 377:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 377:

CUUCCUUUGU GUUAG 15

( 2 ) INFORMATION FOR SEQ ID NO: 378:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 378:

UUUGUGUUAG UUAAU 15

( 2 ) INFORMATION FOR SEQ ID NO: 379:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 379:

UUGUGUUAGU UAAUA 15

( 2 ) INFORMATION FOR SEQ ID NO: 380:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 380:

UGUUAGUUAA UAAAG 15

( 2 ) INFORMATION FOR SEQ ID NO: 381:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 381:

GUUAGUUAAU AAAGC 15

( 2 ) INFORMATION FOR SEQ ID NO: 382:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 382:

AGUUAAUAAA GCUUU 15

( 2 ) INFORMATION FOR SEQ ID NO: 383:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 383:

UAAAGCUUUC UCAAC 15

( 2 ) INFORMATION FOR SEQ ID NO: 384:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 384:

AAAGCUUUCU CAACU 15

( 2 ) INFORMATION FOR SEQ ID NO: 385:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 385:

AAGCUUUCUC AACUG 15

( 2 ) INFORMATION FOR SEQ ID NO: 386:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 386:

GCUUUCUCAA CUGCC 15

( 2 ) INFORMATION FOR SEQ ID NO: 387:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 387:

CCCUGGUCAC CGUUG 15

(2) INFORMATION FOR SEQ ID NO: 388:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 388:

CAGUGGUUCU CUGCU 15

(2) INFORMATION FOR SEQ ID NO: 389:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 389:

UGGUUCUCUG CUCCU 15

(2) INFORMATION FOR SEQ ID NO: 390:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 390:

CUCUGCUCCU CCACA 15

(2) INFORMATION FOR SEQ ID NO: 391:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 391:

UUCUCAUAAG GGUCG 15

(2) INFORMATION FOR SEQ ID NO: 392:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 392:

GCACACUUGU AGCCU 15

(2) INFORMATION FOR SEQ ID NO: 393:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 393:

AGGACCUCAG CCUGG 15

( 2 ) INFORMATION FOR SEQ ID NO: 394:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 394:

UGGGCCUCGU GAUGG 15

( 2 ) INFORMATION FOR SEQ ID NO: 395:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 395:

CAUGCCUUUA GCUCC 15

( 2 ) INFORMATION FOR SEQ ID NO: 396:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 396:

CACCCUCCC AGCAG 15

( 2 ) INFORMATION FOR SEQ ID NO: 397:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 397:

CUCUGCUCCU GGCCC 15

( 2 ) INFORMATION FOR SEQ ID NO: 398:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 398:

UGCCAGUACU GCUGG 15

( 2 ) INFORMATION FOR SEQ ID NO: 399:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 399:

CUCUGCUCCU GGCCC 15

( 2 ) INFORMATION FOR SEQ ID NO: 400:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 400:

UGGUUCUCUG CUCCU 15

( 2 ) INFORMATION FOR SEQ ID NO: 401:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 401:

GGAAUGUCAC CAGGA 15

( 2 ) INFORMATION FOR SEQ ID NO: 402:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 402:

CUCUGCUCCU GGCCC 15

( 2 ) INFORMATION FOR SEQ ID NO: 403:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 403:

CAGUCGUCCG CUUCC 15

( 2 ) INFORMATION FOR SEQ ID NO: 404:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 404:

UCUGUGUCAG CCACU 15

( 2 ) INFORMATION FOR SEQ ID NO: 405:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 405:

UCCUGUUUAA AAACC 15

( 2 ) INFORMATION FOR SEQ ID NO: 406:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 406:

CAGAAGUUGU UUUGC 15

(2) INFORMATION FOR SEQ ID NO: 407:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 407:

AAGCCUUCCU GCCCC 15

(2) INFORMATION FOR SEQ ID NO: 408:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 408:

GGUGGGUCCG UGCAG 15

(2) INFORMATION FOR SEQ ID NO: 409:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 409:

GCCACUUCCU CUGGC 15

(2) INFORMATION FOR SEQ ID NO: 410:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 410:

CAGAAGUUGU UUUGC 15

(2) INFORMATION FOR SEQ ID NO: 411:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 411:

AAGUUGUUUU GCUCC 15

(2) INFORMATION FOR SEQ ID NO: 412:

(i) SEQUENCE CHARACTERISTICS:
(A) LENGTH: 15 base pairs
(B) TYPE: nucleic acid (C) STRANDEDNESS: single
(D) TOPOLOGY: linear (x i) SEQUENCE DESCRIPTION: SEQ ID NO: 412:

UGUGCUUUGA GAACU 15

(2) INFORMATION FOR SEQ ID NO: 413:

(i) SEQUENCE CHARACTERISTICS:
 (A) LENGTH: 15 base pairs
 (B) TYPE: nucleic acid
 (C) STRANDEDNESS: single
 (D) TOPOLOGY: linear (x i) SEQUENCE DESCRIPTION: SEQ ID NO: 413:

AACCCAUCUC CUAAA 15

(2) INFORMATION FOR SEQ ID NO: 414:

(i) SEQUENCE CHARACTERISTICS:
 (A) LENGTH: 15 base pairs
 (B) TYPE: nucleic acid
 (C) STRANDEDNESS: single
 (D) TOPOLOGY: linear (x i) SEQUENCE DESCRIPTION: SEQ ID NO: 414:

CCUGCCUAAG GAAGA 15

(2) INFORMATION FOR SEQ ID NO: 415:

(i) SEQUENCE CHARACTERISTICS:
 (A) LENGTH: 15 base pairs
 (B) TYPE: nucleic acid
 (C) STRANDEDNESS: single
 (D) TOPOLOGY: linear (x i) SEQUENCE DESCRIPTION: SEQ ID NO: 415:

AGGGUUUCUC UACUG 15

(2) INFORMATION FOR SEQ ID NO: 416:

(i) SEQUENCE CHARACTERISTICS:
 (A) LENGTH: 15 base pairs
 (B) TYPE: nucleic acid
 (C) STRANDEDNESS: single
 (D) TOPOLOGY: linear (x i) SEQUENCE DESCRIPTION: SEQ ID NO: 416:

AGGGGCUCCU GCCUA 15

(2) INFORMATION FOR SEQ ID NO: 417:

(i) SEQUENCE CHARACTERISTICS:
 (A) LENGTH: 15 base pairs
 (B) TYPE: nucleic acid
 (C) STRANDEDNESS: single
 (D) TOPOLOGY: linear (x i) SEQUENCE DESCRIPTION: SEQ ID NO: 417:

AAGCUGUUUG AGCUG 15

(2) INFORMATION FOR SEQ ID NO: 418:

(i) SEQUENCE CHARACTERISTICS:
 (A) LENGTH: 15 base pairs
 (B) TYPE: nucleic acid
 (C) STRANDEDNESS: single
 (D) TOPOLOGY: linear ( x i ) SEQUENCE DESCRIPTION: SEQ ID NO: 418:

AGGAGAUACU GAGCC  15

( 2 ) INFORMATION FOR SEQ ID NO: 419:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 419:

CUGUGCUUUG AGAAC  15

( 2 ) INFORMATION FOR SEQ ID NO: 420:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 420:

GUCCAAUUCA CACUG  15

( 2 ) INFORMATION FOR SEQ ID NO: 421:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 421:

AGCUGUUUGA GCUGA  15

( 2 ) INFORMATION FOR SEQ ID NO: 422:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 422:

GUGCAGUCGU CCGCU  15

( 2 ) INFORMATION FOR SEQ ID NO: 423:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 423:

GGCCUGUUUC CUGCC  15

( 2 ) INFORMATION FOR SEQ ID NO: 424:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 424:

GCCUGUUUCC UGCCU                         15

( 2 ) INFORMATION FOR SEQ ID NO: 425:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 425:

UGGAGGUCUC GGAAG                         15

( 2 ) INFORMATION FOR SEQ ID NO: 426:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 426:

CUGGGCUUGG AGACU                         15

( 2 ) INFORMATION FOR SEQ ID NO: 427:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 427:

CUCGGAUAUA CCUGG                         15

( 2 ) INFORMATION FOR SEQ ID NO: 428:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 428:

CAAAGCUCGA CACCC                         15

( 2 ) INFORMATION FOR SEQ ID NO: 429:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 429:

CCCUGGUCAC CGUUG                         15

( 2 ) INFORMATION FOR SEQ ID NO: 430:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 430:

GAGACCUCUA CCAGC                         15

( 2 ) INFORMATION FOR SEQ ID NO: 431:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 431:

AGCCACUUCC UCUGG                                                                 15

( 2 ) INFORMATION FOR SEQ ID NO: 432:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 432:

GAAGCCUUCC UGCCC                                                                 15

( 2 ) INFORMATION FOR SEQ ID NO: 433:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 433:

AUUCGUUUCC GGAGA                                                                 15

( 2 ) INFORMATION FOR SEQ ID NO: 434:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 434:

UCUUCCUCAU GCAAG                                                                 15

( 2 ) INFORMATION FOR SEQ ID NO: 435:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 435:

AUGGCUUCAA CCCGU                                                                 15

( 2 ) INFORMATION FOR SEQ ID NO: 436:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 436:

CCUUGGUAGA GGUGA                                                                 15

( 2 ) INFORMATION FOR SEQ ID NO: 437:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 437:

CUAUAAUCAU UCUGG          15

( 2 ) INFORMATION FOR SEQ ID NO: 438:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 438:

UAAUCAUUCU GGUGC          15

( 2 ) INFORMATION FOR SEQ ID NO: 439:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 439:

UAACAGUCUA CAACU          15

( 2 ) INFORMATION FOR SEQ ID NO: 440:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 440:

ACAGUCUACA ACUUU          15

( 2 ) INFORMATION FOR SEQ ID NO: 441:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 441:

UACAACUUUU CAGCU          15

( 2 ) INFORMATION FOR SEQ ID NO: 442:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 442:

ACAACUUUUC AGCUC          15

( 2 ) INFORMATION FOR SEQ ID NO: 443:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 443:

CAACUUUUCA GCUCC                                          15

( 2 ) INFORMATION FOR SEQ ID NO: 444:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 444:

ACCAGAUCCU GGAGA                                          15

( 2 ) INFORMATION FOR SEQ ID NO: 445:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 445:

UGAGAGUCUG GGGAA                                          15

( 2 ) INFORMATION FOR SEQ ID NO: 446:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 446:

UGGAGGUCUC GGAAG                                          15

( 2 ) INFORMATION FOR SEQ ID NO: 447:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 447:

GAGGUCUCGG AAGGG                                          15

( 2 ) INFORMATION FOR SEQ ID NO: 448:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 448:

CCACUCUCAA AAUAA                                          15

( 2 ) INFORMATION FOR SEQ ID NO: 449:

( i ) SEQUENCE CHARACTERISTICS:
        ( A ) LENGTH: 15 base pairs (B) TYPE: nucleic acid
        (C) STRANDEDNESS: single
        (D) TOPOLOGY: linear (xi) SEQUENCE DESCRIPTION: SEQ ID NO: 449:

ACUGGAUCUC AGGCC 15

(2) INFORMATION FOR SEQ ID NO: 450:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 450:

UGGACCUUCA GCCAA 15

(2) INFORMATION FOR SEQ ID NO: 451:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 451:

CCCAACUCUU CUUGA 15

(2) INFORMATION FOR SEQ ID NO: 452:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 452:

CGAAGCUUCU UUUGC 15

(2) INFORMATION FOR SEQ ID NO: 453:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 453:

GAAGCUUCUU UUGCU 15

(2) INFORMATION FOR SEQ ID NO: 454:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 454:

AGCUUCUUUU GCUCU 15

(2) INFORMATION FOR SEQ ID NO: 455:

(i) SEQUENCE CHARACTERISTICS:
        (A) LENGTH: 15 base pairs
        (B) TYPE: nucleic acid
        (C) STRANDEDNESS: single ( D ) TOPOLOGY: linear ( x i ) SEQUENCE DESCRIPTION: SEQ ID NO: 455:

UCCUGUUUAA AAACC 15

( 2 ) INFORMATION FOR SEQ ID NO: 456:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 456:

CUCUGCUCCU CCACA 15

( 2 ) INFORMATION FOR SEQ ID NO: 457:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 457:

GCUGCUUUUG AACAG 15

( 2 ) INFORMATION FOR SEQ ID NO: 458:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 458:

ACUUUUUUCA CCAGU 15

( 2 ) INFORMATION FOR SEQ ID NO: 459:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 459:

GGUACAUACG UGUGC 15

( 2 ) INFORMATION FOR SEQ ID NO: 460:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 460:

GAAGCUUCUU UUGCU 15

( 2 ) INFORMATION FOR SEQ ID NO: 461:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 461:

UUCGUUUCCG GAGAG 15

( 2 ) INFORMATION FOR SEQ ID NO: 462:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 462:

GUGCUGUAUG GUCCU 15

( 2 ) INFORMATION FOR SEQ ID NO: 463:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 463:

GAAGGGUCGU GCAAG 15

( 2 ) INFORMATION FOR SEQ ID NO: 464:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 464:

UGAGAGUCUG GGGAA 15

( 2 ) INFORMATION FOR SEQ ID NO: 465:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 465:

AGGAGAUACU GAGCC 15

( 2 ) INFORMATION FOR SEQ ID NO: 466:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 466:

GAGGGUCUC AGCAG 15

( 2 ) INFORMATION FOR SEQ ID NO: 467:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 467:

```
          GCAGACUCUG AAAUG                                                                                     15

( 2 ) INFORMATION FOR SEQ ID NO: 468:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 468:

GAAGGCUCAG GAGGA                                                                                     15

( 2 ) INFORMATION FOR SEQ ID NO: 469:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 469:

AACCCAUCUC CUAAA                                                                                     15

( 2 ) INFORMATION FOR SEQ ID NO: 470:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 470:

AUGAGCUCGA GAGUG                                                                                     15

( 2 ) INFORMATION FOR SEQ ID NO: 471:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 471:

UGAAUGUAUA AGUUA                                                                                     15

( 2 ) INFORMATION FOR SEQ ID NO: 472:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 472:

UGGUCCUCGG CUGGA                                                                                     15

( 2 ) INFORMATION FOR SEQ ID NO: 473:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 473:

CACCAGUCAC AUAAA                                                                                     15
```

( 2 ) INFORMATION FOR SEQ ID NO: 474:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 474:

ACCAGAUCCU GGAGA 15

( 2 ) INFORMATION FOR SEQ ID NO: 475:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 475:

ACUGGAUCUC AGGCC 15

( 2 ) INFORMATION FOR SEQ ID NO: 476:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 476:

CAGCAUUUAC CCUCA 15

( 2 ) INFORMATION FOR SEQ ID NO: 477:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 477:

CCACGCUACC UCUGC 15

( 2 ) INFORMATION FOR SEQ ID NO: 478:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 478:

CAUGCCUUUA GCUCC 15

( 2 ) INFORMATION FOR SEQ ID NO: 479:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 479:

CGAGCCUAGG CCACC 15

( 2 ) INFORMATION FOR SEQ ID NO: 480:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 480:

CGGACUUUCG AUCUU 15

( 2 ) INFORMATION FOR SEQ ID NO: 481:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 481:

ACAUGAUAUC CAGUA 15

( 2 ) INFORMATION FOR SEQ ID NO: 482:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 482:

CACUUGUAGC CUCAG 15

( 2 ) INFORMATION FOR SEQ ID NO: 483:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 483:

CACCAGUCAC AUAAA 15

( 2 ) INFORMATION FOR SEQ ID NO: 484:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 484:

CAUGCCUUAG CAGCU 15

( 2 ) INFORMATION FOR SEQ ID NO: 485:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 485:

UAAAACUCAA GGGAC 15

( 2 ) INFORMATION FOR SEQ ID NO: 486:

( i ) SEQUENCE CHARACTERISTICS:

(A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 486:

AUAUAGUAGA UCAGU                                                                             15

(2) INFORMATION FOR SEQ ID NO: 487:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 487:

UGAAUGUAUA AGUUA                                                                             15

(2) INFORMATION FOR SEQ ID NO: 488:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 488:

UGAUGCUCAG GUAUC                                                                             15

(2) INFORMATION FOR SEQ ID NO: 489:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 489:

UUAGAGUUUU ACCAG                                                                             15

(2) INFORMATION FOR SEQ ID NO: 490:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 490:

AGAGUUUUAC CAGCU                                                                             15

(2) INFORMATION FOR SEQ ID NO: 491:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 491:

GAGACAUUGU CCCCA                                                                             15

(2) INFORMATION FOR SEQ ID NO: 492:

(i) SEQUENCE CHARACTERISTICS:
                (A) LENGTH: 15 base pairs
                (B) TYPE: nucleic acid ( C ) STRANDEDNESS: single
        ( D ) TOPOLOGY: linear ( x i ) SEQUENCE DESCRIPTION: SEQ ID NO: 492:

AGGAUAUACA AGUUA 15

( 2 ) INFORMATION FOR SEQ ID NO: 493:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 493:

AGGAGAUACU GAGCC 15

( 2 ) INFORMATION FOR SEQ ID NO: 494:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 494:

UGGAGCUAGC GGACC 15

( 2 ) INFORMATION FOR SEQ ID NO: 495:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 495:

GCUAUUUAUU GAGUA 15

( 2 ) INFORMATION FOR SEQ ID NO: 496:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 496:

UGCCCAUCGG GGUGG 15

( 2 ) INFORMATION FOR SEQ ID NO: 497:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 497:

GGUGGUUCUU CUGAG 15

( 2 ) INFORMATION FOR SEQ ID NO: 498:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 498:

GCUGGCUAGC AGAGG    15

( 2 ) INFORMATION FOR SEQ ID NO: 499:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 499:

CUGACCUCCU GGAGG    15

( 2 ) INFORMATION FOR SEQ ID NO: 500:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 500:

UGCUCCUCCA CAUCC    15

( 2 ) INFORMATION FOR SEQ ID NO: 501:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 501:

CUACCAUCAC CGUGU    15

( 2 ) INFORMATION FOR SEQ ID NO: 502:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 502:

CACUUGUAGC CUCAG    15

( 2 ) INFORMATION FOR SEQ ID NO: 503:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 503:

GUAGCCUCAG AGCUA    15

( 2 ) INFORMATION FOR SEQ ID NO: 504:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 504:

CAACUCUUCU UGAUG 15

( 2 ) INFORMATION FOR SEQ ID NO: 505:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 505:

CACACUUCCC CCCCG 15

( 2 ) INFORMATION FOR SEQ ID NO: 506:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 506:

GCCAGCUCGG AGGAU 15

( 2 ) INFORMATION FOR SEQ ID NO: 507:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 507:

CAGCUAUUUA UUGAG 15

( 2 ) INFORMATION FOR SEQ ID NO: 508:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 508:

CCUGUUUCCU GCCUC 15

( 2 ) INFORMATION FOR SEQ ID NO: 509:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 509:

CAACUCUUCU UGAUG 15

( 2 ) INFORMATION FOR SEQ ID NO: 510:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 510:

UAUUAAUUUA GAGUU 15

( 2 ) INFORMATION FOR SEQ ID NO: 511:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 511:

UUGAUGUAUU UAUUA 15

( 2 ) INFORMATION FOR SEQ ID NO: 512:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 512:

GAUGUAUUUA UUAAU 15

( 2 ) INFORMATION FOR SEQ ID NO: 513:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 513:

AUGUAUUUAU UAAUU 15

( 2 ) INFORMATION FOR SEQ ID NO: 514:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 514:

UGUAUUUAUU AAUUU 15

( 2 ) INFORMATION FOR SEQ ID NO: 515:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 515:

UAUUUAUUAA UUUAG 15

( 2 ) INFORMATION FOR SEQ ID NO: 516:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 516:

AUGUAUUUAU UAAUU 15

(2) INFORMATION FOR SEQ ID NO: 517:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 517:

ACUUCAUUCU CUAUU 15

(2) INFORMATION FOR SEQ ID NO: 518:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 518:

AUGUAUUUAU UAAUU 15

(2) INFORMATION FOR SEQ ID NO: 519:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 519:

UAUUUAUUAA UUUAG 15

(2) INFORMATION FOR SEQ ID NO: 520:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 520:

AGUUGUUUUG CUCCC 15

(2) INFORMATION FOR SEQ ID NO: 521:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 521:

GAAUGGUACA UACGU 15

(2) INFORMATION FOR SEQ ID NO: 522:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 522:

ACUGGAUCUC AGGCC 15

(2) INFORMATION FOR SEQ ID NO: 523:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 523:

CAUGGGUCGA GGGUU 15

( 2 ) INFORMATION FOR SEQ ID NO: 524:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 524:

AUUAAUUUAG AGUUU 15

( 2 ) INFORMATION FOR SEQ ID NO: 525:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 525:

UAGAGUUUUA CCAGC 15

( 2 ) INFORMATION FOR SEQ ID NO: 526:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 526:

AGAGUUUUAC CAGCU 15

( 2 ) INFORMATION FOR SEQ ID NO: 527:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 527:

GAAGCCUUCC UGCCC 15

( 2 ) INFORMATION FOR SEQ ID NO: 528:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 528:

AAGCCUUCCU GCCCC 15

( 2 ) INFORMATION FOR SEQ ID NO: 529:

( i ) SEQUENCE CHARACTERISTICS:
    ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO: 529:

GCCUGUUUCC UGCCU 15

(2) INFORMATION FOR SEQ ID NO: 530:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 530:

CCUGUUUCCU GCCUC 15

(2) INFORMATION FOR SEQ ID NO: 531:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 531:

GAAGCCUUCC UGCCC 15

(2) INFORMATION FOR SEQ ID NO: 532:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 532:

CCACACUUCC CCCCC 15

(2) INFORMATION FOR SEQ ID NO: 533:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 533:

CACACUUCCC CCCCG 15

(2) INFORMATION FOR SEQ ID NO: 534:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 534:

GAGACCUCUA CCAGC 15

(2) INFORMATION FOR SEQ ID NO: 535:

(i) SEQUENCE CHARACTERISTICS:
(A) LENGTH: 15 base pairs
(B) TYPE: nucleic acid
(C) STRANDEDNESS: single ( D ) TOPOLOGY: linear ( x i ) SEQUENCE DESCRIPTION: SEQ ID NO: 535:

UCACCGUUGU GAUCC 15

( 2 ) INFORMATION FOR SEQ ID NO: 536:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 536:

CCAAUGUCAG CCACC 15

( 2 ) INFORMATION FOR SEQ ID NO: 537:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 537:

CUUUUUUCAC CAGUC 15

( 2 ) INFORMATION FOR SEQ ID NO: 538:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 538:

AGCACCUCCC CACCU 15

( 2 ) INFORMATION FOR SEQ ID NO: 539:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 539:

CCCACCUACU UUUGU 15

( 2 ) INFORMATION FOR SEQ ID NO: 540:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 540:

UAUCCAUCCA UCCCA 15

( 2 ) INFORMATION FOR SEQ ID NO: 541:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 541:

UUAGAGUUUU ACCAG                                                                                             15

( 2 ) INFORMATION FOR SEQ ID NO: 542:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 542:

UAGAGUUUUA CCAGC                                                                                             15

( 2 ) INFORMATION FOR SEQ ID NO: 543:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 543:

CUUUUGUUCC CAAUG                                                                                             15

( 2 ) INFORMATION FOR SEQ ID NO: 544:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 544:

CAGCAUUUAC CCUCA                                                                                             15

( 2 ) INFORMATION FOR SEQ ID NO: 545:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 545:

UGAUGCUCAG GUAUC                                                                                             15

( 2 ) INFORMATION FOR SEQ ID NO: 546:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 546:

CAGCAGUCCG CUGUG                                                                                             15

( 2 ) INFORMATION FOR SEQ ID NO: 547:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 547:

```
GUGCUGUAUG GUCCU                                                                        15
```

( 2 ) INFORMATION FOR SEQ ID NO: 548:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 548:

```
GUGAAGUCUG UCAAA                                                                        15
```

( 2 ) INFORMATION FOR SEQ ID NO: 549:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 549:

```
AUAAGUUAUG GCCUG                                                                        15
```

( 2 ) INFORMATION FOR SEQ ID NO: 550:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 550:

```
CUGGCAUUGU UCUCU                                                                        15
```

( 2 ) INFORMATION FOR SEQ ID NO: 551:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 551:

```
GCAUUGUUCU CUAAU                                                                        15
```

( 2 ) INFORMATION FOR SEQ ID NO: 552:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 552:

```
UGGUUCUCUG CUCCU                                                                        15
```

( 2 ) INFORMATION FOR SEQ ID NO: 553:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 553:

```
CUUCUUUUGC UCUGC                                                                        15
```

( 2 ) INFORMATION FOR SEQ ID NO: 554:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 554:

CUUUUGUUCC CAAUG 15

( 2 ) INFORMATION FOR SEQ ID NO: 555:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 555:

ACCGUGUAUU CGUUU 15

( 2 ) INFORMATION FOR SEQ ID NO: 556:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 556:

UCCAGCUACC AUCCC 15

( 2 ) INFORMATION FOR SEQ ID NO: 557:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 557:

CUCGGAUAUA CCUGG 15

( 2 ) INFORMATION FOR SEQ ID NO: 558:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 558:

CAGCAGUCCG CUGUG 15

( 2 ) INFORMATION FOR SEQ ID NO: 559:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 559:

GGAAUGUCAC CAGGA 15

( 2 ) INFORMATION FOR SEQ ID NO: 560:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 560:

AGGACCUCAC CCUGC 15

( 2 ) INFORMATION FOR SEQ ID NO: 561:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 561:

UUUCGAUCUU CCAGC 15

( 2 ) INFORMATION FOR SEQ ID NO: 562:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 562:

GCACACUUGU AGCCU 15

( 2 ) INFORMATION FOR SEQ ID NO: 563:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 563:

UUCAGCUCCG GUCCU 15

( 2 ) INFORMATION FOR SEQ ID NO: 564:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 564:

GGCCUGUUUC CUGCC 15

( 2 ) INFORMATION FOR SEQ ID NO: 565:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 565:

CCCAGCUCUC AGCAG 15

( 2 ) INFORMATION FOR SEQ ID NO: 566:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 566:

CCUGUUUCCU GCCUC 15

(2) INFORMATION FOR SEQ ID NO: 567:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 567:

UACUGGUCAG GAUGC 15

(2) INFORMATION FOR SEQ ID NO: 568:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 568:

GAAGGGUCGU GCAAG 15

(2) INFORMATION FOR SEQ ID NO: 569:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 569:

CUAAUGUCUC CGAGG 15

(2) INFORMATION FOR SEQ ID NO: 570:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 570:

GAGACAUUGU CCCCA 15

(2) INFORMATION FOR SEQ ID NO: 571:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 571:

CCACGCUACC UCUGC 15

(2) INFORMATION FOR SEQ ID NO: 572:

(i) SEQUENCE CHARACTERISTICS:
(A) LENGTH: 15 base pairs
(B) TYPE: nucleic acid ( C ) STRANDEDNESS: single
            ( D ) TOPOLOGY: linear ( x i ) SEQUENCE DESCRIPTION: SEQ ID NO: 572:

CAGCAGUCCG CUGUG                                                                    15

( 2 ) INFORMATION FOR SEQ ID NO: 573:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 573:

AGUGACUCUG UGUCA                                                                    15

( 2 ) INFORMATION FOR SEQ ID NO: 574:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 574:

UUUCCUUUGA AUCAA                                                                    15

( 2 ) INFORMATION FOR SEQ ID NO: 575:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 575:

UCUGUGUCAG CCACU                                                                    15

( 2 ) INFORMATION FOR SEQ ID NO: 576:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 576:

AUGUAUUUAU UAAUU                                                                    15

( 2 ) INFORMATION FOR SEQ ID NO: 577:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 577:

UUUGAAUCAA UAAAG                                                                    15

( 2 ) INFORMATION FOR SEQ ID NO: 578:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 578:

GCUGGCUAGC AGAGG 15

( 2 ) INFORMATION FOR SEQ ID NO: 579:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 579:

AAUCAAUAAA GUUUU 15

( 2 ) INFORMATION FOR SEQ ID NO: 580:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 580:

UAGAGUUUUA CCAGC 15

( 2 ) INFORMATION FOR SEQ ID NO: 581:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 581:

GAGGGUUUCU CUACU 15

( 2 ) INFORMATION FOR SEQ ID NO: 582:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 582:

AAGCUGUUUG AGCUG 15

( 2 ) INFORMATION FOR SEQ ID NO: 583:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 583:

UCAUUCUCUA UUGCC 15

( 2 ) INFORMATION FOR SEQ ID NO: 584:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 584:

AAUGGCUUCA ACCCG 15

(2) INFORMATION FOR SEQ ID NO: 585:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 585:

GAAGCCUUCC UGCCC 15

(2) INFORMATION FOR SEQ ID NO: 586:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 586:

AAGCCUUCCU GCCCC 15

(2) INFORMATION FOR SEQ ID NO: 587:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 587:

CUACCAUCAC CGUGU 15

(2) INFORMATION FOR SEQ ID NO: 588:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 588:

ACCGUGUAUU CGUUU 15

(2) INFORMATION FOR SEQ ID NO: 589:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 589:

CCGGACUUUC GAUCU 15

(2) INFORMATION FOR SEQ ID NO: 590:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 590:

CACACUUCCC CCCCG 15

( 2 ) INFORMATION FOR SEQ ID NO: 591:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 591:

CACCCCUCCC AGCAG 15

( 2 ) INFORMATION FOR SEQ ID NO: 592:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 592:

CAGCUCUCAG CAGUG 15

( 2 ) INFORMATION FOR SEQ ID NO: 593:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 593:

AGGACCUCAC CCUGC 15

( 2 ) INFORMATION FOR SEQ ID NO: 594:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 594:

GAAACCUUUC CUUUG 15

( 2 ) INFORMATION FOR SEQ ID NO: 595:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 595:

UUACCCUCAG CCACU 15

( 2 ) INFORMATION FOR SEQ ID NO: 596:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 596:

CUACCAUCAC CGUGU 15

( 2 ) INFORMATION FOR SEQ ID NO: 597:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 597:

UGCUGCUCCG UGGGG     15

( 2 ) INFORMATION FOR SEQ ID NO: 598:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 598:

CUCAGGUAUC CAUCC     15

( 2 ) INFORMATION FOR SEQ ID NO: 599:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 599:

GAAAGAUCAC AUGGG     15

( 2 ) INFORMATION FOR SEQ ID NO: 600:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 600:

AGCCAAUUUC UCAUG     15

( 2 ) INFORMATION FOR SEQ ID NO: 601:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 601:

GCCAAUUUCU CAUGC     15

( 2 ) INFORMATION FOR SEQ ID NO: 602:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 602:

CCAAUUUCUC AUGCC     15

( 2 ) INFORMATION FOR SEQ ID NO: 603:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 603:

AAUUCUCAU GCCGC                                                              15

( 2 ) INFORMATION FOR SEQ ID NO: 604:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 604:

AAGCUGUUUG AGCUG                                                             15

( 2 ) INFORMATION FOR SEQ ID NO: 605:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 605:

AGCUGUUUGA GCUGA                                                             15

( 2 ) INFORMATION FOR SEQ ID NO: 606:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 606:

CGAGCCUAGG CCACC                                                             15

( 2 ) INFORMATION FOR SEQ ID NO: 607:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 607:

GACCUCUACC AGCCU                                                             15

( 2 ) INFORMATION FOR SEQ ID NO: 608:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 608:

UUCAGCUCCG GUCCU                                                             15

( 2 ) INFORMATION FOR SEQ ID NO: 609:

( i ) SEQUENCE CHARACTERISTICS:
      ( A ) LENGTH: 15 base pairs ( B ) TYPE: nucleic acid
( C ) STRANDEDNESS: single
( D ) TOPOLOGY: linear ( x i ) SEQUENCE DESCRIPTION: SEQ ID NO: 609:

CGGACUUUCG AUCUU                                                                                        15

( 2 ) INFORMATION FOR SEQ ID NO: 610:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 610:

AGGACCUCAC CCUGC                                                                                        15

( 2 ) INFORMATION FOR SEQ ID NO: 611:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 611:

CCUGUUUCCU GCCUC                                                                                        15

( 2 ) INFORMATION FOR SEQ ID NO: 612:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 612:

GGCGGCUCCA CCUCA                                                                                        15

( 2 ) INFORMATION FOR SEQ ID NO: 613:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 613:

UACAACUUUU CAGCU                                                                                        15

( 2 ) INFORMATION FOR SEQ ID NO: 614:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO: 614:

AACUUUUCAG CUCCG                                                                                        15

( 2 ) INFORMATION FOR SEQ ID NO: 615:

( i ) SEQUENCE CHARACTERISTICS:
( A ) LENGTH: 15 base pairs
( B ) TYPE: nucleic acid
( C ) STRANDEDNESS: single (D) TOPOLOGY: linear (x i) SEQUENCE DESCRIPTION: SEQ ID NO: 615:

ACCAGAUCCU GGAGA 15

(2) INFORMATION FOR SEQ ID NO: 616:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 616:

UGGGCCUCGU GAUGG 15

(2) INFORMATION FOR SEQ ID NO: 617:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 617:

CAGUCGUCCG CUUCC 15

(2) INFORMATION FOR SEQ ID NO: 618:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 618:

GGCCUGUUUC CUGCC 15

(2) INFORMATION FOR SEQ ID NO: 619:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 619:

UUUUGCUCCC UGGAA 15

(2) INFORMATION FOR SEQ ID NO: 620:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO: 620:

AGUGGGUCGA AGGUG 15

(2) INFORMATION FOR SEQ ID NO: 621:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO: 621:

UAACAGUCUA CAACU 15

( 2 ) INFORMATION FOR SEQ ID NO: 622:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 622:

AGCACCUCCC CACCU 15

( 2 ) INFORMATION FOR SEQ ID NO: 623:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 623:

GUACUGUACC ACUCU 15

( 2 ) INFORMATION FOR SEQ ID NO: 624:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 624:

UGCCCAUCGG GGUGG 15

( 2 ) INFORMATION FOR SEQ ID NO: 625:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 625:

GGAGACUCAG UGGCU 15

( 2 ) INFORMATION FOR SEQ ID NO: 626:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 626:

UGGCUGUCAC AGAAC 15

( 2 ) INFORMATION FOR SEQ ID NO: 627:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 627:

UGUGCUUUGA GAACU 15

( 2 ) INFORMATION FOR SEQ ID NO: 628:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 628:

GCGAGAUCGG GGAGG 15

( 2 ) INFORMATION FOR SEQ ID NO: 629:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 629:

GAGGUCUCGG AAGGG 15

( 2 ) INFORMATION FOR SEQ ID NO: 630:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 630:

CCCACCUACU UUUGU 15

( 2 ) INFORMATION FOR SEQ ID NO: 631:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 631:

ACUGCCUUGG UAGAG 15

( 2 ) INFORMATION FOR SEQ ID NO: 632:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 632:

UCUCUAUUGC CCCUG 15

( 2 ) INFORMATION FOR SEQ ID NO: 633:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 633:

GAAGGCUCAG GAGGA 15

-continued ( 2 ) INFORMATION FOR SEQ ID NO: 634:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 634:

GGAAUGUCAC CAGGA  15

( 2 ) INFORMATION FOR SEQ ID NO: 635:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 635:

AGUUGUUUUG CUCCC  15

( 2 ) INFORMATION FOR SEQ ID NO: 636:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 636:

CUGUUCUUCC UCAUG  15

( 2 ) INFORMATION FOR SEQ ID NO: 637:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 637:

CUGUGCUUUG AGAAC  15

( 2 ) INFORMATION FOR SEQ ID NO: 638:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 638:

AUGAAAUCAU GGUCC  15

( 2 ) INFORMATION FOR SEQ ID NO: 639:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 639:

GGACUAUAAU CAUUC  15

( 2 ) INFORMATION FOR SEQ ID NO: 640:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 640:

UUAUGUUUAU AACCG  15

( 2 ) INFORMATION FOR SEQ ID NO: 641:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 641:

CUACCAUCAC CGUGU  15

( 2 ) INFORMATION FOR SEQ ID NO: 642:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 642:

UCAUGGUCCC AGGCG  15

( 2 ) INFORMATION FOR SEQ ID NO: 643:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 643:

CUAUAAUCAU UCUGG  15

( 2 ) INFORMATION FOR SEQ ID NO: 644:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 644:

UGGUCAUUGU GGGCC  15

( 2 ) INFORMATION FOR SEQ ID NO: 645:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 645:

CAUGCCUUAG CAGCU  15

( 2 ) INFORMATION FOR SEQ ID NO: 646:

( i ) SEQUENCE CHARACTERISTICS:

(A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 646:

AGCACCUCCC CACCU 15

(2) INFORMATION FOR SEQ ID NO: 647:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 647:

CUUAUGUUUA UAACC 15

(2) INFORMATION FOR SEQ ID NO: 648:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 648:

UAUGUUUAUA ACCGC 15

(2) INFORMATION FOR SEQ ID NO: 649:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 649:

UGUUUAUAAC CGCCA 15

(2) INFORMATION FOR SEQ ID NO: 650:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 650:

GAAAGAUCAG GAUAU 15

(2) INFORMATION FOR SEQ ID NO: 651:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 651:

AGGAUAUACA AGUUA 15

(2) INFORMATION FOR SEQ ID NO: 652:

(i) SEQUENCE CHARACTERISTICS:
        (A) LENGTH: 15 base pairs
        (B) TYPE: nucleic acid ( C ) STRANDEDNESS: single
            ( D ) TOPOLOGY: linear ( x i ) SEQUENCE DESCRIPTION: SEQ ID NO: 652:

ACAAGUUACA GAAGG                                                                                        15

( 2 ) INFORMATION FOR SEQ ID NO: 653:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 653:

CCCACCUCCC UGAGC                                                                                        15

( 2 ) INFORMATION FOR SEQ ID NO: 654:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 654:

GAAACCUUUC CUUUG                                                                                        15

( 2 ) INFORMATION FOR SEQ ID NO: 655:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 655:

AACCUUUCCU UUGAA                                                                                        15

( 2 ) INFORMATION FOR SEQ ID NO: 656:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 656:

AGGACCUCAG CCUGG                                                                                        15

( 2 ) INFORMATION FOR SEQ ID NO: 657:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 657:

AGCCACUUCC UCUGG                                                                                        15

( 2 ) INFORMATION FOR SEQ ID NO: 658:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 658:

GCCACUUCCU CUGGC 15

( 2 ) INFORMATION FOR SEQ ID NO: 659:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 659:

ACUUCCUCUG GCUGU 15

( 2 ) INFORMATION FOR SEQ ID NO: 660:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 660:

CCGGACUUUC GAUCU 15

( 2 ) INFORMATION FOR SEQ ID NO: 661:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 661:

CGGACUUUCG AUCUU 15

( 2 ) INFORMATION FOR SEQ ID NO: 662:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 662:

UGCCCAUCGG GGUGG 15

( 2 ) INFORMATION FOR SEQ ID NO: 663:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 663:

CGGAUAUACC UGGAG 15

( 2 ) INFORMATION FOR SEQ ID NO: 664:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 664:

GAGACCUCUA CCAGC 15

( 2 ) INFORMATION FOR SEQ ID NO: 665:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 665:

GGCGGCUCCA CCUCA 15

( 2 ) INFORMATION FOR SEQ ID NO: 666:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 666:

GAAGCCUUCC UGCCC 15

( 2 ) INFORMATION FOR SEQ ID NO: 667:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 667:

GAGACAUUGU CCCCA 15

( 2 ) INFORMATION FOR SEQ ID NO: 668:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 668:

GCAUUGUUCU CUAAU 15

( 2 ) INFORMATION FOR SEQ ID NO: 669:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 669:

UUAGAGUUUU ACCAG 15

( 2 ) INFORMATION FOR SEQ ID NO: 670:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( x i ) SEQUENCE DESCRIPTION: SEQ ID NO: 670:

UAGAGUUUUA CCAGC 15

( 2 ) INFORMATION FOR SEQ ID NO: 671:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 671:

AGAGUUUUAC CAGCU     15

( 2 ) INFORMATION FOR SEQ ID NO: 672:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 672:

GAGUUUUACC AGCUA     15

( 2 ) INFORMATION FOR SEQ ID NO: 673:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 673:

ACCAGCUAUU UAUUG     15

( 2 ) INFORMATION FOR SEQ ID NO: 674:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 674:

CAGCUAUUUA UUGAG     15

( 2 ) INFORMATION FOR SEQ ID NO: 675:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 675:

AGCUAUUUAU UGAGU     15

( 2 ) INFORMATION FOR SEQ ID NO: 676:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 676:

GCUAUUUAUU GAGUA     15

( 2 ) INFORMATION FOR SEQ ID NO: 677:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 677:

UAUUUAUUGA GUACC         15

( 2 ) INFORMATION FOR SEQ ID NO: 678:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 678:

CAACUCUUCU UGAUG         15

( 2 ) INFORMATION FOR SEQ ID NO: 679:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 679:

GCAGCCUCUU AUGUU         15

( 2 ) INFORMATION FOR SEQ ID NO: 680:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 680:

GCCUCUUAUG UUUAU         15

( 2 ) INFORMATION FOR SEQ ID NO: 681:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 681:

UCUUCCUCAU GCAAG         15

( 2 ) INFORMATION FOR SEQ ID NO: 682:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 682:

AAGUUUUAUG UCGGC         15

( 2 ) INFORMATION FOR SEQ ID NO: 683:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 683:

UUUAUGUCGG CCUGA 15

( 2 ) INFORMATION FOR SEQ ID NO: 684:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 684:

GGAGACUCAG UGGCU 15

( 2 ) INFORMATION FOR SEQ ID NO: 685:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 685:

CUGGCAUUGU UCUCU 15

( 2 ) INFORMATION FOR SEQ ID NO: 686:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 686:

CUCAGGUAUC CAUCC 15

( 2 ) INFORMATION FOR SEQ ID NO: 687:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 687:

UGGAUCUCAG GCCGC 15

( 2 ) INFORMATION FOR SEQ ID NO: 688:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 688:

CUGACCUCCU GGAGG 15

( 2 ) INFORMATION FOR SEQ ID NO: 689:

( i ) SEQUENCE CHARACTERISTICS:
    ( A ) LENGTH: 15 base pairs ( B ) TYPE: nucleic acid
            ( C ) STRANDEDNESS: single
            ( D ) TOPOLOGY: linear ( x i ) SEQUENCE DESCRIPTION: SEQ ID NO: 689:

UGGAGCUAGC GGACC                                                                                           15

( 2 ) INFORMATION FOR SEQ ID NO: 690:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 690:

UAUCCAUCCA UCCCA                                                                                           15

( 2 ) INFORMATION FOR SEQ ID NO: 691:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 691:

UCCAAUUCAC ACUGA                                                                                           15

( 2 ) INFORMATION FOR SEQ ID NO: 692:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 692:

AUCACAUUCA CGGUG                                                                                           15

( 2 ) INFORMATION FOR SEQ ID NO: 693:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 693:

UCACAUUCAC GGUGC                                                                                           15

( 2 ) INFORMATION FOR SEQ ID NO: 694:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 694:

GGAAUGUCAC CAGGA                                                                                           15

( 2 ) INFORMATION FOR SEQ ID NO: 695:

( i ) SEQUENCE CHARACTERISTICS:
            ( A ) LENGTH: 15 base pairs
            ( B ) TYPE: nucleic acid
            ( C ) STRANDEDNESS: single ( D ) TOPOLOGY: linear ( x i ) SEQUENCE DESCRIPTION: SEQ ID NO: 695:

ACCAGAUCCU GGAGA 15

( 2 ) INFORMATION FOR SEQ ID NO: 696:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 696:

GAAGGGUCGU GCAAG 15

( 2 ) INFORMATION FOR SEQ ID NO: 697:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 697:

AAGCUGUUUG AGCUG 15

( 2 ) INFORMATION FOR SEQ ID NO: 698:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 698:

UAUAAGUUAU GGCCU 15

( 2 ) INFORMATION FOR SEQ ID NO: 699:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 699:

CAGUGGUUCU CUGCU 15

( 2 ) INFORMATION FOR SEQ ID NO: 700:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 700:

GAAAGAUCAC AUGGG 15

( 2 ) INFORMATION FOR SEQ ID NO: 701:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 701:

UGAGACUCCU GCCUG                                                                                              15

( 2 ) INFORMATION FOR SEQ ID NO: 702:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 702:

GAAACCUUUC CUUUG                                                                                              15

( 2 ) INFORMATION FOR SEQ ID NO: 703:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 703:

GACCUCUACC AGCCU                                                                                              15

( 2 ) INFORMATION FOR SEQ ID NO: 704:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 704:

UUUCGAUCUU CCAGC                                                                                              15

( 2 ) INFORMATION FOR SEQ ID NO: 705:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 705:

CCCAGCUCUC AGCAG                                                                                              15

( 2 ) INFORMATION FOR SEQ ID NO: 706:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 706:

CUGCUUUUGA ACAGA                                                                                              15

( 2 ) INFORMATION FOR SEQ ID NO: 707:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 707:

```
AACCUUUCCU UUGAA                                                                    15
```

(2) INFORMATION FOR SEQ ID NO: 708:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 708:

```
AGGUGGUUCU UCUGA                                                                    15
```

(2) INFORMATION FOR SEQ ID NO: 709:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 709:

```
GGUGGUUCUU CUGAG                                                                    15
```

(2) INFORMATION FOR SEQ ID NO: 710:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 710:

```
AGGGUUUCUC UACUG                                                                    15
```

(2) INFORMATION FOR SEQ ID NO: 711:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 711:

```
UGCUUUUCUC AUAAG                                                                    15
```

(2) INFORMATION FOR SEQ ID NO: 712:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 712:

```
AAGUUUUAUG UCGGC                                                                    15
```

(2) INFORMATION FOR SEQ ID NO: 713:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 713:

```
AUUCUCUAUU GCCCC                                                                    15
```

( 2 ) INFORMATION FOR SEQ ID NO: 714:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 714:

AUCCAGUAGA CACAA       15

( 2 ) INFORMATION FOR SEQ ID NO: 715:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 715:

AAACACUAUG UGGAC       15

( 2 ) INFORMATION FOR SEQ ID NO: 716:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 716:

AAGCUGUUUG AGCUG       15

( 2 ) INFORMATION FOR SEQ ID NO: 717:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 717:

UACUGGUCAG GAUGC       15

( 2 ) INFORMATION FOR SEQ ID NO: 718:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 718:

AAUGUCUCCG AGGCC       15

( 2 ) INFORMATION FOR SEQ ID NO: 719:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 719:

GAAGCCUUCC UGCCC       15

( 2 ) INFORMATION FOR SEQ ID NO: 720:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 720:

GACCUCUACC AGCCU 15

( 2 ) INFORMATION FOR SEQ ID NO: 721:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 721:

CCCAGCUCUC AGCAG 15

( 2 ) INFORMATION FOR SEQ ID NO: 722:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 722:

GAGGUCUCGG AAGGG 15

( 2 ) INFORMATION FOR SEQ ID NO: 723:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 723:

GAAGGGUCGU GCAAG 15

( 2 ) INFORMATION FOR SEQ ID NO: 724:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 724:

GGUACAUACG UGUGC 15

( 2 ) INFORMATION FOR SEQ ID NO: 725:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 725:

GGUGGGUCCG UGCAG 15

( 2 ) INFORMATION FOR SEQ ID NO: 726:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 726:

UAUUUAUUGA GUACC 15

(2) INFORMATION FOR SEQ ID NO: 727:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 727:

CCGGACUUUC GAUCU 15

(2) INFORMATION FOR SEQ ID NO: 728:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 728:

AGGACCUCAC CCUGC 15

(2) INFORMATION FOR SEQ ID NO: 729:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 729:

UUUUGCUCUG CCGCU 15

(2) INFORMATION FOR SEQ ID NO: 730:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 730:

AGUCUGUCAA ACAGG 15

(2) INFORMATION FOR SEQ ID NO: 731:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO: 731:

AUGAAAUCAU GGUCC 15

(2) INFORMATION FOR SEQ ID NO: 732:

(i) SEQUENCE CHARACTERISTICS:
(A) LENGTH: 15 base pairs
(B) TYPE: nucleic acid ( C ) STRANDEDNESS: single
            ( D ) TOPOLOGY: linear ( x i ) SEQUENCE DESCRIPTION: SEQ ID NO: 732:

UCAUGGUCCC AGGCG                                                                    15

( 2 ) INFORMATION FOR SEQ ID NO: 733:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 733:

GGUGGGUCCG UGCAG                                                                    15

( 2 ) INFORMATION FOR SEQ ID NO: 734:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 734:

CUCCGGUCCU GACCC                                                                    15

( 2 ) INFORMATION FOR SEQ ID NO: 735:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 735:

ACAGUCUACA ACUUU                                                                    15

( 2 ) INFORMATION FOR SEQ ID NO: 736:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 736:

CUGACCUCCU GGAGG                                                                    15

( 2 ) INFORMATION FOR SEQ ID NO: 737:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 737:

GGAGCCUCCG GACUU                                                                    15

( 2 ) INFORMATION FOR SEQ ID NO: 738:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 738:

UGCCUUUAGC UCCCA 15

( 2 ) INFORMATION FOR SEQ ID NO: 739:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 739:

CUGGACUAUA AUCAU 15

( 2 ) INFORMATION FOR SEQ ID NO: 740:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 740:

AGGUGGUUCU UCUGA 15

( 2 ) INFORMATION FOR SEQ ID NO: 741:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 741:

UGAGACUCCU GCCUG 15

( 2 ) INFORMATION FOR SEQ ID NO: 742:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 742:

CCAAUGUCAG CCACC 15

( 2 ) INFORMATION FOR SEQ ID NO: 743:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 743:

GCAGCCUCUU AUGUU 15

( 2 ) INFORMATION FOR SEQ ID NO: 744:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 744:

```
GCCAAGUAAC  UGUGA                                                                                   15
```

( 2 ) INFORMATION FOR SEQ ID NO: 745:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 745:

```
GGACCUUCAG  CCAAG                                                                                   15
```

( 2 ) INFORMATION FOR SEQ ID NO: 746:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 746:

```
UUCCGCUACC  AUCAC                                                                                   15
```

( 2 ) INFORMATION FOR SEQ ID NO: 747:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 747:

```
CGGACUUUCG  AUCUU                                                                                   15
```

( 2 ) INFORMATION FOR SEQ ID NO: 748:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 748:

```
UUAAUUUAGA  GUUUU                                                                                   15
```

( 2 ) INFORMATION FOR SEQ ID NO: 749:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 749:

```
ACUUCAUUCU  CUAUU                                                                                   15
```

( 2 ) INFORMATION FOR SEQ ID NO: 750:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 750:

```
CUUCAUUCUC  UAUUG                                                                                   15
```

( 2 ) INFORMATION FOR SEQ ID NO: 751:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 751:

UUGAUGUAUU UAUUA 15

( 2 ) INFORMATION FOR SEQ ID NO: 752:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 752:

UGUAUUUAUU AAUUU 15

( 2 ) INFORMATION FOR SEQ ID NO: 753:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 753:

GAAGCUUCUU UUGCU 15

( 2 ) INFORMATION FOR SEQ ID NO: 754:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 754:

AGCUUCUUUU GCUCU 15

( 2 ) INFORMATION FOR SEQ ID NO: 755:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 755:

UGUAUUUAUU AAUUU 15

( 2 ) INFORMATION FOR SEQ ID NO: 756:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 756:

UGUAUUUAUU AAUUU 15

(2) INFORMATION FOR SEQ ID NO: 757:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 757:

UUGUUCUCUA AUGUC         15

(2) INFORMATION FOR SEQ ID NO: 758:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 758:

UUUCUCUACU GGUCA         15

(2) INFORMATION FOR SEQ ID NO: 759:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 759:

UGCUUUUCUC AUAAG         15

(2) INFORMATION FOR SEQ ID NO: 760:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 760:

AUUUAUUAAU UUAGA         15

(2) INFORMATION FOR SEQ ID NO: 761:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 761:

UAUUCGUUUC CGGAG         15

(2) INFORMATION FOR SEQ ID NO: 762:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 762:

AUUCGUUUCC GGAGA         15

(2) INFORMATION FOR SEQ ID NO: 763:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 763:

UUCGUUUCCG GAGAG 15

( 2 ) INFORMATION FOR SEQ ID NO: 764:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 764:

UUCUCAUAAG GGUCG 15

( 2 ) INFORMATION FOR SEQ ID NO: 765:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 765:

UGGAGGUCUC GGAAG 15

( 2 ) INFORMATION FOR SEQ ID NO: 766:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 766:

GAGGUCUCGG AAGGG 15

( 2 ) INFORMATION FOR SEQ ID NO: 767:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 767:

CAGCGUCCUG AUGAGGCCGA AAGGCCGAAA CUGGGG 36

( 2 ) INFORMATION FOR SEQ ID NO: 768:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 768:

AGCAGAGCUG AUGAGGCCGA AAGGCCGAAA GCUCAG 36

( 2 ) INFORMATION FOR SEQ ID NO: 769:

( i ) SEQUENCE CHARACTERISTICS:
      ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO: 769:

AGUAGCACUG AUGAGGCCGA AAGGCCGAAA GGAGCU  36

(2) INFORMATION FOR SEQ ID NO: 770:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 770:

CUCUGAGCUG AUGAGGCCGA AAGGCCGAAA GCAGAG  36

(2) INFORMATION FOR SEQ ID NO: 771:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 771:

CAACUCUCUG AUGAGGCCGA AAGGCCGAAA GUAGCA  36

(2) INFORMATION FOR SEQ ID NO: 772:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 772:

AGGUUGCCUG AUGAGGCCGA AAGGCCGAAA CUCUGA  36

(2) INFORMATION FOR SEQ ID NO: 773:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 773:

CGAGGCUCUG AUGAGGCCGA AAGGCCGAAA GGUUGC  36

(2) INFORMATION FOR SEQ ID NO: 774:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 774:

CCAUAGCCUG AUGAGGCCGA AAGGCCGAAA GGCUGA  36

(2) INFORMATION FOR SEQ ID NO: 775:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO: 775:

GGAGCCACUG AUGAGGCCGA AAGGCCGAAA GCGAGG 36

(2) INFORMATION FOR SEQ ID NO: 776:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 776:

CUGCUGGCUG AUGAGGCCGA AAGGCCGAAA GCCAUA 36

(2) INFORMATION FOR SEQ ID NO: 777:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 777:

GGACCAGCUG AUGAGGCCGA AAGGCCGAAA GUGCGG 36

(2) INFORMATION FOR SEQ ID NO: 778:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 778:

CGAGCAGCUG AUGAGGCCGA AAGGCCGAAA CCAGGA 36

(2) INFORMATION FOR SEQ ID NO: 779:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 779:

GAGCCCCUG AUGAGGCCGA AAGGCCGAAA GCAGGA 36

(2) INFORMATION FOR SEQ ID NO: 780:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 780:

GGGAACACUG AUGAGGCCGA AAGGCCGAAA GCCCCG 36

(2) INFORMATION FOR SEQ ID NO: 781:

(i) SEQUENCE CHARACTERISTICS:
        (A) LENGTH: 36 base pairs
        (B) TYPE: nucleic acid
        (C) STRANDEDNESS: single
        (D) TOPOLOGY: linear -continued ( x i ) SEQUENCE DESCRIPTION: SEQ ID NO: 781:

UCCUGGGCUG AUGAGGCCGA AAGGCCGAAA CAGAGC　　　　　　　　　　　　　　36

( 2 ) INFORMATION FOR SEQ ID NO: 782:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 782:

GUCCUGGCUG AUGAGGCCGA AAGGCCGAAA ACAGAG　　　　　　　　　　　　　　36

( 2 ) INFORMATION FOR SEQ ID NO: 783:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 783:

GGACACACUG AUGAGGCCGA AAGGCCGAAA UGUCUG　　　　　　　　　　　　　　36

( 2 ) INFORMATION FOR SEQ ID NO: 784:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 784:

UGAGGGGCUG AUGAGGCCGA AAGGCCGAAA CACAGA　　　　　　　　　　　　　　36

( 2 ) INFORMATION FOR SEQ ID NO: 785:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 785:

GACUUUUCUG AUGAGGCCGA AAGGCCGAAA GGGGGA　　　　　　　　　　　　　　36

( 2 ) INFORMATION FOR SEQ ID NO: 786:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 786:

GCAGGAUCUG AUGAGGCCGA AAGGCCGAAA CUUUUG　　　　　　　　　　　　　　36

( 2 ) INFORMATION FOR SEQ ID NO: 787:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 787:

GGGGCAGCUG AUGAGGCCGA AAGGCCGAAA UGACUU 36

(2) INFORMATION FOR SEQ ID NO: 788:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 788:

CAGCACGCUG AUGAGGCCGA AAGGCCGAAA GCCUCC 36

(2) INFORMATION FOR SEQ ID NO: 789:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 789:

GUCACAGCUG AUGAGGCCGA AAGGCCGAAA GGUGCU 36

(2) INFORMATION FOR SEQ ID NO: 790:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 790:

GCCCAACCUG AUGAGGCCGA AAGGCCGAAA CUUGGG 36

(2) INFORMATION FOR SEQ ID NO: 791:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 791:

UAUGCCCCUG AUGAGGCCGA AAGGCCGAAA CAACUU 36

(2) INFORMATION FOR SEQ ID NO: 792:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 792:

GGGUCUCCUG AUGAGGCCGA AAGGCCGAAA UGCCCA 36

(2) INFORMATION FOR SEQ ID NO: 793:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 793:

UUUAGGCCUG AUGAGGCCGA AAGGCCGAAA CGGGGU 36

( 2 ) INFORMATION FOR SEQ ID NO: 794:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 794:

UCCUUUUCUG AUGAGGCCGA AAGGCCGAAA GGCAAC    36

( 2 ) INFORMATION FOR SEQ ID NO: 795:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 795:

CAGGAGCCUG AUGAGGCCGA AAGGCCGAAA CUCCUU    36

( 2 ) INFORMATION FOR SEQ ID NO: 796:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 796:

CAGGCAGCUG AUGAGGCCGA AAGGCCGAAA GCAACU    36

( 2 ) INFORMATION FOR SEQ ID NO: 797:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 797:

CAGUUCACUG AUGAGGCCGA AAGGCCGAAA CACCUU    36

( 2 ) INFORMATION FOR SEQ ID NO: 798:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 798:

GGUUGGCCUG AUGAGGCCGA AAGGCCGAAA UCUUCU    36

( 2 ) INFORMATION FOR SEQ ID NO: 799:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 799:

GUUUGAACUG AUGAGGCCGA AAGGCCGAAA GCACAU    36

( 2 ) INFORMATION FOR SEQ ID NO: 800:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO: 800:

CAGUUUGCUG AUGAGGCCGA AAGGCCGAAA UAGCAC   36

( 2 ) INFORMATION FOR SEQ ID NO: 801:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 801:

GCAGUUUCUG AUGAGGCCGA AAGGCCGAAA AUAGCA   36

( 2 ) INFORMATION FOR SEQ ID NO: 802:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 802:

AGCUGUUCUG AUGAGGCCGA AAGGCCGAAA CUGCCC   36

( 2 ) INFORMATION FOR SEQ ID NO: 803:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 803:

AAGGUUUCUG AUGAGGCCGA AAGGCCGAAA GCUGUU   36

( 2 ) INFORMATION FOR SEQ ID NO: 804:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 804:

GGUGAGGCUG AUGAGGCCGA AAGGCCGAAA GGUUUU   36

( 2 ) INFORMATION FOR SEQ ID NO: 805:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 805:

CGGUGAGCUG AUGAGGCCGA AAGGCCGAAA AGGUUU   36

( 2 ) INFORMATION FOR SEQ ID NO: 806:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 806:

ACACGGUCUG AUGAGGCCGA AAGGCCGAAA GGAAGG 36

( 2 ) INFORMATION FOR SEQ ID NO: 807:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 807:

AGUCCAGCUG AUGAGGCCGA AAGGCCGAAA CACGGU 36

( 2 ) INFORMATION FOR SEQ ID NO: 808:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 808:

CGUUCUGCUG AUGAGGCCGA AAGGCCGAAA GUCCAG 36

( 2 ) INFORMATION FOR SEQ ID NO: 809:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 809:

AAGAGGGCUG AUGAGGCCGA AAGGCCGAAA GGGGUG 36

( 2 ) INFORMATION FOR SEQ ID NO: 810:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 810:

CUGCCAACUG AUGAGGCCGA AAGGCCGAAA GGGGAG 36

( 2 ) INFORMATION FOR SEQ ID NO: 811:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 811:

GGCUGCCCUG AUGAGGCCGA AAGGCCGAAA GAGGGG 36

( 2 ) INFORMATION FOR SEQ ID NO: 812:

( i ) SEQUENCE CHARACTERISTICS:
( A ) LENGTH: 36 base pairs
( B ) TYPE: nucleic acid ( C ) STRANDEDNESS: single
( D ) TOPOLOGY: linear ( x i ) SEQUENCE DESCRIPTION: SEQ ID NO: 812:

GUAGGGUCUG AUGAGGCCGA AAGGCCGAAA GGUUCU 36

( 2 ) INFORMATION FOR SEQ ID NO: 813:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 813:

CGUAGGGCUG AUGAGGCCGA AAGGCCGAAA AGGUUC 36

( 2 ) INFORMATION FOR SEQ ID NO: 814:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 814:

GGCAGCGCUG AUGAGGCCGA AAGGCCGAAA GGGUAA 36

( 2 ) INFORMATION FOR SEQ ID NO: 815:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 815:

CCACGGUCUG AUGAGGCCGA AAGGCCGAAA GGUUGG 36

( 2 ) INFORMATION FOR SEQ ID NO: 816:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 816:

CCCCACGCUG AUGAGGCCGA AAGGCCGAAA GCAGCA 36

( 2 ) INFORMATION FOR SEQ ID NO: 817:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 817:

UGGUCGUCUG AUGAGGCCGA AAGGCCGAAA CCUCAG 36

( 2 ) INFORMATION FOR SEQ ID NO: 818:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 818:

CCAUGGUCUG AUGAGGCCGA AAGGCCGAAA UCUCUC 36

( 2 ) INFORMATION FOR SEQ ID NO: 819:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 819:

CACGAGACUG AUGAGGCCGA AAGGCCGAAA UUGGCU 36

( 2 ) INFORMATION FOR SEQ ID NO: 820:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 820:

GCACGAGCUG AUGAGGCCGA AAGGCCGAAA AUUGGC 36

( 2 ) INFORMATION FOR SEQ ID NO: 821:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 821:

GGCACGACUG AUGAGGCCGA AAGGCCGAAA AAUUGG 36

( 2 ) INFORMATION FOR SEQ ID NO: 822:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 822:

GCGGCACCUG AUGAGGCCGA AAGGCCGAAA GAAAUU 36

( 2 ) INFORMATION FOR SEQ ID NO: 823:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 823:

GUUCUCACUG AUGAGGCCGA AAGGCCGAAA CAGCUC 36

( 2 ) INFORMATION FOR SEQ ID NO: 824:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 824:

UGUUCUCCUG AUGAGGCCGA AAGGCCGAAA ACAGCU 36

( 2 ) INFORMATION FOR SEQ ID NO: 825:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 825:

GGGGGCCCUG AUGAGGCCGA AAGGCCGAAA GGUGUU 36

( 2 ) INFORMATION FOR SEQ ID NO: 826:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 826:

GAGCUGGCUG AUGAGGCCGA AAGGCCGAAA GGGGGC 36

( 2 ) INFORMATION FOR SEQ ID NO: 827:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 827:

AGGUCUGCUG AUGAGGCCGA AAGGCCGAAA GCUGGU 36

( 2 ) INFORMATION FOR SEQ ID NO: 828:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 828:

CAGGACACUG AUGAGGCCGA AAGGCCGAAA GGUCUG 36

( 2 ) INFORMATION FOR SEQ ID NO: 829:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 829:

GCAGGACCUG AUGAGGCCGA AAGGCCGAAA AGGUCU 36

( 2 ) INFORMATION FOR SEQ ID NO: 830:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 830:

CUGGCAGCUG AUGAGGCCGA AAGGCCGAAA CAAAGG 36

( 2 ) INFORMATION FOR SEQ ID NO: 831:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 831:

UGUGGGGCUG AUGAGGCCGA AAGGCCGAAA GUCGCU      36

( 2 ) INFORMATION FOR SEQ ID NO: 832:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 832:

GGCUGACCUG AUGAGGCCGA AAGGCCGAAA GUUGUG      36

( 2 ) INFORMATION FOR SEQ ID NO: 833:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 833:

GGGGGCUCUG AUGAGGCCGA AAGGCCGAAA CAAGUU      36

( 2 ) INFORMATION FOR SEQ ID NO: 834:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 834:

CCUCUAGCUG AUGAGGCCGA AAGGCCGAAA CCCGGG      36

( 2 ) INFORMATION FOR SEQ ID NO: 835:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 835:

CCACCUCCUG AUGAGGCCGA AAGGCCGAAA GGACCC      36

( 2 ) INFORMATION FOR SEQ ID NO: 836:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 836:

GGGAACACUG AUGAGGCCGA AAGGCCGAAA CCACGG      36

( 2 ) INFORMATION FOR SEQ ID NO: 837:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 837:

UCCAGGGCUG AUGAGGCCGA AAGGCCGAAA CAGACC    36

( 2 ) INFORMATION FOR SEQ ID NO: 838:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 838:

GUCCAGGCUG AUGAGGCCGA AAGGCCGAAA ACAGAC    36

( 2 ) INFORMATION FOR SEQ ID NO: 839:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 839:

GACUGGGCUG AUGAGGCCGA AAGGCCGAAA CAGCCC    36

( 2 ) INFORMATION FOR SEQ ID NO: 840:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 840:

AGACUGGCUG AUGAGGCCGA AAGGCCGAAA ACAGCC    36

( 2 ) INFORMATION FOR SEQ ID NO: 841:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 841:

CCUCCGACUG AUGAGGCCGA AAGGCCGAAA CUGGGA    36

( 2 ) INFORMATION FOR SEQ ID NO: 842:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 842:

GGCCUCCCUG AUGAGGCCGA AAGGCCGAAA GACUGG    36

( 2 ) INFORMATION FOR SEQ ID NO: 843:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 843:

CCAGGUGCUG AUGAGGCCGA AAGGCCGAAA CCUGGG      36

( 2 ) INFORMATION FOR SEQ ID NO: 844:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 844:

GGGGUUCCUG AUGAGGCCGA AAGGCCGAAA CCUCUG      36

( 2 ) INFORMATION FOR SEQ ID NO: 845:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 845:

CAUAGGUCUG AUGAGGCCGA AAGGCCGAAA CUGUGG      36

( 2 ) INFORMATION FOR SEQ ID NO: 846:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 846:

GUUGCCACUG AUGAGGCCGA AAGGCCGAAA GGUGAC      36

( 2 ) INFORMATION FOR SEQ ID NO: 847:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 847:

CGAGAAGCUG AUGAGGCCGA AAGGCCGAAA GUCGUU      36

( 2 ) INFORMATION FOR SEQ ID NO: 848:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 848:

GGCCGAGCUG AUGAGGCCGA AAGGCCGAAA GGAGUC      36

( 2 ) INFORMATION FOR SEQ ID NO: 849:

( i ) SEQUENCE CHARACTERISTICS:
    ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO: 849:

UGGCCGACUG AUGAGGCCGA AAGGCCGAAA AGGAGU 36

(2) INFORMATION FOR SEQ ID NO: 850:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 850:

CUUGGCCCUG AUGAGGCCGA AAGGCCGAAA GAAGGA 36

(2) INFORMATION FOR SEQ ID NO: 851:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 851:

ACUGACUCUG AUGAGGCCGA AAGGCCGAAA GGCCUU 36

(2) INFORMATION FOR SEQ ID NO: 852:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 852:

UCACACUCUG AUGAGGCCGA AAGGCCGAAA CUGAGG 36

(2) INFORMATION FOR SEQ ID NO: 853:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 853:

CCAGUAUCUG AUGAGGCCGA AAGGCCGAAA CUGCAC 36

(2) INFORMATION FOR SEQ ID NO: 854:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 854:

UCCCCAGCUG AUGAGGCCGA AAGGCCGAAA UUACUG 36

(2) INFORMATION FOR SEQ ID NO: 855:

(i) SEQUENCE CHARACTERISTICS:
(A) LENGTH: 36 base pairs
(B) TYPE: nucleic acid
(C) STRANDEDNESS: single ( D ) TOPOLOGY: linear ( x i ) SEQUENCE DESCRIPTION: SEQ ID NO: 855:

AGCUGUACUG AUGAGGCGA AAGGCCGAAA UGGUCA          36

( 2 ) INFORMATION FOR SEQ ID NO: 856:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 856:

AAAGCUGCUG AUGAGGCCGA AAGGCCGAAA GAUGGU          36

( 2 ) INFORMATION FOR SEQ ID NO: 857:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 857:

CGCCGGACUG AUGAGGCCGA AAGGCCGAAA GCUGUA          36

( 2 ) INFORMATION FOR SEQ ID NO: 858:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 858:

GCGCCGGCUG AUGAGGCCGA AAGGCCGAAA AGCUGU          36

( 2 ) INFORMATION FOR SEQ ID NO: 859:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 859:

GGCGCCGCUG AUGAGGCCGA AAGGCCGAAA AAGCUG          36

( 2 ) INFORMATION FOR SEQ ID NO: 860:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 860:

UCGUCAGCUG AUGAGGCCGA AAGGCCGAAA UCACGU          36

( 2 ) INFORMATION FOR SEQ ID NO: 861:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 861:

UUCGUCACUG AUGAGGCCGA AAGGCCGAAA AUCACG 36

( 2 ) INFORMATION FOR SEQ ID NO: 862:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 862:

CUUCUGACUG AUGAGGCCGA AAGGCCGAAA CCUCUG 36

( 2 ) INFORMATION FOR SEQ ID NO: 863:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 863:

CCCUUCUCUG AUGAGGCCGA AAGGCCGAAA GACCUC 36

( 2 ) INFORMATION FOR SEQ ID NO: 864:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 864:

UUGGCUCCUG AUGAGGCCGA AAGGCCGAAA GGGUGG 36

( 2 ) INFORMATION FOR SEQ ID NO: 865:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 865:

GGGCUGGCUG AUGAGGCCGA AAGGCCGAAA CCCCAU 36

( 2 ) INFORMATION FOR SEQ ID NO: 866:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 866:

UGGGCUGCUG AUGAGGCCGA AAGGCCGAAA ACCCCA 36

( 2 ) INFORMATION FOR SEQ ID NO: 867:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 867:

UCAGCAGCUG AUGAGGCCGA AAGGCCGAAA GCUGGG 36

(2) INFORMATION FOR SEQ ID NO: 868:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 868:

GCAGGAGCUG AUGAGGCCGA AAGGCCGAAA GCUGCG 36

(2) INFORMATION FOR SEQ ID NO: 869:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 869:

AGCAGGACUG AUGAGGCCGA AAGGCCGAAA AGCUGC 36

(2) INFORMATION FOR SEQ ID NO: 870:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 870:

AGAGCAGCUG AUGAGGCCGA AAGGCCGAAA GAAGCU 36

(2) INFORMATION FOR SEQ ID NO: 871:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 871:

GGUUGCACUG AUGAGGCCGA AAGGCCGAAA GCAGGA 36

(2) INFORMATION FOR SEQ ID NO: 872:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 872:

UGUGUAUCUG AUGAGGCCGA AAGGCCGAAA GCUGGC 36

(2) INFORMATION FOR SEQ ID NO: 873:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 873:

UUGUGUACUG AUGAGGCCGA AAGGCCGAAA AGCUGG 36

( 2 ) INFORMATION FOR SEQ ID NO: 874:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 874:

UCUUGUGCUG AUGAGGCCGA AAGGCCGAAA UAAGCU     36

( 2 ) INFORMATION FOR SEQ ID NO: 875:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 875:

GGACACGCUG AUGAGGCCGA AAGGCCGAAA GCUCCC     36

( 2 ) INFORMATION FOR SEQ ID NO: 876:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 876:

AGGACACCUG AUGAGGCCGA AAGGCCGAAA AGCUCC     36

( 2 ) INFORMATION FOR SEQ ID NO: 877:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 877:

CAUACAGCUG AUGAGGCCGA AAGGCCGAAA CACGAA     36

( 2 ) INFORMATION FOR SEQ ID NO: 878:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 878:

GGGGCCACUG AUGAGGCCGA AAGGCCGAAA CAGGAC     36

( 2 ) INFORMATION FOR SEQ ID NO: 879:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 879:

CCCGGACCUG AUGAGGCCGA AAGGCCGAAA UCCCUC     36

( 2 ) INFORMATION FOR SEQ ID NO: 880:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 880:

UUUCCCGCUG AUGAGGCCGA AAGGCCGAAA CAAUCC    36

( 2 ) INFORMATION FOR SEQ ID NO: 881:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 881:

UGCUGGGCUG AUGAGGCCGA AAGGCCGAAA UUUUCU    36

( 2 ) INFORMATION FOR SEQ ID NO: 882:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 882:

CUGCUGGCUG AUGAGGCCGA AAGGCCGAAA AUUUUC    36

( 2 ) INFORMATION FOR SEQ ID NO: 883:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 883:

CACAUUGCUG AUGAGGCCGA AAGGCCGAAA GUCUGC    36

( 2 ) INFORMATION FOR SEQ ID NO: 884:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 884:

UUCCCCCCUG AUGAGGCCGA AAGGCCGAAA GCCUGG    36

( 2 ) INFORMATION FOR SEQ ID NO: 885:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 885:

CUCGGGCCUG AUGAGGCCGA AAGGCCGAAA UGGGUU    36

( 2 ) INFORMATION FOR SEQ ID NO: 886:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 886:

GACACUUCUG AUGAGGCCGA AAGGCCGAAA GCUCGG 36

(2) INFORMATION FOR SEQ ID NO: 887:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 887:

UCCUUUACUG AUGAGGCCGA AAGGCCGAAA CACUUG 36

(2) INFORMATION FOR SEQ ID NO: 888:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 888:

CAUCCUUCUG AUGAGGCCGA AAGGCCGAAA GACACU 36

(2) INFORMATION FOR SEQ ID NO: 889:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 889:

AGUGGGACUG AUGAGGCCGA AAGGCCGAAA GUGCCA 36

(2) INFORMATION FOR SEQ ID NO: 890:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 890:

CAGUGGGCUG AUGAGGCCGA AAGGCCGAAA AGUGCC 36

(2) INFORMATION FOR SEQ ID NO: 891:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 891:

GCAGUGGCUG AUGAGGCCGA AAGGCCGAAA AAGUGC 36

(2) INFORMATION FOR SEQ ID NO: 892:

(i) SEQUENCE CHARACTERISTICS:
        (A) LENGTH: 36 base pairs
        (B) TYPE: nucleic acid (C) STRANDEDNESS: single
(D) TOPOLOGY: linear (xi) SEQUENCE DESCRIPTION: SEQ ID NO: 892:

AUUCCCCUG AUGAGGCCGA AAGGCCGAAA UGGGCA 36

(2) INFORMATION FOR SEQ ID NO: 893:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 893:

AGUCACUCUG AUGAGGCCGA AAGGCCGAAA UUCCCC 36

(2) INFORMATION FOR SEQ ID NO: 894:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 894:

CUCGAGUCUG AUGAGGCCGA AAGGCCGAAA CAGUCA 36

(2) INFORMATION FOR SEQ ID NO: 895:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 895:

AGAUCUCCUG AUGAGGCCGA AAGGCCGAAA GUGACA 36

(2) INFORMATION FOR SEQ ID NO: 896:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 896:

CCCUCAACUG AUGAGGCCGA AAGGCCGAAA UCUCGA 36

(2) INFORMATION FOR SEQ ID NO: 897:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 897:

UGCCCUCCUG AUGAGGCCGA AAGGCCGAAA GAUCUC 36

(2) INFORMATION FOR SEQ ID NO: 898:

(i) SEQUENCE CHARACTERISTICS:
(A) LENGTH: 36 base pairs
(B) TYPE: nucleic acid
(C) STRANDEDNESS: single
(D) TOPOLOGY: linear ( x i ) SEQUENCE DESCRIPTION: SEQ ID NO: 898:

ACAGAGGCUG AUGAGGCCGA AAGGCCGAAA GGUGCC  36

( 2 ) INFORMATION FOR SEQ ID NO: 899:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 899:

CCCGACACUG AUGAGGCCGA AAGGCCGAAA GGUAGG  36

( 2 ) INFORMATION FOR SEQ ID NO: 900:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 900:

CUGGCCCUG AUGAGGCCGA AAGGCCGAAA CAGAGG  36

( 2 ) INFORMATION FOR SEQ ID NO: 901:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 901:

UCCCCUUCUG AUGAGGCCGA AAGGCCGAAA GUGCUC  36

( 2 ) INFORMATION FOR SEQ ID NO: 902:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 902:

CGCGGGUCUG AUGAGGCCGA AAGGCCGAAA CCUCCC  36

( 2 ) INFORMATION FOR SEQ ID NO: 903:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 903:

GGGGGGACUG AUGAGGCCGA AAGGCCGAAA GCACAU  36

( 2 ) INFORMATION FOR SEQ ID NO: 904:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 904:

CCGGGGGCUG AUGAGGCCGA AAGGCCGAAA GAGCAC 36

(2) INFORMATION FOR SEQ ID NO: 905:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 905:

AAUCUCACUG AUGAGGCCGA AAGGCCGAAA CCGGGG 36

(2) INFORMATION FOR SEQ ID NO: 906:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 906:

UGAUGACCUG AUGAGGCCGA AAGGCCGAAA UCUCAU 36

(2) INFORMATION FOR SEQ ID NO: 907:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 907:

UGAUGAUCUG AUGAGGCCGA AAGGCCGAAA CAAUCU 36

(2) INFORMATION FOR SEQ ID NO: 908:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 908:

CAGUGAUCUG AUGAGGCCGA AAGGCCGAAA UGACAA 36

(2) INFORMATION FOR SEQ ID NO: 909:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 909:

CCACAGUCUG AUGAGGCCGA AAGGCCGAAA UGAUGA 36

(2) INFORMATION FOR SEQ ID NO: 910:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 910:

CGGCUGCCUG AUGAGGCCGA AAGGCCGAAA CCACAG 36

( 2 ) INFORMATION FOR SEQ ID NO: 911:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 911:

CCAUUACUG AUGAGGCCGA AAGGCCGAAA CUGCGG    36

( 2 ) INFORMATION FOR SEQ ID NO: 912:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 912:

UGCCCAUCUG AUGAGGCCGA AAGGCCGAAA UGACUG    36

( 2 ) INFORMATION FOR SEQ ID NO: 913:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 913:

ACGUGCUCUG AUGAGGCCGA AAGGCCGAAA GGCCUG    36

( 2 ) INFORMATION FOR SEQ ID NO: 914:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 914:

AUAGAGGCUG AUGAGGCCGA AAGGCCGAAA CGUGCU    36

( 2 ) INFORMATION FOR SEQ ID NO: 915:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 915:

GGUUAUACUG AUGAGGCCGA AAGGCCGAAA GGUACG    36

( 2 ) INFORMATION FOR SEQ ID NO: 916:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 916:

GCGGUUACUG AUGAGGCCGA AAGGCCGAAA GAGGUA    36

( 2 ) INFORMATION FOR SEQ ID NO: 917:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 917:

UGGCGGUCUG AUGAGGCCGA AAGGCCGAAA UAGAGG   36

( 2 ) INFORMATION FOR SEQ ID NO: 918:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 918:

AUUUCUUCUG AUGAGGCCGA AAGGCCGAAA UCUUCC   36

( 2 ) INFORMATION FOR SEQ ID NO: 919:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 919:

UAGUCUGCUG AUGAGGCCGA AAGGCCGAAA UUUCUU   36

( 2 ) INFORMATION FOR SEQ ID NO: 920:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 920:

CCUGUUGCUG AUGAGGCCGA AAGGCCGAAA GUCUGU   36

( 2 ) INFORMATION FOR SEQ ID NO: 921:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 921:

GUUCAGGCUG AUGAGGCCGA AAGGCCGAAA GGCGUG   36

( 2 ) INFORMATION FOR SEQ ID NO: 922:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 922:

CCCGGGACUG AUGAGGCCGA AAGGCCGAAA GGUUCA   36

( 2 ) INFORMATION FOR SEQ ID NO: 923:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 923:

GUCCCGGCUG AUGAGGCCGA AAGGCCGAAA UAGGUU    36

( 2 ) INFORMATION FOR SEQ ID NO: 924:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 924:

CGAGGAACUG AUGAGGCCGA AAGGCCGAAA GGCCCU    36

( 2 ) INFORMATION FOR SEQ ID NO: 925:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 925:

GCCGAGGCUG AUGAGGCCGA AAGGCCGAAA GAGGCC    36

( 2 ) INFORMATION FOR SEQ ID NO: 926:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 926:

GGCCGAGCUG AUGAGGCCGA AAGGCCGAAA AGAGGC    36

( 2 ) INFORMATION FOR SEQ ID NO: 927:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 927:

GAAGGCCCUG AUGAGGCCGA AAGGCCGAAA GGAAGA    36

( 2 ) INFORMATION FOR SEQ ID NO: 928:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 928:

AUAUGGGCUG AUGAGGCCGA AAGGCCGAAA GGCCGA    36

( 2 ) INFORMATION FOR SEQ ID NO: 929:

( i ) SEQUENCE CHARACTERISTICS:
        ( A ) LENGTH: 36 base pairs (B) TYPE: nucleic acid
        (C) STRANDEDNESS: single
        (D) TOPOLOGY: linear (xi) SEQUENCE DESCRIPTION: SEQ ID NO: 929:

AAUAUGGCUG AUGAGGCCGA AAGGCCGAAA AGGCCG                                    36

(2) INFORMATION FOR SEQ ID NO: 930:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 930:

CCACCAACUG AUGAGGCCGA AAGGCCGAAA UGGGAA                                    36

(2) INFORMATION FOR SEQ ID NO: 931:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 931:

UGCCACCCUG AUGAGGCCGA AAGGCCGAAA UAUGGG                                    36

(2) INFORMATION FOR SEQ ID NO: 932:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 932:

CAUGGCACUG AUGAGGCCGA AAGGCCGAAA UGUCUU                                    36

(2) INFORMATION FOR SEQ ID NO: 933:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 933:

GUAGGUGCUG AUGAGGCCGA AAGGCCGAAA GCUGCA                                    36

(2) INFORMATION FOR SEQ ID NO: 934:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 934:

GGGCCGGCUG AUGAGGCCGA AAGGCCGAAA GGUGUA                                    36

(2) INFORMATION FOR SEQ ID NO: 935:

(i) SEQUENCE CHARACTERISTICS:
        (A) LENGTH: 36 base pairs
        (B) TYPE: nucleic acid
        (C) STRANDEDNESS: single (D) TOPOLOGY: linear (xi) SEQUENCE DESCRIPTION: SEQ ID NO: 935:

UGAGGACCUG AUGAGGCCGA AAGGCCGAAA UGCCCU  36

(2) INFORMATION FOR SEQ ID NO: 936:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 936:

GACUGAGCUG AUGAGGCCGA AAGGCCGAAA CAAUGC  36

(2) INFORMATION FOR SEQ ID NO: 937:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 937:

UCUGACUCUG AUGAGGCCGA AAGGCCGAAA GGACAA  36

(2) INFORMATION FOR SEQ ID NO: 938:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 938:

UGUAUCUCUG AUGAGGCCGA AAGGCCGAAA CUGAGG  36

(2) INFORMATION FOR SEQ ID NO: 939:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 939:

GCUGUUGCUG AUGAGGCCGA AAGGCCGAAA UCUGAC  36

(2) INFORMATION FOR SEQ ID NO: 940:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 940:

GGCCCCACUG AUGAGGCCGA AAGGCCGAAA UGCUGU  36

(2) INFORMATION FOR SEQ ID NO: 941:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO: 941:

UGGCCCCUG AUGAGGCCGA AAGGCCGAAA AUGCUG 36

( 2 ) INFORMATION FOR SEQ ID NO: 942:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 942:

GUGCAGGCUG AUGAGGCCGA AAGGCCGAAA CCAUGG 36

( 2 ) INFORMATION FOR SEQ ID NO: 943:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 943:

AGUGUUUCUG AUGAGGCCGA AAGGCCGAAA GGUGUG 36

( 2 ) INFORMATION FOR SEQ ID NO: 944:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 944:

CGUGGCCCUG AUGAGGCCGA AAGGCCGAAA GUGUUU 36

( 2 ) INFORMATION FOR SEQ ID NO: 945:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 945:

CAGAUCACUG AUGAGGCCGA AAGGCCGAAA UGCGUG 36

( 2 ) INFORMATION FOR SEQ ID NO: 946:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 946:

GACUACACUG AUGAGGCCGA AAGGCCGAAA UCAGAU 36

( 2 ) INFORMATION FOR SEQ ID NO: 947:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 947:

AUGUGACCUG AUGAGGCCGA AAGGCCGAAA CAGAUC                                36

( 2 ) INFORMATION FOR SEQ ID NO: 948:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 948:

GUCAUGUCUG AUGAGGCCGA AAGGCCGAAA CUACAG                                36

( 2 ) INFORMATION FOR SEQ ID NO: 949:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 949:

CUUGGCUCUG AUGAGGCCGA AAGGCCGAAA GUCAUG                                36

( 2 ) INFORMATION FOR SEQ ID NO: 950:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 950:

AUGUCUUCUG AUGAGGCCGA AAGGCCGAAA GUCUUG                                36

( 2 ) INFORMATION FOR SEQ ID NO: 951:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 951:

AUCCAUCCUG AUGAGGCCGA AAGGCCGAAA UCAUGU                                36

( 2 ) INFORMATION FOR SEQ ID NO: 952:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 952:

AGACUUUCUG AUGAGGCCGA AAGGCCGAAA CAUCCA                                36

( 2 ) INFORMATION FOR SEQ ID NO: 953:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 953:

UAGACUUCUG AUGAGGCCGA AAGGCCGAAA ACAUCC                                36

( 2 ) INFORMATION FOR SEQ ID NO: 954:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 954:

CAGGCUACUG AUGAGGCCGA AAGGCCGAAA CUUUAA  36

( 2 ) INFORMATION FOR SEQ ID NO: 955:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 955:

AUCAGGCCUG AUGAGGCCGA AAGGCCGAAA GACUUU  36

( 2 ) INFORMATION FOR SEQ ID NO: 956:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 956:

GUGGGGCCUG AUGAGGCCGA AAGGCCGAAA UGUCUC  36

( 2 ) INFORMATION FOR SEQ ID NO: 957:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 957:

CCAGUUGCUG AUGAGGCCGA AAGGCCGAAA UGUCCU  36

( 2 ) INFORMATION FOR SEQ ID NO: 958:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 958:

GUUUCAGCUG AUGAGGCCGA AAGGCCGAAA UUUCCC  36

( 2 ) INFORMATION FOR SEQ ID NO: 959:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 959:

AGGCAGCUG AUGAGGCCGA AAGGCCGAAA GUUUCA  36

( 2 ) INFORMATION FOR SEQ ID NO: 960:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 960:

UACCCAACUG AUGAGGCCGA AAGGCCGAAA GGCAGC    36

( 2 ) INFORMATION FOR SEQ ID NO: 961:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 961:

CAUACCCUG AUGAGGCCGA AAGGCCGAAA UAGGCA    36

( 2 ) INFORMATION FOR SEQ ID NO: 962:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 962:

CUCAGCACUG AUGAGGCCGA AAGGCCGAAA CCCAAU    36

( 2 ) INFORMATION FOR SEQ ID NO: 963:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 963:

CUUCUGUCUG AUGAGGCCGA AAGGCCGAAA GUCUGU    36

( 2 ) INFORMATION FOR SEQ ID NO: 964:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 964:

UCUUCUGCUG AUGAGGCCGA AAGGCCGAAA AGUCUG    36

( 2 ) INFORMATION FOR SEQ ID NO: 965:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 965:

GUCUAUGCUG AUGAGGCCGA AAGGCCGAAA GGGCCA    36

( 2 ) INFORMATION FOR SEQ ID NO: 966:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 966:

ACAUGUCCUG AUGAGGCCGA AAGGCCGAAA UGGAGG 36

(2) INFORMATION FOR SEQ ID NO: 967:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 967:

UUGAUGCCUG AUGAGGCCGA AAGGCCGAAA CACAUG 36

(2) INFORMATION FOR SEQ ID NO: 968:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 968:

GUGUUUUCUG AUGAGGCCGA AAGGCCGAAA UGCUAC 36

(2) INFORMATION FOR SEQ ID NO: 969:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 969:

CGUCAGGCUG AUGAGGCCGA AAGGCCGAAA GUGUGG 36

(2) INFORMATION FOR SEQ ID NO: 970:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 970:

CCGUCAGCUG AUGAGGCCGA AAGGCCGAAA AGUGUG 36

(2) INFORMATION FOR SEQ ID NO: 971:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 971:

AGUGCCCUG AUGAGGCCGA AAGGCCGAAA GCUGGC 36

(2) INFORMATION FOR SEQ ID NO: 972:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO: 972:

GUCAGUACUG AUGAGGCCGA AAGGCCGAAA CAGCAG 36

( 2 ) INFORMATION FOR SEQ ID NO: 973:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 973:

GGGUCAGCUG AUGAGGCCGA AAGGCCGAAA GACAGC 36

( 2 ) INFORMATION FOR SEQ ID NO: 974:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 974:

UAUCAUCCUG AUGAGGCCGA AAGGCCGAAA GGGUUG 36

( 2 ) INFORMATION FOR SEQ ID NO: 975:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 975:

AAAUACACUG AUGAGGCCGA AAGGCCGAAA UCAUCA 36

( 2 ) INFORMATION FOR SEQ ID NO: 976:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 976:

GAAUAAACUG AUGAGGCCGA AAGGCCGAAA CAUAUC 36

( 2 ) INFORMATION FOR SEQ ID NO: 977:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 977:

AUGAAUACUG AUGAGGCCGA AAGGCCGAAA UACAUA 36

( 2 ) INFORMATION FOR SEQ ID NO: 978:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 978:

AAUGAAUCUG AUGAGGCCGA AAGGCCGAAA AUACAU    36

( 2 ) INFORMATION FOR SEQ ID NO: 979:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 979:

AAAUGAACUG AUGAGGCCGA AAGGCCGAAA AAUACA    36

( 2 ) INFORMATION FOR SEQ ID NO: 980:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 980:

ACAAAUGCUG AUGAGGCCGA AAGGCCGAAA UAAAUA    36

( 2 ) INFORMATION FOR SEQ ID NO: 981:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 981:

AACAAAUCUG AUGAGGCCGA AAGGCCGAAA AUAAAU    36

( 2 ) INFORMATION FOR SEQ ID NO: 982:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 982:

AAUAACACUG AUGAGGCCGA AAGGCCGAAA UGAAUA    36

( 2 ) INFORMATION FOR SEQ ID NO: 983:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 983:

AAAUAACCUG AUGAGGCCGA AAGGCCGAAA AUGAAU    36

( 2 ) INFORMATION FOR SEQ ID NO: 984:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 984:

```
GUAAAAUCUG AUGAGGCCGA AAGGCCGAAA CAAAUG                                    36
```

( 2 ) INFORMATION FOR SEQ ID NO: 985:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 985:

```
GGUAAAACUG AUGAGGCCGA AAGGCCGAAA ACAAAU                                    36
```

( 2 ) INFORMATION FOR SEQ ID NO: 986:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 986:

```
CUGGUAACUG AUGAGGCCGA AAGGCCGAAA UAACAA                                    36
```

( 2 ) INFORMATION FOR SEQ ID NO: 987:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 987:

```
GCUGGUACUG AUGAGGCCGA AAGGCCGAAA AUAACA                                    36
```

( 2 ) INFORMATION FOR SEQ ID NO: 988:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 988:

```
AGCUGGUCUG AUGAGGCCGA AAGGCCGAAA AAUAAC                                    36
```

( 2 ) INFORMATION FOR SEQ ID NO: 989:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 989:

```
UAGCUGGCUG AUGAGGCCGA AAGGCCGAAA AAAUAA                                    36
```

( 2 ) INFORMATION FOR SEQ ID NO: 990:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 990:

```
CAAUAAACUG AUGAGGCCGA AAGGCCGAAA GCUGGU                                    36
```

( 2 ) INFORMATION FOR SEQ ID NO: 991:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 991:

CUCAAUACUG AUGAGGCCGA AAGGCCGAAA UAGCUG    36

( 2 ) INFORMATION FOR SEQ ID NO: 992:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 992:

ACUCAAUCUG AUGAGGCCGA AAGGCCGAAA AUAGCU    36

( 2 ) INFORMATION FOR SEQ ID NO: 993:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 993:

CACUCAACUG AUGAGGCCGA AAGGCCGAAA AAUAGC    36

( 2 ) INFORMATION FOR SEQ ID NO: 994:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 994:

GACACUCCUG AUGAGGCCGA AAGGCCGAAA UAAAUA    36

( 2 ) INFORMATION FOR SEQ ID NO: 995:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 995:

CAUAAAACUG AUGAGGCCGA AAGGCCGAAA CACUCA    36

( 2 ) INFORMATION FOR SEQ ID NO: 996:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 996:

UACAUAACUG AUGAGGCCGA AAGGCCGAAA GACACU    36

( 2 ) INFORMATION FOR SEQ ID NO: 997:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 997:

CUACAUACUG AUGAGGCCGA AAGGCCGAAA AGACAC　　　　　　　　　　36

( 2 ) INFORMATION FOR SEQ ID NO: 998:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 998:

CCUACAUCUG AUGAGGCCGA AAGGCCGAAA AAGACA　　　　　　　　　　36

( 2 ) INFORMATION FOR SEQ ID NO: 999:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 999:

GCCUACACUG AUGAGGCCGA AAGGCCGAAA AAAGAC　　　　　　　　　　36

( 2 ) INFORMATION FOR SEQ ID NO: 1000:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1000:

UUUAGCCCUG AUGAGGCCGA AAGGCCGAAA CAUAAA　　　　　　　　　　36

( 2 ) INFORMATION FOR SEQ ID NO: 1001:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1001:

GUUCAUUCUG AUGAGGCCGA AAGGCCGAAA GCCUAC　　　　　　　　　　36

( 2 ) INFORMATION FOR SEQ ID NO: 1002:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1002:

AGAGACCCUG AUGAGGCCGA AAGGCCGAAA UGUUCA　　　　　　　　　　36

( 2 ) INFORMATION FOR SEQ ID NO: 1003:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1003:

GGCCAGACUG AUGAGGCCGA AAGGCCGAAA CCUAUG 36

( 2 ) INFORMATION FOR SEQ ID NO: 1004:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1004:

GAGGCCACUG AUGAGGCCGA AAGGCCGAAA GACCUA 36

( 2 ) INFORMATION FOR SEQ ID NO: 1005:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1005:

GCUCCGUCUG AUGAGGCCGA AAGGCCGAAA GGCCAG 36

( 2 ) INFORMATION FOR SEQ ID NO: 1006:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1006:

GGACUGGCUG AUGAGGCCGA AAGGCCGAAA GCUCCG 36

( 2 ) INFORMATION FOR SEQ ID NO: 1007:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1007:

UGACAUGCUG AUGAGGCCGA AAGGCCGAAA CUGGGA 36

( 2 ) INFORMATION FOR SEQ ID NO: 1008:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1008:

UGAAUGUCUG AUGAGGCCGA AAGGCCGAAA CAUGGA 36

( 2 ) INFORMATION FOR SEQ ID NO: 1009:

( i ) SEQUENCE CHARACTERISTICS:
    ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO: 1009:

GACCUUGCUG AUGAGGCCGA AAGGCCGAAA UGUGAC 36

(2) INFORMATION FOR SEQ ID NO: 1010:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1010:

UGACCUUCUG AUGAGGCCGA AAGGCCGAAA AUGUGA 36

(2) INFORMATION FOR SEQ ID NO: 1011:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1011:

ACCUGGUCUG AUGAGGCCGA AAGGCCGAAA CCUUGA 36

(2) INFORMATION FOR SEQ ID NO: 1012:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1012:

ACAACUGCUG AUGAGGCCGA AAGGCCGAAA CCUGGU 36

(2) INFORMATION FOR SEQ ID NO: 1013:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1013:

CCUGUACCUG AUGAGGCCGA AAGGCCGAAA CUGUAC 36

(2) INFORMATION FOR SEQ ID NO: 1014:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1014:

CAACCUGCUG AUGAGGCCGA AAGGCCGAAA CAACUG 36

(2) INFORMATION FOR SEQ ID NO: 1015:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO: 1015:

AGUGUACCUG AUGAGGCGA AAGGCCGAAA CCUGUA 36

(2) INFORMATION FOR SEQ ID NO: 1016:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1016:

UGCAGUGCUG AUGAGGCCGA AAGGCCGAAA CAACCU 36

(2) INFORMATION FOR SEQ ID NO: 1017:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1017:

CCCAUUUCUG AUGAGGCCGA AAGGCCGAAA UCUUUU 36

(2) INFORMATION FOR SEQ ID NO: 1018:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1018:

CAAUGAGCUG AUGAGGCCGA AAGGCCGAAA GUCCCA 36

(2) INFORMATION FOR SEQ ID NO: 1019:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1019:

CCAAUGACUG AUGAGGCCGA AAGGCCGAAA AGUCCC 36

(2) INFORMATION FOR SEQ ID NO: 1020:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1020:

GGCCAAUCUG AUGAGGCCGA AAGGCCGAAA GAAGUC 36

(2) INFORMATION FOR SEQ ID NO: 1021:

(i) SEQUENCE CHARACTERISTICS:
        (A) LENGTH: 36 base pairs
        (B) TYPE: nucleic acid
        (C) STRANDEDNESS: single
        (D) TOPOLOGY: linear -continued (x i) SEQUENCE DESCRIPTION: SEQ ID NO: 1021:

GUUGGCCCUG AUGAGGCCGA AAGGCCGAAA UGAGAA 36

(2) INFORMATION FOR SEQ ID NO: 1022:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1022:

CUGGGGACUG AUGAGGCCGA AAGGCCGAAA GGCAGG 36

(2) INFORMATION FOR SEQ ID NO: 1023:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1023:

UCUGGGGCUG AUGAGGCCGA AAGGCCGAAA AGGCAG 36

(2) INFORMATION FOR SEQ ID NO: 1024:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1024:

UUCUGGGCUG AUGAGGCCGA AAGGCCGAAA AAGGCA 36

(2) INFORMATION FOR SEQ ID NO: 1025:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1025:

AUAGAAACUG AUGAGGCCGA AAGGCCGAAA UCACUC 36

(2) INFORMATION FOR SEQ ID NO: 1026:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1026:

GAUAGAACUG AUGAGGCCGA AAGGCCGAAA AUCACU 36

(2) INFORMATION FOR SEQ ID NO: 1027:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1027:

CGAUAGACUG AUGAGGCCGA AAGGCCGAAA AAUCAC 36

( 2 ) INFORMATION FOR SEQ ID NO: 1028:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1028:

CCGAUAGCUG AUGAGGCCGA AAGGCCGAAA AAAUCA 36

( 2 ) INFORMATION FOR SEQ ID NO: 1029:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1029:

GCCGAUACUG AUGAGGCCGA AAGGCCGAAA AAAAUC 36

( 2 ) INFORMATION FOR SEQ ID NO: 1030:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1030:

GUGCCGACUG AUGAGGCCGA AAGGCCGAAA GAAAAA 36

( 2 ) INFORMATION FOR SEQ ID NO: 1031:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1031:

UUGUGCCCUG AUGAGGCCGA AAGGCCGAAA UAGAAA 36

( 2 ) INFORMATION FOR SEQ ID NO: 1032:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1032:

GUCCAUACUG AUGAGGCCGA AAGGCCGAAA GUGCUU 36

( 2 ) INFORMATION FOR SEQ ID NO: 1033:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1033:

CAGUCCACUG AUGAGGCCGA AAGGCCGAAA UAGUGC 36

( 2 ) INFORMATION FOR SEQ ID NO: 1034:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1034:

GAACCAUCUG AUGAGGCCGA AAGGCCGAAA CCAGUC    36

( 2 ) INFORMATION FOR SEQ ID NO: 1035:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1035:

ACCUGUGCUG AUGAGGCCGA AAGGCCGAAA CCAUUA    36

( 2 ) INFORMATION FOR SEQ ID NO: 1036:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1036:

AACCUGUCUG AUGAGGCCGA AAGGCCGAAA ACCAUU    36

( 2 ) INFORMATION FOR SEQ ID NO: 1037:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1037:

AUCUCUGCUG AUGAGGCCGA AAGGCCGAAA CCUGUG    36

( 2 ) INFORMATION FOR SEQ ID NO: 1038:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1038:

AAUCUCUCUG AUGAGGCCGA AAGGCCGAAA ACCUGU    36

( 2 ) INFORMATION FOR SEQ ID NO: 1039:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1039:

ACUGGGUCUG AUGAGGCCGA AAGGCCGAAA UCUCUG    36

( 2 ) INFORMATION FOR SEQ ID NO: 1040:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1040:

CACUGGGCUG AUGAGGCCGA AAGGCCGAAA AUCUCU   36

( 2 ) INFORMATION FOR SEQ ID NO: 1041:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1041:

GAGGAAUCUG AUGAGGCCGA AAGGCCGAAA GGCCUC   36

( 2 ) INFORMATION FOR SEQ ID NO: 1042:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1042:

GGAGGAACUG AUGAGGCCGA AAGGCCGAAA AGGCCU   36

( 2 ) INFORMATION FOR SEQ ID NO: 1043:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1043:

AGGGAGGCUG AUGAGGCCGA AAGGCCGAAA UAAGGC   36

( 2 ) INFORMATION FOR SEQ ID NO: 1044:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1044:

AAGGGAGCUG AUGAGGCCGA AAGGCCGAAA AUAAGG   36

( 2 ) INFORMATION FOR SEQ ID NO: 1045:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1045:

GGGAAGGCUG AUGAGGCCGA AAGGCCGAAA GGAAUA   36

( 2 ) INFORMATION FOR SEQ ID NO: 1046:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1046:

UGGGGGCUG AUGAGGCCGA AAGGCCGAAA GGGAGG 36

(2) INFORMATION FOR SEQ ID NO: 1047:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1047:

UUGGGGGCUG AUGAGGCCGA AAGGCCGAAA AGGGAG 36

(2) INFORMATION FOR SEQ ID NO: 1048:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1048:

GCUAACACUG AUGAGGCCGA AAGGCCGAAA GGUGUC 36

(2) INFORMATION FOR SEQ ID NO: 1049:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1049:

GGCUAACCUG AUGAGGCCGA AAGGCCGAAA AGGUGU 36

(2) INFORMATION FOR SEQ ID NO: 1050:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1050:

GGUGGCUCUG AUGAGGCCGA AAGGCCGAAA CAAAGG 36

(2) INFORMATION FOR SEQ ID NO: 1051:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1051:

AGGUGGCCUG AUGAGGCCGA AAGGCCGAAA ACAAAG 36

(2) INFORMATION FOR SEQ ID NO: 1052:

(i) SEQUENCE CHARACTERISTICS:
        (A) LENGTH: 36 base pairs
        (B) TYPE: nucleic acid (C) STRANDEDNESS: single
(D) TOPOLOGY: linear (xi) SEQUENCE DESCRIPTION: SEQ ID NO: 1052:

GGGUGGGCUG AUGAGGCCGA AAGGCCGAAA GGUGGC 36

(2) INFORMATION FOR SEQ ID NO: 1053:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1053:

AGAAAUGCUG AUGAGGCCGA AAGGCCGAAA UGUGGG 36

(2) INFORMATION FOR SEQ ID NO: 1054:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1054:

UGGCAGACUG AUGAGGCCGA AAGGCCGAAA UGUAUG 36

(2) INFORMATION FOR SEQ ID NO: 1055:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1055:

CUGGCAGCUG AUGAGGCCGA AAGGCCGAAA AUGUAU 36

(2) INFORMATION FOR SEQ ID NO: 1056:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1056:

ACUGGCACUG AUGAGGCCGA AAGGCCGAAA AAUGUA 36

(2) INFORMATION FOR SEQ ID NO: 1057:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1057:

CAUUGUGCUG AUGAGGCCGA AAGGCCGAAA CACUGG 36

(2) INFORMATION FOR SEQ ID NO: 1058:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO: 1058:

UCAUUGUCUG AUGAGGCCGA AAGGCCGAAA ACACUG 36

( 2 ) INFORMATION FOR SEQ ID NO: 1059:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1059:

GACCGCUCUG AUGAGGCCGA AAGGCCGAAA GUGUCA 36

( 2 ) INFORMATION FOR SEQ ID NO: 1060:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1060:

CAGACAUCUG AUGAGGCCGA AAGGCCGAAA CCGCUG 36

( 2 ) INFORMATION FOR SEQ ID NO: 1061:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1061:

AUGUCCACUG AUGAGGCCGA AAGGCCGAAA CAUGAC 36

( 2 ) INFORMATION FOR SEQ ID NO: 1062:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1062:

UUGGGCACUG AUGAGGCCGA AAGGCCGAAA UUCCCU 36

( 2 ) INFORMATION FOR SEQ ID NO: 1063:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1063:

CAAGGCACUG AUGAGGCCGA AAGGCCGAAA GCUUGG 36

( 2 ) INFORMATION FOR SEQ ID NO: 1064:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1064:

```
AGAGGACCUG AUGAGGCCGA AAGGCCGAAA GGCAUA                                  36
```

( 2 ) INFORMATION FOR SEQ ID NO: 1065:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1065:

```
ACAAGAGCUG AUGAGGCCGA AAGGCCGAAA CAAGGC                                  36
```

( 2 ) INFORMATION FOR SEQ ID NO: 1066:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1066:

```
AGGACAACUG AUGAGGCCGA AAGGCCGAAA GGACAA                                  36
```

( 2 ) INFORMATION FOR SEQ ID NO: 1067:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1067:

```
ACAGGACCUG AUGAGGCCGA AAGGCCGAAA GAGGAC                                  36
```

( 2 ) INFORMATION FOR SEQ ID NO: 1068:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1068:

```
CAAACAGCUG AUGAGGCCGA AAGGCCGAAA CAAGAG                                  36
```

( 2 ) INFORMATION FOR SEQ ID NO: 1069:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1069:

```
AAAUGCACUG AUGAGGCCGA AAGGCCGAAA CAGGAC                                  36
```

( 2 ) INFORMATION FOR SEQ ID NO: 1070:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1070:

```
GAAAUGCCUG AUGAGGCCGA AAGGCCGAAA ACAGGA                                  36
```

( 2 ) INFORMATION FOR SEQ ID NO: 1071:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1071:

CCAGUGACUG AUGAGGCCGA AAGGCCGAAA UGCAAA     36

( 2 ) INFORMATION FOR SEQ ID NO: 1072:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1072:

CCCAGUGCUG AUGAGGCCGA AAGGCCGAAA AUGCAA     36

( 2 ) INFORMATION FOR SEQ ID NO: 1073:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1073:

UCCCAGUCUG AUGAGGCCGA AAGGCCGAAA AAUGCA     36

( 2 ) INFORMATION FOR SEQ ID NO: 1074:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1074:

AUAGUGCCUG AUGAGGCCGA AAGGCCGAAA GCUCCC     36

( 2 ) INFORMATION FOR SEQ ID NO: 1075:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1075:

GCUGCAACUG AUGAGGCCGA AAGGCCGAAA GUGCAA     36

( 2 ) INFORMATION FOR SEQ ID NO: 1076:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1076:

GAGCUGCCUG AUGAGGCCGA AAGGCCGAAA UAGUGC     36

( 2 ) INFORMATION FOR SEQ ID NO: 1077:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1077:

GAAACUGCUG AUGAGGCCGA AAGGCCGAAA GCUGCA     36

( 2 ) INFORMATION FOR SEQ ID NO: 1078:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1078:

UGCAGGACUG AUGAGGCCGA AAGGCCGAAA CUGGAG     36

( 2 ) INFORMATION FOR SEQ ID NO: 1079:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1079:

CUGCAGGCUG AUGAGGCCGA AAGGCCGAAA ACUGGA     36

( 2 ) INFORMATION FOR SEQ ID NO: 1080:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1080:

ACUGCAGCUG AUGAGGCCGA AAGGCCGAAA AACUGG     36

( 2 ) INFORMATION FOR SEQ ID NO: 1081:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1081:

GGACCCUCUG AUGAGGCCGA AAGGCCGAAA UCACUG     36

( 2 ) INFORMATION FOR SEQ ID NO: 1082:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1082:

CUUGCAGCUG AUGAGGCCGA AAGGCCGAAA CCCUGA     36

( 2 ) INFORMATION FOR SEQ ID NO: 1083:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1083:

CCUCCAACUG AUGAGGCCGA AAGGCCGAAA CCUUGG 36

( 2 ) INFORMATION FOR SEQ ID NO: 1084:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1084:

GUCCUCCUG AUGAGGCCGA AAGGCCGAAA UACCUU 36

( 2 ) INFORMATION FOR SEQ ID NO: 1085:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1085:

UGGGAGGCUG AUGAGGCCGA AAGGCCGAAA GUCCUC 36

( 2 ) INFORMATION FOR SEQ ID NO: 1086:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1086:

AAGCUGGCUG AUGAGGCCGA AAGGCCGAAA GGGAGU 36

( 2 ) INFORMATION FOR SEQ ID NO: 1087:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1087:

CCUUCCACUG AUGAGGCCGA AAGGCCGAAA GCUGGG 36

( 2 ) INFORMATION FOR SEQ ID NO: 1088:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1088:

CCCUUCCCUG AUGAGGCCGA AAGGCCGAAA AGCUGG 36

( 2 ) INFORMATION FOR SEQ ID NO: 1089:

( i ) SEQUENCE CHARACTERISTICS:
  ( A ) LENGTH: 36 base pairs ( B ) TYPE: nucleic acid
        ( C ) STRANDEDNESS: single
        ( D ) TOPOLOGY: linear ( x i ) SEQUENCE DESCRIPTION: SEQ ID NO: 1089:

CGCGGAUCUG AUGAGGCCGA AAGGCCGAAA CCCUUC 36

( 2 ) INFORMATION FOR SEQ ID NO: 1090:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1090:

ACACGCGCUG AUGAGGCCGA AAGGCCGAAA UGACCC 36

( 2 ) INFORMATION FOR SEQ ID NO: 1091:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1091:

CUACACACUG AUGAGGCCGA AAGGCCGAAA CACACA 36

( 2 ) INFORMATION FOR SEQ ID NO: 1092:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1092:

GCUUGUCCUG AUGAGGCCGA AAGGCCGAAA CACAUA 36

( 2 ) INFORMATION FOR SEQ ID NO: 1093:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1093:

AGAGCGACUG AUGAGGCCGA AAGGCCGAAA GCUUGU 36

( 2 ) INFORMATION FOR SEQ ID NO: 1094:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1094:

ACAGAGCCUG AUGAGGCCGA AAGGCCGAAA GAGCUU 36

( 2 ) INFORMATION FOR SEQ ID NO: 1095:

( i ) SEQUENCE CHARACTERISTICS:
        ( A ) LENGTH: 36 base pairs
        ( B ) TYPE: nucleic acid
        ( C ) STRANDEDNESS: single (D) TOPOLOGY: linear (xi) SEQUENCE DESCRIPTION: SEQ ID NO: 1095:

GGUGACACUG AUGAGGCCGA AAGGCCGAAA GCGAGA 36

(2) INFORMATION FOR SEQ ID NO: 1096:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1096:

CCUGGGUCUG AUGAGGCCGA AAGGCCGAAA CAGAGC 36

(2) INFORMATION FOR SEQ ID NO: 1097:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1097:

GAACCAUCUG AUGAGGCCGA AAGGCCGAAA UUGCAC 36

(2) INFORMATION FOR SEQ ID NO: 1098:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1098:

UGCAGUGCUG AUGAGGCCGA AAGGCCGAAA CCAUGA 36

(2) INFORMATION FOR SEQ ID NO: 1099:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1099:

CUGCAGUCUG AUGAGGCCGA AAGGCCGAAA ACCAUG 36

(2) INFORMATION FOR SEQ ID NO: 1100:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1100:

AGGUCAACUG AUGAGGCCGA AAGGCCGAAA CUGCAG 36

(2) INFORMATION FOR SEQ ID NO: 1101:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO: 1101:

AAAGGUCCUG AUGAGGCCGA AAGGCCGAAA GACUGC 36

( 2 ) INFORMATION FOR SEQ ID NO: 1102:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1102:

AGCCCAACUG AUGAGGCCGA AAGGCCGAAA GGUCAA 36

( 2 ) INFORMATION FOR SEQ ID NO: 1103:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1103:

GAGCCCACUG AUGAGGCCGA AAGGCCGAAA AGGUCA 36

( 2 ) INFORMATION FOR SEQ ID NO: 1104:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1104:

UGAGCCCUG AUGAGGCCGA AAGGCCGAAA AAGGUC 36

( 2 ) INFORMATION FOR SEQ ID NO: 1105:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1105:

AUCACUUCUG AUGAGGCCGA AAGGCCGAAA GCCCAA 36

( 2 ) INFORMATION FOR SEQ ID NO: 1106:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1106:

GUGGGAGCUG AUGAGGCCGA AAGGCCGAAA UCACUU 36

( 2 ) INFORMATION FOR SEQ ID NO: 1107:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1107:

GAGGUGGCUG AUGAGGCCGA AAGGCCGAAA GGAUCA  36

(2) INFORMATION FOR SEQ ID NO: 1108:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1108:

GGAGGCUCUG AUGAGGCCGA AAGGCCGAAA GGUGGG  36

(2) INFORMATION FOR SEQ ID NO: 1109:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1109:

UACUCAGCUG AUGAGGCCGA AAGGCCGAAA GGCUGA  36

(2) INFORMATION FOR SEQ ID NO: 1110:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1110:

UCCCAGCCUG AUGAGGCCGA AAGGCCGAAA CUCAGG  36

(2) INFORMATION FOR SEQ ID NO: 1111:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1111:

GUGAGCCCUG AUGAGGCCGA AAGGCCGAAA UGGUCC  36

(2) INFORMATION FOR SEQ ID NO: 1112:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1112:

GUGUUGUCUG AUGAGGCCGA AAGGCCGAAA GCCUAU  36

(2) INFORMATION FOR SEQ ID NO: 1113:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1113:

AAAAUCACUG AUGAGGCCGA AAGGCCGAAA UUUGCC  36

( 2 ) INFORMATION FOR SEQ ID NO: 1114:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1114:

AAAAAUCCUG AUGAGGCCGA AAGGCCGAAA AUUUGC    36

( 2 ) INFORMATION FOR SEQ ID NO: 1115:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1115:

AAAAAAACUG AUGAGGCCGA AAGGCCGAAA UCAAAU    36

( 2 ) INFORMATION FOR SEQ ID NO: 1116:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1116:

AAAAAAACUG AUGAGGCCGA AAGGCCGAAA AUCAAA    36

( 2 ) INFORMATION FOR SEQ ID NO: 1117:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1117:

AAAAAAACUG AUGAGGCCGA AAGGCCGAAA AAUCAA    36

( 2 ) INFORMATION FOR SEQ ID NO: 1118:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1118:

AAAAAAACUG AUGAGGCCGA AAGGCCGAAA AAAUCA    36

( 2 ) INFORMATION FOR SEQ ID NO: 1119:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1119:

AAAAAAACUG AUGAGGCCGA AAGGCCGAAA AAAAUC    36

( 2 ) INFORMATION FOR SEQ ID NO: 1120:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1120:

AAAAAACUG AUGAGGCCGA AAGGCCGAAA AAAAAU      36

( 2 ) INFORMATION FOR SEQ ID NO: 1121:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1121:

AAAAAACUG AUGAGGCCGA AAGGCCGAAA AAAAAA      36

( 2 ) INFORMATION FOR SEQ ID NO: 1122:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1122:

AAAAAACUG AUGAGGCCGA AAGGCCGAAA AAAAAA      36

( 2 ) INFORMATION FOR SEQ ID NO: 1123:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1123:

GAAAAACUG AUGAGGCCGA AAGGCCGAAA AAAAAA      36

( 2 ) INFORMATION FOR SEQ ID NO: 1124:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1124:

UGAAAAACUG AUGAGGCCGA AAGGCCGAAA AAAAAA      36

( 2 ) INFORMATION FOR SEQ ID NO: 1125:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1125:

CUGAAAACUG AUGAGGCCGA AAGGCCGAAA AAAAAA      36

( 2 ) INFORMATION FOR SEQ ID NO: 1126:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1126:

UCUGAAACUG AUGAGGCCGA AAGGCCGAAA AAAAAA 36

(2) INFORMATION FOR SEQ ID NO: 1127:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1127:

CUCUGAACUG AUGAGGCCGA AAGGCCGAAA AAAAAA 36

(2) INFORMATION FOR SEQ ID NO: 1128:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1128:

UCUCUGACUG AUGAGGCCGA AAGGCCGAAA AAAAAA 36

(2) INFORMATION FOR SEQ ID NO: 1129:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1129:

GUCUCUGCUG AUGAGGCCGA AAGGCCGAAA AAAAAA 36

(2) INFORMATION FOR SEQ ID NO: 1130:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1130:

CGUCUCUCUG AUGAGGCCGA AAGGCCGAAA AAAAAA 36

(2) INFORMATION FOR SEQ ID NO: 1131:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1131:

GUUGCGACUG AUGAGGCCGA AAGGCCGAAA CCCCGU 36

(2) INFORMATION FOR SEQ ID NO: 1132:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO: 1132:

AUGUUGCCUG AUGAGGCCGA AAGGCCGAAA GACCCC 36

( 2 ) INFORMATION FOR SEQ ID NO: 1133:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1133:

UCUGGGCCUG AUGAGGCCGA AAGGCCGAAA UGUUGC 36

( 2 ) INFORMATION FOR SEQ ID NO: 1134:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1134:

ACAAAGGCUG AUGAGGCCGA AAGGCCGAAA GUCUGG 36

( 2 ) INFORMATION FOR SEQ ID NO: 1135:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1135:

CACAAAGCUG AUGAGGCCGA AAGGCCGAAA AGUCUG 36

( 2 ) INFORMATION FOR SEQ ID NO: 1136:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1136:

UAACACACUG AUGAGGCCGA AAGGCCGAAA GGAAGU 36

( 2 ) INFORMATION FOR SEQ ID NO: 1137:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1137:

CUAACACCUG AUGAGGCCGA AAGGCCGAAA AGGAAG 36

( 2 ) INFORMATION FOR SEQ ID NO: 1138:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1138:

AUUAACUCUG AUGAGGCCGA AAGGCCGAAA CACAAA    36

( 2 ) INFORMATION FOR SEQ ID NO: 1139:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1139:

UAUUAACCUG AUGAGGCCGA AAGGCCGAAA ACACAA    36

( 2 ) INFORMATION FOR SEQ ID NO: 1140:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1140:

CUUUAUUCUG AUGAGGCCGA AAGGCCGAAA CUAACA    36

( 2 ) INFORMATION FOR SEQ ID NO: 1141:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1141:

GCUUUAUCUG AUGAGGCCGA AAGGCCGAAA ACUAAC    36

( 2 ) INFORMATION FOR SEQ ID NO: 1142:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1142:

AAAGCUUCUG AUGAGGCCGA AAGGCCGAAA UUAACU    36

( 2 ) INFORMATION FOR SEQ ID NO: 1143:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1143:

GUUGAGACUG AUGAGGCCGA AAGGCCGAAA GCUUUA    36

( 2 ) INFORMATION FOR SEQ ID NO: 1144:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1144:

AGUUGAGCUG AUGAGGCCGA AAGGCCGAAA AGCUUU 36

( 2 ) INFORMATION FOR SEQ ID NO: 1145:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1145:

CAGUUGACUG AUGAGGCCGA AAGGCCGAAA AAGCUU 36

( 2 ) INFORMATION FOR SEQ ID NO: 1146:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1146:

GGCAGUUCUG AUGAGGCCGA AAGGCCGAAA GAAAGC 36

( 2 ) INFORMATION FOR SEQ ID NO: 1147:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1147:

CAACGGUCUG AUGAGGCCGA AAGGCCGAAA CCAGGG 36

( 2 ) INFORMATION FOR SEQ ID NO: 1148:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1148:

AGCAGAGCUG AUGAGGCCGA AAGGCCGAAA CCACUG 36

( 2 ) INFORMATION FOR SEQ ID NO: 1149:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1149:

AGGAGCACUG AUGAGGCCGA AAGGCCGAAA GAACCA 36

( 2 ) INFORMATION FOR SEQ ID NO: 1150:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1150:

UGUGGAGCUG AUGAGGCCGA AAGGCCGAAA GCAGAG 36

( 2 ) INFORMATION FOR SEQ ID NO: 1151:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1151:

CGACCCUCUG AUGAGGCCGA AAGGCCGAAA UGAGAA    36

( 2 ) INFORMATION FOR SEQ ID NO: 1152:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1152:

AGGCUACCUG AUGAGGCCGA AAGGCCGAAA GUGUGC    36

( 2 ) INFORMATION FOR SEQ ID NO: 1153:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1153:

CCAGGCUCUG AUGAGGCCGA AAGGCCGAAA GGUCCU    36

( 2 ) INFORMATION FOR SEQ ID NO: 1154:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1154:

CCAUCACCUG AUGAGGCCGA AAGGCCGAAA GGCCCA    36

( 2 ) INFORMATION FOR SEQ ID NO: 1155:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1155:

GGAGCUACUG AUGAGGCCGA AAGGCCGAAA GGCAUG    36

( 2 ) INFORMATION FOR SEQ ID NO: 1156:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1156:

CUGCUGGCUG AUGAGGCCGA AAGGCCGAAA GGGGUG    36

( 2 ) INFORMATION FOR SEQ ID NO: 1157:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1157:

GGGCCAGCUG AUGAGGCCGA AAGGCCGAAA GCAGAG   36

( 2 ) INFORMATION FOR SEQ ID NO: 1158:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1158:

CCAGCAGCUG AUGAGGCCGA AAGGCCGAAA CUGGCA   36

( 2 ) INFORMATION FOR SEQ ID NO: 1159:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1159:

GGGCCAGCUG AUGAGGCCGA AAGGCCGAAA GCAGAG   36

( 2 ) INFORMATION FOR SEQ ID NO: 1160:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1160:

AGGAGCACUG AUGAGGCCGA AAGGCCGAAA GAACCA   36

( 2 ) INFORMATION FOR SEQ ID NO: 1161:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1161:

UCCUGGUCUG AUGAGGCCGA AAGGCCGAAA CAUUCC   36

( 2 ) INFORMATION FOR SEQ ID NO: 1162:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1162:

GGGCCAGCUG AUGAGGCCGA AAGGCCGAAA GCAGAG   36

( 2 ) INFORMATION FOR SEQ ID NO: 1163:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1163:

GGAAGCGCUG AUGAGGCCGA AAGGCCGAAA CGACUG                36

( 2 ) INFORMATION FOR SEQ ID NO: 1164:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1164:

AGUGGCUCUG AUGAGGCCGA AAGGCCGAAA CACAGA                36

( 2 ) INFORMATION FOR SEQ ID NO: 1165:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1165:

GGUUUUUCUG AUGAGGCCGA AAGGCCGAAA ACAGGA                36

( 2 ) INFORMATION FOR SEQ ID NO: 1166:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1166:

GCAAAACCUG AUGAGGCCGA AAGGCCGAAA CUUCUG                36

( 2 ) INFORMATION FOR SEQ ID NO: 1167:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1167:

GGGGCAGCUG AUGAGGCCGA AAGGCCGAAA AGGCUU                36

( 2 ) INFORMATION FOR SEQ ID NO: 1168:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1168:

CUGCACGCUG AUGAGGCCGA AAGGCCGAAA CCCACC                36

( 2 ) INFORMATION FOR SEQ ID NO: 1169:

( i ) SEQUENCE CHARACTERISTICS:
      ( A ) LENGTH: 36 base pairs (B) TYPE: nucleic acid
                (C) STRANDEDNESS: single
                (D) TOPOLOGY: linear (xi) SEQUENCE DESCRIPTION: SEQ ID NO: 1169:

GCCAGAGCUG AUGAGGCCGA AAGGCCGAAA AGUGGC                    36

(2) INFORMATION FOR SEQ ID NO: 1170:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 1170:

GCAAAACCUG AUGAGGCCGA AAGGCCGAAA CUUCUG                    36

(2) INFORMATION FOR SEQ ID NO: 1171:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 1171:

GGAGCAACUG AUGAGGCCGA AAGGCCGAAA CAACUU                    36

(2) INFORMATION FOR SEQ ID NO: 1172:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 1172:

AGUUCUCCUG AUGAGGCCGA AAGGCCGAAA AGCACA                    36

(2) INFORMATION FOR SEQ ID NO: 1173:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 1173:

UUUAGGACUG AUGAGGCCGA AAGGCCGAAA UGGGUU                    36

(2) INFORMATION FOR SEQ ID NO: 1174:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 1174:

UCUUCCUCUG AUGAGGCCGA AAGGCCGAAA GGCAGG                    36

(2) INFORMATION FOR SEQ ID NO: 1175:

(i) SEQUENCE CHARACTERISTICS:
                (A) LENGTH: 36 base pairs
                (B) TYPE: nucleic acid
                (C) STRANDEDNESS: single (D) TOPOLOGY: linear (xi) SEQUENCE DESCRIPTION: SEQ ID NO: 1175:

CAGUAGACUG AUGAGGCGA AAGGCCGAAA AACCCU    36

(2) INFORMATION FOR SEQ ID NO: 1176:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 1176:

UAGGCAGCUG AUGAGGCCGA AAGGCCGAAA GCCCCU    36

(2) INFORMATION FOR SEQ ID NO: 1177:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 1177:

CAGCUCACUG AUGAGGCCGA AAGGCCGAAA CAGCUU    36

(2) INFORMATION FOR SEQ ID NO: 1178:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 1178:

GGCUCAGCUG AUGAGGCCGA AAGGCCGAAA UCUCCU    36

(2) INFORMATION FOR SEQ ID NO: 1179:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 1179:

GUUCUCACUG AUGAGGCCGA AAGGCCGAAA GCACAG    36

(2) INFORMATION FOR SEQ ID NO: 1180:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO: 1180:

CAGUGUGCUG AUGAGGCCGA AAGGCCGAAA UUGGAC    36

(2) INFORMATION FOR SEQ ID NO: 1181:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO: 1181:

UCAGCUCCUG AUGAGGCCGA AAGGCCGAAA ACAGCU    36

(2) INFORMATION FOR SEQ ID NO: 1182:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1182:

AGCGGACCUG AUGAGGCCGA AAGGCCGAAA CUGCAC    36

(2) INFORMATION FOR SEQ ID NO: 1183:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1183:

CGGGUUGCUG AUGAGGCCGA AAGGCCGAAA GCCAUU    36

(2) INFORMATION FOR SEQ ID NO: 1184:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1184:

GGGCAGGCUG AUGAGGCCGA AAGGCCGAAA GGCUUC    36

(2) INFORMATION FOR SEQ ID NO: 1185:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1185:

GGGGCAGCUG AUGAGGCCGA AAGGCCGAAA AGGCUU    36

(2) INFORMATION FOR SEQ ID NO: 1186:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1186:

ACACGGUCUG AUGAGGCCGA AAGGCCGAAA UGGUAG    36

(2) INFORMATION FOR SEQ ID NO: 1187:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1187:

AAACGAACUG AUGAGGCCGA AAGGCCGAAA CACGGU  36

(2) INFORMATION FOR SEQ ID NO: 1188:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1188:

AGAUCGACUG AUGAGGCCGA AAGGCCGAAA GUCCGG  36

(2) INFORMATION FOR SEQ ID NO: 1189:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1189:

CGGGGGGCUG AUGAGGCCGA AAGGCCGAAA AGUGUG  36

(2) INFORMATION FOR SEQ ID NO: 1190:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1190:

CUGCUGGCUG AUGAGGCCGA AAGGCCGAAA GGGGUG  36

(2) INFORMATION FOR SEQ ID NO: 1191:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1191:

CACUGCUCUG AUGAGGCCGA AAGGCCGAAA GAGCUG  36

(2) INFORMATION FOR SEQ ID NO: 1192:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1192:

GCAGGGUCUG AUGAGGCCGA AAGGCCGAAA GGUCCU  36

(2) INFORMATION FOR SEQ ID NO: 1193:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1193:

CAAAGGACUG AUGAGGCCGA AAGGCCGAAA GGUUUC  36

( 2 ) INFORMATION FOR SEQ ID NO: 1194:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1194:

AGUGGCUCUG AUGAGGCCGA AAGGCCGAAA GGGUAA    36

( 2 ) INFORMATION FOR SEQ ID NO: 1195:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1195:

ACACGGUCUG AUGAGGCCGA AAGGCCGAAA UGGUAG    36

( 2 ) INFORMATION FOR SEQ ID NO: 1196:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1196:

CCCCACGCUG AUGAGGCCGA AAGGCCGAAA GCAGCA    36

( 2 ) INFORMATION FOR SEQ ID NO: 1197:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1197:

GGAUGGACUG AUGAGGCCGA AAGGCCGAAA CCUGAG    36

( 2 ) INFORMATION FOR SEQ ID NO: 1198:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1198:

CCCAUGUCUG AUGAGGCCGA AAGGCCGAAA UCUUUC    36

( 2 ) INFORMATION FOR SEQ ID NO: 1199:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1199:

CAUGAGACUG AUGAGGCCGA AAGGCCGAAA UUGGCU    36

( 2 ) INFORMATION FOR SEQ ID NO: 1200:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1200:

GCAUGAGCUG AUGAGGCCGA AAGGCCGAAA AUUGGC     36

( 2 ) INFORMATION FOR SEQ ID NO: 1201:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1201:

GGCAUGACUG AUGAGGCCGA AAGGCCGAAA AAUUGG     36

( 2 ) INFORMATION FOR SEQ ID NO: 1202:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1202:

GCGGCAUCUG AUGAGGCCGA AAGGCCGAAA GAAAUU     36

( 2 ) INFORMATION FOR SEQ ID NO: 1203:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1203:

CAGCUCACUG AUGAGGCCGA AAGGCCGAAA CAGCUU     36

( 2 ) INFORMATION FOR SEQ ID NO: 1204:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1204:

UCAGCUCCUG AUGAGGCCGA AAGGCCGAAA ACAGCU     36

( 2 ) INFORMATION FOR SEQ ID NO: 1205:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1205:

GGUGGCCCUG AUGAGGCCGA AAGGCCGAAA GGCUCG     36

( 2 ) INFORMATION FOR SEQ ID NO: 1206:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1206:

AGGCUGGCUG AUGAGGCCGA AAGGCCGAAA GAGGUC 36

(2) INFORMATION FOR SEQ ID NO: 1207:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1207:

AGGACCGCUG AUGAGGCCGA AAGGCCGAAA GCUGAA 36

(2) INFORMATION FOR SEQ ID NO: 1208:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1208:

AAGAUCGCUG AUGAGGCCGA AAGGCCGAAA AGUCCG 36

(2) INFORMATION FOR SEQ ID NO: 1209:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1209:

GCAGGGUCUG AUGAGGCCGA AAGGCCGAAA GGUCCU 36

(2) INFORMATION FOR SEQ ID NO: 1210:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1210:

GAGGCAGCUG AUGAGGCCGA AAGGCCGAAA AACAGG 36

(2) INFORMATION FOR SEQ ID NO: 1211:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1211:

UGAGGUGCUG AUGAGGCCGA AAGGCCGAAA GCCGCC 36

(2) INFORMATION FOR SEQ ID NO: 1212:

(i) SEQUENCE CHARACTERISTICS:
(A) LENGTH: 36 base pairs
(B) TYPE: nucleic acid

-continued (C) STRANDEDNESS: single
(D) TOPOLOGY: linear (xi) SEQUENCE DESCRIPTION: SEQ ID NO: 1212:

AGCUGAACUG AUGAGGCCGA AAGGCCGAAA GUUGUA 36

(2) INFORMATION FOR SEQ ID NO: 1213:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1213:

CGGAGCUCUG AUGAGGCCGA AAGGCCGAAA AAAGUU 36

(2) INFORMATION FOR SEQ ID NO: 1214:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1214:

UCUCCAGCUG AUGAGGCCGA AAGGCCGAAA UCUGGU 36

(2) INFORMATION FOR SEQ ID NO: 1215:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1215:

CCAUCACCUG AUGAGGCCGA AAGGCCGAAA GGCCCA 36

(2) INFORMATION FOR SEQ ID NO: 1216:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1216:

GGAAGCGCUG AUGAGGCCGA AAGGCCGAAA CGACUG 36

(2) INFORMATION FOR SEQ ID NO: 1217:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1217:

GGCAGGACUG AUGAGGCCGA AAGGCCGAAA CAGGCC 36

(2) INFORMATION FOR SEQ ID NO: 1218:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO: 1218:

UUCCAGGCUG AUGAGGCCGA AAGGCCGAAA GCAAAA 36

(2) INFORMATION FOR SEQ ID NO: 1219:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1219:

GGCAGGACUG AUGAGGCCGA AAGGCCGAAA CAGGCC 36

(2) INFORMATION FOR SEQ ID NO: 1220:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1220:

AGGCAGGCUG AUGAGGCCGA AAGGCCGAAA ACAGGC 36

(2) INFORMATION FOR SEQ ID NO: 1221:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1221:

CUUCCGACUG AUGAGGCCGA AAGGCCGAAA CCUCCA 36

(2) INFORMATION FOR SEQ ID NO: 1222:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1222:

AGUCUCCCUG AUGAGGCCGA AAGGCCGAAA GCCCAG 36

(2) INFORMATION FOR SEQ ID NO: 1223:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1223:

CCAGGUACUG AUGAGGCCGA AAGGCCGAAA UCCGAG 36

(2) INFORMATION FOR SEQ ID NO: 1224:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1224:

GGGUGUCCUG AUGAGGCCGA AAGGCCGAAA GCUUUG    36

(2) INFORMATION FOR SEQ ID NO: 1225:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1225:

CAACGGUCUG AUGAGGCCGA AAGGCCGAAA CCAGGG    36

(2) INFORMATION FOR SEQ ID NO: 1226:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1226:

GCUGGUACUG AUGAGGCCGA AAGGCCGAAA GGUCUC    36

(2) INFORMATION FOR SEQ ID NO: 1227:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1227:

CCAGAGGCUG AUGAGGCCGA AAGGCCGAAA GUGGCU    36

(2) INFORMATION FOR SEQ ID NO: 1228:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1228:

GGGCAGGCUG AUGAGGCCGA AAGGCCGAAA GGCUUC    36

(2) INFORMATION FOR SEQ ID NO: 1229:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1229:

UCUCCGGCUG AUGAGGCCGA AAGGCCGAAA ACGAAU    36

(2) INFORMATION FOR SEQ ID NO: 1230:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1230:

CUUGCAUCUG AUGAGGCCGA AAGGCCGAAA GGAAGA    36

( 2 ) INFORMATION FOR SEQ ID NO: 1231:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1231:

ACGGGUUCUG AUGAGGCCGA AAGGCCGAAA AGCCAU    36

( 2 ) INFORMATION FOR SEQ ID NO: 1232:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1232:

UCACCUCCUG AUGAGGCCGA AAGGCCGAAA CCAAGG    36

( 2 ) INFORMATION FOR SEQ ID NO: 1233:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1233:

CCAGAAUCUG AUGAGGCCGA AAGGCCGAAA UUAUAG    36

( 2 ) INFORMATION FOR SEQ ID NO: 1234:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1234:

GCACCAGCUG AUGAGGCCGA AAGGCCGAAA UGAUUA    36

( 2 ) INFORMATION FOR SEQ ID NO: 1235:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1235:

AGUUGUACUG AUGAGGCCGA AAGGCCGAAA CUGUUA    36

( 2 ) INFORMATION FOR SEQ ID NO: 1236:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1236:

AAAGUUGCUG AUGAGGCCGA AAGGCCGAAA GACUGU    36

( 2 ) INFORMATION FOR SEQ ID NO: 1237:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1237:

AGCUGAACUG AUGAGGCCGA AAGGCCGAAA GUUGUA    36

( 2 ) INFORMATION FOR SEQ ID NO: 1238:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1238:

GAGCUGACUG AUGAGGCCGA AAGGCCGAAA AGUUGU    36

( 2 ) INFORMATION FOR SEQ ID NO: 1239:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1239:

GGAGCUGCUG AUGAGGCCGA AAGGCCGAAA AAGUUG    36

( 2 ) INFORMATION FOR SEQ ID NO: 1240:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1240:

UCUCCAGCUG AUGAGGCCGA AAGGCCGAAA UCUGGU    36

( 2 ) INFORMATION FOR SEQ ID NO: 1241:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1241:

UUCCCCACUG AUGAGGCCGA AAGGCCGAAA CUCUCA    36

( 2 ) INFORMATION FOR SEQ ID NO: 1242:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1242:

CUUCCGACUG AUGAGGCCGA AAGGCCGAAA CCUCCA    36

( 2 ) INFORMATION FOR SEQ ID NO: 1243:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1243:

CCCUUCCCUG AUGAGGCCGA AAGGCCGAAA GACCUC 36

( 2 ) INFORMATION FOR SEQ ID NO: 1244:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1244:

UUAUUUUCUG AUGAGGCCGA AAGGCCGAAA GAGUGG 36

( 2 ) INFORMATION FOR SEQ ID NO: 1245:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1245:

GGCCUGACUG AUGAGGCCGA AAGGCCGAAA UCCAGU 36

( 2 ) INFORMATION FOR SEQ ID NO: 1246:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1246:

UUGGCUGCUG AUGAGGCCGA AAGGCCGAAA GGUCCA 36

( 2 ) INFORMATION FOR SEQ ID NO: 1247:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1247:

UCAAGAACUG AUGAGGCCGA AAGGCCGAAA GUUGGG 36

( 2 ) INFORMATION FOR SEQ ID NO: 1248:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1248:

GCAAAAGCUG AUGAGGCCGA AAGGCCGAAA GCUUCG 36

( 2 ) INFORMATION FOR SEQ ID NO: 1249:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO: 1249:

AGCAAAACUG AUGAGGCCGA AAGGCCGAAA AGCUUC 36

(2) INFORMATION FOR SEQ ID NO: 1250:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1250:

AGAGCAACUG AUGAGGCCGA AAGGCCGAAA GAAGCU 36

(2) INFORMATION FOR SEQ ID NO: 1251:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1251:

GGUUUUUCUG AUGAGGCCGA AAGGCCGAAA ACAGGA 36

(2) INFORMATION FOR SEQ ID NO: 1252:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1252:

UGUGGAGCUG AUGAGGCCGA AAGGCCGAAA GCAGAG 36

(2) INFORMATION FOR SEQ ID NO: 1253:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1253:

CUGUUCACUG AUGAGGCCGA AAGGCCGAAA AGCAGC 36

(2) INFORMATION FOR SEQ ID NO: 1254:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1254:

ACUGGUGCUG AUGAGGCCGA AAGGCCGAAA AAAAGU 36

(2) INFORMATION FOR SEQ ID NO: 1255:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO: 1255:

GCACACGCUG AUGAGGCCGA AAGGCCGAAA UGUACC 36

(2) INFORMATION FOR SEQ ID NO: 1256:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1256:

AGCAAAACUG AUGAGGCCGA AAGGCCGAAA AGCUUC 36

(2) INFORMATION FOR SEQ ID NO: 1257:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1257:

CUCUCCGCUG AUGAGGCCGA AAGGCCGAAA AACGAA 36

(2) INFORMATION FOR SEQ ID NO: 1258:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1258:

AGGACCACUG AUGAGGCCGA AAGGCCGAAA CAGCAC 36

(2) INFORMATION FOR SEQ ID NO: 1259:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1259:

CUUGCACCUG AUGAGGCCGA AAGGCCGAAA CCCUUC 36

(2) INFORMATION FOR SEQ ID NO: 1260:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1260:

UUCCCCACUG AUGAGGCCGA AAGGCCGAAA CUCUCA 36

(2) INFORMATION FOR SEQ ID NO: 1261:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO: 1261:

GGCUCAGCUG AUGAGGCCGA AAGGCCGAAA UCUCCU 36

( 2 ) INFORMATION FOR SEQ ID NO: 1262:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1262:

CUGCUGACUG AUGAGGCCGA AAGGCCGAAA CCCCUC 36

( 2 ) INFORMATION FOR SEQ ID NO: 1263:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1263:

CAUUUCACUG AUGAGGCCGA AAGGCCGAAA GUCUGC 36

( 2 ) INFORMATION FOR SEQ ID NO: 1264:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1264:

UCCUCCUCUG AUGAGGCCGA AAGGCCGAAA GCCUUC 36

( 2 ) INFORMATION FOR SEQ ID NO: 1265:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1265:

UUUAGGACUG AUGAGGCCGA AAGGCCGAAA UGGGUU 36

( 2 ) INFORMATION FOR SEQ ID NO: 1266:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1266:

CACUCUCCUG AUGAGGCCGA AAGGCCGAAA GCUCAU 36

( 2 ) INFORMATION FOR SEQ ID NO: 1267:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1267:

```
UAACUUACUG  AUGAGGCCGA  AAGGCCGAAA  CAUUCA                                          36
```

( 2 ) INFORMATION FOR SEQ ID NO: 1268:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1268:

```
CACCUUCCUG  AUGAGGCCGA  AAGGCCGAAA  CCCACU                                          36
```

( 2 ) INFORMATION FOR SEQ ID NO: 1269:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1269:

```
AGUUGUACUG  AUGAGGCCGA  AAGGCCGAAA  CUGUUA                                          36
```

( 2 ) INFORMATION FOR SEQ ID NO: 1270:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1270:

```
AGGUGGGCUG  AUGAGGCCGA  AAGGCCGAAA  GGUGCU                                          36
```

( 2 ) INFORMATION FOR SEQ ID NO: 1271:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1271:

```
AGAGUGGCUG  AUGAGGCCGA  AAGGCCGAAA  CAGUAC                                          36
```

( 2 ) INFORMATION FOR SEQ ID NO: 1272:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1272:

```
CCACCCCCUG  AUGAGGCCGA  AAGGCCGAAA  UGGGCA                                          36
```

( 2 ) INFORMATION FOR SEQ ID NO: 1273:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1273:

```
AGCCACUCUG  AUGAGGCCGA  AAGGCCGAAA  GUCUCC                                          36
```

( 2 ) INFORMATION FOR SEQ ID NO: 1274:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1274:

GUUCUGUCUG AUGAGGCCGA AAGGCCGAAA CAGCCA 36

( 2 ) INFORMATION FOR SEQ ID NO: 1275:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1275:

AGUUCUCCUG AUGAGGCCGA AAGGCCGAAA AGCACA 36

( 2 ) INFORMATION FOR SEQ ID NO: 1276:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1276:

CCUCCCCUG AUGAGGCCGA AAGGCCGAAA UCUCGC 36

( 2 ) INFORMATION FOR SEQ ID NO: 1277:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1277:

CCCUUCCCUG AUGAGGCCGA AAGGCCGAAA GACCUC 36

( 2 ) INFORMATION FOR SEQ ID NO: 1278:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1278:

ACAAAAGCUG AUGAGGCCGA AAGGCCGAAA GGUGGG 36

( 2 ) INFORMATION FOR SEQ ID NO: 1279:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1279:

CUCUACCCUG AUGAGGCCGA AAGGCCGAAA GGCAGU 36

( 2 ) INFORMATION FOR SEQ ID NO: 1280:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO: 1280:

CAGGGGCCUG AUGAGGCCGA AAGGCCGAAA UAGAGA 36

( 2 ) INFORMATION FOR SEQ ID NO: 1281:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO: 1281:

UCCUCCUCUG AUGAGGCCGA AAGGCCGAAA GCCUUC 36

( 2 ) INFORMATION FOR SEQ ID NO: 1282:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO: 1282:

UCCUGGUCUG AUGAGGCCGA AAGGCCGAAA CAUUCC 36

( 2 ) INFORMATION FOR SEQ ID NO: 1283:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO: 1283:

GGGAGCACUG AUGAGGCCGA AAGGCCGAAA ACAACU 36

( 2 ) INFORMATION FOR SEQ ID NO: 1284:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO: 1284:

CAUGAGGCUG AUGAGGCCGA AAGGCCGAAA GAACAG 36

( 2 ) INFORMATION FOR SEQ ID NO: 1285:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO: 1285:

GUUCUCACUG AUGAGGCCGA AAGGCCGAAA GCACAG 36

( 2 ) INFORMATION FOR SEQ ID NO: 1286:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1286:

GGACCAUCUG AUGAGGCCGA AAGGCCGAAA UUUCAU    36

( 2 ) INFORMATION FOR SEQ ID NO: 1287:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1287:

GAAUGAUCUG AUGAGGCCGA AAGGCCGAAA UAGUCC    36

( 2 ) INFORMATION FOR SEQ ID NO: 1288:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1288:

CGGUUAUCUG AUGAGGCCGA AAGGCCGAAA ACAUAA    36

( 2 ) INFORMATION FOR SEQ ID NO: 1289:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1289:

ACACGGUCUG AUGAGGCCGA AAGGCCGAAA UGGUAG    36

( 2 ) INFORMATION FOR SEQ ID NO: 1290:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1290:

CGCCUGGCUG AUGAGGCCGA AAGGCCGAAA CCAUGA    36

( 2 ) INFORMATION FOR SEQ ID NO: 1291:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1291:

CCAGAAUCUG AUGAGGCCGA AAGGCCGAAA UUAUAG    36

( 2 ) INFORMATION FOR SEQ ID NO: 1292:

( i ) SEQUENCE CHARACTERISTICS:
( A ) LENGTH: 36 base pairs
( B ) TYPE: nucleic acid ( C ) STRANDEDNESS: single
( D ) TOPOLOGY: linear ( x i ) SEQUENCE DESCRIPTION: SEQ ID NO: 1292:

GGCCCACCUG AUGAGGCCGA AAGGCCGAAA UGACCA    36

( 2 ) INFORMATION FOR SEQ ID NO: 1293:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1293:

AGCUGCUCUG AUGAGGCCGA AAGGCCGAAA GGCAUG    36

( 2 ) INFORMATION FOR SEQ ID NO: 1294:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1294:

AGGUGGGCUG AUGAGGCCGA AAGGCCGAAA GGUGCU    36

( 2 ) INFORMATION FOR SEQ ID NO: 1295:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1295:

GGUUAUACUG AUGAGGCCGA AAGGCCGAAA CAUAAG    36

( 2 ) INFORMATION FOR SEQ ID NO: 1296:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1296:

GCGGUUACUG AUGAGGCCGA AAGGCCGAAA AACAUA    36

( 2 ) INFORMATION FOR SEQ ID NO: 1297:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1297:

UGGCGGUCUG AUGAGGCCGA AAGGCCGAAA UAAACA    36

( 2 ) INFORMATION FOR SEQ ID NO: 1298:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear (x i) SEQUENCE DESCRIPTION: SEQ ID NO: 1298:

AUAUCCUCUG AUGAGGCCGA AAGGCCGAAA UCUUUC  36

(2) INFORMATION FOR SEQ ID NO: 1299:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1299:

UAACUUGCUG AUGAGGCCGA AAGGCCGAAA UAUCCU  36

(2) INFORMATION FOR SEQ ID NO: 1300:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1300:

CCUUCUGCUG AUGAGGCCGA AAGGCCGAAA ACUUGU  36

(2) INFORMATION FOR SEQ ID NO: 1301:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1301:

GCUCAGGCUG AUGAGGCCGA AAGGCCGAAA GGUGGG  36

(2) INFORMATION FOR SEQ ID NO: 1302:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1302:

CAAAGGACUG AUGAGGCCGA AAGGCCGAAA GGUUUC  36

(2) INFORMATION FOR SEQ ID NO: 1303:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1303:

UUCAAAGCUG AUGAGGCCGA AAGGCCGAAA AAGGUU  36

(2) INFORMATION FOR SEQ ID NO: 1304:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1304:

CCAGGCUCUG AUGAGGCCGA AAGGCCGAAA GGUCCU 36

(2) INFORMATION FOR SEQ ID NO: 1305:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1305:

CCAGAGGCUG AUGAGGCCGA AAGGCCGAAA GUGGCU 36

(2) INFORMATION FOR SEQ ID NO: 1306:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1306:

GCCAGAGCUG AUGAGGCCGA AAGGCCGAAA AGUGGC 36

(2) INFORMATION FOR SEQ ID NO: 1307:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1307:

ACAGCCACUG AUGAGGCCGA AAGGCCGAAA GGAAGU 36

(2) INFORMATION FOR SEQ ID NO: 1308:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1308:

AGAUCGACUG AUGAGGCCGA AAGGCCGAAA GUCCGG 36

(2) INFORMATION FOR SEQ ID NO: 1309:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1309:

AAGAUCGCUG AUGAGGCCGA AAGGCCGAAA AGUCCG 36

(2) INFORMATION FOR SEQ ID NO: 1310:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1310:

CCACCCCCUG AUGAGGCCGA AAGGCCGAAA UGGGCA 36

( 2 ) INFORMATION FOR SEQ ID NO: 1311:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1311:

CUCCAGGCUG AUGAGGCCGA AAGGCCGAAA UAUCCG    36

( 2 ) INFORMATION FOR SEQ ID NO: 1312:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1312:

GCUGGUACUG AUGAGGCCGA AAGGCCGAAA GGUCUC    36

( 2 ) INFORMATION FOR SEQ ID NO: 1313:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1313:

UGAGGUGCUG AUGAGGCCGA AAGGCCGAAA GCCGCC    36

( 2 ) INFORMATION FOR SEQ ID NO: 1314:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1314:

GGGCAGGCUG AUGAGGCCGA AAGGCCGAAA GGCUUC    36

( 2 ) INFORMATION FOR SEQ ID NO: 1315:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1315:

UGGGGACCUG AUGAGGCCGA AAGGCCGAAA UGUCUC    36

( 2 ) INFORMATION FOR SEQ ID NO: 1316:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1316:

AUUAGAGCUG AUGAGGCCGA AAGGCCGAAA CAAUGC    36

( 2 ) INFORMATION FOR SEQ ID NO: 1317:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1317:

UCCAGCCCUG AUGAGGCCGA AAGGCCGAAA GGACCA    36

( 2 ) INFORMATION FOR SEQ ID NO: 1318:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1318:

UUUAUGUCUG AUGAGGCCGA AAGGCCGAAA CUGGUG    36

( 2 ) INFORMATION FOR SEQ ID NO: 1319:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1319:

UCUCCAGCUG AUGAGGCCGA AAGGCCGAAA UCUGGU    36

( 2 ) INFORMATION FOR SEQ ID NO: 1320:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1320:

GGCCUGACUG AUGAGGCCGA AAGGCCGAAA UCCAGU    36

( 2 ) INFORMATION FOR SEQ ID NO: 1321:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1321:

UGAGGGUCUG AUGAGGCCGA AAGGCCGAAA AUGCUG    36

( 2 ) INFORMATION FOR SEQ ID NO: 1322:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1322:

GCAGAGGCUG AUGAGGCCGA AAGGCCGAAA GCGUGG    36

( 2 ) INFORMATION FOR SEQ ID NO: 1323:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1323:

GGAGCUACUG AUGAGGCCGA AAGGCCGAAA GGCAUG    36

( 2 ) INFORMATION FOR SEQ ID NO: 1324:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1324:

GGUGGCCCUG AUGAGGCCGA AAGGCCGAAA GGCUCG    36

( 2 ) INFORMATION FOR SEQ ID NO: 1325:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1325:

AAGAUCGCUG AUGAGGCCGA AAGGCCGAAA AGUCCG    36

( 2 ) INFORMATION FOR SEQ ID NO: 1326:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1326:

UACUGGACUG AUGAGGCCGA AAGGCCGAAA UCAUGU    36

( 2 ) INFORMATION FOR SEQ ID NO: 1327:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1327:

CUGAGGCCUG AUGAGGCCGA AAGGCCGAAA CAAGUG    36

( 2 ) INFORMATION FOR SEQ ID NO: 1328:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1328:

UUUAUGUCUG AUGAGGCCGA AAGGCCGAAA CUGGUG    36

( 2 ) INFORMATION FOR SEQ ID NO: 1329:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO: 1329:

AGCUGCUCUG AUGAGGCCGA AAGGCCGAAA GGCAUG 36

(2) INFORMATION FOR SEQ ID NO: 1330:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1330:

GUCCCUUCUG AUGAGGCCGA AAGGCCGAAA GUUUUA 36

(2) INFORMATION FOR SEQ ID NO: 1331:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1331:

ACUGAUCCUG AUGAGGCCGA AAGGCCGAAA CUAUAU 36

(2) INFORMATION FOR SEQ ID NO: 1332:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1332:

UAACUUACUG AUGAGGCCGA AAGGCCGAAA CAUUCA 36

(2) INFORMATION FOR SEQ ID NO: 1333:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1333:

GAUACCUCUG AUGAGGCCGA AAGGCCGAAA GCAUCA 36

(2) INFORMATION FOR SEQ ID NO: 1334:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1334:

CUGGUAACUG AUGAGGCCGA AAGGCCGAAA CUCUAA 36

(2) INFORMATION FOR SEQ ID NO: 1335:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO: 1335:

AGCUGGUCUG AUGAGGCCGA AAGGCCGAAA AACUCU                36

(2) INFORMATION FOR SEQ ID NO: 1336:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 1336:

UGGGGACCUG AUGAGGCCGA AAGGCCGAAA UGUCUC                36

(2) INFORMATION FOR SEQ ID NO: 1337:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 1337:

UAACUUGCUG AUGAGGCCGA AAGGCCGAAA UAUCCU                36

(2) INFORMATION FOR SEQ ID NO: 1338:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 1338:

GGCUCAGCUG AUGAGGCCGA AAGGCCGAAA UCUCCU                36

(2) INFORMATION FOR SEQ ID NO: 1339:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 1339:

GGUCCGCCUG AUGAGGCCGA AAGGCCGAAA GCUCCA                36

(2) INFORMATION FOR SEQ ID NO: 1340:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO: 1340:

UACUCAACUG AUGAGGCCGA AAGGCCGAAA AAUAGC                36

(2) INFORMATION FOR SEQ ID NO: 1341:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO: 1341:

CCACCCCUG AUGAGGCCGA AAGGCCGAAA UGGGCA 36

(2) INFORMATION FOR SEQ ID NO: 1342:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1342:

CUCAGAACUG AUGAGGCCGA AAGGCCGAAA ACCACC 36

(2) INFORMATION FOR SEQ ID NO: 1343:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1343:

CCUCUGCCUG AUGAGGCCGA AAGGCCGAAA GCCAGC 36

(2) INFORMATION FOR SEQ ID NO: 1344:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1344:

CCUCCAGCUG AUGAGGCCGA AAGGCCGAAA GGUCAG 36

(2) INFORMATION FOR SEQ ID NO: 1345:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1345:

GGAUGUGCUG AUGAGGCCGA AAGGCCGAAA GGAGCA 36

(2) INFORMATION FOR SEQ ID NO: 1346:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1346:

ACACGGUCUG AUGAGGCCGA AAGGCCGAAA UGGUAG 36

(2) INFORMATION FOR SEQ ID NO: 1347:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1347:

```
CUGAGGCUG AUGAGGCGA AAGGCCGAAA CAAGUG                                36
```

(2) INFORMATION FOR SEQ ID NO: 1348:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1348:

```
UAGCUCUCUG AUGAGGCCGA AAGGCCGAAA GGCUAC                              36
```

(2) INFORMATION FOR SEQ ID NO: 1349:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1349:

```
CAUCAAGCUG AUGAGGCCGA AAGGCCGAAA GAGUUG                              36
```

(2) INFORMATION FOR SEQ ID NO: 1350:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1350:

```
CGGGGGGCUG AUGAGGCCGA AAGGCCGAAA AGUGUG                              36
```

(2) INFORMATION FOR SEQ ID NO: 1351:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1351:

```
AUCCUCCCUG AUGAGGCCGA AAGGCCGAAA GCUGGC                              36
```

(2) INFORMATION FOR SEQ ID NO: 1352:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1352:

```
CUCAAUACUG AUGAGGCCGA AAGGCCGAAA UAGCUG                              36
```

(2) INFORMATION FOR SEQ ID NO: 1353:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1353:

```
GAGGCAGCUG AUGAGGCCGA AAGGCCGAAA AACAGG                              36
```

( 2 ) INFORMATION FOR SEQ ID NO: 1354:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1354:

CAUCAAGCUG AUGAGGCCGA AAGGCCGAAA GAGUUG     36

( 2 ) INFORMATION FOR SEQ ID NO: 1355:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1355:

AACUCUACUG AUGAGGCCGA AAGGCCGAAA UUAAUA     36

( 2 ) INFORMATION FOR SEQ ID NO: 1356:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1356:

UAAUAAACUG AUGAGGCCGA AAGGCCGAAA CAUCAA     36

( 2 ) INFORMATION FOR SEQ ID NO: 1357:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1357:

AUUAAUACUG AUGAGGCCGA AAGGCCGAAA UACAUC     36

( 2 ) INFORMATION FOR SEQ ID NO: 1358:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1358:

AAUUAAUCUG AUGAGGCCGA AAGGCCGAAA AUACAU     36

( 2 ) INFORMATION FOR SEQ ID NO: 1359:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1359:

AAAUUAACUG AUGAGGCCGA AAGGCCGAAA AAUACA     36

( 2 ) INFORMATION FOR SEQ ID NO: 1360:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1360:

CUAAAUUCUG AUGAGGCCGA AAGGCCGAAA UAAAUA    36

( 2 ) INFORMATION FOR SEQ ID NO: 1361:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1361:

AAUUAAUCUG AUGAGGCCGA AAGGCCGAAA AUACAU    36

( 2 ) INFORMATION FOR SEQ ID NO: 1362:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1362:

AAUAGAGCUG AUGAGGCCGA AAGGCCGAAA UGAAGU    36

( 2 ) INFORMATION FOR SEQ ID NO: 1363:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1363:

AAUUAAUCUG AUGAGGCCGA AAGGCCGAAA AUACAU    36

( 2 ) INFORMATION FOR SEQ ID NO: 1364:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1364:

CUAAAUUCUG AUGAGGCCGA AAGGCCGAAA UAAAUA    36

( 2 ) INFORMATION FOR SEQ ID NO: 1365:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1365:

GGGAGCACUG AUGAGGCCGA AAGGCCGAAA ACAACU    36

( 2 ) INFORMATION FOR SEQ ID NO: 1366:

( i ) SEQUENCE CHARACTERISTICS:

(A) LENGTH: 36 base pairs
              (B) TYPE: nucleic acid
              (C) STRANDEDNESS: single
              (D) TOPOLOGY: linear (xi) SEQUENCE DESCRIPTION: SEQ ID NO: 1366:

CUGGUACUG AUGAGGCCGA AAGGCCGAAA CUCUAA					36

(2) INFORMATION FOR SEQ ID NO: 1367:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (xi) SEQUENCE DESCRIPTION: SEQ ID NO: 1367:

GCUGGUACUG AUGAGGCCGA AAGGCCGAAA ACUCUA					36

(2) INFORMATION FOR SEQ ID NO: 1368:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (xi) SEQUENCE DESCRIPTION: SEQ ID NO: 1368:

AGCUGGUCUG AUGAGGCCGA AAGGCCGAAA AACUCU					36

(2) INFORMATION FOR SEQ ID NO: 1369:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (xi) SEQUENCE DESCRIPTION: SEQ ID NO: 1369:

UAGCUGGCUG AUGAGGCCGA AAGGCCGAAA AAACUC					36

(2) INFORMATION FOR SEQ ID NO: 1370:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (xi) SEQUENCE DESCRIPTION: SEQ ID NO: 1370:

CAAUAAACUG AUGAGGCCGA AAGGCCGAAA GCUGGU					36

(2) INFORMATION FOR SEQ ID NO: 1371:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (xi) SEQUENCE DESCRIPTION: SEQ ID NO: 1371:

CUCAAUACUG AUGAGGCCGA AAGGCCGAAA UAGCUG					36

(2) INFORMATION FOR SEQ ID NO: 1372:

(i) SEQUENCE CHARACTERISTICS:
              (A) LENGTH: 36 base pairs
              (B) TYPE: nucleic acid

```
           ( C ) STRANDEDNESS: single
           ( D ) TOPOLOGY: linear ( x i ) SEQUENCE DESCRIPTION: SEQ ID NO: 1372:

ACUCAAUCUG  AUGAGGCCGA  AAGGCCGAAA  AUAGCU                                    36

( 2 ) INFORMATION FOR SEQ ID NO: 1373:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1373:

UACUCAACUG  AUGAGGCCGA  AAGGCCGAAA  AAUAGC                                    36

( 2 ) INFORMATION FOR SEQ ID NO: 1374:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1374:

GGUACUCCUG  AUGAGGCCGA  AAGGCCGAAA  UAAAUA                                    36

( 2 ) INFORMATION FOR SEQ ID NO: 1375:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1375:

CAUCAAGCUG  AUGAGGCCGA  AAGGCCGAAA  GAGUUG                                    36

( 2 ) INFORMATION FOR SEQ ID NO: 1376:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1376:

AACAUAACUG  AUGAGGCCGA  AAGGCCGAAA  GGCUGC                                    36

( 2 ) INFORMATION FOR SEQ ID NO: 1377:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1377:

AUAAACACUG  AUGAGGCCGA  AAGGCCGAAA  AGAGGC                                    36

( 2 ) INFORMATION FOR SEQ ID NO: 1378:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear
```

(x i) SEQUENCE DESCRIPTION: SEQ ID NO: 1378:

CUUGCAUCUG AUGAGGCCGA AAGGCCGAAA GGAAGA 36

(2) INFORMATION FOR SEQ ID NO: 1379:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (x i) SEQUENCE DESCRIPTION: SEQ ID NO: 1379:

GCCGACACUG AUGAGGCCGA AAGGCCGAAA AAACUU 36

(2) INFORMATION FOR SEQ ID NO: 1380:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (x i) SEQUENCE DESCRIPTION: SEQ ID NO: 1380:

UCAGGCCCUG AUGAGGCCGA AAGGCCGAAA CAUAAA 36

(2) INFORMATION FOR SEQ ID NO: 1381:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (x i) SEQUENCE DESCRIPTION: SEQ ID NO: 1381:

AGCCACUCUG AUGAGGCCGA AAGGCCGAAA GUCUCC 36

(2) INFORMATION FOR SEQ ID NO: 1382:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (x i) SEQUENCE DESCRIPTION: SEQ ID NO: 1382:

AGAGAACCUG AUGAGGCCGA AAGGCCGAAA UGCCAG 36

(2) INFORMATION FOR SEQ ID NO: 1383:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (x i) SEQUENCE DESCRIPTION: SEQ ID NO: 1383:

GGAUGGACUG AUGAGGCCGA AAGGCCGAAA CCUGAG 36

(2) INFORMATION FOR SEQ ID NO: 1384:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (x i) SEQUENCE DESCRIPTION: SEQ ID NO: 1384:

GCGGCCUCUG AUGAGGCCGA AAGGCCGAAA GAUCCA                36

( 2 ) INFORMATION FOR SEQ ID NO: 1385:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1385:

CCUCCAGCUG AUGAGGCCGA AAGGCCGAAA GGUCAG                36

( 2 ) INFORMATION FOR SEQ ID NO: 1386:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1386:

GGUCCGCCUG AUGAGGCCGA AAGGCCGAAA GCUCCA                36

( 2 ) INFORMATION FOR SEQ ID NO: 1387:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1387:

UGGGAUGCUG AUGAGGCCGA AAGGCCGAAA UGGAUA                36

( 2 ) INFORMATION FOR SEQ ID NO: 1388:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1388:

UCAGUGUCUG AUGAGGCCGA AAGGCCGAAA AUUGGA                36

( 2 ) INFORMATION FOR SEQ ID NO: 1389:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1389:

CACCGUGCUG AUGAGGCCGA AAGGCCGAAA UGUGAU                36

( 2 ) INFORMATION FOR SEQ ID NO: 1390:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1390:

GCACCGUCUG AUGAGGCCGA AAGGCCGAAA AUGUGA                36

( 2 ) INFORMATION FOR SEQ ID NO: 1391:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1391:

UCCUGGUCUG AUGAGGCCGA AAGGCCGAAA CAUUCC    36

( 2 ) INFORMATION FOR SEQ ID NO: 1392:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1392:

UCUCCAGCUG AUGAGGCCGA AAGGCCGAAA UCUGGU    36

( 2 ) INFORMATION FOR SEQ ID NO: 1393:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1393:

CUUGCACCUG AUGAGGCCGA AAGGCCGAAA CCCUUC    36

( 2 ) INFORMATION FOR SEQ ID NO: 1394:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1394:

CAGCUCACUG AUGAGGCCGA AAGGCCGAAA CAGCUU    36

( 2 ) INFORMATION FOR SEQ ID NO: 1395:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1395:

AGGCCAUCUG AUGAGGCCGA AAGGCCGAAA CUUAUA    36

( 2 ) INFORMATION FOR SEQ ID NO: 1396:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1396:

AGCAGAGCUG AUGAGGCCGA AAGGCCGAAA CCACUG    36

( 2 ) INFORMATION FOR SEQ ID NO: 1397:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1397:

CCCAUGUCUG AUGAGGCCGA AAGGCCGAAA UCUUUC        36

( 2 ) INFORMATION FOR SEQ ID NO: 1398:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1398:

CAGGCAGCUG AUGAGGCCGA AAGGCCGAAA GUCUCA        36

( 2 ) INFORMATION FOR SEQ ID NO: 1399:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1399:

CAAAGGACUG AUGAGGCCGA AAGGCCGAAA GGUUUC        36

( 2 ) INFORMATION FOR SEQ ID NO: 1400:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1400:

AGGCUGGCUG AUGAGGCCGA AAGGCCGAAA GAGGUC        36

( 2 ) INFORMATION FOR SEQ ID NO: 1401:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1401:

GCUGGAACUG AUGAGGCCGA AAGGCCGAAA UCGAAA        36

( 2 ) INFORMATION FOR SEQ ID NO: 1402:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1402:

CUGCUGACUG AUGAGGCCGA AAGGCCGAAA GCUGGG        36

( 2 ) INFORMATION FOR SEQ ID NO: 1403:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1403:

UCUGUUCCUG AUGAGGCCGA AAGGCCGAAA AAGCAG    36

( 2 ) INFORMATION FOR SEQ ID NO: 1404:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1404:

UUCAAAGCUG AUGAGGCCGA AAGGCCGAAA AAGGUU    36

( 2 ) INFORMATION FOR SEQ ID NO: 1405:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1405:

UCAGAAGCUG AUGAGGCCGA AAGGCCGAAA CCACCU    36

( 2 ) INFORMATION FOR SEQ ID NO: 1406:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1406:

CUCAGAACUG AUGAGGCCGA AAGGCCGAAA ACCACC    36

( 2 ) INFORMATION FOR SEQ ID NO: 1407:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1407:

CAGUAGACUG AUGAGGCCGA AAGGCCGAAA AACCCU    36

( 2 ) INFORMATION FOR SEQ ID NO: 1408:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1408:

CUUAUGACUG AUGAGGCCGA AAGGCCGAAA AAAGCA    36

( 2 ) INFORMATION FOR SEQ ID NO: 1409:

( i ) SEQUENCE CHARACTERISTICS:
    ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO: 1409:

GCCGACACUG AUGAGGCCGA AAGGCCGAAA AAACUU 36

( 2 ) INFORMATION FOR SEQ ID NO: 1410:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1410:

GGGGCAACUG AUGAGGCCGA AAGGCCGAAA GAGAAU 36

( 2 ) INFORMATION FOR SEQ ID NO: 1411:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1411:

UUGUGUCCUG AUGAGGCCGA AAGGCCGAAA CUGGAU 36

( 2 ) INFORMATION FOR SEQ ID NO: 1412:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1412:

GUCCACACUG AUGAGGCCGA AAGGCCGAAA GUGUUU 36

( 2 ) INFORMATION FOR SEQ ID NO: 1413:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1413:

CAGCUCACUG AUGAGGCCGA AAGGCCGAAA CAGCUU 36

( 2 ) INFORMATION FOR SEQ ID NO: 1414:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1414:

GCAUCCUCUG AUGAGGCCGA AAGGCCGAAA CCAGUA 36

( 2 ) INFORMATION FOR SEQ ID NO: 1415:

( i ) SEQUENCE CHARACTERISTICS:
( A ) LENGTH: 36 base pairs
( B ) TYPE: nucleic acid
( C ) STRANDEDNESS: single (D) TOPOLOGY: linear (xi) SEQUENCE DESCRIPTION: SEQ ID NO: 1415:

ACGUAUGCUG AUGAGGCCGA AAGGCCGAAA CCAUUC                36

(2) INFORMATION FOR SEQ ID NO: 1416:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1416:

GGCCUGACUG AUGAGGCCGA AAGGCCGAAA UCCAGU                36

(2) INFORMATION FOR SEQ ID NO: 1417:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1417:

AACCUCCUG AUGAGGCCGA AAGGCCGAAA CCCAUG                 36

(2) INFORMATION FOR SEQ ID NO: 1418:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1418:

AAACUCUCUG AUGAGGCCGA AAGGCCGAAA AUUAAU                36

(2) INFORMATION FOR SEQ ID NO: 1419:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1419:

GCUGGUACUG AUGAGGCCGA AAGGCCGAAA ACUCUA                36

(2) INFORMATION FOR SEQ ID NO: 1420:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1420:

AGCUGGUCUG AUGAGGCCGA AAGGCCGAAA AACUCU                36

(2) INFORMATION FOR SEQ ID NO: 1421:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1421:

GGGCAGGCUG AUGAGGCCGA AAGGCCGAAA GGCUUC 36

(2) INFORMATION FOR SEQ ID NO: 1422:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1422:

GGGGCAGCUG AUGAGGCCGA AAGGCCGAAA AGGCUU 36

(2) INFORMATION FOR SEQ ID NO: 1423:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1423:

AGGCAGGCUG AUGAGGCCGA AAGGCCGAAA ACAGGC 36

(2) INFORMATION FOR SEQ ID NO: 1424:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1424:

GAGGCAGCUG AUGAGGCCGA AAGGCCGAAA AACAGG 36

(2) INFORMATION FOR SEQ ID NO: 1425:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1425:

GGGCAGGCUG AUGAGGCCGA AAGGCCGAAA GGCUUC 36

(2) INFORMATION FOR SEQ ID NO: 1426:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1426:

GGGGGGGCUG AUGAGGCCGA AAGGCCGAAA GUGUGG 36

(2) INFORMATION FOR SEQ ID NO: 1427:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO: 1427:

CGGGGGGCUG AUGAGGCCGA AAGGCCGAAA AGUGUG 36

( 2 ) INFORMATION FOR SEQ ID NO: 1428:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1428:

GCUGGUACUG AUGAGGCCGA AAGGCCGAAA GGUCUC 36

( 2 ) INFORMATION FOR SEQ ID NO: 1429:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1429:

GGAUCACCUG AUGAGGCCGA AAGGCCGAAA CGGUGA 36

( 2 ) INFORMATION FOR SEQ ID NO: 1430:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1430:

GGUGGCUCUG AUGAGGCCGA AAGGCCGAAA CAUUGG 36

( 2 ) INFORMATION FOR SEQ ID NO: 1431:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1431:

GACUGGUCUG AUGAGGCCGA AAGGCCGAAA AAAAAG 36

( 2 ) INFORMATION FOR SEQ ID NO: 1432:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1432:

AGGUGGGCUG AUGAGGCCGA AAGGCCGAAA GGUGCU 36

( 2 ) INFORMATION FOR SEQ ID NO: 1433:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1433:

ACAAAAGCUG AUGAGGCCGA AAGGCCGAAA GGUGGG 36

( 2 ) INFORMATION FOR SEQ ID NO: 1434:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1434:

UGGGAUGCUG AUGAGGCCGA AAGGCCGAAA UGGAUA    36

( 2 ) INFORMATION FOR SEQ ID NO: 1435:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1435:

CUGGUAACUG AUGAGGCCGA AAGGCCGAAA CUCUAA    36

( 2 ) INFORMATION FOR SEQ ID NO: 1436:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1436:

GCUGGUACUG AUGAGGCCGA AAGGCCGAAA ACUCUA    36

( 2 ) INFORMATION FOR SEQ ID NO: 1437:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1437:

CAUUGGGCUG AUGAGGCCGA AAGGCCGAAA CAAAAG    36

( 2 ) INFORMATION FOR SEQ ID NO: 1438:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1438:

UGAGGGUCUG AUGAGGCCGA AAGGCCGAAA AUGCUG    36

( 2 ) INFORMATION FOR SEQ ID NO: 1439:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1439:

GAUACCUCUG AUGAGGCCGA AAGGCCGAAA GCAUCA    36

( 2 ) INFORMATION FOR SEQ ID NO: 1440:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1440:

CACAGCGCUG AUGAGGCCGA AAGGCCGAAA CUGCUG    36

( 2 ) INFORMATION FOR SEQ ID NO: 1441:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1441:

AGGACCACUG AUGAGGCCGA AAGGCCGAAA CAGCAC    36

( 2 ) INFORMATION FOR SEQ ID NO: 1442:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1442:

UUUGACACUG AUGAGGCCGA AAGGCCGAAA CUUCAC    36

( 2 ) INFORMATION FOR SEQ ID NO: 1443:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1443:

CAGGCCACUG AUGAGGCCGA AAGGCCGAAA ACUUAU    36

( 2 ) INFORMATION FOR SEQ ID NO: 1444:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1444:

AGAGAACCUG AUGAGGCCGA AAGGCCGAAA UGCCAG    36

( 2 ) INFORMATION FOR SEQ ID NO: 1445:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1445:

AUUAGAGCUG AUGAGGCCGA AAGGCCGAAA CAAUGC    36

( 2 ) INFORMATION FOR SEQ ID NO: 1446:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1446:

AGGAGCACUG AUGAGGCCGA AAGGCCGAAA GAACCA 36

( 2 ) INFORMATION FOR SEQ ID NO: 1447:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1447:

GCAGAGCCUG AUGAGGCCGA AAGGCCGAAA AAGAAG 36

( 2 ) INFORMATION FOR SEQ ID NO: 1448:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1448:

CAUUGGGCUG AUGAGGCCGA AAGGCCGAAA CAAAAG 36

( 2 ) INFORMATION FOR SEQ ID NO: 1449:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1449:

AAACGAACUG AUGAGGCCGA AAGGCCGAAA CACGGU 36

( 2 ) INFORMATION FOR SEQ ID NO: 1450:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1450:

GGGAUGGCUG AUGAGGCCGA AAGGCCGAAA GCUGGA 36

( 2 ) INFORMATION FOR SEQ ID NO: 1451:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1451:

CCAGGUACUG AUGAGGCCGA AAGGCCGAAA UCCGAG 36

( 2 ) INFORMATION FOR SEQ ID NO: 1452:

( i ) SEQUENCE CHARACTERISTICS:
( A ) LENGTH: 36 base pairs
( B ) TYPE: nucleic acid ( C ) STRANDEDNESS: single
( D ) TOPOLOGY: linear ( x i ) SEQUENCE DESCRIPTION: SEQ ID NO: 1452:

CACAGCGCUG AUGAGGCCGA AAGGCCGAAA CUGCUG 36

( 2 ) INFORMATION FOR SEQ ID NO: 1453:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1453:

UCCUGGUCUG AUGAGGCCGA AAGGCCGAAA CAUUCC 36

( 2 ) INFORMATION FOR SEQ ID NO: 1454:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1454:

GCAGGGUCUG AUGAGGCCGA AAGGCCGAAA GGUCCU 36

( 2 ) INFORMATION FOR SEQ ID NO: 1455:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1455:

GCUGGAACUG AUGAGGCCGA AAGGCCGAAA UCGAAA 36

( 2 ) INFORMATION FOR SEQ ID NO: 1456:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1456:

AGGCUACCUG AUGAGGCCGA AAGGCCGAAA GUGUGC 36

( 2 ) INFORMATION FOR SEQ ID NO: 1457:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1457:

AGGACCGCUG AUGAGGCCGA AAGGCCGAAA GCUGAA 36

( 2 ) INFORMATION FOR SEQ ID NO: 1458:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 1458:

GGCAGGACUG AUGAGGCGA AAGGCCGAAA CAGGCC    36

( 2 ) INFORMATION FOR SEQ ID NO: 1459:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1459:

CUGCUGACUG AUGAGGCCGA AAGGCCGAAA GCUGGG    36

( 2 ) INFORMATION FOR SEQ ID NO: 1460:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1460:

GAGGCAGCUG AUGAGGCCGA AAGGCCGAAA AACAGG    36

( 2 ) INFORMATION FOR SEQ ID NO: 1461:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1461:

GCAUCCUCUG AUGAGGCCGA AAGGCCGAAA CCAGUA    36

( 2 ) INFORMATION FOR SEQ ID NO: 1462:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1462:

CUUGCACCUG AUGAGGCCGA AAGGCCGAAA CCCUUC    36

( 2 ) INFORMATION FOR SEQ ID NO: 1463:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1463:

CCUCGGACUG AUGAGGCCGA AAGGCCGAAA CAUUAG    36

( 2 ) INFORMATION FOR SEQ ID NO: 1464:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1464:

```
GGCCUCGCUG  AUGAGGCCGA  AAGGCCGAAA  GACAUU                                                36
```

( 2 ) INFORMATION FOR SEQ ID NO: 1465:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1465:

```
GGGCAGGCUG  AUGAGGCCGA  AAGGCCGAAA  GGCUUC                                                36
```

( 2 ) INFORMATION FOR SEQ ID NO: 1466:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1466:

```
AGGCUGGCUG  AUGAGGCCGA  AAGGCCGAAA  GAGGUC                                                36
```

( 2 ) INFORMATION FOR SEQ ID NO: 1467:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1467:

```
CUGCUGACUG  AUGAGGCCGA  AAGGCCGAAA  GCUGGG                                                36
```

( 2 ) INFORMATION FOR SEQ ID NO: 1468:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1468:

```
CCCUUCCCUG  AUGAGGCCGA  AAGGCCGAAA  GACCUC                                                36
```

( 2 ) INFORMATION FOR SEQ ID NO: 1469:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1469:

```
CUUGCACCUG  AUGAGGCCGA  AAGGCCGAAA  CCCUUC                                                36
```

( 2 ) INFORMATION FOR SEQ ID NO: 1470:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1470:

```
GCACACGCUG  AUGAGGCCGA  AAGGCCGAAA  UGUACC                                                36
```

( 2 ) INFORMATION FOR SEQ ID NO: 1471:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1471:

CUGCACGCUG AUGAGGCCGA AAGGCCGAAA CCCACC      36

( 2 ) INFORMATION FOR SEQ ID NO: 1472:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1472:

GGUACUCCUG AUGAGGCCGA AAGGCCGAAA UAAAUA      36

( 2 ) INFORMATION FOR SEQ ID NO: 1473:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1473:

AGAUCGACUG AUGAGGCCGA AAGGCCGAAA GUCCGG      36

( 2 ) INFORMATION FOR SEQ ID NO: 1474:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1474:

GCAGGGUCUG AUGAGGCCGA AAGGCCGAAA GGUCCU      36

( 2 ) INFORMATION FOR SEQ ID NO: 1475:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1475:

AGCGGCACUG AUGAGGCCGA AAGGCCGAAA GCAAAA      36

( 2 ) INFORMATION FOR SEQ ID NO: 1476:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1476:

CCUGUUUCUG AUGAGGCCGA AAGGCCGAAA CAGACU      36

( 2 ) INFORMATION FOR SEQ ID NO: 1477:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1477:

GGACCAUCUG AUGAGGCCGA AAGGCCGAAA UUUCAU    36

( 2 ) INFORMATION FOR SEQ ID NO: 1478:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1478:

CGCCUGGCUG AUGAGGCCGA AAGGCCGAAA CCAUGA    36

( 2 ) INFORMATION FOR SEQ ID NO: 1479:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1479:

CUGCACGCUG AUGAGGCCGA AAGGCCGAAA CCCACC    36

( 2 ) INFORMATION FOR SEQ ID NO: 1480:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1480:

GGGUCAGCUG AUGAGGCCGA AAGGCCGAAA CCGGAG    36

( 2 ) INFORMATION FOR SEQ ID NO: 1481:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1481:

AAAGUUGCUG AUGAGGCCGA AAGGCCGAAA GACUGU    36

( 2 ) INFORMATION FOR SEQ ID NO: 1482:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1482:

CCUCCAGCUG AUGAGGCCGA AAGGCCGAAA GGUCAG    36

( 2 ) INFORMATION FOR SEQ ID NO: 1483:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1483:

AAGUCCGCUG AUGAGGCCGA AAGGCCGAAA GGCUCC 36

( 2 ) INFORMATION FOR SEQ ID NO: 1484:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1484:

UGGGAGCCUG AUGAGGCCGA AAGGCCGAAA AAGGCA 36

( 2 ) INFORMATION FOR SEQ ID NO: 1485:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1485:

AUGAUUACUG AUGAGGCCGA AAGGCCGAAA GUCCAG 36

( 2 ) INFORMATION FOR SEQ ID NO: 1486:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1486:

UCAGAAGCUG AUGAGGCCGA AAGGCCGAAA CCACCU 36

( 2 ) INFORMATION FOR SEQ ID NO: 1487:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1487:

CAGGCAGCUG AUGAGGCCGA AAGGCCGAAA GUCUCA 36

( 2 ) INFORMATION FOR SEQ ID NO: 1488:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1488:

GGUGGCUCUG AUGAGGCCGA AAGGCCGAAA CAUUGG 36

( 2 ) INFORMATION FOR SEQ ID NO: 1489:

( i ) SEQUENCE CHARACTERISTICS:
      ( A ) LENGTH: 36 base pairs ( B ) TYPE: nucleic acid
        ( C ) STRANDEDNESS: single
        ( D ) TOPOLOGY: linear ( x i ) SEQUENCE DESCRIPTION: SEQ ID NO: 1489:

AACAUAACUG AUGAGGCCGA AAGGCCGAAA GGCUGC        36

( 2 ) INFORMATION FOR SEQ ID NO: 1490:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1490:

UCACAGUCUG AUGAGGCCGA AAGGCCGAAA CUUGGC        36

( 2 ) INFORMATION FOR SEQ ID NO: 1491:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1491:

CUUGGCUCUG AUGAGGCCGA AAGGCCGAAA AGGUCC        36

( 2 ) INFORMATION FOR SEQ ID NO: 1492:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1492:

GUGAUGGCUG AUGAGGCCGA AAGGCCGAAA GCGGAA        36

( 2 ) INFORMATION FOR SEQ ID NO: 1493:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1493:

AAGAUCGCUG AUGAGGCCGA AAGGCCGAAA AGUCCG        36

( 2 ) INFORMATION FOR SEQ ID NO: 1494:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1494:

AAAACUCCUG AUGAGGCCGA AAGGCCGAAA AAUUAA        36

( 2 ) INFORMATION FOR SEQ ID NO: 1495:

( i ) SEQUENCE CHARACTERISTICS:
        ( A ) LENGTH: 36 base pairs
        ( B ) TYPE: nucleic acid
        ( C ) STRANDEDNESS: single (D) TOPOLOGY: linear (xi) SEQUENCE DESCRIPTION: SEQ ID NO: 1495:

AAUAGAGCUG AUGAGGCCGA AAGGCCGAAA UGAAGU    36

(2) INFORMATION FOR SEQ ID NO: 1496:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1496:

CAAUAGACUG AUGAGGCCGA AAGGCCGAAA AUGAAG    36

(2) INFORMATION FOR SEQ ID NO: 1497:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1497:

UAAUAAACUG AUGAGGCCGA AAGGCCGAAA CAUCAA    36

(2) INFORMATION FOR SEQ ID NO: 1498:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1498:

AAAUUAACUG AUGAGGCCGA AAGGCCGAAA AAUACA    36

(2) INFORMATION FOR SEQ ID NO: 1499:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1499:

AGCAAAACUG AUGAGGCCGA AAGGCCGAAA AGCUUC    36

(2) INFORMATION FOR SEQ ID NO: 1500:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1500:

AGAGCAACUG AUGAGGCCGA AAGGCCGAAA GAAGCU    36

(2) INFORMATION FOR SEQ ID NO: 1501:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO: 1501:

AAAUUAACUG AUGAGGCCGA AAGGCCGAAA AAUACA   36

( 2 ) INFORMATION FOR SEQ ID NO: 1502:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1502:

AAAUUAACUG AUGAGGCCGA AAGGCCGAAA AAUACA   36

( 2 ) INFORMATION FOR SEQ ID NO: 1503:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1503:

GACAUUACUG AUGAGGCCGA AAGGCCGAAA GAACAA   36

( 2 ) INFORMATION FOR SEQ ID NO: 1504:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1504:

UGACCAGCUG AUGAGGCCGA AAGGCCGAAA GAGAAA   36

( 2 ) INFORMATION FOR SEQ ID NO: 1505:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1505:

CUUAUGACUG AUGAGGCCGA AAGGCCGAAA AAAGCA   36

( 2 ) INFORMATION FOR SEQ ID NO: 1506:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1506:

UCUAAAUCUG AUGAGGCCGA AAGGCCGAAA AUAAAU   36

( 2 ) INFORMATION FOR SEQ ID NO: 1507:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1507:

CUCCGGACUG AUGAGGCCGA AAGGCCGAAA CGAAUA 36

(2) INFORMATION FOR SEQ ID NO: 1508:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1508:

UCUCCGGCUG AUGAGGCCGA AAGGCCGAAA ACGAAU 36

(2) INFORMATION FOR SEQ ID NO: 1509:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1509:

CUCUCCGCUG AUGAGGCCGA AAGGCCGAAA AACGAA 36

(2) INFORMATION FOR SEQ ID NO: 1510:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1510:

CGACCCUCUG AUGAGGCCGA AAGGCCGAAA UGAGAA 36

(2) INFORMATION FOR SEQ ID NO: 1511:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1511:

CUUCCGACUG AUGAGGCCGA AAGGCCGAAA CCUCCA 36

(2) INFORMATION FOR SEQ ID NO: 1512:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1512:

CCCUUCCCUG AUGAGGCCGA AAGGCCGAAA GACCUC 36

(2) INFORMATION FOR SEQ ID NO: 1513:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1513:

UGGGGACCUG AUGAGGCCGA AAGGCCGAAA UGUCUC 36

( 2 ) INFORMATION FOR SEQ ID NO: 1514:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1514:

GCAGAGGCUG AUGAGGCCGA AAGGCCGAAA GCGUGG    36

( 2 ) INFORMATION FOR SEQ ID NO: 1515:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1515:

CACAGCGCUG AUGAGGCCGA AAGGCCGAAA CUGCUG    36

( 2 ) INFORMATION FOR SEQ ID NO: 1516:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1516:

UGACACACUG AUGAGGCCGA AAGGCCGAAA GUCACU    36

( 2 ) INFORMATION FOR SEQ ID NO: 1517:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1517:

UUGAUUCCUG AUGAGGCCGA AAGGCCGAAA AGGAAA    36

( 2 ) INFORMATION FOR SEQ ID NO: 1518:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1518:

AGUGGCUCUG AUGAGGCCGA AAGGCCGAAA CACAGA    36

( 2 ) INFORMATION FOR SEQ ID NO: 1519:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1519:

AAUUAAUCUG AUGAGGCCGA AAGGCCGAAA AUACAU    36

( 2 ) INFORMATION FOR SEQ ID NO: 1520:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1520:

CUUUAUUCUG AUGAGGCCGA AAGGCCGAAA UUCAAA      36

( 2 ) INFORMATION FOR SEQ ID NO: 1521:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1521:

CCUCUGCCUG AUGAGGCCGA AAGGCCGAAA GCCAGC      36

( 2 ) INFORMATION FOR SEQ ID NO: 1522:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1522:

AAAACUUCUG AUGAGGCCGA AAGGCCGAAA UUGAUU      36

( 2 ) INFORMATION FOR SEQ ID NO: 1523:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1523:

GCUGGUACUG AUGAGGCCGA AAGGCCGAAA ACUCUA      36

( 2 ) INFORMATION FOR SEQ ID NO: 1524:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1524:

AGUAGAGCUG AUGAGGCCGA AAGGCCGAAA ACCCUC      36

( 2 ) INFORMATION FOR SEQ ID NO: 1525:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1525:

CAGCUCACUG AUGAGGCCGA AAGGCCGAAA CAGCUU      36

( 2 ) INFORMATION FOR SEQ ID NO: 1526:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 1526:

GGCAAUACUG AUGAGGCCGA AAGGCCGAAA GAAUGA 36

(2) INFORMATION FOR SEQ ID NO: 1527:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO: 1527:

GGGCCGGGAG AAGCUGACCA GAGAAACACA CGUUGUGGUA CAUUACCUGG UA 52

(2) INFORMATION FOR SEQ ID NO: 1528:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO: 1528:

GGAGUGCGAG AAGCGCACCA GAGAAACACA CGUUGUGGUA CAUUACCUGG UA 52

(2) INFORMATION FOR SEQ ID NO: 1529:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO: 1529:

CCCAUCAGAG AAGUUUACCA GAGAAACACA CGUUGUGGUA CAUUACCUGG UA 52

(2) INFORMATION FOR SEQ ID NO: 1530:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO: 1530:

GCCCUUGGAG AAGCAGACCA GAGAAACACA CGUUGUGGUA CAUUACCUGG UA 52

(2) INFORMATION FOR SEQ ID NO: 1531:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO: 1531:

UGUUCUCAAG AAGCUCACCA GAGAAACACA CGUUGUGGUA CAUUACCUGG UA 52

(2) INFORMATION FOR SEQ ID NO: 1532:

(i) SEQUENCE CHARACTERISTICS:
(A) LENGTH: 52 base pairs
(B) TYPE: nucleic acid ( C ) STRANDEDNESS: single
( D ) TOPOLOGY: linear ( x i ) SEQUENCE DESCRIPTION: SEQ ID NO: 1532:

AGACUGGGAG AAGCCCACCA GAGAAACACA CGUUGUGGUA CAUUACCUGG UA  52

( 2 ) INFORMATION FOR SEQ ID NO: 1533:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1533:

CUGCACACAG AAGCCGACCA GAGAAACACA CGUUGUGGUA CAUUACCUGG UA  52

( 2 ) INFORMATION FOR SEQ ID NO: 1534:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1534:

ACAUUGGAAG AAGCUGACCA GAGAAACACA CGUUGUGGUA CAUUACCUGG UA  52

( 2 ) INFORMATION FOR SEQ ID NO: 1535:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1535:

CCCCGAUGAG AAGUGGACCA GAGAAACACA CGUUGUGGUA CAUUACCUGG UA  52

( 2 ) INFORMATION FOR SEQ ID NO: 1536:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1536:

AUGACUGCAG AAGCUAACCA GAGAAACACA CGUUGUGGUA CAUUACCUGG UA  52

( 2 ) INFORMATION FOR SEQ ID NO: 1537:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1537:

CUGUUGUAAG AAGUAUACCA GAGAAACACA CGUUGUGGUA CAUUACCUGG UA  52

( 2 ) INFORMATION FOR SEQ ID NO: 1538:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1538:

ACCCAAUAAG AAGCAAACCA GAGAAACACA CGUUGUGGUA CAUUACCUGG UA    52

( 2 ) INFORMATION FOR SEQ ID NO: 1539:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1539:

UUCUGUAAAG AAGUGGACCA GAGAAACACA CGUUGUGGUA CAUUACCUGG UA    52

( 2 ) INFORMATION FOR SEQ ID NO: 1540:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1540:

GGUCAGUAAG AAGCAGACCA GAGAAACACA CGUUGUGGUA CAUUACCUGG UA    52

( 2 ) INFORMATION FOR SEQ ID NO: 1541:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1541:

GGGUUGGGAG AAGUAGACCA GAGAAACACA CGUUGUGGUA CAUUACCUGG UA    52

( 2 ) INFORMATION FOR SEQ ID NO: 1542:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1542:

ACCUGUACAG AAGUACACCA GAGAAACACA CGUUGUGGUA CAUUACCUGG UA    52

( 2 ) INFORMATION FOR SEQ ID NO: 1543:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1543:

AAGGUCAAAG AAGCAGACCA GAGAAACACA CGUUGUGGUA CAUUACCUGG UA    52

( 2 ) INFORMATION FOR SEQ ID NO: 1544:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1544:

CAGCAGCCCC CGGCCC                                                                        16

( 2 ) INFORMATION FOR SEQ ID NO: 1545:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1545:

GCGCUGCCCG CACUCC                                                                        16

( 2 ) INFORMATION FOR SEQ ID NO: 1546:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1546:

AAACUGCCCU GAUGGG                                                                        16

( 2 ) INFORMATION FOR SEQ ID NO: 1547:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1547:

CUGCGGCCCC AAGGGC                                                                        16

( 2 ) INFORMATION FOR SEQ ID NO: 1548:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1548:

GAGCUGUUUG AGAACA                                                                        16

( 2 ) INFORMATION FOR SEQ ID NO: 1549:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1549:

GGGCUGUUCC CAGUCU                                                                        16

( 2 ) INFORMATION FOR SEQ ID NO: 1550:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1550:

CGGCUGACGU GUGCAG                                                                        16

( 2 ) INFORMATION FOR SEQ ID NO: 1551:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1551:

CAGCAGACUC CAAUGU  16

( 2 ) INFORMATION FOR SEQ ID NO: 1552:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1552:

CCACUGCCCA UCGGGG  16

( 2 ) INFORMATION FOR SEQ ID NO: 1553:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1553:

UAGCAGCCGC AGUCAU  16

( 2 ) INFORMATION FOR SEQ ID NO: 1554:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1554:

AUACAGACUA CAACAG  16

( 2 ) INFORMATION FOR SEQ ID NO: 1555:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1555:

UUGCUGCCUA UUGGGU  16

( 2 ) INFORMATION FOR SEQ ID NO: 1556:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1556:

CCACAGACUU ACAGAA  16

( 2 ) INFORMATION FOR SEQ ID NO: 1557:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1557:

CUGCUGUCUA CUGACC         16

( 2 ) INFORMATION FOR SEQ ID NO: 1558:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1558:

CUACUGACCC CAACCC         16

( 2 ) INFORMATION FOR SEQ ID NO: 1559:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1559:

GUACAGUUGU ACAGGU         16

( 2 ) INFORMATION FOR SEQ ID NO: 1560:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1560:

CUGCAGUCUU GACCUU         16

( 2 ) INFORMATION FOR SEQ ID NO: 1561:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1561:

GGGAUCACAG AAGUGAACCA GAGAAACACA CGUUGUGGUA CAUUACCUGG UA         52

( 2 ) INFORMATION FOR SEQ ID NO: 1562:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1562:

UGAGGAAGAG AAGUUCACCA GAGAAACACA CGUUGUGGUA CAUUACCUGG UA         52

( 2 ) INFORMATION FOR SEQ ID NO: 1563:

(i) SEQUENCE CHARACTERISTICS:
              (A) LENGTH: 52 base pairs
              (B) TYPE: nucleic acid
              (C) STRANDEDNESS: single
              (D) TOPOLOGY: linear (xi) SEQUENCE DESCRIPTION: SEQ ID NO: 1563:

UCAGCUCAAG AAGCUUACCA GAGAAACACA CGUUGUGGUA CAUUACCUGG UA          52

(2) INFORMATION FOR SEQ ID NO: 1564:

(i) SEQUENCE CHARACTERISTICS:
              (A) LENGTH: 52 base pairs
              (B) TYPE: nucleic acid
              (C) STRANDEDNESS: single
              (D) TOPOLOGY: linear (xi) SEQUENCE DESCRIPTION: SEQ ID NO: 1564:

GCACAGCGAG AAGCUGACCA GAGAAACACA CGUUGUGGUA CAUUACCUGG UA          52

(2) INFORMATION FOR SEQ ID NO: 1565:

(i) SEQUENCE CHARACTERISTICS:
              (A) LENGTH: 52 base pairs
              (B) TYPE: nucleic acid
              (C) STRANDEDNESS: single
              (D) TOPOLOGY: linear (xi) SEQUENCE DESCRIPTION: SEQ ID NO: 1565:

AAGCGGACAG AAGCACACCA GAGAAACACA CGUUGUGGUA CAUUACCUGG UA          52

(2) INFORMATION FOR SEQ ID NO: 1566:

(i) SEQUENCE CHARACTERISTICS:
              (A) LENGTH: 52 base pairs
              (B) TYPE: nucleic acid
              (C) STRANDEDNESS: single
              (D) TOPOLOGY: linear (xi) SEQUENCE DESCRIPTION: SEQ ID NO: 1566:

AGAGCUGGAG AAGCGGACCA GAGAAACACA CGUUGUGGUA CAUUACCUGG UA          52

(2) INFORMATION FOR SEQ ID NO: 1567:

(i) SEQUENCE CHARACTERISTICS:
              (A) LENGTH: 52 base pairs
              (B) TYPE: nucleic acid
              (C) STRANDEDNESS: single
              (D) TOPOLOGY: linear (xi) SEQUENCE DESCRIPTION: SEQ ID NO: 1567:

UCUCCUGGAG AAGCAUACCA GAGAAACACA CGUUGUGGUA CAUUACCUGG UA          52

(2) INFORMATION FOR SEQ ID NO: 1568:

(i) SEQUENCE CHARACTERISTICS:
              (A) LENGTH: 52 base pairs
              (B) TYPE: nucleic acid
              (C) STRANDEDNESS: single
              (D) TOPOLOGY: linear (xi) SEQUENCE DESCRIPTION: SEQ ID NO: 1568:

UCUACCAAAG AAGUGGACCA GAGAAACACA CGUUGUGGUA CAUUACCUGG UA          52

(2) INFORMATION FOR SEQ ID NO: 1569:

(i) SEQUENCE CHARACTERISTICS:
              (A) LENGTH: 52 base pairs ( B ) TYPE: nucleic acid
        ( C ) STRANDEDNESS: single
        ( D ) TOPOLOGY: linear ( x i ) SEQUENCE DESCRIPTION: SEQ ID NO: 1569:

AGGAUCUGAG AAGCUAACCA GAGAAACACA CGUUGUGGUA CAUUACCUGG UA               52

( 2 ) INFORMATION FOR SEQ ID NO: 1570:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1570:

AAGUUGUAAG AAGUUAACCA GAGAAACACA CGUUGUGGUA CAUUACCUGG UA               52

( 2 ) INFORMATION FOR SEQ ID NO: 1571:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1571:

CCCAAGCAAG AAGUCUACCA GAGAAACACA CGUUGUGGUA CAUUACCUGG UA               52

( 2 ) INFORMATION FOR SEQ ID NO: 1572:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1572:

AUUUCAGAAG AAGCUGACCA GAGAAACACA CGUUGUGGUA CAUUACCUGG UA               52

( 2 ) INFORMATION FOR SEQ ID NO: 1573:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1573:

UGCCUUCCAG AAGCAGACCA GAGAAACACA CGUUGUGGUA CAUUACCUGG UA               52

( 2 ) INFORMATION FOR SEQ ID NO: 1574:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1574:

CCCCGAUGAG AAGCAGACCA GAGAAACACA CGUUGUGGUA CAUUACCUGG UA               52

( 2 ) INFORMATION FOR SEQ ID NO: 1575:

( i ) SEQUENCE CHARACTERISTICS:
        ( A ) LENGTH: 52 base pairs
        ( B ) TYPE: nucleic acid
        ( C ) STRANDEDNESS: single (D) TOPOLOGY: linear (xi) SEQUENCE DESCRIPTION: SEQ ID NO: 1575:

ACAUAAGAAG AAGCCAACCA GAGAAACACA CGUUGUGGUA CAUUACCUGG UA        52

(2) INFORMATION FOR SEQ ID NO: 1576:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 1576:

GUCCACCGAG AAGUAGACCA GAGAAACACA CGUUGUGGUA CAUUACCUGG UA        52

(2) INFORMATION FOR SEQ ID NO: 1577:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 1577:

AGAAUGAAAG AAGCGUACCA GAGAAACACA CGUUGUGGUA CAUUACCUGG UA        52

(2) INFORMATION FOR SEQ ID NO: 1578:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 1578:

UCACCGUUGU GAUCCC        16

(2) INFORMATION FOR SEQ ID NO: 1579:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 1579:

GAACUGUUCU UCCUCA        16

(2) INFORMATION FOR SEQ ID NO: 1580:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 1580:

AAGCUGUUUG AGCUGA        16

(2) INFORMATION FOR SEQ ID NO: 1581:

(i) SEQUENCE CHARACTERISTICS:
        (A) LENGTH: 16 base pairs
        (B) TYPE: nucleic acid
        (C) STRANDEDNESS: single
        (D) TOPOLOGY: linear -continued ( x i ) SEQUENCE DESCRIPTION: SEQ ID NO: 1581:

CAGCAGUCCG CUGUGC 16

( 2 ) INFORMATION FOR SEQ ID NO: 1582:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1582:

GUGCAGUCGU CCGCUU 16

( 2 ) INFORMATION FOR SEQ ID NO: 1583:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1583:

CCGCGGACCC AGCUCU 16

( 2 ) INFORMATION FOR SEQ ID NO: 1584:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1584:

AUGCCGACCC AGGAGA 16

( 2 ) INFORMATION FOR SEQ ID NO: 1585:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1585:

CCACUGCCUU GGUAGA 16

( 2 ) INFORMATION FOR SEQ ID NO: 1586:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1586:

UAGCGGACCA GAUCCU 16

( 2 ) INFORMATION FOR SEQ ID NO: 1587:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1587:

UAACAGUCUA CAACUU 16

(2) INFORMATION FOR SEQ ID NO: 1588:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO: 1588:

AGACGGACUG CUUGGG 16

(2) INFORMATION FOR SEQ ID NO: 1589:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO: 1589:

CAGCAGACUC UGAAAU 16

(2) INFORMATION FOR SEQ ID NO: 1590:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO: 1590:

CUGCAGACGG AAGGCA 16

(2) INFORMATION FOR SEQ ID NO: 1591:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO: 1591:

CUGCUGCCCA UCGGGG 16

(2) INFORMATION FOR SEQ ID NO: 1592:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO: 1592:

UGGCAGCCUC UUAUGU 16

(2) INFORMATION FOR SEQ ID NO: 1593:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO: 1593:

CUACAGCCCG GUGGAC 16

( 2 ) INFORMATION FOR SEQ ID NO: 1594:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1594:

ACGCUGACUU CAUUCU     16

( 2 ) INFORMATION FOR SEQ ID NO: 1595:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1595:

AAAGUGCAAG AAGCAGACCA GAGAAACACA CGUUGUGGUA CAUUACCUGG UA     52

( 2 ) INFORMATION FOR SEQ ID NO: 1596:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1596:

GGAGCAGAAG AAGCAUACCA GAGAAACACA CGUUGUGGUA CAUUACCUGG UA     52

( 2 ) INFORMATION FOR SEQ ID NO: 1597:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1597:

GGGAUCACAG AAGCGAACCA GAGAAACACA CGUUGUGGUA CAUUACCUGG UA     52

( 2 ) INFORMATION FOR SEQ ID NO: 1598:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1598:

GCACAGUGAG AAGCUGACCA GAGAAACACA CGUUGUGGUA CAUUACCUGG UA     52

( 2 ) INFORMATION FOR SEQ ID NO: 1599:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1599:

AAGCCGAGAG AAGCGUACCA GAGAAACACA CGUUGUGGUA CAUUACCUGG UA     52

( 2 ) INFORMATION FOR SEQ ID NO: 1600:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1600:

UUCCACCAAG AAGCGCACCA GAGAAACACA CGUUGUGGUA CAUUACCUGG UA    52

( 2 ) INFORMATION FOR SEQ ID NO: 1601:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1601:

CAUUCUUGAG AAGUGAACCA GAGAAACACA CGUUGUGGUA CAUUACCUGG UA    52

( 2 ) INFORMATION FOR SEQ ID NO: 1602:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1602:

UCUCCAGGAG AAGCAUACCA GAGAAACACA CGUUGUGGUA CAUUACCUGG UA    52

( 2 ) INFORMATION FOR SEQ ID NO: 1603:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1603:

UCCACUGAAG AAGUGGACCA GAGAAACACA CGUUGUGGUA CAUUACCUGG UA    52

( 2 ) INFORMATION FOR SEQ ID NO: 1604:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1604:

AGGGUCUGAG AAGCCAACCA GAGAAACACA CGUUGUGGUA CAUUACCUGG UA    52

( 2 ) INFORMATION FOR SEQ ID NO: 1605:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1605:

ACCUCCAAAG AAGCAGACCA GAGAAACACA CGUUGUGGUA CAUUACCUGG UA    52

( 2 ) INFORMATION FOR SEQ ID NO: 1606:

( i ) SEQUENCE CHARACTERISTICS:

( A ) LENGTH: 52 base pairs
( B ) TYPE: nucleic acid
( C ) STRANDEDNESS: single
( D ) TOPOLOGY: linear ( x i ) SEQUENCE DESCRIPTION: SEQ ID NO: 1606:

AUGUAAGAAG AAGCUGACCA GAGAAACACA CGUUGUGGUA CAUUACCUGG UA          52

( 2 ) INFORMATION FOR SEQ ID NO: 1607:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( x i ) SEQUENCE DESCRIPTION: SEQ ID NO: 1607:

UGCUUUCCAG AAGCAGACCA GAGAAACACA CGUUGUGGUA CAUUACCUGG UA          52

( 2 ) INFORMATION FOR SEQ ID NO: 1608:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( x i ) SEQUENCE DESCRIPTION: SEQ ID NO: 1608:

UCCCGAUAAG AAGCGGACCA GAGAAACACA CGUUGUGGUA CAUUACCUGG UA          52

( 2 ) INFORMATION FOR SEQ ID NO: 1609:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( x i ) SEQUENCE DESCRIPTION: SEQ ID NO: 1609:

GCCCACCAAG AAGUAGACCA GAGAAACACA CGUUGUGGUA CAUUACCUGG UA          52

( 2 ) INFORMATION FOR SEQ ID NO: 1610:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( x i ) SEQUENCE DESCRIPTION: SEQ ID NO: 1610:

AGAAGGAAAG AAGCCUACCA GAGAAACACA CGUUGUGGUA CAUUACCUGG UA          52

( 2 ) INFORMATION FOR SEQ ID NO: 1611:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( x i ) SEQUENCE DESCRIPTION: SEQ ID NO: 1611:

GAGUUGGGAG AAGUGUACCA GAGAAACACA CGUUGUGGUA CAUUACCUGG UA          52

( 2 ) INFORMATION FOR SEQ ID NO: 1612:

( i ) SEQUENCE CHARACTERISTICS:
( A ) LENGTH: 52 base pairs
( B ) TYPE: nucleic acid ( C ) STRANDEDNESS: single
             ( D ) TOPOLOGY: linear ( x i ) SEQUENCE DESCRIPTION: SEQ ID NO: 1612:

AGACUCCAAG  AAGUGGACCA  GAGAAACACA  CGUUGUGGUA  CAUUACCUGG  UA                52

( 2 ) INFORMATION FOR SEQ ID NO: 1613:

( i ) SEQUENCE CHARACTERISTICS:
             ( A ) LENGTH: 52 base pairs
             ( B ) TYPE: nucleic acid
             ( C ) STRANDEDNESS: single
             ( D ) TOPOLOGY: linear ( x i ) SEQUENCE DESCRIPTION: SEQ ID NO: 1613:

CCUCCCACAG  AAGCUUACCA  GAGAAACACA  CGUUGUGGUA  CAUUACCUGG  UA                52

( 2 ) INFORMATION FOR SEQ ID NO: 1614:

( i ) SEQUENCE CHARACTERISTICS:
             ( A ) LENGTH: 16 base pairs
             ( B ) TYPE: nucleic acid
             ( C ) STRANDEDNESS: single
             ( D ) TOPOLOGY: linear ( x i ) SEQUENCE DESCRIPTION: SEQ ID NO: 1614:

CUGCUGCCUG  CACUUU                                                            16

( 2 ) INFORMATION FOR SEQ ID NO: 1615:

( i ) SEQUENCE CHARACTERISTICS:
             ( A ) LENGTH: 16 base pairs
             ( B ) TYPE: nucleic acid
             ( C ) STRANDEDNESS: single
             ( D ) TOPOLOGY: linear ( x i ) SEQUENCE DESCRIPTION: SEQ ID NO: 1615:

AUGCUGCCUC  UGCUCC                                                            16

( 2 ) INFORMATION FOR SEQ ID NO: 1616:

( i ) SEQUENCE CHARACTERISTICS:
             ( A ) LENGTH: 16 base pairs
             ( B ) TYPE: nucleic acid
             ( C ) STRANDEDNESS: single
             ( D ) TOPOLOGY: linear ( x i ) SEQUENCE DESCRIPTION: SEQ ID NO: 1616:

UCGCCGUUGU  GAUCCC                                                            16

( 2 ) INFORMATION FOR SEQ ID NO: 1617:

( i ) SEQUENCE CHARACTERISTICS:
             ( A ) LENGTH: 16 base pairs
             ( B ) TYPE: nucleic acid
             ( C ) STRANDEDNESS: single
             ( D ) TOPOLOGY: linear ( x i ) SEQUENCE DESCRIPTION: SEQ ID NO: 1617:

CAGCAGACCA  CUGUGC                                                            16

( 2 ) INFORMATION FOR SEQ ID NO: 1618:

( i ) SEQUENCE CHARACTERISTICS:
             ( A ) LENGTH: 16 base pairs
             ( B ) TYPE: nucleic acid
             ( C ) STRANDEDNESS: single
             ( D ) TOPOLOGY: linear ( x i ) SEQUENCE DESCRIPTION: SEQ ID NO: 1618:

ACGCAGUCCU CGGCUU 16

( 2 ) INFORMATION FOR SEQ ID NO: 1619:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1619:

GCGCUGCCUG GUGGAA 16

( 2 ) INFORMATION FOR SEQ ID NO: 1620:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1620:

UCACUGUUCA AGAAUG 16

( 2 ) INFORMATION FOR SEQ ID NO: 1621:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1621:

AUGCUGACCC UGGAGA 16

( 2 ) INFORMATION FOR SEQ ID NO: 1622:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1622:

CCACUGCCUC AGUGGA 16

( 2 ) INFORMATION FOR SEQ ID NO: 1623:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1623:

UGGCGGACCA GACCCU 16

( 2 ) INFORMATION FOR SEQ ID NO: 1624:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1624:

CUGCGGCCUU GGAGGU 16

( 2 ) INFORMATION FOR SEQ ID NO: 1625:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1625:

CAGCAGACUC UUACAU 16

( 2 ) INFORMATION FOR SEQ ID NO: 1626:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1626:

CUGCAGCCGG AAAGCA 16

( 2 ) INFORMATION FOR SEQ ID NO: 1627:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1627:

CCGCUGCCUA UCGGGA 16

( 2 ) INFORMATION FOR SEQ ID NO: 1628:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1628:

CUACAGCCUG GUGGGC 16

( 2 ) INFORMATION FOR SEQ ID NO: 1629:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1629:

AGGCUGACUU CCUUCU 16

( 2 ) INFORMATION FOR SEQ ID NO: 1630:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1630:

ACACUGUCCC CAACUC 16

( 2 ) INFORMATION FOR SEQ ID NO: 1631:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1631:

CCACAGCCUG GAGUCU                         16

( 2 ) INFORMATION FOR SEQ ID NO: 1632:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1632:

AAGCUGUUGU GGGAGG                         16

( 2 ) INFORMATION FOR SEQ ID NO: 1633:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1633:

GAUCCAAUUC ACACUGA                        17

( 2 ) INFORMATION FOR SEQ ID NO: 1634:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1634:

GCUGACUUCC UUCUCUA                        17

( 2 ) INFORMATION FOR SEQ ID NO: 1635:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1635:

GAACUGCUCU UCCUCUU                        17

( 2 ) INFORMATION FOR SEQ ID NO: 1636:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1636:

CCUCUGCUCC UGGUCCU                        17

( 2 ) INFORMATION FOR SEQ ID NO: 1637:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1637:

CUGAAGCUCA GAUAUAC        17

( 2 ) INFORMATION FOR SEQ ID NO: 1638:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1638:

CUCAAGGUAC AAGCCCC        17

( 2 ) INFORMATION FOR SEQ ID NO: 1639:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1639:

GAGAACCUCG GCCUGGG        17

( 2 ) INFORMATION FOR SEQ ID NO: 1640:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1640:

CCCCGCCUCC CUGAGCC        17

( 2 ) INFORMATION FOR SEQ ID NO: 1641:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1641:

CCGUGCCUUU AGCUCCC        17

( 2 ) INFORMATION FOR SEQ ID NO: 1642:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1642:

CAAUGGCUUC AACCCGU        17

( 2 ) INFORMATION FOR SEQ ID NO: 1643:

-continued ( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1643:

CCUCUGCUCC UGGUCCU 17

( 2 ) INFORMATION FOR SEQ ID NO: 1644:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1644:

CUCCUGGUCC UGGUCGC 17

( 2 ) INFORMATION FOR SEQ ID NO: 1645:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1645:

GGACUGCUUG GGGAACU 17

( 2 ) INFORMATION FOR SEQ ID NO: 1646:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1646:

UCCUACCUUU GUUCCCA 17

( 2 ) INFORMATION FOR SEQ ID NO: 1647:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1647:

GACACUGUCC CCAACUC 17

( 2 ) INFORMATION FOR SEQ ID NO: 1648:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1648:

GUUGUGAUCC CCGGGCC 17

( 2 ) INFORMATION FOR SEQ ID NO: 1649:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 1649:

CCAGACCUUG GAACUCC                                                                                           17

(2) INFORMATION FOR SEQ ID NO: 1650:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1650:

ACCCGGCUCC ACCUCAA                                                                                           17

(2) INFORMATION FOR SEQ ID NO: 1651:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1651:

AUUUCUUUCA CGAGUCA                                                                                           17

(2) INFORMATION FOR SEQ ID NO: 1652:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1652:

UGAACAGUAC UUCCCCC                                                                                           17

(2) INFORMATION FOR SEQ ID NO: 1653:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1653:

GAAGCCUUCC UGCCUCG                                                                                           17

(2) INFORMATION FOR SEQ ID NO: 1654:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1654:

GGGUGGAUCC GUGCAGG                                                                                           17

(2) INFORMATION FOR SEQ ID NO: 1655:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 1655:

CAGCCCCUAA UCUGACC 17

( 2 ) INFORMATION FOR SEQ ID NO: 1656:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1656:

GACCAAGUAA CUGUGAA 17

( 2 ) INFORMATION FOR SEQ ID NO: 1657:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1657:

CAAGCUGUUG UGGGAGG 17

( 2 ) INFORMATION FOR SEQ ID NO: 1658:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1658:

CUGAAGCUCG ACACCCC 17

( 2 ) INFORMATION FOR SEQ ID NO: 1659:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1659:

GGCCCCCUAC CUUAGGA 17

( 2 ) INFORMATION FOR SEQ ID NO: 1660:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1660:

CACUGCCUCA GUGGAGG 17

( 2 ) INFORMATION FOR SEQ ID NO: 1661:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (x i) SEQUENCE DESCRIPTION: SEQ ID NO: 1661:

GAGCCAAUUU CUCAUGC                                                                                   17

(2) INFORMATION FOR SEQ ID NO: 1662:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1662:

GAAGCCUUCC UGCCUCG                                                                                   17

(2) INFORMATION FOR SEQ ID NO: 1663:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1663:

GAAGCUCUUC AAGCUGA                                                                                   17

(2) INFORMATION FOR SEQ ID NO: 1664:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1664:

CGGAGGAUCA CAAACGA                                                                                   17

(2) INFORMATION FOR SEQ ID NO: 1665:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1665:

ACUGUGCUUU GAGAACU                                                                                   17

(2) INFORMATION FOR SEQ ID NO: 1666:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1666:

UGUGCUAUAU GGUCCUC                                                                                   17

(2) INFORMATION FOR SEQ ID NO: 1667:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1667:

```
AAGCUCUUCA AGCUGAG                                                                        17
```

(2) INFORMATION FOR SEQ ID NO: 1668:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1668:

```
CACGCAGUCC UCGGCUU                                                                        17
```

(2) INFORMATION FOR SEQ ID NO: 1669:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1669:

```
CAAUGGCUUC AACCCGU                                                                        17
```

(2) INFORMATION FOR SEQ ID NO: 1670:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1670:

```
UUACCCCUCA CCCACCU                                                                        17
```

(2) INFORMATION FOR SEQ ID NO: 1671:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1671:

```
AGAAGCCUUC CUGCCUC                                                                        17
```

(2) INFORMATION FOR SEQ ID NO: 1672:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1672:

```
ACCCACCUCA CAGGGUA                                                                        17
```

(2) INFORMATION FOR SEQ ID NO: 1673:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1673:

```
CGCUGUGUUU UGGAGCU                                                                        17
```

( 2 ) INFORMATION FOR SEQ ID NO: 1674:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1674:

GUGGUGCUUC UGAACAG    17

( 2 ) INFORMATION FOR SEQ ID NO: 1675:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1675:

GCACCCUCC CAGCGCA    17

( 2 ) INFORMATION FOR SEQ ID NO: 1676:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1676:

CCUCGGCUUC UGCCACC    17

( 2 ) INFORMATION FOR SEQ ID NO: 1677:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1677:

UCCCUGUUUA AAAACCA    17

( 2 ) INFORMATION FOR SEQ ID NO: 1678:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1678:

AAGAACCUCA UCCUGCG    17

( 2 ) INFORMATION FOR SEQ ID NO: 1679:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1679:

GGGUACUUCC CCCAGGC    17

( 2 ) INFORMATION FOR SEQ ID NO: 1680:

( i ) SEQUENCE CHARACTERISTICS:
                  ( A ) LENGTH: 17 base pairs
                  ( B ) TYPE: nucleic acid
                  ( C ) STRANDEDNESS: single
                  ( D ) TOPOLOGY: linear ( x i ) SEQUENCE DESCRIPTION: SEQ ID NO: 1680:

CUCGGCUUCU GCCACCA                                                                                          17

( 2 ) INFORMATION FOR SEQ ID NO: 1681:

( i ) SEQUENCE CHARACTERISTICS:
                  ( A ) LENGTH: 17 base pairs
                  ( B ) TYPE: nucleic acid
                  ( C ) STRANDEDNESS: single
                  ( D ) TOPOLOGY: linear ( x i ) SEQUENCE DESCRIPTION: SEQ ID NO: 1681:

GCCACCAUCA CUGUGUA                                                                                          17

( 2 ) INFORMATION FOR SEQ ID NO: 1682:

( i ) SEQUENCE CHARACTERISTICS:
                  ( A ) LENGTH: 17 base pairs
                  ( B ) TYPE: nucleic acid
                  ( C ) STRANDEDNESS: single
                  ( D ) TOPOLOGY: linear ( x i ) SEQUENCE DESCRIPTION: SEQ ID NO: 1682:

GUGCUGCUCC GUGGGAA                                                                                          17

( 2 ) INFORMATION FOR SEQ ID NO: 1683:

( i ) SEQUENCE CHARACTERISTICS:
                  ( A ) LENGTH: 17 base pairs
                  ( B ) TYPE: nucleic acid
                  ( C ) STRANDEDNESS: single
                  ( D ) TOPOLOGY: linear ( x i ) SEQUENCE DESCRIPTION: SEQ ID NO: 1683:

GAAAAUGUUC CAACCAC                                                                                          17

( 2 ) INFORMATION FOR SEQ ID NO: 1684:

( i ) SEQUENCE CHARACTERISTICS:
                  ( A ) LENGTH: 17 base pairs
                  ( B ) TYPE: nucleic acid
                  ( C ) STRANDEDNESS: single
                  ( D ) TOPOLOGY: linear ( x i ) SEQUENCE DESCRIPTION: SEQ ID NO: 1684:

GGGAGUAUCA CCAGGGA                                                                                          17

( 2 ) INFORMATION FOR SEQ ID NO: 1685:

( i ) SEQUENCE CHARACTERISTICS:
                  ( A ) LENGTH: 17 base pairs
                  ( B ) TYPE: nucleic acid
                  ( C ) STRANDEDNESS: single
                  ( D ) TOPOLOGY: linear ( x i ) SEQUENCE DESCRIPTION: SEQ ID NO: 1685:

GAGCCAAUUU CUCAUGC                                                                                          17

( 2 ) INFORMATION FOR SEQ ID NO: 1686:

( i ) SEQUENCE CHARACTERISTICS:

(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1686:

AGCCAAUUUC UCAUGCU 17

(2) INFORMATION FOR SEQ ID NO: 1687:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1687:

GCCAAUUUCU CAUGCUU 17

(2) INFORMATION FOR SEQ ID NO: 1688:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1688:

CAAUUUCUCA UGCUUCA 17

(2) INFORMATION FOR SEQ ID NO: 1689:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1689:

GUCACUGUUC AAGAAUG 17

(2) INFORMATION FOR SEQ ID NO: 1690:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1690:

UCACUGUUCA AGAAUGU 17

(2) INFORMATION FOR SEQ ID NO: 1691:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1691:

GAACUGCUCU UCCUCUU 17

(2) INFORMATION FOR SEQ ID NO: 1692:

(i) SEQUENCE CHARACTERISTICS:
(A) LENGTH: 17 base pairs
(B) TYPE: nucleic acid ( C ) STRANDEDNESS: single
          ( D ) TOPOLOGY: linear ( x i ) SEQUENCE DESCRIPTION: SEQ ID NO: 1692:

GCACCCCUCC CAGCGCA                                                                                  17

( 2 ) INFORMATION FOR SEQ ID NO: 1693:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 1693:

AGGCAGCUCC GGACUUU                                                                                  17

( 2 ) INFORMATION FOR SEQ ID NO: 1694:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 1694:

CCAGACCUUG GAACUCC                                                                                  17

( 2 ) INFORMATION FOR SEQ ID NO: 1695:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 1695:

CGGACUUUCG AUCUUCC                                                                                  17

( 2 ) INFORMATION FOR SEQ ID NO: 1696:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 1696:

GCCUGUUUCC UGCCUCU                                                                                  17

( 2 ) INFORMATION FOR SEQ ID NO: 1697:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO: 1697:

CAGCAUUUAC CCCUCAC                                                                                  17

( 2 ) INFORMATION FOR SEQ ID NO: 1698:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear (x i) SEQUENCE DESCRIPTION: SEQ ID NO: 1698:

CUACAACUUU UCAGCUC    17

(2) INFORMATION FOR SEQ ID NO: 1699:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1699:

CAACUUUUCA GCUCCCA    17

(2) INFORMATION FOR SEQ ID NO: 1700:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1700:

CUCCUGGUCC UGGUCGC    17

(2) INFORMATION FOR SEQ ID NO: 1701:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1701:

UCCUGCCUCG GGGUGGA    17

(2) INFORMATION FOR SEQ ID NO: 1702:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1702:

ACUGUGCUUU GAGAACU    17

(2) INFORMATION FOR SEQ ID NO: 1703:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1703:

UCUUGUGUUC CCUGGAA    17

(2) INFORMATION FOR SEQ ID NO: 1704:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1704:

CUUGUGUUCC CUGGAAG 17

(2) INFORMATION FOR SEQ ID NO: 1705:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1705:

AGGCCUGUUU CCUGCCU 17

(2) INFORMATION FOR SEQ ID NO: 1706:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1706:

GGCCUGUUUC CUGCCUC 17

(2) INFORMATION FOR SEQ ID NO: 1707:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1707:

CUCCUGGUCC UGGUCGC 17

(2) INFORMATION FOR SEQ ID NO: 1708:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1708:

UCCUGCCUCU GAAGCUC 17

(2) INFORMATION FOR SEQ ID NO: 1709:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1709:

GCUCAGAUAU ACCUGGA 17

(2) INFORMATION FOR SEQ ID NO: 1710:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1710:

CCUGGGGUUG GAGACUA 17

( 2 ) INFORMATION FOR SEQ ID NO: 1711:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1711:

CUGACAGUUA UUUAUUG                                                                          17

( 2 ) INFORMATION FOR SEQ ID NO: 1712:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1712:

GCUCACCUUU AGCAGCU                                                                          17

( 2 ) INFORMATION FOR SEQ ID NO: 1713:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1713:

CAAUGGCUUC AACCCGU                                                                          17

( 2 ) INFORMATION FOR SEQ ID NO: 1714:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1714:

CCAUGCUUCC UCUGACA                                                                          17

( 2 ) INFORMATION FOR SEQ ID NO: 1715:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1715:

GACCACCUCC CCACCUA                                                                          17

( 2 ) INFORMATION FOR SEQ ID NO: 1716:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1716:

CUCUUCCUCU UGCGAAG                                                                          17

( 2 ) INFORMATION FOR SEQ ID NO: 1717:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1717:

AAUGGCUUCA ACCCGUG    17

( 2 ) INFORMATION FOR SEQ ID NO: 1718:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1718:

GACCAAGUAA CUGUGAA    17

( 2 ) INFORMATION FOR SEQ ID NO: 1719:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1719:

UGUGUAUUCG UUCCCAG    17

( 2 ) INFORMATION FOR SEQ ID NO: 1720:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1720:

GCAGAGAUUU UGUGUCA    17

( 2 ) INFORMATION FOR SEQ ID NO: 1721:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1721:

UUGAGAAUCU ACAACUU    17

( 2 ) INFORMATION FOR SEQ ID NO: 1722:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1722:

GAGAAUCUAC AACUUUU    17

( 2 ) INFORMATION FOR SEQ ID NO: 1723:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1723:

CUACAACUUU UCAGCUC 17

( 2 ) INFORMATION FOR SEQ ID NO: 1724:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1724:

UACAACUUUU CAGCUCC 17

( 2 ) INFORMATION FOR SEQ ID NO: 1725:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1725:

ACAACUUUUC AGCUCCC 17

( 2 ) INFORMATION FOR SEQ ID NO: 1726:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1726:

UUCGUGAUCG UGGCGUC 17

( 2 ) INFORMATION FOR SEQ ID NO: 1727:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1727:

GUGGGAGUAU CACCAGG 17

( 2 ) INFORMATION FOR SEQ ID NO: 1728:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1728:

CCGGAGGUCU CAGAAGG 17

( 2 ) INFORMATION FOR SEQ ID NO: 1729:

( i ) SEQUENCE CHARACTERISTICS:
  ( A ) LENGTH: 17 base pairs (B) TYPE: nucleic acid
                (C) STRANDEDNESS: single
                (D) TOPOLOGY: linear (xi) SEQUENCE DESCRIPTION: SEQ ID NO: 1729:

GGAGGUCUCA GAAGGG                                                                    17

(2) INFORMATION FOR SEQ ID NO: 1730:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 1730:

CCUACCUUUG UUCCCAA                                                                   17

(2) INFORMATION FOR SEQ ID NO: 1731:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 1731:

AGAGGGGUCU CAGCAGA                                                                   17

(2) INFORMATION FOR SEQ ID NO: 1732:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 1732:

AGGGGAAUCC AGCCCCU                                                                   17

(2) INFORMATION FOR SEQ ID NO: 1733:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 1733:

CCCCAACUCU UGUUGAU                                                                   17

(2) INFORMATION FOR SEQ ID NO: 1734:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 1734:

ACGACGCUUC UUUUGCU                                                                   17

(2) INFORMATION FOR SEQ ID NO: 1735:

(i) SEQUENCE CHARACTERISTICS:
                (A) LENGTH: 17 base pairs
                (B) TYPE: nucleic acid
                (C) STRANDEDNESS: single ( D ) TOPOLOGY: linear ( x i ) SEQUENCE DESCRIPTION: SEQ ID NO: 1735:

CGACGCUUCU UUUGCUC                                                                              17

( 2 ) INFORMATION FOR SEQ ID NO: 1736:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1736:

ACGCUUCUUU UGCUCUG                                                                              17

( 2 ) INFORMATION FOR SEQ ID NO: 1737:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1737:

CUUUUGCUCU GCGGCCU                                                                              17

( 2 ) INFORMATION FOR SEQ ID NO: 1738:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1738:

AUCCAAUUCA CACUGAA                                                                              17

( 2 ) INFORMATION FOR SEQ ID NO: 1739:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1739:

UUGGGCUUCU CCACAGG                                                                              17

( 2 ) INFORMATION FOR SEQ ID NO: 1740:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1740:

GGGCUUCUCC ACAGGUC                                                                              17

( 2 ) INFORMATION FOR SEQ ID NO: 1741:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1741:

UUGGAACUCC AUGUGCU 17

( 2 ) INFORMATION FOR SEQ ID NO: 1742:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1742:

GCGGGCUUCG UGAUCGU 17

( 2 ) INFORMATION FOR SEQ ID NO: 1743:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1743:

CUCCUGGUCC UGGUCGC 17

( 2 ) INFORMATION FOR SEQ ID NO: 1744:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1744:

UGUGCUAUAU GGUCCUC 17

( 2 ) INFORMATION FOR SEQ ID NO: 1745:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1745:

GGAAAGAUCA UACGGGU 17

( 2 ) INFORMATION FOR SEQ ID NO: 1746:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1746:

GUCACUGUUC AAGAAUG 17

( 2 ) INFORMATION FOR SEQ ID NO: 1747:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1747:

CAGAGAUUUU GUGUCAG 17

( 2 ) INFORMATION FOR SEQ ID NO: 1748:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1748:

AGAGGGUCU CAGCAGA 17

( 2 ) INFORMATION FOR SEQ ID NO: 1749:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1749:

AGCAGACUCU UACAUGC 17

( 2 ) INFORMATION FOR SEQ ID NO: 1750:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1750:

AACAGAGUCU GGGGAAA 17

( 2 ) INFORMATION FOR SEQ ID NO: 1751:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1751:

GUAUUCGUUC CCAGAGC 17

( 2 ) INFORMATION FOR SEQ ID NO: 1752:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1752:

UCGGUGCUCA GGUAUCC 17

( 2 ) INFORMATION FOR SEQ ID NO: 1753:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1753:

UCAGGCCUAA GAGGACU 17

( 2 ) INFORMATION FOR SEQ ID NO: 1754:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1754:

UAGCAGCUCA ACAAUGG 17

( 2 ) INFORMATION FOR SEQ ID NO: 1755:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1755:

AGGGUACUUC CCCCAGG 17

( 2 ) INFORMATION FOR SEQ ID NO: 1756:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1756:

GGGUACUUCC CCCAGGC 17

( 2 ) INFORMATION FOR SEQ ID NO: 1757:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1757:

GAUGGUGUCC CGCUGCC 17

( 2 ) INFORMATION FOR SEQ ID NO: 1758:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1758:

CUGCCUAUCG GGAUGGU 17

( 2 ) INFORMATION FOR SEQ ID NO: 1759:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1759:

UGGAGACUAA CUGGAUG 17

( 2 ) INFORMATION FOR SEQ ID NO: 1760:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1760:

CUGGCUGUCA CAGGACA 17

( 2 ) INFORMATION FOR SEQ ID NO: 1761:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1761:

CUGUGCUUUG AGAACUG 17

( 2 ) INFORMATION FOR SEQ ID NO: 1762:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1762:

UUCGUGAUCG UGGCGUC 17

( 2 ) INFORMATION FOR SEQ ID NO: 1763:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1763:

CGAACUAUCG AGUGGAC 17

( 2 ) INFORMATION FOR SEQ ID NO: 1764:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1764:

GGGUACUUCC CCCAGGC 17

( 2 ) INFORMATION FOR SEQ ID NO: 1765:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1765:

ACCCACCUCC UCUGGCU 17

( 2 ) INFORMATION FOR SEQ ID NO: 1766:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1766:

AUACUUGUAG CCUCAGG                                                                                17

(2) INFORMATION FOR SEQ ID NO: 1767:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1767:

AGAAGGCUCA GGAGGAG                                                                                17

(2) INFORMATION FOR SEQ ID NO: 1768:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1768:

GGGAGUAUCA CCAGGGA                                                                                17

(2) INFORMATION FOR SEQ ID NO: 1769:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1769:

AGGGUACUUC CCCCAGG                                                                                17

(2) INFORMATION FOR SEQ ID NO: 1770:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1770:

ACUGCUCUUC CUCUUGC                                                                                17

(2) INFORMATION FOR SEQ ID NO: 1771:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1771:

CCUGGGGUUG GAGACUA                                                                                17

(2) INFORMATION FOR SEQ ID NO: 1772:

(i) SEQUENCE CHARACTERISTICS:
        (A) LENGTH: 17 base pairs
        (B) TYPE: nucleic acid ( C ) STRANDEDNESS: single
            ( D ) TOPOLOGY: linear ( x i ) SEQUENCE DESCRIPTION: SEQ ID NO: 1772:

CGUGAAAUUA UGGUCAA                                                                            17

( 2 ) INFORMATION FOR SEQ ID NO: 1773:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1773:

GAAAAUGUUC CAACCAC                                                                            17

( 2 ) INFORMATION FOR SEQ ID NO: 1774:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1774:

UGGGUCAUAA UUGUUGG                                                                            17

( 2 ) INFORMATION FOR SEQ ID NO: 1775:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1775:

GCCACCAUCA CUGUGUA                                                                            17

( 2 ) INFORMATION FOR SEQ ID NO: 1776:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1776:

GUCCUGGUCG CCGUUGU                                                                            17

( 2 ) INFORMATION FOR SEQ ID NO: 1777:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1777:

ACCUGGGUCA UAAUUGU                                                                            17

( 2 ) INFORMATION FOR SEQ ID NO: 1778:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear (x i) SEQUENCE DESCRIPTION: SEQ ID NO: 1778:

CUGAUCAUUG CGGGCUU 17

(2) INFORMATION FOR SEQ ID NO: 1779:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1779:

GUGGCCCUCU GCUCGUA 17

(2) INFORMATION FOR SEQ ID NO: 1780:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1780:

UGGGAAGUCC CUGUUUA 17

(2) INFORMATION FOR SEQ ID NO: 1781:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1781:

UCCUACCUUU GUUCCCA 17

(2) INFORMATION FOR SEQ ID NO: 1782:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1782:

UUACACCUAU UACCGCC 17

(2) INFORMATION FOR SEQ ID NO: 1783:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1783:

ACACCUAUUA CCGCCAG 17

(2) INFORMATION FOR SEQ ID NO: 1784:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 1784:

```
AGGAAGAUCA GGAUAUA                                                                         17
```

( 2 ) INFORMATION FOR SEQ ID NO: 1785:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1785:

```
CAGGAUAUAC AAGUUAC                                                                         17
```

( 2 ) INFORMATION FOR SEQ ID NO: 1786:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1786:

```
UACAAGUUAC AGAAGGC                                                                         17
```

( 2 ) INFORMATION FOR SEQ ID NO: 1787:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1787:

```
CCCCGCCUCC CUGAGCC                                                                         17
```

( 2 ) INFORMATION FOR SEQ ID NO: 1788:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1788:

```
CUGCACUUUG CCCUGGU                                                                         17
```

( 2 ) INFORMATION FOR SEQ ID NO: 1789:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1789:

```
GAACAGAUCA AUGGACA                                                                         17
```

( 2 ) INFORMATION FOR SEQ ID NO: 1790:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1790:

```
GAGAACCUCG GCCUGGG                                                                         17
```

( 2 ) INFORMATION FOR SEQ ID NO: 1791:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1791:

GGGCUUCUCC ACAGGUC 17

( 2 ) INFORMATION FOR SEQ ID NO: 1792:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1792:

GGCCUGUUUC CUGCCUC 17

( 2 ) INFORMATION FOR SEQ ID NO: 1793:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1793:

CUGCUCGUAG ACCUCUC 17

( 2 ) INFORMATION FOR SEQ ID NO: 1794:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1794:

CCCCACCUAC AUACAUU 17

( 2 ) INFORMATION FOR SEQ ID NO: 1795:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1795:

CCGGACUUUC GAUCUUC 17

( 2 ) INFORMATION FOR SEQ ID NO: 1796:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1796:

CUCCUGGUCC UGGUCGC 17

(2) INFORMATION FOR SEQ ID NO: 1797:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1797:

UCAGAUAUAC CUGGAGA        17

(2) INFORMATION FOR SEQ ID NO: 1798:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1798:

GAUCACAUUC ACGGUGC        17

(2) INFORMATION FOR SEQ ID NO: 1799:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1799:

GUCCAUUUAC ACCUAUU        17

(2) INFORMATION FOR SEQ ID NO: 1800:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1800:

CCUCUGCUCC UGGUCCU        17

(2) INFORMATION FOR SEQ ID NO: 1801:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1801:

GAGAACCUCG GCCUGGG        17

(2) INFORMATION FOR SEQ ID NO: 1802:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1802:

GACACUGUCC CCAACUC        17

(2) INFORMATION FOR SEQ ID NO: 1803:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1803:

AUGGUCCUCA CCUGGAC            17

( 2 ) INFORMATION FOR SEQ ID NO: 1804:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1804:

UCCCUGUUUA AAAACCA            17

( 2 ) INFORMATION FOR SEQ ID NO: 1805:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1805:

GCUCAGAUAU ACCUGGA            17

( 2 ) INFORMATION FOR SEQ ID NO: 1806:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1806:

AACAGAGUCU GGGGAAA            17

( 2 ) INFORMATION FOR SEQ ID NO: 1807:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1807:

GCGGGCUUCG UGAUCGU            17

( 2 ) INFORMATION FOR SEQ ID NO: 1808:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1808:

GCCACCAUCA CUGUGUA            17

( 2 ) INFORMATION FOR SEQ ID NO: 1809:

( i ) SEQUENCE CHARACTERISTICS:
        ( A ) LENGTH: 17 base pairs ( B ) TYPE: nucleic acid
( C ) STRANDEDNESS: single
( D ) TOPOLOGY: linear ( x i ) SEQUENCE DESCRIPTION: SEQ ID NO: 1809:

ACCCACCUCA CAGGGUA 17

( 2 ) INFORMATION FOR SEQ ID NO: 1810:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1810:

AGAGGACUCG GAGGGGC 17

( 2 ) INFORMATION FOR SEQ ID NO: 1811:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1811:

CCCCUAAUCU GACCUGC 17

( 2 ) INFORMATION FOR SEQ ID NO: 1812:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1812:

CAUGUGCUAU AUGGUCC 17

( 2 ) INFORMATION FOR SEQ ID NO: 1813:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1813:

UAUCCGGUAG ACACAAG 17

( 2 ) INFORMATION FOR SEQ ID NO: 1814:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1814:

UCACGAGUCA UAUAAAU 17

( 2 ) INFORMATION FOR SEQ ID NO: 1815:

( i ) SEQUENCE CHARACTERISTICS:
( A ) LENGTH: 17 base pairs
( B ) TYPE: nucleic acid
( C ) STRANDEDNESS: single ( D ) TOPOLOGY: linear ( x i ) SEQUENCE DESCRIPTION: SEQ ID NO: 1815:

ACAGUACUUC CCCCAGG 17

( 2 ) INFORMATION FOR SEQ ID NO: 1816:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1816:

CUAAAACUCA AGGUACA 17

( 2 ) INFORMATION FOR SEQ ID NO: 1817:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1817:

GAACAGAUCA AUGGACA 17

( 2 ) INFORMATION FOR SEQ ID NO: 1818:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1818:

AUGUAAGUUA UUGCCUA 17

( 2 ) INFORMATION FOR SEQ ID NO: 1819:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1819:

UGGACGCUCA CCUUUAG 17

( 2 ) INFORMATION FOR SEQ ID NO: 1820:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1820:

GCUCAGAUAU ACCUGGA 17

( 2 ) INFORMATION FOR SEQ ID NO: 1821:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (x i) SEQUENCE DESCRIPTION: SEQ ID NO: 1821:

UGGAGACUAA CUGGAUG 17

(2) INFORMATION FOR SEQ ID NO: 1822:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1822:

AGAGAUUUUG UGUCAGC 17

(2) INFORMATION FOR SEQ ID NO: 1823:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1823:

GAGAACCUCG GCCUGGG 17

(2) INFORMATION FOR SEQ ID NO: 1824:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1824:

UGGAAGCUCU UCAAGCU 17

(2) INFORMATION FOR SEQ ID NO: 1825:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1825:

AUGUAAGUUA UUGCCUA 17

(2) INFORMATION FOR SEQ ID NO: 1826:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1826:

CGCUGCCUAU CGGGAUG 17

(2) INFORMATION FOR SEQ ID NO: 1827:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1827:

```
CUGCCUAUCG GGAUGGU                                                              17
```

( 2 ) INFORMATION FOR SEQ ID NO: 1828:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1828:

```
UAUUGAGUAC CCUGUAC                                                              17
```

( 2 ) INFORMATION FOR SEQ ID NO: 1829:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1829:

```
CGGAGGAUCA CAAACGA                                                              17
```

( 2 ) INFORMATION FOR SEQ ID NO: 1830:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1830:

```
CCUGACCUCC UGGAGGU                                                              17
```

( 2 ) INFORMATION FOR SEQ ID NO: 1831:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1831:

```
CUGGUCCUCC AAUGGCU                                                              17
```

( 2 ) INFORMATION FOR SEQ ID NO: 1832:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1832:

```
GCGUCCAUUU ACACCUA                                                              17
```

( 2 ) INFORMATION FOR SEQ ID NO: 1833:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1833:

```
AUACUUGUAG CCUCAGG                                                              17
```

( 2 ) INFORMATION FOR SEQ ID NO: 1834:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1834:

UGUAGCCUCA GGCCUAA 17

( 2 ) INFORMATION FOR SEQ ID NO: 1835:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1835:

CCAACUCUUG UUGAUGU 17

( 2 ) INFORMATION FOR SEQ ID NO: 1836:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1836:

CCUGACCUCC UGGAGGU 17

( 2 ) INFORMATION FOR SEQ ID NO: 1837:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1837:

UUCCGACUAG GGUCCUG 17

( 2 ) INFORMATION FOR SEQ ID NO: 1838:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1838:

AGUGCUGUAC CAUGAUC 17

( 2 ) INFORMATION FOR SEQ ID NO: 1839:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1839:

GCCUGUUUCC UGCCUCU 17

( 2 ) INFORMATION FOR SEQ ID NO: 1840:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1840:

CCAACUCUUG UUGAUGU 17

( 2 ) INFORMATION FOR SEQ ID NO: 1841:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1841:

UUGAGAAUCU ACAACUU 17

( 2 ) INFORMATION FOR SEQ ID NO: 1842:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1842:

UGACAGUUAU UUAUUGA 17

( 2 ) INFORMATION FOR SEQ ID NO: 1843:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1843:

UGAUGUAUUU AUUAAUU 17

( 2 ) INFORMATION FOR SEQ ID NO: 1844:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1844:

GAUGUAUUUA UUAAUUC 17

( 2 ) INFORMATION FOR SEQ ID NO: 1845:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1845:

AUGUAUUUAU UAAUUCA 17

( 2 ) INFORMATION FOR SEQ ID NO: 1846:

( i ) SEQUENCE CHARACTERISTICS:

(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1846:

ACAUUCCUAC CUUUGUU 17

(2) INFORMATION FOR SEQ ID NO: 1847:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1847:

UAUUUAUUAA UUCAGAG 17

(2) INFORMATION FOR SEQ ID NO: 1848:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1848:

UGAUGUAUUU AUUAAUU 17

(2) INFORMATION FOR SEQ ID NO: 1849:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1849:

GAUGUAUUUA UUAAUUC 17

(2) INFORMATION FOR SEQ ID NO: 1850:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1850:

GUAUUUAUUA AUUCAGA 17

(2) INFORMATION FOR SEQ ID NO: 1851:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1851:

CAGUUAUUUA UUGAGUA 17

(2) INFORMATION FOR SEQ ID NO: 1852:

(i) SEQUENCE CHARACTERISTICS:
(A) LENGTH: 17 base pairs
(B) TYPE: nucleic acid ( C ) STRANDEDNESS: single
( D ) TOPOLOGY: linear ( x i ) SEQUENCE DESCRIPTION: SEQ ID NO: 1852:

UGUGCUAUAU GGUCCUC 17

( 2 ) INFORMATION FOR SEQ ID NO: 1853:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1853:

UCUCUAUUAC CCCUGCU 17

( 2 ) INFORMATION FOR SEQ ID NO: 1854:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1854:

AUUUCUUUCA CGAGUCA 17

( 2 ) INFORMATION FOR SEQ ID NO: 1855:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1855:

GAAAAUGUUC CAACCAC 17

( 2 ) INFORMATION FOR SEQ ID NO: 1856:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1856:

UGACAGUUAU UUAUUGA 17

( 2 ) INFORMATION FOR SEQ ID NO: 1857:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1857:

ACAGUUAUUU AUUGAGU 17

( 2 ) INFORMATION FOR SEQ ID NO: 1858:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1858:

CAGUUAUUUA UUGAGUA 17

( 2 ) INFORMATION FOR SEQ ID NO: 1859:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1859:

AGUUAUUUAU UGAGUAC 17

( 2 ) INFORMATION FOR SEQ ID NO: 1860:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1860:

UUAUUUAUUG AGUACCC 17

( 2 ) INFORMATION FOR SEQ ID NO: 1861:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1861:

CUGACAGUUA UUUAUUG 17

( 2 ) INFORMATION FOR SEQ ID NO: 1862:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1862:

GAAUGUCUCC GAGGUCA 17

( 2 ) INFORMATION FOR SEQ ID NO: 1863:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1863:

AGACUCUUAC AUGCCAG 17

( 2 ) INFORMATION FOR SEQ ID NO: 1864:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1864:

GGGUACUUCC CCCAGGC      17

(2) INFORMATION FOR SEQ ID NO: 1865:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1865:

GGGCUUCUCC ACAGGUC      17

(2) INFORMATION FOR SEQ ID NO: 1866:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1866:

UUUUGUGUCA GCCACUG      17

(2) INFORMATION FOR SEQ ID NO: 1867:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1867:

UGGAGACUAA CUGGAUG      17

(2) INFORMATION FOR SEQ ID NO: 1868:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1868:

GAGAACCUCG GCCUGGG      17

(2) INFORMATION FOR SEQ ID NO: 1869:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1869:

ACAUACAUUC CUACCUU      17

(2) INFORMATION FOR SEQ ID NO: 1870:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1870:

CUGGACCUCA GGCCACA      17

( 2 ) INFORMATION FOR SEQ ID NO: 1871:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1871:

UCAUGCUUCA CAGAACU 17

( 2 ) INFORMATION FOR SEQ ID NO: 1872:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1872:

ACACAGCUCU CAGUAGU 17

( 2 ) INFORMATION FOR SEQ ID NO: 1873:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1873:

CUCCUGGUCC UGGUCGC 17

( 2 ) INFORMATION FOR SEQ ID NO: 1874:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1874:

AUCCAAUUCA CACUGAA 17

( 2 ) INFORMATION FOR SEQ ID NO: 1875:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1875:

GAUCACAUUC ACGGUGC 17

( 2 ) INFORMATION FOR SEQ ID NO: 1876:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1876:

AUCACAUUCA CGGUGCU 17

( 2 ) INFORMATION FOR SEQ ID NO: 1877:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1877:

AUCAGGAUAU ACAAGUU  17

( 2 ) INFORMATION FOR SEQ ID NO: 1878:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1878:

GAGCAGGUUA ACAUGUA  17

( 2 ) INFORMATION FOR SEQ ID NO: 1879:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1879:

GGAAAGAUCA UACGGGU  17

( 2 ) INFORMATION FOR SEQ ID NO: 1880:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1880:

ACAGUUAUUU AUUGAGU  17

( 2 ) INFORMATION FOR SEQ ID NO: 1881:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1881:

GCCCUGGUCC UCCAAUG  17

( 2 ) INFORMATION FOR SEQ ID NO: 1882:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1882:

CAGGAUAUAC AAGUUAC  17

( 2 ) INFORMATION FOR SEQ ID NO: 1883:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1883:

GGAAAGAUCA UACGGGU  17

( 2 ) INFORMATION FOR SEQ ID NO: 1884:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1884:

UUGGGCUUCU CCACAGG  17

( 2 ) INFORMATION FOR SEQ ID NO: 1885:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1885:

GGGUACUUCC CCCAGGC  17

( 2 ) INFORMATION FOR SEQ ID NO: 1886:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1886:

GGGCCUGUCG GUGCUCA  17

( 2 ) INFORMATION FOR SEQ ID NO: 1887:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1887:

CUGCUCGUAG ACCUCUC  17

( 2 ) INFORMATION FOR SEQ ID NO: 1888:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1888:

CCCUGCCUCC UCCACA  17

( 2 ) INFORMATION FOR SEQ ID NO: 1889:

( i ) SEQUENCE CHARACTERISTICS:
  ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 1889:

CCAUCCAUCC CACAGAA 17

(2) INFORMATION FOR SEQ ID NO: 1890:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1890:

CUUGUGUUCC CUGGAAG 17

(2) INFORMATION FOR SEQ ID NO: 1891:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1891:

GAACUGCUCU UCCUCUU 17

(2) INFORMATION FOR SEQ ID NO: 1892:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1892:

GACUUCCUUC UCUAUUA 17

(2) INFORMATION FOR SEQ ID NO: 1893:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1893:

GCUGAUUUCU UUCACGA 17

(2) INFORMATION FOR SEQ ID NO: 1894:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1894:

CUGCUCUUCC UCUUGCG 17

(2) INFORMATION FOR SEQ ID NO: 1895:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO: 1895:

UGAUUUCUUU CACGAGU 17

(2) INFORMATION FOR SEQ ID NO: 1896:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1896:

AUUUCUUUCA CGAGUCA 17

(2) INFORMATION FOR SEQ ID NO: 1897:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1897:

UAUCCGGUAG ACACAAG 17

(2) INFORMATION FOR SEQ ID NO: 1898:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1898:

UAAAUACUAU GUGGACG 17

(2) INFORMATION FOR SEQ ID NO: 1899:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1899:

UGUGCUAUAU GGUCCUC 17

(2) INFORMATION FOR SEQ ID NO: 1900:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1900:

CAAUUUCUCA UGCUUCA 17

(2) INFORMATION FOR SEQ ID NO: 1901:

(i) SEQUENCE CHARACTERISTICS:
        (A) LENGTH: 17 base pairs
        (B) TYPE: nucleic acid
        (C) STRANDEDNESS: single
        (D) TOPOLOGY: linear -continued ( x i ) SEQUENCE DESCRIPTION: SEQ ID NO: 1901:

AUCAGGAUAU ACAAGUU                                                                              17

( 2 ) INFORMATION FOR SEQ ID NO: 1902:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1902:

UCAUGCUUCA CAGAACU                                                                              17

( 2 ) INFORMATION FOR SEQ ID NO: 1903:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1903:

UUAUUAAUUC AGAGUUC                                                                              17

( 2 ) INFORMATION FOR SEQ ID NO: 1904:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1904:

CCUGGGGUUG GAGACUA                                                                              17

( 2 ) INFORMATION FOR SEQ ID NO: 1905:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1905:

UCAGAGUUCU GACAGUU                                                                              17

( 2 ) INFORMATION FOR SEQ ID NO: 1906:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1906:

CGGAGGAUCA CAAACGA                                                                              17

( 2 ) INFORMATION FOR SEQ ID NO: 1907:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1907:

```
UGAACAGUAC UUCCCCC                                                                                17
```

(2) INFORMATION FOR SEQ ID NO: 1908:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1908:

```
GAAGCCUUCC UGCCUCG                                                                                17
```

(2) INFORMATION FOR SEQ ID NO: 1909:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1909:

```
GGCCUGUUUC CUGCCUC                                                                                17
```

(2) INFORMATION FOR SEQ ID NO: 1910:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1910:

```
GCCUGUUUCC UGCCUCU                                                                                17
```

(2) INFORMATION FOR SEQ ID NO: 1911:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1911:

```
ACAUUCCUAC CUUUGUU                                                                                17
```

(2) INFORMATION FOR SEQ ID NO: 1912:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1912:

```
CCCUGCCUCC UCCACA                                                                                 17
```

(2) INFORMATION FOR SEQ ID NO: 1913:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1913:

```
CCUACCUUUG UUCCCAA                                                                                17
```

( 2 ) INFORMATION FOR SEQ ID NO: 1914:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1914:

UUACACCUAU UACCGCC 17

( 2 ) INFORMATION FOR SEQ ID NO: 1915:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1915:

GUCGCCGUUG UGAUCCC 17

( 2 ) INFORMATION FOR SEQ ID NO: 1916:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1916:

ACCUUUGUUC CCAAUGU 17

( 2 ) INFORMATION FOR SEQ ID NO: 1917:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1917:

CCUUUGUUCC CAAUGUC 17

( 2 ) INFORMATION FOR SEQ ID NO: 1918:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1918:

GACCACCUCC CCACCUA 17

( 2 ) INFORMATION FOR SEQ ID NO: 1919:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1919:

ACCUACAUAC AUUCCUA 17

( 2 ) INFORMATION FOR SEQ ID NO: 1920:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1920:

ACAUACAUUC CUACCUU                                                                    17

( 2 ) INFORMATION FOR SEQ ID NO: 1921:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1921:

CAUACAUUCC UACCUUU                                                                    17

( 2 ) INFORMATION FOR SEQ ID NO: 1922:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1922:

GUCCAUUUAC ACCUAUU                                                                    17

( 2 ) INFORMATION FOR SEQ ID NO: 1923:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1923:

ACCUUUGUUC CCAAUGU                                                                    17

( 2 ) INFORMATION FOR SEQ ID NO: 1924:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1924:

CCUUUGUUCC CAAUGUC                                                                    17

( 2 ) INFORMATION FOR SEQ ID NO: 1925:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1925:

ACAGCAUUUA CCCCUCA                                                                    17

( 2 ) INFORMATION FOR SEQ ID NO: 1926:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1926:

UCGGUGCUCA GGUAUCC 17

( 2 ) INFORMATION FOR SEQ ID NO: 1927:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1927:

AGGCAGCUCC GGACUUU 17

( 2 ) INFORMATION FOR SEQ ID NO: 1928:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1928:

CAGAGAUUUU GUGUCAG 17

( 2 ) INFORMATION FOR SEQ ID NO: 1929:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1929:

CCUGCACUUU GCCCUGG 17

( 2 ) INFORMATION FOR SEQ ID NO: 1930:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1930:

CUGCUCGUAG ACCUCUC 17

( 2 ) INFORMATION FOR SEQ ID NO: 1931:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1931:

UGCCUCCUCC CACAGCC 17

( 2 ) INFORMATION FOR SEQ ID NO: 1932:

( i ) SEQUENCE CHARACTERISTICS:
( A ) LENGTH: 17 base pairs
( B ) TYPE: nucleic acid ( C ) STRANDEDNESS: single
( D ) TOPOLOGY: linear ( x i ) SEQUENCE DESCRIPTION: SEQ ID NO: 1932:

CUCUUCCUCU UGCGAAG 17

( 2 ) INFORMATION FOR SEQ ID NO: 1933:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1933:

UCUCUAUUAC CCCUGCU 17

( 2 ) INFORMATION FOR SEQ ID NO: 1934:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1934:

CUCCUGGUCC UGGUCGC 17

( 2 ) INFORMATION FOR SEQ ID NO: 1935:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1935:

UGUGCUAUAU GGUCCUC 17

( 2 ) INFORMATION FOR SEQ ID NO: 1936:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1936:

GUCCUGGUCG CCGUUGU 17

( 2 ) INFORMATION FOR SEQ ID NO: 1937:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1937:

GUGGGAGUAU CACCAGG 17

( 2 ) INFORMATION FOR SEQ ID NO: 1938:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear (x i) SEQUENCE DESCRIPTION: SEQ ID NO: 1938:

CUUUAGCUCC CGUGGGA 17

(2) INFORMATION FOR SEQ ID NO: 1939:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1939:

UGGAGACUAA CUGGAUG 17

(2) INFORMATION FOR SEQ ID NO: 1940:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1940:

UCAGAGUUCU GACAGUU 17

(2) INFORMATION FOR SEQ ID NO: 1941:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1941:

CUCUCAGUAG UGCUGCU 17

(2) INFORMATION FOR SEQ ID NO: 1942:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1942:

UACAACUUUU CAGCUCC 17

(2) INFORMATION FOR SEQ ID NO: 1943:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1943:

UCACAGAUCC AAUUCAC 17

(2) INFORMATION FOR SEQ ID NO: 1944:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1944:

GCUCAGGUAU CCAUCCA 17

(2) INFORMATION FOR SEQ ID NO: 1945:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1945:

CCCCACCUAC AUACAUU 17

(2) INFORMATION FOR SEQ ID NO: 1946:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1946:

GCCUGUUUCC UGCCUCU 17

(2) INFORMATION FOR SEQ ID NO: 1947:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1947:

CCACAGGUCA GGGUGCU 17

(2) INFORMATION FOR SEQ ID NO: 1948:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1948:

AGAAGGGUCC UGCAAGC 17

(2) INFORMATION FOR SEQ ID NO: 1949:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1949:

ACUAGGGUCC UGAAGCU 17

(2) INFORMATION FOR SEQ ID NO: 1950:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1950:

UCAGGCCUAA GAGGACU 17

( 2 ) INFORMATION FOR SEQ ID NO: 1951:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1951:

AGGGUACUUC CCCCAGG 17

( 2 ) INFORMATION FOR SEQ ID NO: 1952:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1952:

GACCACCUCC CCACCUA 17

( 2 ) INFORMATION FOR SEQ ID NO: 1953:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1953:

CCCUACCUUA GGAAGGU 17

( 2 ) INFORMATION FOR SEQ ID NO: 1954:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1954:

CCUACCUUAG GAAGGUG 17

( 2 ) INFORMATION FOR SEQ ID NO: 1955:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1955:

GGAAAGAUCA UACGGGU 17

( 2 ) INFORMATION FOR SEQ ID NO: 1956:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1956:

AAGAUCAUAC GGGUUUG 17

(2) INFORMATION FOR SEQ ID NO: 1957:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1957:

GGGUGGAUCC GUGCAGG 17

(2) INFORMATION FOR SEQ ID NO: 1958:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1958:

GUCCCUGUUU AAAAACC 17

(2) INFORMATION FOR SEQ ID NO: 1959:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1959:

GACGAACUAU CGAGUGG 17

(2) INFORMATION FOR SEQ ID NO: 1960:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1960:

CGGACUUUCG AUCUUCC 17

(2) INFORMATION FOR SEQ ID NO: 1961:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1961:

CUUUUGCUCU GCGGCCU 17

(2) INFORMATION FOR SEQ ID NO: 1962:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1962:

UUCUCUAUUA CCCCUGC 17

(2) INFORMATION FOR SEQ ID NO: 1963:

-continued (i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 1963:

CGUGAAAUUA UGGUCAA                                                                          17

(2) INFORMATION FOR SEQ ID NO: 1964:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 1964:

CUCAUGCUUC ACAGAAC                                                                          17

(2) INFORMATION FOR SEQ ID NO: 1965:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 1965:

UCAUGCUUCA CAGAACU                                                                          17

(2) INFORMATION FOR SEQ ID NO: 1966:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 1966:

GCUCCCAUCC UGACCCU                                                                          17

(2) INFORMATION FOR SEQ ID NO: 1967:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 1967:

CGGACUUUCG AUCUUCC                                                                          17

(2) INFORMATION FOR SEQ ID NO: 1968:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 1968:

CCUGACCUCC UGGAGGU                                                                          17

(2) INFORMATION FOR SEQ ID NO: 1969:

(i) SEQUENCE CHARACTERISTICS:
            (A) LENGTH: 17 base pairs ( B ) TYPE: nucleic acid
            ( C ) STRANDEDNESS: single
            ( D ) TOPOLOGY: linear ( x i ) SEQUENCE DESCRIPTION: SEQ ID NO: 1969:

UACAACUUUU CAGCUCC                                                                                              17

( 2 ) INFORMATION FOR SEQ ID NO: 1970:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1970:

CAACUUUUCA GCUCCCA                                                                                              17

( 2 ) INFORMATION FOR SEQ ID NO: 1971:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1971:

UCGGUGCUCA GGUAUCC                                                                                              17

( 2 ) INFORMATION FOR SEQ ID NO: 1972:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1972:

CACAGGGUAC UUCCCCC                                                                                              17

( 2 ) INFORMATION FOR SEQ ID NO: 1973:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1973:

GCACCCCUCC CAGCGCA                                                                                              17

( 2 ) INFORMATION FOR SEQ ID NO: 1974:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1974:

UUACCCCUCA CCCACCU                                                                                              17

( 2 ) INFORMATION FOR SEQ ID NO: 1975:

( i ) SEQUENCE CHARACTERISTICS:
            ( A ) LENGTH: 17 base pairs
            ( B ) TYPE: nucleic acid
            ( C ) STRANDEDNESS: single ( D ) TOPOLOGY: linear ( x i ) SEQUENCE DESCRIPTION: SEQ ID NO: 1975:

UUCGAUCUUC CGACUAG 17

( 2 ) INFORMATION FOR SEQ ID NO: 1976:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1976:

UCUUGUGUUC CCUGGAA 17

( 2 ) INFORMATION FOR SEQ ID NO: 1977:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1977:

GGGCCUGUCG GUGCUCA 17

( 2 ) INFORMATION FOR SEQ ID NO: 1978:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1978:

UGGAGUCUCC CAGCACC 17

( 2 ) INFORMATION FOR SEQ ID NO: 1979:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1979:

AGGCAGCUCC GGACUUU 17

( 2 ) INFORMATION FOR SEQ ID NO: 1980:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1980:

GGCUGACUUC CUUCUCU 17

( 2 ) INFORMATION FOR SEQ ID NO: 1981:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1981:

GAACUGCUCU UCCUCUU 17

( 2 ) INFORMATION FOR SEQ ID NO: 1982:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1982:

GGCUGACUUC CUUCUCU 17

( 2 ) INFORMATION FOR SEQ ID NO: 1983:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1983:

GUUGAUGUAU UUAUUAA 17

( 2 ) INFORMATION FOR SEQ ID NO: 1984:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1984:

CUGCUCUUCC UCUUGCG 17

( 2 ) INFORMATION FOR SEQ ID NO: 1985:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1985:

UGAUGUAUUU AUUAAUU 17

( 2 ) INFORMATION FOR SEQ ID NO: 1986:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1986:

GAACUGCUCU UCCUCUU 17

( 2 ) INFORMATION FOR SEQ ID NO: 1987:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1987:

-continued

ACUUCCUUCU CUAUUAC 17

( 2 ) INFORMATION FOR SEQ ID NO: 1988:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1988:

UUCCUUCUCU AUUACCC 17

( 2 ) INFORMATION FOR SEQ ID NO: 1989:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1989:

AUGUAUUUAU UAAUUCA 17

( 2 ) INFORMATION FOR SEQ ID NO: 1990:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1990:

UGUGUAUUCG UUCCCAG 17

( 2 ) INFORMATION FOR SEQ ID NO: 1991:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1991:

GUAUUUAUUA AUUCAGA 17

( 2 ) INFORMATION FOR SEQ ID NO: 1992:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1992:

UAUUUAUUAA UUCAGAG 17

( 2 ) INFORMATION FOR SEQ ID NO: 1993:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1993:

CUCUUCCUCU UGCGAAG 17

( 2 ) INFORMATION FOR SEQ ID NO: 1994:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1994:

CUUCCUCUUG CGAAGAC 17

( 2 ) INFORMATION FOR SEQ ID NO: 1995:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1995:

AUUUCUUUCA CGAGUCA 17

( 2 ) INFORMATION FOR SEQ ID NO: 1996:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1996:

UUUUGUGUCA GCCACUG 17

( 2 ) INFORMATION FOR SEQ ID NO: 1997:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1997:

GAUGGUGUCC CGCUGCC 17

( 2 ) INFORMATION FOR SEQ ID NO: 1998:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1998:

UGGAGUCUCC CAGCACC 17

( 2 ) INFORMATION FOR SEQ ID NO: 1999:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1999:

CAGUACUUCC CCCAGGC 17

( 2 ) INFORMATION FOR SEQ ID NO: 2000:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2000:

ACCAUGCUUC CUCUGAC 17

( 2 ) INFORMATION FOR SEQ ID NO: 2001:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2001:

CCGGACUUUC GAUCUUC 17

( 2 ) INFORMATION FOR SEQ ID NO: 2002:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2002:

UGCUUCCUCU GACAUGG 17

( 2 ) INFORMATION FOR SEQ ID NO: 2003:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2003:

CUUUCCUUUG AAUCAAU 17

( 2 ) INFORMATION FOR SEQ ID NO: 2004:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2004:

UUUUGUGUCA GCCACUG 17

( 2 ) INFORMATION FOR SEQ ID NO: 2005:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2005:

UGUGUAUUCG UUCCCAG 17

( 2 ) INFORMATION FOR SEQ ID NO: 2006:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 2006:

CUUUGAAUCA AUAAAGU 17

( 2 ) INFORMATION FOR SEQ ID NO: 2007:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 2007:

UGGAAGCUCU UCAAGCU 17

( 2 ) INFORMATION FOR SEQ ID NO: 2008:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 2008:

GAAUCAAUAA AGUUUUA 17

( 2 ) INFORMATION FOR SEQ ID NO: 2009:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 2009:

UGGAAGCUCU UCAAGCU 17

( 2 ) INFORMATION FOR SEQ ID NO: 2010:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 2010:

UAUAUGGUCC UCACCUG 17

( 2 ) INFORMATION FOR SEQ ID NO: 2011:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 2011:

GAAGCUCUUC AAGCUGA 17

( 2 ) INFORMATION FOR SEQ ID NO: 2012:

( i ) SEQUENCE CHARACTERISTICS:
( A ) LENGTH: 38 base pairs
( B ) TYPE: nucleic acid (C) STRANDEDNESS: single
(D) TOPOLOGY: linear (xi) SEQUENCE DESCRIPTION: SEQ ID NO: 2012:

UCAGUGUGCU GAUGAGGCCG AAAGGCCGAA AUUGGAUC     38

(2) INFORMATION FOR SEQ ID NO: 2013:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2013:

UAGAGAAGCU GAUGAGGCCG AAAGGCCGAA AAGUCAGC     38

(2) INFORMATION FOR SEQ ID NO: 2014:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2014:

AAGAGGAACU GAUGAGGCCG AAAGGCCGAA AGCAGUUC     38

(2) INFORMATION FOR SEQ ID NO: 2015:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2015:

AGGACCAGCU GAUGAGGCCG AAAGGCCGAA AGCAGAGG     38

(2) INFORMATION FOR SEQ ID NO: 2016:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2016:

GUAUAUCUCU GAUGAGGCCG AAAGGCCGAA AGCUUCAG     38

(2) INFORMATION FOR SEQ ID NO: 2017:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2017:

GGGGCUUGCU GAUGAGGCCG AAAGGCCGAA ACCUUGAG     38

(2) INFORMATION FOR SEQ ID NO: 2018:

(i) SEQUENCE CHARACTERISTICS:
      (A) LENGTH: 38 base pairs
      (B) TYPE: nucleic acid
      (C) STRANDEDNESS: single
      (D) TOPOLOGY: linear ( x i ) SEQUENCE DESCRIPTION: SEQ ID NO: 2018:

CCCAGGCCCU GAUGAGGCCG AAAGGCCGAA AGGUUCUC 38

( 2 ) INFORMATION FOR SEQ ID NO: 2019:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2019:

GGCUCAGGCU GAUGAGGCCG AAAGGCCGAA AGGCGGGG 38

( 2 ) INFORMATION FOR SEQ ID NO: 2020:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2020:

GGGAGCUACU GAUGAGGCCG AAAGGCCGAA AGGCACGG 38

( 2 ) INFORMATION FOR SEQ ID NO: 2021:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2021:

ACGGGUUGCU GAUGAGGCCG AAAGGCCGAA AGCCAUUG 38

( 2 ) INFORMATION FOR SEQ ID NO: 2022:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2022:

AGGACCAGCU GAUGAGGCCG AAAGGCCGAA AGCAGAGG 38

( 2 ) INFORMATION FOR SEQ ID NO: 2023:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2023:

GCGACCAGCU GAUGAGGCCG AAAGGCCGAA ACCAGGAG 38

( 2 ) INFORMATION FOR SEQ ID NO: 2024:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2024:

AGUUCCCCCU GAUGAGGCCG AAAGGCCGAA AGCAGUCC 38

( 2 ) INFORMATION FOR SEQ ID NO: 2025:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2025:

UGGGAACACU GAUGAGGCCG AAAGGCCGAA AGGUAGGA 38

( 2 ) INFORMATION FOR SEQ ID NO: 2026:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2026:

GAGUUGGGCU GAUGAGGCCG AAAGGCCGAA ACAGUGUC 38

( 2 ) INFORMATION FOR SEQ ID NO: 2027:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2027:

GGCCCGGGCU GAUGAGGCCG AAAGGCCGAA AUCACAAC 38

( 2 ) INFORMATION FOR SEQ ID NO: 2028:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2028:

GGAGUUCCCU GAUGAGGCCG AAAGGCCGAA AGGUCUGG 38

( 2 ) INFORMATION FOR SEQ ID NO: 2029:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2029:

UUGAGGUGCU GAUGAGGCCG AAAGGCCGAA AGCCGGGU 38

( 2 ) INFORMATION FOR SEQ ID NO: 2030:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2030:

UGACUCGUCU GAUGAGGCCG AAAGGCCGAA AAAGAAAU 38

( 2 ) INFORMATION FOR SEQ ID NO: 2031:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2031:

GGGGGAAGCU GAUGAGGCCG AAAGGCCGAA ACUGUUCA    38

( 2 ) INFORMATION FOR SEQ ID NO: 2032:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2032:

CGAGGCAGCU GAUGAGGCCG AAAGGCCGAA AAGGCUUC    38

( 2 ) INFORMATION FOR SEQ ID NO: 2033:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2033:

CCUGCACGCU GAUGAGGCCG AAAGGCCGAA AUCCACCC    38

( 2 ) INFORMATION FOR SEQ ID NO: 2034:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2034:

GGUCAGAUCU GAUGAGGCCG AAAGGCCGAA AGGGGCUG    38

( 2 ) INFORMATION FOR SEQ ID NO: 2035:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2035:

UUCACAGUCU GAUGAGGCCG AAAGGCCGAA ACUUGGUC    38

( 2 ) INFORMATION FOR SEQ ID NO: 2036:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2036:

CCUCCCACCU GAUGAGGCCG AAAGGCCGAA ACAGCUUG    38

( 2 ) INFORMATION FOR SEQ ID NO: 2037:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2037:

GGGGUGUCCU GAUGAGGCCG AAAGGCCGAA AGCUUCAG    38

( 2 ) INFORMATION FOR SEQ ID NO: 2038:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2038:

UCCUAAGGCU GAUGAGGCCG AAAGGCCGAA AGGGGGCC    38

( 2 ) INFORMATION FOR SEQ ID NO: 2039:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2039:

CCUCCACUCU GAUGAGGCCG AAAGGCCGAA AGGCAGUG    38

( 2 ) INFORMATION FOR SEQ ID NO: 2040:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2040:

GCAUGAGACU GAUGAGGCCG AAAGGCCGAA AUUGGCUC    38

( 2 ) INFORMATION FOR SEQ ID NO: 2041:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2041:

CGAGGCAGCU GAUGAGGCCG AAAGGCCGAA AAGGCUUC    38

( 2 ) INFORMATION FOR SEQ ID NO: 2042:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2042:

UCAGCUUGCU GAUGAGGCCG AAAGGCCGAA AGAGCUUC    38

( 2 ) INFORMATION FOR SEQ ID NO: 2043:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2043:

UCGUUUGUCU GAUGAGGCCG AAAGGCCGAA AUCCUCCG 38

( 2 ) INFORMATION FOR SEQ ID NO: 2044:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2044:

AGUUCUCACU GAUGAGGCCG AAAGGCCGAA AGCACAGU 38

( 2 ) INFORMATION FOR SEQ ID NO: 2045:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2045:

GAGGACCACU GAUGAGGCCG AAAGGCCGAA AUAGCACA 38

( 2 ) INFORMATION FOR SEQ ID NO: 2046:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2046:

CUCAGCUUCU GAUGAGGCCG AAAGGCCGAA AAGAGCUU 38

( 2 ) INFORMATION FOR SEQ ID NO: 2047:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2047:

AAGCCGAGCU GAUGAGGCCG AAAGGCCGAA ACUGCGUG 38

( 2 ) INFORMATION FOR SEQ ID NO: 2048:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2048:

ACGGUUGCU GAUGAGGCCG AAAGGCCGAA AGCCAUUG 38

( 2 ) INFORMATION FOR SEQ ID NO: 2049:

( i ) SEQUENCE CHARACTERISTICS:
( A ) LENGTH: 38 base pairs (B) TYPE: nucleic acid
(C) STRANDEDNESS: single
(D) TOPOLOGY: linear (xi) SEQUENCE DESCRIPTION: SEQ ID NO: 2049:

AGGUGGGUCU GAUGAGGCCG AAAGGCCGAA AGGGGUAA                    38

(2) INFORMATION FOR SEQ ID NO: 2050:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2050:

GAGGCAGGCU GAUGAGGCCG AAAGGCCGAA AGGCUUCU                    38

(2) INFORMATION FOR SEQ ID NO: 2051:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2051:

UACCCUGUCU GAUGAGGCCG AAAGGCCGAA AGGUGGGU                    38

(2) INFORMATION FOR SEQ ID NO: 2052:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2052:

AGCUCCAACU GAUGAGGCCG AAAGGCCGAA ACACAGCG                    38

(2) INFORMATION FOR SEQ ID NO: 2053:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2053:

CUGUUCAGCU GAUGAGGCCG AAAGGCCGAA AGCACCAC                    38

(2) INFORMATION FOR SEQ ID NO: 2054:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 2054:

UGCGCUGGCU GAUGAGGCCG AAAGGCCGAA AGGGGUGC                    38

(2) INFORMATION FOR SEQ ID NO: 2055:

(i) SEQUENCE CHARACTERISTICS:
      (A) LENGTH: 38 base pairs
      (B) TYPE: nucleic acid
      (C) STRANDEDNESS: single (D) TOPOLOGY: linear (x i) SEQUENCE DESCRIPTION: SEQ ID NO: 2055:

GGUGGCAGCU GAUGAGGCCG AAAGGCCGAA AGCCGAGG 38

(2) INFORMATION FOR SEQ ID NO: 2056:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO: 2056:

UGGUUUUUCU GAUGAGGCCG AAAGGCCGAA AACAGGGA 38

(2) INFORMATION FOR SEQ ID NO: 2057:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO: 2057:

CGCAGGAUCU GAUGAGGCCG AAAGGCCGAA AGGUUCUU 38

(2) INFORMATION FOR SEQ ID NO: 2058:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO: 2058:

GCCUGGGGCU GAUGAGGCCG AAAGGCCGAA AAGUACCC 38

(2) INFORMATION FOR SEQ ID NO: 2059:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO: 2059:

UGGUGGCACU GAUGAGGCCG AAAGGCCGAA AAGCCGAG 38

(2) INFORMATION FOR SEQ ID NO: 2060:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO: 2060:

UACACAGUCU GAUGAGGCCG AAAGGCCGAA AUGGUGGC 38

(2) INFORMATION FOR SEQ ID NO: 2061:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO: 2061:

UUCCCACGCU GAUGAGGCCG AAAGGCCGAA AGCAGCAC 38

(2) INFORMATION FOR SEQ ID NO: 2062:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO: 2062:

GUGGUUGGCU GAUGAGGCCG AAAGGCCGAA ACAUUUC 38

(2) INFORMATION FOR SEQ ID NO: 2063:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO: 2063:

UCCCUGGUCU GAUGAGGCCG AAAGGCCGAA AUACUCCC 38

(2) INFORMATION FOR SEQ ID NO: 2064:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO: 2064:

GCAUGAGACU GAUGAGGCCG AAAGGCCGAA AUUGGCUC 38

(2) INFORMATION FOR SEQ ID NO: 2065:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO: 2065:

AGCAUGAGCU GAUGAGGCCG AAAGGCCGAA AAUUGGCU 38

(2) INFORMATION FOR SEQ ID NO: 2066:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO: 2066:

AAGCAUGACU GAUGAGGCCG AAAGGCCGAA AAAUUGGC 38

(2) INFORMATION FOR SEQ ID NO: 2067:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO: 2067:

| | |
|---|---|
| UGAAGCAUCU GAUGAGGCCG AAAGGCCGAA AGAAAUUG | 38 |

( 2 ) INFORMATION FOR SEQ ID NO: 2068:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2068:

| | |
|---|---|
| CAUUCUUGCU GAUGAGGCCG AAAGGCCGAA ACAGUGAC | 38 |

( 2 ) INFORMATION FOR SEQ ID NO: 2069:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2069:

| | |
|---|---|
| ACAUUCUUCU GAUGAGGCCG AAAGGCCGAA AACAGUGA | 38 |

( 2 ) INFORMATION FOR SEQ ID NO: 2070:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2070:

| | |
|---|---|
| AAGAGGAACU GAUGAGGCCG AAAGGCCGAA AGCAGUUC | 38 |

( 2 ) INFORMATION FOR SEQ ID NO: 2071:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2071:

| | |
|---|---|
| UGCGCUGGCU GAUGAGGCCG AAAGGCCGAA AGGGGUGC | 38 |

( 2 ) INFORMATION FOR SEQ ID NO: 2072:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2072:

| | |
|---|---|
| AAAGUCCGCU GAUGAGGCCG AAAGGCCGAA AGCUGCCU | 38 |

( 2 ) INFORMATION FOR SEQ ID NO: 2073:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2073:

| | |
|---|---|
| GGAGUUCCCU GAUGAGGCCG AAAGGCCGAA AGGUCUGG | 38 |

( 2 ) INFORMATION FOR SEQ ID NO: 2074:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2074:

GGAAGAUCCU GAUGAGGCCG AAAGGCCGAA AAAGUCCG    38

( 2 ) INFORMATION FOR SEQ ID NO: 2075:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2075:

AGAGGCAGCU GAUGAGGCCG AAAGGCCGAA AAACAGGC    38

( 2 ) INFORMATION FOR SEQ ID NO: 2076:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2076:

GUGAGGGGCU GAUGAGGCCG AAAGGCCGAA AAAUGCUG    38

( 2 ) INFORMATION FOR SEQ ID NO: 2077:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2077:

GAGCUGAACU GAUGAGGCCG AAAGGCCGAA AGUUGUAG    38

( 2 ) INFORMATION FOR SEQ ID NO: 2078:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2078:

UGGGAGCUCU GAUGAGGCCG AAAGGCCGAA AAAAGUUG    38

( 2 ) INFORMATION FOR SEQ ID NO: 2079:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2079:

GCGACCAGCU GAUGAGGCCG AAAGGCCGAA ACCAGGAG    38

( 2 ) INFORMATION FOR SEQ ID NO: 2080:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2080:

UCCACCCCCU GAUGAGGCCG AAAGGCCGAA AGGCAGGA 38

( 2 ) INFORMATION FOR SEQ ID NO: 2081:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2081:

AGUUCUCACU GAUGAGGCCG AAAGGCCGAA AGCACAGU 38

( 2 ) INFORMATION FOR SEQ ID NO: 2082:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2082:

UUCCAGGGCU GAUGAGGCCG AAAGGCCGAA ACACAAGA 38

( 2 ) INFORMATION FOR SEQ ID NO: 2083:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2083:

CUUCCAGGCU GAUGAGGCCG AAAGGCCGAA AACACAAG 38

( 2 ) INFORMATION FOR SEQ ID NO: 2084:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2084:

AGGCAGGACU GAUGAGGCCG AAAGGCCGAA ACAGGCCU 38

( 2 ) INFORMATION FOR SEQ ID NO: 2085:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2085:

GAGGCAGGCU GAUGAGGCCG AAAGGCCGAA AACAGGCC 38

( 2 ) INFORMATION FOR SEQ ID NO: 2086:

( i ) SEQUENCE CHARACTERISTICS:

( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2086:

GCGACCAGCU GAUGAGGCCG AAAGGCCGAA ACCAGGAG                    38

( 2 ) INFORMATION FOR SEQ ID NO: 2087:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2087:

GAGCUUCACU GAUGAGGCCG AAAGGCCGAA AGGCAGGA                    38

( 2 ) INFORMATION FOR SEQ ID NO: 2088:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2088:

UCCAGGUACU GAUGAGGCCG AAAGGCCGAA AUCUGAGC                    38

( 2 ) INFORMATION FOR SEQ ID NO: 2089:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2089:

UAGUCUCCCU GAUGAGGCCG AAAGGCCGAA ACCCCAGG                    38

( 2 ) INFORMATION FOR SEQ ID NO: 2090:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2090:

CAAUAAAUCU GAUGAGGCCG AAAGGCCGAA ACUGUCAG                    38

( 2 ) INFORMATION FOR SEQ ID NO: 2091:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2091:

AGCUGCUACU GAUGAGGCCG AAAGGCCGAA AGGUGAGC                    38

( 2 ) INFORMATION FOR SEQ ID NO: 2092:

( i ) SEQUENCE CHARACTERISTICS:
        ( A ) LENGTH: 38 base pairs
        ( B ) TYPE: nucleic acid (C) STRANDEDNESS: single
(D) TOPOLOGY: linear (xi) SEQUENCE DESCRIPTION: SEQ ID NO: 2092:

ACGGGUUGCU GAUGAGGCCG AAAGGCCGAA AGCCAUUG 38

(2) INFORMATION FOR SEQ ID NO: 2093:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2093:

UGUCAGAGCU GAUGAGGCCG AAAGGCCGAA AAGCAUGG 38

(2) INFORMATION FOR SEQ ID NO: 2094:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2094:

UAGGUGGGCU GAUGAGGCCG AAAGGCCGAA AGGUGGUC 38

(2) INFORMATION FOR SEQ ID NO: 2095:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2095:

CUUCGCAACU GAUGAGGCCG AAAGGCCGAA AGGAAGAG 38

(2) INFORMATION FOR SEQ ID NO: 2096:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2096:

CACGGGUUCU GAUGAGGCCG AAAGGCCGAA AAGCCAUU 38

(2) INFORMATION FOR SEQ ID NO: 2097:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2097:

UUCACAGUCU GAUGAGGCCG AAAGGCCGAA ACUUGGUC 38

(2) INFORMATION FOR SEQ ID NO: 2098:

(i) SEQUENCE CHARACTERISTICS:
(A) LENGTH: 38 base pairs
(B) TYPE: nucleic acid
(C) STRANDEDNESS: single
(D) TOPOLOGY: linear ( x i ) SEQUENCE DESCRIPTION: SEQ ID NO: 2098:

CUGGGAACCU GAUGAGGCCG AAAGGCCGAA AAUACACA 38

( 2 ) INFORMATION FOR SEQ ID NO: 2099:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2099:

UGACACAACU GAUGAGGCCG AAAGGCCGAA AUCUCUGC 38

( 2 ) INFORMATION FOR SEQ ID NO: 2100:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2100:

AAGUUGUACU GAUGAGGCCG AAAGGCCGAA AUUCUCAA 38

( 2 ) INFORMATION FOR SEQ ID NO: 2101:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2101:

AAAAGUUGCU GAUGAGGCCG AAAGGCCGAA AGAUUCUC 38

( 2 ) INFORMATION FOR SEQ ID NO: 2102:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2102:

GAGCUGAACU GAUGAGGCCG AAAGGCCGAA AGUUGUAG 38

( 2 ) INFORMATION FOR SEQ ID NO: 2103:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2103:

GGAGCUGACU GAUGAGGCCG AAAGGCCGAA AAGUUGUA 38

( 2 ) INFORMATION FOR SEQ ID NO: 2104:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2104:

GGGAGCUGCU GAUGAGGCCG AAAGGCCGAA AAAGUUGU  38

( 2 ) INFORMATION FOR SEQ ID NO: 2105:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2105:

GACGCCACCU GAUGAGGCCG AAAGGCCGAA AUCACGAA  38

( 2 ) INFORMATION FOR SEQ ID NO: 2106:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2106:

CCUGGUGACU GAUGAGGCCG AAAGGCCGAA ACUCCCAC  38

( 2 ) INFORMATION FOR SEQ ID NO: 2107:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2107:

CCUUCUGACU GAUGAGGCCG AAAGGCCGAA ACCUCCGG  38

( 2 ) INFORMATION FOR SEQ ID NO: 2108:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2108:

CCCCUUCUCU GAUGAGGCCG AAAGGCCGAA AGACCUCC  38

( 2 ) INFORMATION FOR SEQ ID NO: 2109:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2109:

UUGGGAACCU GAUGAGGCCG AAAGGCCGAA AAGGUAGG  38

( 2 ) INFORMATION FOR SEQ ID NO: 2110:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2110:

UCUGCUGACU GAUGAGGCCG AAAGGCCGAA ACCCCUCU  38

( 2 ) INFORMATION FOR SEQ ID NO: 2111:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2111:

AGGGGCUGCU GAUGAGGCCG AAAGGCCGAA AUUCCCCU    38

( 2 ) INFORMATION FOR SEQ ID NO: 2112:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2112:

AUCAACAACU GAUGAGGCCG AAAGGCCGAA AGUUGGGG    38

( 2 ) INFORMATION FOR SEQ ID NO: 2113:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2113:

AGCAAAAGCU GAUGAGGCCG AAAGGCCGAA AGCGUCGU    38

( 2 ) INFORMATION FOR SEQ ID NO: 2114:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2114:

GAGCAAAACU GAUGAGGCCG AAAGGCCGAA AAGCGUCG    38

( 2 ) INFORMATION FOR SEQ ID NO: 2115:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2115:

CAGAGCAACU GAUGAGGCCG AAAGGCCGAA AGAAGCGU    38

( 2 ) INFORMATION FOR SEQ ID NO: 2116:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2116:

AGGCCGCACU GAUGAGGCCG AAAGGCCGAA AGCAAAAG    38

( 2 ) INFORMATION FOR SEQ ID NO: 2117:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2117:

UUCAGUGUCU GAUGAGGCCG AAAGGCCGAA AAUUGGAU     38

( 2 ) INFORMATION FOR SEQ ID NO: 2118:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2118:

CCUGUGGACU GAUGAGGCCG AAAGGCCGAA AAGCCCAA     38

( 2 ) INFORMATION FOR SEQ ID NO: 2119:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2119:

GACCUGUGCU GAUGAGGCCG AAAGGCCGAA AGAAGCCC     38

( 2 ) INFORMATION FOR SEQ ID NO: 2120:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2120:

AGCACAUGCU GAUGAGGCCG AAAGGCCGAA AGUUCCAA     38

( 2 ) INFORMATION FOR SEQ ID NO: 2121:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2121:

ACGAUCACCU GAUGAGGCCG AAAGGCCGAA AAGCCCGC     38

( 2 ) INFORMATION FOR SEQ ID NO: 2122:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2122:

GCGACCAGCU GAUGAGGCCG AAAGGCCGAA ACCAGGAG     38

( 2 ) INFORMATION FOR SEQ ID NO: 2123:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2123:

GAGGACCACU GAUGAGGCCG AAAGGCCGAA AUAGCACA                    38

( 2 ) INFORMATION FOR SEQ ID NO: 2124:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2124:

ACCCGUAUCU GAUGAGGCCG AAAGGCCGAA AUCUUUCC                    38

( 2 ) INFORMATION FOR SEQ ID NO: 2125:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2125:

CAUUCUUGCU GAUGAGGCCG AAAGGCCGAA ACAGUGAC                    38

( 2 ) INFORMATION FOR SEQ ID NO: 2126:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2126:

CUGACACACU GAUGAGGCCG AAAGGCCGAA AAUCUCUG                    38

( 2 ) INFORMATION FOR SEQ ID NO: 2127:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2127:

UCUGCUGACU GAUGAGGCCG AAAGGCCGAA ACCCCUCU                    38

( 2 ) INFORMATION FOR SEQ ID NO: 2128:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2128:

GCAUGUAACU GAUGAGGCCG AAAGGCCGAA AGUCUGCU                    38

( 2 ) INFORMATION FOR SEQ ID NO: 2129:

( i ) SEQUENCE CHARACTERISTICS:
    ( A ) LENGTH: 38 base pairs ( B ) TYPE: nucleic acid
( C ) STRANDEDNESS: single
( D ) TOPOLOGY: linear ( x i ) SEQUENCE DESCRIPTION: SEQ ID NO: 2129:

UUUCCCACU GAUGAGGCCG AAAGGCCGAA ACUCUGUU 38

( 2 ) INFORMATION FOR SEQ ID NO: 2130:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2130:

GCUCUGGGCU GAUGAGGCCG AAAGGCCGAA ACGAAUAC 38

( 2 ) INFORMATION FOR SEQ ID NO: 2131:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2131:

GGAUACCUCU GAUGAGGCCG AAAGGCCGAA AGCACCGA 38

( 2 ) INFORMATION FOR SEQ ID NO: 2132:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2132:

AGUCCUCUCU GAUGAGGCCG AAAGGCCGAA AGGCCUGA 38

( 2 ) INFORMATION FOR SEQ ID NO: 2133:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2133:

CCAUUGUUCU GAUGAGGCCG AAAGGCCGAA AGCUGCUA 38

( 2 ) INFORMATION FOR SEQ ID NO: 2134:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2134:

CCUGGGGCU GAUGAGGCCG AAAGGCCGAA AGUACCCU 38

( 2 ) INFORMATION FOR SEQ ID NO: 2135:

( i ) SEQUENCE CHARACTERISTICS:
( A ) LENGTH: 38 base pairs
( B ) TYPE: nucleic acid
( C ) STRANDEDNESS: single ( D ) TOPOLOGY: linear ( x i ) SEQUENCE DESCRIPTION: SEQ ID NO: 2135:

GCCUGGGGCU GAUGAGGCCG AAAGGCCGAA AAGUACCC 38

( 2 ) INFORMATION FOR SEQ ID NO: 2136:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2136:

GGCAGCGGCU GAUGAGGCCG AAAGGCCGAA ACACCAUC 38

( 2 ) INFORMATION FOR SEQ ID NO: 2137:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2137:

ACCAUCCCCU GAUGAGGCCG AAAGGCCGAA AUAGGCAG 38

( 2 ) INFORMATION FOR SEQ ID NO: 2138:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2138:

CAUCCAGUCU GAUGAGGCCG AAAGGCCGAA AGUCUCCA 38

( 2 ) INFORMATION FOR SEQ ID NO: 2139:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2139:

UGUCCUGUCU GAUGAGGCCG AAAGGCCGAA ACAGCCAG 38

( 2 ) INFORMATION FOR SEQ ID NO: 2140:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2140:

CAGUUCUCCU GAUGAGGCCG AAAGGCCGAA AAGCACAG 38

( 2 ) INFORMATION FOR SEQ ID NO: 2141:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2141:

GACGCCACCU GAUGAGGCCG AAAGGCCGAA AUCACGAA 38

( 2 ) INFORMATION FOR SEQ ID NO: 2142:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2142:

GUCCACUCCU GAUGAGGCCG AAAGGCCGAA AUAGUUCG 38

( 2 ) INFORMATION FOR SEQ ID NO: 2143:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2143:

GCCUGGGGCU GAUGAGGCCG AAAGGCCGAA AAGUACCC 38

( 2 ) INFORMATION FOR SEQ ID NO: 2144:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2144:

AGCCAGAGCU GAUGAGGCCG AAAGGCCGAA AGGUGGGU 38

( 2 ) INFORMATION FOR SEQ ID NO: 2145:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2145:

CCUGAGGCCU GAUGAGGCCG AAAGGCCGAA ACAAGUAU 38

( 2 ) INFORMATION FOR SEQ ID NO: 2146:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2146:

CUCCUCCUCU GAUGAGGCCG AAAGGCCGAA AGCCUUCU 38

( 2 ) INFORMATION FOR SEQ ID NO: 2147:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2147:

```
UCCCUGGUCU  GAUGAGGCCG  AAAGGCCGAA  AUACUCCC                    38
```

( 2 ) INFORMATION FOR SEQ ID NO: 2148:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2148:

```
CCUGGGGCU  GAUGAGGCCG  AAAGGCCGAA  AGUACCCU                     38
```

( 2 ) INFORMATION FOR SEQ ID NO: 2149:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2149:

```
GCAAGAGGCU  GAUGAGGCCG  AAAGGCCGAA  AGAGCAGU                    38
```

( 2 ) INFORMATION FOR SEQ ID NO: 2150:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2150:

```
UAGUCUCCCU  GAUGAGGCCG  AAAGGCCGAA  ACCCCAGG                    38
```

( 2 ) INFORMATION FOR SEQ ID NO: 2151:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2151:

```
UUGACCAUCU  GAUGAGGCCG  AAAGGCCGAA  AUUUCACG                    38
```

( 2 ) INFORMATION FOR SEQ ID NO: 2152:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2152:

```
GUGGUUGGCU  GAUGAGGCCG  AAAGGCCGAA  ACAUUUUC                    38
```

( 2 ) INFORMATION FOR SEQ ID NO: 2153:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2153:

```
CCAACAAUCU  GAUGAGGCCG  AAAGGCCGAA  AUGACCCA                    38
```

( 2 ) INFORMATION FOR SEQ ID NO: 2154:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2154:

UACACAGUCU GAUGAGGCCG AAAGGCCGAA AUGGUGGC 38

( 2 ) INFORMATION FOR SEQ ID NO: 2155:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2155:

ACAACGGCCU GAUGAGGCCG AAAGGCCGAA ACCAGGAC 38

( 2 ) INFORMATION FOR SEQ ID NO: 2156:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2156:

ACAAUUAUCU GAUGAGGCCG AAAGGCCGAA ACCCAGGU 38

( 2 ) INFORMATION FOR SEQ ID NO: 2157:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2157:

AAGCCCGCCU GAUGAGGCCG AAAGGCCGAA AUGAUCAG 38

( 2 ) INFORMATION FOR SEQ ID NO: 2158:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2158:

UACGAGCACU GAUGAGGCCG AAAGGCCGAA AGGGCCAC 38

( 2 ) INFORMATION FOR SEQ ID NO: 2159:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2159:

UAAACAGGCU GAUGAGGCCG AAAGGCCGAA ACUUCCCA 38

( 2 ) INFORMATION FOR SEQ ID NO: 2160:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2160:

UGGGAACACU GAUGAGGCCG AAAGGCCGAA AGGUAGGA 38

( 2 ) INFORMATION FOR SEQ ID NO: 2161:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2161:

GGCGGUAACU GAUGAGGCCG AAAGGCCGAA AGGUGUAA 38

( 2 ) INFORMATION FOR SEQ ID NO: 2162:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2162:

CUGGCGGUCU GAUGAGGCCG AAAGGCCGAA AUAGGUGU 38

( 2 ) INFORMATION FOR SEQ ID NO: 2163:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2163:

UAUAUCCUCU GAUGAGGCCG AAAGGCCGAA AUCUUCCU 38

( 2 ) INFORMATION FOR SEQ ID NO: 2164:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2164:

GUAACUUGCU GAUGAGGCCG AAAGGCCGAA AUAUCCUG 38

( 2 ) INFORMATION FOR SEQ ID NO: 2165:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2165:

GCCUUCUGCU GAUGAGGCCG AAAGGCCGAA AACUUGUA 38

( 2 ) INFORMATION FOR SEQ ID NO: 2166:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2166:

GGCUCAGGCU GAUGAGGCCG AAAGGCCGAA AGGCGGGG     38

(2) INFORMATION FOR SEQ ID NO: 2167:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2167:

ACCAGGGCCU GAUGAGGCCG AAAGGCCGAA AAGUGCAG     38

(2) INFORMATION FOR SEQ ID NO: 2168:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2168:

UGUCCAUUCU GAUGAGGCCG AAAGGCCGAA AUCUGUUC     38

(2) INFORMATION FOR SEQ ID NO: 2169:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2169:

CCCAGGCCCU GAUGAGGCCG AAAGGCCGAA AGGUUCUC     38

(2) INFORMATION FOR SEQ ID NO: 2170:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2170:

GACCUGUGCU GAUGAGGCCG AAAGGCCGAA AGAAGCCC     38

(2) INFORMATION FOR SEQ ID NO: 2171:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2171:

GAGGCAGGCU GAUGAGGCCG AAAGGCCGAA AACAGGCC     38

(2) INFORMATION FOR SEQ ID NO: 2172:

(i) SEQUENCE CHARACTERISTICS:
(A) LENGTH: 38 base pairs
(B) TYPE: nucleic acid (C) STRANDEDNESS: single
(D) TOPOLOGY: linear (x i) SEQUENCE DESCRIPTION: SEQ ID NO: 2172:

GAGAGGUCCU GAUGAGGCCG AAAGGCCGAA ACGAGCAG 38

(2) INFORMATION FOR SEQ ID NO: 2173:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO: 2173:

AAUGUAUGCU GAUGAGGCCG AAAGGCCGAA AGGUGGGG 38

(2) INFORMATION FOR SEQ ID NO: 2174:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO: 2174:

GAAGAUCGCU GAUGAGGCCG AAAGGCCGAA AAGUCCGG 38

(2) INFORMATION FOR SEQ ID NO: 2175:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO: 2175:

GCGACCAGCU GAUGAGGCCG AAAGGCCGAA ACCAGGAG 38

(2) INFORMATION FOR SEQ ID NO: 2176:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO: 2176:

UCUCCAGGCU GAUGAGGCCG AAAGGCCGAA AUAUCUGA 38

(2) INFORMATION FOR SEQ ID NO: 2177:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO: 2177:

GCACCGUGCU GAUGAGGCCG AAAGGCCGAA AUGUGAUC 38

(2) INFORMATION FOR SEQ ID NO: 2178:

(i) SEQUENCE CHARACTERISTICS:
(A) LENGTH: 38 base pairs
(B) TYPE: nucleic acid
(C) STRANDEDNESS: single
(D) TOPOLOGY: linear ( x i ) SEQUENCE DESCRIPTION: SEQ ID NO: 2178:

AAUAGGUGCU GAUGAGGCCG AAAGGCCGAA AAAUGGAC 38

( 2 ) INFORMATION FOR SEQ ID NO: 2179:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2179:

AGGACCAGCU GAUGAGGCCG AAAGGCCGAA AGCAGAGG 38

( 2 ) INFORMATION FOR SEQ ID NO: 2180:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2180:

CCCAGGCCCU GAUGAGGCCG AAAGGCCGAA AGGUUCUC 38

( 2 ) INFORMATION FOR SEQ ID NO: 2181:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2181:

GAGUUGGGCU GAUGAGGCCG AAAGGCCGAA ACAGUGUC 38

( 2 ) INFORMATION FOR SEQ ID NO: 2182:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2182:

GUCCAGGUCU GAUGAGGCCG AAAGGCCGAA AGGACCAU 38

( 2 ) INFORMATION FOR SEQ ID NO: 2183:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2183:

UGGUUUUUCU GAUGAGGCCG AAAGGCCGAA AACAGGGA 38

( 2 ) INFORMATION FOR SEQ ID NO: 2184:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2184:

UCCAGGUACU GAUGAGGCCG AAAGGCCGAA AUCUGAGC 38

(2) INFORMATION FOR SEQ ID NO: 2185:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2185:

UUUCCCCACU GAUGAGGCCG AAAGGCCGAA ACUCUGUU 38

(2) INFORMATION FOR SEQ ID NO: 2186:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2186:

ACGAUCACCU GAUGAGGCCG AAAGGCCGAA AAGCCCGC 38

(2) INFORMATION FOR SEQ ID NO: 2187:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2187:

UACACAGUCU GAUGAGGCCG AAAGGCCGAA AUGGUGGC 38

(2) INFORMATION FOR SEQ ID NO: 2188:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2188:

UACCCUGUCU GAUGAGGCCG AAAGGCCGAA AGGUGGGU 38

(2) INFORMATION FOR SEQ ID NO: 2189:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2189:

GCCCUCCCU GAUGAGGCCG AAAGGCCGAA AGUCCUCU 38

(2) INFORMATION FOR SEQ ID NO: 2190:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2190:

GCAGGUCACU GAUGAGGCCG AAAGGCCGAA AUUAGGGG 38

( 2 ) INFORMATION FOR SEQ ID NO: 2191:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2191:

GGACCAUACU GAUGAGGCCG AAAGGCCGAA AGCACAUG      38

( 2 ) INFORMATION FOR SEQ ID NO: 2192:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2192:

CUUGUGUCCU GAUGAGGCCG AAAGGCCGAA ACCGGAUA      38

( 2 ) INFORMATION FOR SEQ ID NO: 2193:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2193:

AUUUAUAUCU GAUGAGGCCG AAAGGCCGAA ACUCGUGA      38

( 2 ) INFORMATION FOR SEQ ID NO: 2194:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2194:

CCUGGGGCU GAUGAGGCCG AAAGGCCGAA AGUACUGU      38

( 2 ) INFORMATION FOR SEQ ID NO: 2195:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2195:

UGUACCUUCU GAUGAGGCCG AAAGGCCGAA AGUUUUAG      38

( 2 ) INFORMATION FOR SEQ ID NO: 2196:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2196:

UGUCCAUUCU GAUGAGGCCG AAAGGCCGAA AUCUGUUC      38

( 2 ) INFORMATION FOR SEQ ID NO: 2197:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2197:

UAGGCAAUCU GAUGAGGCCG AAAGGCCGAA ACUUACAU 38

( 2 ) INFORMATION FOR SEQ ID NO: 2198:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2198:

CUAAAGGUCU GAUGAGGCCG AAAGGCCGAA AGCGUCCA 38

( 2 ) INFORMATION FOR SEQ ID NO: 2199:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2199:

UCCAGGUACU GAUGAGGCCG AAAGGCCGAA AUCUGAGC 38

( 2 ) INFORMATION FOR SEQ ID NO: 2200:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2200:

CAUCCAGUCU GAUGAGGCCG AAAGGCCGAA AGUCUCCA 38

( 2 ) INFORMATION FOR SEQ ID NO: 2201:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2201:

GCUGACACCU GAUGAGGCCG AAAGGCCGAA AAAUCUCU 38

( 2 ) INFORMATION FOR SEQ ID NO: 2202:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2202:

CCCAGGCCCU GAUGAGGCCG AAAGGCCGAA AGGUUCUC 38

( 2 ) INFORMATION FOR SEQ ID NO: 2203:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2203:

AGCUUGAACU GAUGAGGCCG AAAGGCCGAA AGCUUCCA 38

( 2 ) INFORMATION FOR SEQ ID NO: 2204:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2204:

UAGGCAAUCU GAUGAGGCCG AAAGGCCGAA ACUUACAU 38

( 2 ) INFORMATION FOR SEQ ID NO: 2205:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2205:

CAUCCCGACU GAUGAGGCCG AAAGGCCGAA AGGCAGCG 38

( 2 ) INFORMATION FOR SEQ ID NO: 2206:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2206:

ACCAUCCCCU GAUGAGGCCG AAAGGCCGAA AUAGGCAG 38

( 2 ) INFORMATION FOR SEQ ID NO: 2207:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2207:

GUACAGGGCU GAUGAGGCCG AAAGGCCGAA ACUCAAUA 38

( 2 ) INFORMATION FOR SEQ ID NO: 2208:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2208:

UCGUUUGUCU GAUGAGGCCG AAAGGCCGAA AUCCUCCG 38

( 2 ) INFORMATION FOR SEQ ID NO: 2209:

( i ) SEQUENCE CHARACTERISTICS:
    ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO: 2209:

ACCUCCAGCU GAUGAGGCCG AAAGGCCGAA AGGUCAGG 38

(2) INFORMATION FOR SEQ ID NO: 2210:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2210:

AGCCAUUGCU GAUGAGGCCG AAAGGCCGAA AGGACCAG 38

(2) INFORMATION FOR SEQ ID NO: 2211:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2211:

UAGGUGUACU GAUGAGGCCG AAAGGCCGAA AUGGACGC 38

(2) INFORMATION FOR SEQ ID NO: 2212:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2212:

CCUGAGGCCU GAUGAGGCCG AAAGGCCGAA ACAAGUAU 38

(2) INFORMATION FOR SEQ ID NO: 2213:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2213:

UUAGGCCUCU GAUGAGGCCG AAAGGCCGAA AGGCUACA 38

(2) INFORMATION FOR SEQ ID NO: 2214:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2214:

ACAUCAACCU GAUGAGGCCG AAAGGCCGAA AGAGUUGG 38

(2) INFORMATION FOR SEQ ID NO: 2215:

(i) SEQUENCE CHARACTERISTICS:
        (A) LENGTH: 38 base pairs
        (B) TYPE: nucleic acid
        (C) STRANDEDNESS: single ( D ) TOPOLOGY: linear ( x i ) SEQUENCE DESCRIPTION: SEQ ID NO: 2215:

ACCUCCAGCU GAUGAGGCCG AAAGGCCGAA AGGUCAGG                    38

( 2 ) INFORMATION FOR SEQ ID NO: 2216:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2216:

CAGGACCCCU GAUGAGGCCG AAAGGCCGAA AGUCGGAA                    38

( 2 ) INFORMATION FOR SEQ ID NO: 2217:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2217:

GAUCAUGGCU GAUGAGGCCG AAAGGCCGAA ACAGCACU                    38

( 2 ) INFORMATION FOR SEQ ID NO: 2218:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2218:

AGAGGCAGCU GAUGAGGCCG AAAGGCCGAA AAACAGGC                    38

( 2 ) INFORMATION FOR SEQ ID NO: 2219:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2219:

ACAUCAACCU GAUGAGGCCG AAAGGCCGAA AGAGUUGG                    38

( 2 ) INFORMATION FOR SEQ ID NO: 2220:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2220:

AAGUUGUACU GAUGAGGCCG AAAGGCCGAA AUUCUCAA                    38

( 2 ) INFORMATION FOR SEQ ID NO: 2221:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2221:

UCAAUAAACU GAUGAGGCCG AAAGGCCGAA AACUGUCA 38

( 2 ) INFORMATION FOR SEQ ID NO: 2222:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2222:

AAUUAAUACU GAUGAGGCCG AAAGGCCGAA AUACAUCA 38

( 2 ) INFORMATION FOR SEQ ID NO: 2223:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2223:

GAAUUAAUCU GAUGAGGCCG AAAGGCCGAA AAUACAUC 38

( 2 ) INFORMATION FOR SEQ ID NO: 2224:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2224:

UGAAUUAACU GAUGAGGCCG AAAGGCCGAA AAAUACAU 38

( 2 ) INFORMATION FOR SEQ ID NO: 2225:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2225:

AACAAAGGCU GAUGAGGCCG AAAGGCCGAA AGGAAUGU 38

( 2 ) INFORMATION FOR SEQ ID NO: 2226:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2226:

CUCUGAAUCU GAUGAGGCCG AAAGGCCGAA AAUAAAUA 38

( 2 ) INFORMATION FOR SEQ ID NO: 2227:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2227:

AAUUAAUACU GAUGAGGCCG AAAGGCCGAA AUACAUCA 38

( 2 ) INFORMATION FOR SEQ ID NO: 2228:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2228:

GAAUUAAUCU GAUGAGGCCG AAAGGCCGAA AAUACAUC 38

( 2 ) INFORMATION FOR SEQ ID NO: 2229:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2229:

UCUGAAUUCU GAUGAGGCCG AAAGGCCGAA AUAAAUAC 38

( 2 ) INFORMATION FOR SEQ ID NO: 2230:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2230:

UACUCAAUCU GAUGAGGCCG AAAGGCCGAA AAUAACUG 38

( 2 ) INFORMATION FOR SEQ ID NO: 2231:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2231:

GAGGACCACU GAUGAGGCCG AAAGGCCGAA AUAGCACA 38

( 2 ) INFORMATION FOR SEQ ID NO: 2232:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2232:

AGCAGGGGCU GAUGAGGCCG AAAGGCCGAA AAUAGAGA 38

( 2 ) INFORMATION FOR SEQ ID NO: 2233:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2233:

UGACUCGUCU GAUGAGGCCG AAAGGCCGAA AAAGAAAU 38

( 2 ) INFORMATION FOR SEQ ID NO: 2234:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2234:

GUGGUUGGCU GAUGAGGCCG AAAGGCCGAA ACAUUUC 38

( 2 ) INFORMATION FOR SEQ ID NO: 2235:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2235:

UCAAUAAACU GAUGAGGCCG AAAGGCCGAA AACUGUCA 38

( 2 ) INFORMATION FOR SEQ ID NO: 2236:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2236:

ACUCAAUACU GAUGAGGCCG AAAGGCCGAA AUAACUGU 38

( 2 ) INFORMATION FOR SEQ ID NO: 2237:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2237:

UACUCAAUCU GAUGAGGCCG AAAGGCCGAA AAUAACUG 38

( 2 ) INFORMATION FOR SEQ ID NO: 2238:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2238:

GUACUCAACU GAUGAGGCCG AAAGGCCGAA AAAUAACU 38

( 2 ) INFORMATION FOR SEQ ID NO: 2239:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2239:

GGGUACUCCU GAUGAGGCCG AAAGGCCGAA AUAAAUAA 38

( 2 ) INFORMATION FOR SEQ ID NO: 2240:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2240:

CAAUAAAUCU GAUGAGGCCG AAAGGCCGAA ACUGUCAG  38

( 2 ) INFORMATION FOR SEQ ID NO: 2241:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2241:

UGACCUCGCU GAUGAGGCCG AAAGGCCGAA AGACAUUC  38

( 2 ) INFORMATION FOR SEQ ID NO: 2242:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2242:

CUGGCAUGCU GAUGAGGCCG AAAGGCCGAA AAGAGUCU  38

( 2 ) INFORMATION FOR SEQ ID NO: 2243:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2243:

GCCUGGGGCU GAUGAGGCCG AAAGGCCGAA AAGUACCC  38

( 2 ) INFORMATION FOR SEQ ID NO: 2244:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2244:

GACCUGUGCU GAUGAGGCCG AAAGGCCGAA AGAAGCCC  38

( 2 ) INFORMATION FOR SEQ ID NO: 2245:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 2245:

CAGUGGCUCU GAUGAGGCCG AAAGGCCGAA ACACAAAA  38

( 2 ) INFORMATION FOR SEQ ID NO: 2246:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2246:

CAUCCAGUCU GAUGAGGCCG AAAGGCCGAA AGUCUCCA  38

(2) INFORMATION FOR SEQ ID NO: 2247:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2247:

CCCAGGCCCU GAUGAGGCCG AAAGGCCGAA AGGUUCUC  38

(2) INFORMATION FOR SEQ ID NO: 2248:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2248:

AAGGUAGGCU GAUGAGGCCG AAAGGCCGAA AUGUAUGU  38

(2) INFORMATION FOR SEQ ID NO: 2249:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2249:

UGUGGCCUCU GAUGAGGCCG AAAGGCCGAA AGGUCCAG  38

(2) INFORMATION FOR SEQ ID NO: 2250:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2250:

AGUUCUGUCU GAUGAGGCCG AAAGGCCGAA AAGCAUGA  38

(2) INFORMATION FOR SEQ ID NO: 2251:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2251:

ACUACUGACU GAUGAGGCCG AAAGGCCGAA AGCUGUGU  38

(2) INFORMATION FOR SEQ ID NO: 2252:

(i) SEQUENCE CHARACTERISTICS:
(A) LENGTH: 38 base pairs
(B) TYPE: nucleic acid ( C ) STRANDEDNESS: single
( D ) TOPOLOGY: linear ( x i ) SEQUENCE DESCRIPTION: SEQ ID NO: 2252:

GCGACCAGCU GAUGAGGCCG AAAGGCCGAA ACCAGGAG 38

( 2 ) INFORMATION FOR SEQ ID NO: 2253:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2253:

UUCAGUGUCU GAUGAGGCCG AAAGGCCGAA AAUUGGAU 38

( 2 ) INFORMATION FOR SEQ ID NO: 2254:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2254:

GCACCGUGCU GAUGAGGCCG AAAGGCCGAA AUGUGAUC 38

( 2 ) INFORMATION FOR SEQ ID NO: 2255:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2255:

AGCACCGUCU GAUGAGGCCG AAAGGCCGAA AAUGUGAU 38

( 2 ) INFORMATION FOR SEQ ID NO: 2256:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2256:

AACUUGUACU GAUGAGGCCG AAAGGCCGAA AUCCUGAU 38

( 2 ) INFORMATION FOR SEQ ID NO: 2257:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2257:

UACAUGUUCU GAUGAGGCCG AAAGGCCGAA ACCUGCUC 38

( 2 ) INFORMATION FOR SEQ ID NO: 2258:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2258:

ACCCGUAUCU GAUGAGGCCG AAAGGCCGAA AUCUUUCC 38

( 2 ) INFORMATION FOR SEQ ID NO: 2259:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2259:

ACUCAAUACU GAUGAGGCCG AAAGGCCGAA AUAACUGU 38

( 2 ) INFORMATION FOR SEQ ID NO: 2260:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2260:

CAUUGGAGCU GAUGAGGCCG AAAGGCCGAA ACCAGGGC 38

( 2 ) INFORMATION FOR SEQ ID NO: 2261:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2261:

GUAACUUGCU GAUGAGGCCG AAAGGCCGAA AUAUCCUG 38

( 2 ) INFORMATION FOR SEQ ID NO: 2262:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2262:

ACCCGUAUCU GAUGAGGCCG AAAGGCCGAA AUCUUUCC 38

( 2 ) INFORMATION FOR SEQ ID NO: 2263:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2263:

CCUGUGGACU GAUGAGGCCG AAAGGCCGAA AAGCCCAA 38

( 2 ) INFORMATION FOR SEQ ID NO: 2264:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2264:

```
GCCUGGGGCU  GAUGAGGCCG  AAAGGCCGAA  AAGUACCC                                              38
```

( 2 ) INFORMATION FOR SEQ ID NO: 2265:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2265:

```
UGAGCACCCU  GAUGAGGCCG  AAAGGCCGAA  ACAGGCCC                                              38
```

( 2 ) INFORMATION FOR SEQ ID NO: 2266:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2266:

```
GAGAGGUCCU  GAUGAGGCCG  AAAGGCCGAA  ACGAGCAG                                              38
```

( 2 ) INFORMATION FOR SEQ ID NO: 2267:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2267:

```
UGUGGGAGCU  GAUGAGGCCG  AAAGGCCGAA  AGGCAGGG                                              38
```

( 2 ) INFORMATION FOR SEQ ID NO: 2268:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2268:

```
UUCUGUGGCU  GAUGAGGCCG  AAAGGCCGAA  AUGGAUGG                                              38
```

( 2 ) INFORMATION FOR SEQ ID NO: 2269:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2269:

```
CUUCCAGGCU  GAUGAGGCCG  AAAGGCCGAA  AACACAAG                                              38
```

( 2 ) INFORMATION FOR SEQ ID NO: 2270:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2270:

```
AAGAGGAACU  GAUGAGGCCG  AAAGGCCGAA  AGCAGUUC                                              38
```

( 2 ) INFORMATION FOR SEQ ID NO: 2271:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2271:

UAAUAGAGCU GAUGAGGCCG AAAGGCCGAA AGGAAGUC      38

( 2 ) INFORMATION FOR SEQ ID NO: 2272:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2272:

UCGUGAAACU GAUGAGGCCG AAAGGCCGAA AAAUCAGC      38

( 2 ) INFORMATION FOR SEQ ID NO: 2273:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2273:

CGCAAGAGCU GAUGAGGCCG AAAGGCCGAA AAGAGCAG      38

( 2 ) INFORMATION FOR SEQ ID NO: 2274:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2274:

ACUCGUGACU GAUGAGGCCG AAAGGCCGAA AGAAAUCA      38

( 2 ) INFORMATION FOR SEQ ID NO: 2275:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2275:

UGACUCGUCU GAUGAGGCCG AAAGGCCGAA AAAGAAAU      38

( 2 ) INFORMATION FOR SEQ ID NO: 2276:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2276:

CUUGUGUCCU GAUGAGGCCG AAAGGCCGAA ACCGGAUA      38

( 2 ) INFORMATION FOR SEQ ID NO: 2277:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2277:

CGUCCACACU GAUGAGGCCG AAAGGCCGAA AGUAUUUA      38

( 2 ) INFORMATION FOR SEQ ID NO: 2278:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2278:

GAGGACCACU GAUGAGGCCG AAAGGCCGAA AUAGCACA      38

( 2 ) INFORMATION FOR SEQ ID NO: 2279:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2279:

UGAAGCAUCU GAUGAGGCCG AAAGGCCGAA AGAAAUUG      38

( 2 ) INFORMATION FOR SEQ ID NO: 2280:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2280:

AACUUGUACU GAUGAGGCCG AAAGGCCGAA AUCCUGAU      38

( 2 ) INFORMATION FOR SEQ ID NO: 2281:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2281:

AGUUCUGUCU GAUGAGGCCG AAAGGCCGAA AAGCAUGA      38

( 2 ) INFORMATION FOR SEQ ID NO: 2282:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2282:

GAACUCUGCU GAUGAGGCCG AAAGGCCGAA AUUAAUAA      38

( 2 ) INFORMATION FOR SEQ ID NO: 2283:

-continued ( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2283:

UAGUCUCCCU GAUGAGGCCG AAAGGCCGAA ACCCCAGG      38

( 2 ) INFORMATION FOR SEQ ID NO: 2284:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2284:

AACUGUCACU GAUGAGGCCG AAAGGCCGAA AACUCUGA      38

( 2 ) INFORMATION FOR SEQ ID NO: 2285:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2285:

UCGUUUGUCU GAUGAGGCCG AAAGGCCGAA AUCCUCCG      38

( 2 ) INFORMATION FOR SEQ ID NO: 2286:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2286:

GGGGGAAGCU GAUGAGGCCG AAAGGCCGAA ACUGUUCA      38

( 2 ) INFORMATION FOR SEQ ID NO: 2287:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2287:

CGAGGCAGCU GAUGAGGCCG AAAGGCCGAA AAGGCUUC      38

( 2 ) INFORMATION FOR SEQ ID NO: 2288:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2288:

GAGGCAGGCU GAUGAGGCCG AAAGGCCGAA AACAGGCC      38

( 2 ) INFORMATION FOR SEQ ID NO: 2289:

( i ) SEQUENCE CHARACTERISTICS:
        ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO: 2289:

AGAGGCAGCU GAUGAGGCCG AAAGGCCGAA AAACAGGC 38

(2) INFORMATION FOR SEQ ID NO: 2290:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2290:

AACAAAGGCU GAUGAGGCCG AAAGGCCGAA AGGAAUGU 38

(2) INFORMATION FOR SEQ ID NO: 2291:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2291:

UGUGGGAGCU GAUGAGGCCG AAAGGCCGAA AGGCAGGG 38

(2) INFORMATION FOR SEQ ID NO: 2292:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2292:

UUGGGAACCU GAUGAGGCCG AAAGGCCGAA AAGGUAGG 38

(2) INFORMATION FOR SEQ ID NO: 2293:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2293:

GGCGGUAACU GAUGAGGCCG AAAGGCCGAA AGGUGUAA 38

(2) INFORMATION FOR SEQ ID NO: 2294:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2294:

GGGAUCACCU GAUGAGGCCG AAAGGCCGAA ACGGCGAC 38

(2) INFORMATION FOR SEQ ID NO: 2295:

(i) SEQUENCE CHARACTERISTICS:
(A) LENGTH: 38 base pairs
(B) TYPE: nucleic acid
(C) STRANDEDNESS: single (D) TOPOLOGY: linear (xi) SEQUENCE DESCRIPTION: SEQ ID NO: 2295:

ACAUUGGCU GAUGAGGCCG AAAGGCCGAA ACAAAGGU 38

(2) INFORMATION FOR SEQ ID NO: 2296:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2296:

GACAUUGGCU GAUGAGGCCG AAAGGCCGAA AACAAAGG 38

(2) INFORMATION FOR SEQ ID NO: 2297:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2297:

UAGGUGGGCU GAUGAGGCCG AAAGGCCGAA AGGUGGUC 38

(2) INFORMATION FOR SEQ ID NO: 2298:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2298:

UAGGAAUGCU GAUGAGGCCG AAAGGCCGAA AUGUAGGU 38

(2) INFORMATION FOR SEQ ID NO: 2299:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2299:

AAGGUAGGCU GAUGAGGCCG AAAGGCCGAA AUGUAUGU 38

(2) INFORMATION FOR SEQ ID NO: 2300:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2300:

AAAGGUAGCU GAUGAGGCCG AAAGGCCGAA AAUGUAUG 38

(2) INFORMATION FOR SEQ ID NO: 2301:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO: 2301:

AAUAGGUGCU GAUGAGGCCG AAAGGCCGAA AAAUGGAC 38

( 2 ) INFORMATION FOR SEQ ID NO: 2302:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2302:

ACAUUGGCU GAUGAGGCCG AAAGGCCGAA ACAAAGGU 38

( 2 ) INFORMATION FOR SEQ ID NO: 2303:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2303:

GACAUUGGCU GAUGAGGCCG AAAGGCCGAA AACAAAGG 38

( 2 ) INFORMATION FOR SEQ ID NO: 2304:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2304:

UGAGGGUCU GAUGAGGCCG AAAGGCCGAA AAUGCUGU 38

( 2 ) INFORMATION FOR SEQ ID NO: 2305:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2305:

GGAUACCUCU GAUGAGGCCG AAAGGCCGAA AGCACCGA 38

( 2 ) INFORMATION FOR SEQ ID NO: 2306:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2306:

AAAGUCCGCU GAUGAGGCCG AAAGGCCGAA AGCUGCCU 38

( 2 ) INFORMATION FOR SEQ ID NO: 2307:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2307:

CUGACACACU GAUGAGGCCG AAAGGCCGAA AAUCUCUG 38

( 2 ) INFORMATION FOR SEQ ID NO: 2308:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2308:

CCAGGGCACU GAUGAGGCCG AAAGGCCGAA AGUGCAGG 38

( 2 ) INFORMATION FOR SEQ ID NO: 2309:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2309:

GAGAGGUCCU GAUGAGGCCG AAAGGCCGAA ACGAGCAG 38

( 2 ) INFORMATION FOR SEQ ID NO: 2310:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2310:

GGCUGUGGCU GAUGAGGCCG AAAGGCCGAA AGGAGGCA 38

( 2 ) INFORMATION FOR SEQ ID NO: 2311:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2311:

CUUCGCAACU GAUGAGGCCG AAAGGCCGAA AGGAAGAG 38

( 2 ) INFORMATION FOR SEQ ID NO: 2312:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2312:

AGCAGGGCU GAUGAGGCCG AAAGGCCGAA AAUAGAGA 38

( 2 ) INFORMATION FOR SEQ ID NO: 2313:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2313:

GCGACCAGCU GAUGAGGCCG AAAGGCCGAA ACCAGGAG 38

( 2 ) INFORMATION FOR SEQ ID NO: 2314:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2314:

GAGGACCACU GAUGAGGCCG AAAGGCCGAA AUAGCACA        38

( 2 ) INFORMATION FOR SEQ ID NO: 2315:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2315:

ACAACGGCCU GAUGAGGCCG AAAGGCCGAA ACCAGGAC        38

( 2 ) INFORMATION FOR SEQ ID NO: 2316:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2316:

CCUGGUGACU GAUGAGGCCG AAAGGCCGAA ACUCCCAC        38

( 2 ) INFORMATION FOR SEQ ID NO: 2317:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2317:

UCCCACGGCU GAUGAGGCCG AAAGGCCGAA AGCUAAAG        38

( 2 ) INFORMATION FOR SEQ ID NO: 2318:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2318:

CAUCCAGUCU GAUGAGGCCG AAAGGCCGAA AGUCUCCA        38

( 2 ) INFORMATION FOR SEQ ID NO: 2319:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2319:

AACUGUCACU GAUGAGGCCG AAAGGCCGAA AACUCUGA        38

( 2 ) INFORMATION FOR SEQ ID NO: 2320:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2320:

AGCAGCACCU GAUGAGGCCG AAAGGCCGAA ACUGAGAG 38

( 2 ) INFORMATION FOR SEQ ID NO: 2321:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2321:

GGAGCUGACU GAUGAGGCCG AAAGGCCGAA AAGUUGUA 38

( 2 ) INFORMATION FOR SEQ ID NO: 2322:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2322:

GUGAAUUGCU GAUGAGGCCG AAAGGCCGAA AUCUGUGA 38

( 2 ) INFORMATION FOR SEQ ID NO: 2323:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2323:

UGGAUGGACU GAUGAGGCCG AAAGGCCGAA ACCUGAGC 38

( 2 ) INFORMATION FOR SEQ ID NO: 2324:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2324:

AAUGUAUGCU GAUGAGGCCG AAAGGCCGAA AGGUGGGG 38

( 2 ) INFORMATION FOR SEQ ID NO: 2325:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 2325:

AGAGGCAGCU GAUGAGGCCG AAAGGCCGAA AAACAGGC 38

( 2 ) INFORMATION FOR SEQ ID NO: 2326:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2326:

AGCACCCUCU GAUGAGGCCG AAAGGCCGAA ACCUGUGG 38

(2) INFORMATION FOR SEQ ID NO: 2327:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2327:

GCUUGCAGCU GAUGAGGCCG AAAGGCCGAA ACCCUUCU 38

(2) INFORMATION FOR SEQ ID NO: 2328:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2328:

AGCUUCAGCU GAUGAGGCCG AAAGGCCGAA ACCCUAGU 38

(2) INFORMATION FOR SEQ ID NO: 2329:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2329:

AGUCCUCUCU GAUGAGGCCG AAAGGCCGAA AGGCUGA 38

(2) INFORMATION FOR SEQ ID NO: 2330:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2330:

CCUGGGGCU GAUGAGGCCG AAAGGCCGAA AGUACCCU 38

(2) INFORMATION FOR SEQ ID NO: 2331:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2331:

UAGGUGGGCU GAUGAGGCCG AAAGGCCGAA AGGUGGUC 38

(2) INFORMATION FOR SEQ ID NO: 2332:

(i) SEQUENCE CHARACTERISTICS:
(A) LENGTH: 38 base pairs
(B) TYPE: nucleic acid (C) STRANDEDNESS: single
(D) TOPOLOGY: linear (xi) SEQUENCE DESCRIPTION: SEQ ID NO: 2332:

ACCUUCCUCU GAUGAGGCCG AAAGGCCGAA AGGUAGGG 38

(2) INFORMATION FOR SEQ ID NO: 2333:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2333:

CACCUUCCCU GAUGAGGCCG AAAGGCCGAA AAGGUAGG 38

(2) INFORMATION FOR SEQ ID NO: 2334:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2334:

ACCCGUAUCU GAUGAGGCCG AAAGGCCGAA AUCUUUCC 38

(2) INFORMATION FOR SEQ ID NO: 2335:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2335:

CAAACCCGCU GAUGAGGCCG AAAGGCCGAA AUGAUCUU 38

(2) INFORMATION FOR SEQ ID NO: 2336:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2336:

CCUGCACGCU GAUGAGGCCG AAAGGCCGAA AUCCACCC 38

(2) INFORMATION FOR SEQ ID NO: 2337:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2337:

GGUUUUUACU GAUGAGGCCG AAAGGCCGAA ACAGGGAC 38

(2) INFORMATION FOR SEQ ID NO: 2338:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO: 2338:

CCACUCGACU GAUGAGGCCG AAAGGCCGAA AGUUCGUC 38

( 2 ) INFORMATION FOR SEQ ID NO: 2339:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2339:

GGAAGAUCCU GAUGAGGCCG AAAGGCCGAA AAAGUCCG 38

( 2 ) INFORMATION FOR SEQ ID NO: 2340:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2340:

AGGCCGCACU GAUGAGGCCG AAAGGCCGAA AGCAAAAG 38

( 2 ) INFORMATION FOR SEQ ID NO: 2341:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2341:

GCAGGGUCU GAUGAGGCCG AAAGGCCGAA AUAGAGAA 38

( 2 ) INFORMATION FOR SEQ ID NO: 2342:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2342:

UUGACCAUCU GAUGAGGCCG AAAGGCCGAA AUUUCACG 38

( 2 ) INFORMATION FOR SEQ ID NO: 2343:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2343:

GUUCUGUGCU GAUGAGGCCG AAAGGCCGAA AGCAUGAG 38

( 2 ) INFORMATION FOR SEQ ID NO: 2344:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2344:

AGUUCUGUCU GAUGAGGCCG AAAGGCCGAA AAGCAUGA                                38

( 2 ) INFORMATION FOR SEQ ID NO: 2345:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2345:

AGGGUCAGCU GAUGAGGCCG AAAGGCCGAA AUGGGAGC                                38

( 2 ) INFORMATION FOR SEQ ID NO: 2346:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2346:

GGAAGAUCCU GAUGAGGCCG AAAGGCCGAA AAAGUCCG                                38

( 2 ) INFORMATION FOR SEQ ID NO: 2347:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2347:

ACCUCCAGCU GAUGAGGCCG AAAGGCCGAA AGGUCAGG                                38

( 2 ) INFORMATION FOR SEQ ID NO: 2348:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2348:

GGAGCUGACU GAUGAGGCCG AAAGGCCGAA AAGUUGUA                                38

( 2 ) INFORMATION FOR SEQ ID NO: 2349:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2349:

UGGGAGCUCU GAUGAGGCCG AAAGGCCGAA AAAAGUUG                                38

( 2 ) INFORMATION FOR SEQ ID NO: 2350:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2350:

GGAUACCUCU GAUGAGGCCG AAAGGCCGAA AGCACCGA                                38

( 2 ) INFORMATION FOR SEQ ID NO: 2351:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2351:

GGGGGAAGCU GAUGAGGCCG AAAGGCCGAA ACCCUGUG 38

( 2 ) INFORMATION FOR SEQ ID NO: 2352:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2352:

UGCGCUGGCU GAUGAGGCCG AAAGGCCGAA AGGGGUGC 38

( 2 ) INFORMATION FOR SEQ ID NO: 2353:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2353:

AGGUGGGUCU GAUGAGGCCG AAAGGCCGAA AGGGGUAA 38

( 2 ) INFORMATION FOR SEQ ID NO: 2354:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2354:

CUAGUCGGCU GAUGAGGCCG AAAGGCCGAA AGAUCGAA 38

( 2 ) INFORMATION FOR SEQ ID NO: 2355:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2355:

UUCCAGGGCU GAUGAGGCCG AAAGGCCGAA ACACAAGA 38

( 2 ) INFORMATION FOR SEQ ID NO: 2356:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2356:

UGAGCACCCU GAUGAGGCCG AAAGGCCGAA ACAGGCCC 38

-continued ( 2 ) INFORMATION FOR SEQ ID NO: 2357:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2357:

GGUGCUGGCU GAUGAGGCCG AAAGGCCGAA AGACUCCA                         38

( 2 ) INFORMATION FOR SEQ ID NO: 2358:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2358:

AAAGUCCGCU GAUGAGGCCG AAAGGCCGAA AGCUGCCU                         38

( 2 ) INFORMATION FOR SEQ ID NO: 2359:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2359:

AGAGAAGGCU GAUGAGGCCG AAAGGCCGAA AGUCAGCC                         38

( 2 ) INFORMATION FOR SEQ ID NO: 2360:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2360:

AAGAGGAACU GAUGAGGCCG AAAGGCCGAA AGCAGUUC                         38

( 2 ) INFORMATION FOR SEQ ID NO: 2361:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2361:

AGAGAAGGCU GAUGAGGCCG AAAGGCCGAA AGUCAGCC                         38

( 2 ) INFORMATION FOR SEQ ID NO: 2362:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2362:

UUAAUAAACU GAUGAGGCCG AAAGGCCGAA ACAUCAAC                         38

( 2 ) INFORMATION FOR SEQ ID NO: 2363:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 2363:

CGCAAGAGCU GAUGAGGCCG AAAGGCCGAA AAGAGCAG 38

( 2 ) INFORMATION FOR SEQ ID NO: 2364:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2364:

AAUUAAUACU GAUGAGGCCG AAAGGCCGAA AUACAUCA 38

( 2 ) INFORMATION FOR SEQ ID NO: 2365:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2365:

AAGAGGAACU GAUGAGGCCG AAAGGCCGAA AGCAGUUC 38

( 2 ) INFORMATION FOR SEQ ID NO: 2366:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2366:

GUAAUAGACU GAUGAGGCCG AAAGGCCGAA AAGGAAGU 38

( 2 ) INFORMATION FOR SEQ ID NO: 2367:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2367:

GGGUAAUACU GAUGAGGCCG AAAGGCCGAA AGAAGGAA 38

( 2 ) INFORMATION FOR SEQ ID NO: 2368:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2368:

UGAAUUAACU GAUGAGGCCG AAAGGCCGAA AAAUACAU 38

( 2 ) INFORMATION FOR SEQ ID NO: 2369:

( i ) SEQUENCE CHARACTERISTICS:
        ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO: 2369:

CUGGGAACCU GAUGAGGCCG AAAGGCCGAA AAUACACA                                      38

(2) INFORMATION FOR SEQ ID NO: 2370:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2370:

UCUGAAUUCU GAUGAGGCCG AAAGGCCGAA AUAAAUAC                                      38

(2) INFORMATION FOR SEQ ID NO: 2371:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2371:

CUCUGAAUCU GAUGAGGCCG AAAGGCCGAA AAUAAAUA                                      38

(2) INFORMATION FOR SEQ ID NO: 2372:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2372:

CUUCGCAACU GAUGAGGCCG AAAGGCCGAA AGGAAGAG                                      38

(2) INFORMATION FOR SEQ ID NO: 2373:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2373:

GUCUUCGCCU GAUGAGGCCG AAAGGCCGAA AGAGGAAG                                      38

(2) INFORMATION FOR SEQ ID NO: 2374:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2374:

UGACUCGUCU GAUGAGGCCG AAAGGCCGAA AAAGAAAU                                      38

(2) INFORMATION FOR SEQ ID NO: 2375:

(i) SEQUENCE CHARACTERISTICS:
(A) LENGTH: 38 base pairs
(B) TYPE: nucleic acid
(C) STRANDEDNESS: single (D) TOPOLOGY: linear (xi) SEQUENCE DESCRIPTION: SEQ ID NO: 2375:

CAGUGGCUCU GAUGAGGCCG AAAGGCCGAA ACACAAAA 38

(2) INFORMATION FOR SEQ ID NO: 2376:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2376:

GGCAGCGGCU GAUGAGGCCG AAAGGCCGAA ACACCAUC 38

(2) INFORMATION FOR SEQ ID NO: 2377:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2377:

GGUGCUGGCU GAUGAGGCCG AAAGGCCGAA AGACUCCA 38

(2) INFORMATION FOR SEQ ID NO: 2378:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2378:

GCCUGGGGCU GAUGAGGCCG AAAGGCCGAA AAGUACUG 38

(2) INFORMATION FOR SEQ ID NO: 2379:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2379:

GUCAGAGGCU GAUGAGGCCG AAAGGCCGAA AGCAUGGU 38

(2) INFORMATION FOR SEQ ID NO: 2380:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2380:

GAAGAUCGCU GAUGAGGCCG AAAGGCCGAA AAGUCCGG 38

(2) INFORMATION FOR SEQ ID NO: 2381:

(i) SEQUENCE CHARACTERISTICS:
(A) LENGTH: 38 base pairs
(B) TYPE: nucleic acid
(C) STRANDEDNESS: single
(D) TOPOLOGY: linear ( x i ) SEQUENCE DESCRIPTION: SEQ ID NO: 2381:

CCAUGCACU GAUGAGGCCG AAAGGCCGAA AGGAAGCA 38

( 2 ) INFORMATION FOR SEQ ID NO: 2382:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2382:

AUUGAUUCCU GAUGAGGCCG AAAGGCCGAA AAGGAAAG 38

( 2 ) INFORMATION FOR SEQ ID NO: 2383:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2383:

CAGUGGCUCU GAUGAGGCCG AAAGGCCGAA ACACAAAA 38

( 2 ) INFORMATION FOR SEQ ID NO: 2384:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2384:

CUGGGAACCU GAUGAGGCCG AAAGGCCGAA AAUACACA 38

( 2 ) INFORMATION FOR SEQ ID NO: 2385:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2385:

ACUUUAUUCU GAUGAGGCCG AAAGGCCGAA AUUCAAAG 38

( 2 ) INFORMATION FOR SEQ ID NO: 2386:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2386:

AGCUUGAACU GAUGAGGCCG AAAGGCCGAA AGCUUCCA 38

( 2 ) INFORMATION FOR SEQ ID NO: 2387:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2387:

```
UAAAACUUCU    GAUGAGGCCG    AAAGGCCGAA    AUUGAUUC                                    38
```

( 2 ) INFORMATION FOR SEQ ID NO: 2388:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2388:

```
AGCUUGAACU    GAUGAGGCCG    AAAGGCCGAA    AGCUUCCA                                    38
```

( 2 ) INFORMATION FOR SEQ ID NO: 2389:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2389:

```
CAGGUGAGCU    GAUGAGGCCG    AAAGGCCGAA    ACCAUAUA                                    38
```

( 2 ) INFORMATION FOR SEQ ID NO: 2390:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2390:

```
UCAGCUUGCU    GAUGAGGCCG    AAAGGCCGAA    AGAGCUUC                                    38
```